United States Patent
Haynes et al.

(10) Patent No.: US 10,232,034 B2
(45) Date of Patent: Mar. 19, 2019

(54) COMPOSITIONS COMPRISING CH505 ENVELOPES, AND TRIMERS

(71) Applicants: Duke University, Durham, NC (

(56) References Cited

OTHER PUBLICATIONS

Chen, C., et al., "The site and stage of anti-DNA B-cell deletion," Nature, vol. 373, pp. 252-255 (Jan. 19, 1995).

Gao, F., et al., "Cooperation of B Cell Lineages in Induction of HIV-1-Broadly Neutralizing Antibodies," Cell, vol. 158, No. 3, pp. 481-491, Author Manuscript—15 total pages (Jul. 31, 2014).

Goepfert, P. A., et al., "Specificity and 6-Month Durability of Immune Responses Induced by DNA and Recombinant Modified Vaccinia Ankara Vaccines Expressing HIV-1 Virus-Like Particles," J. Infect. Dis., vol. 210, pp. 99-110 (Jul. 1, 2014).

Graham, B. S., et al., "DNA Vaccine Delivered by a Needle-Free Injection Device Improves Potency of Priming for Antibody and CD8+ T-Cell Responses after rAd5 Boost in a Randomized Clinical Trial," PLoS One, vol. 8, Issue 4, e59340, pp. 1-11 (Apr. 2013).

Haynes, B. F., et al., "B-cell-lineage immunogen design in vaccine development with HIV-1 as a case study," Nature Biotech., vol. 30, No. 5, pp. 423-433 (May 2012).

Jalah, R., et al., "DNA and Protein Co-Immunization Improves the Magnitude and Longevity of Humoral Immune Responses in Macaques," PLoS One, vol. 9, Issue 3, e91550, pp. 1-13 (Mar. 2014).

Kepler, T. B., et al., "Somatic Hypermutation in B Cells: An Optimal Control Treatment," J. Theor. Biol., vol. 164, pp. 37-64 (1993).

Kibler, K. V., et al., "Improved NYVAC-Based Vaccine Vectors," PLoS One, vol. 6, Issue 11, e25674, pp. 1-13 (Nov. 2011).

Liao, H.-X., et al., "A group M consensus envelope glycoprotein induces antibodies that neutralize subsets of subtype B and C HIV-1 primary viruses," Virology, vol. 353, pp. 268-282 (2006).

Liao, H.-X., et al., "Co-evolution of a broadly neutralizing HIV-1 antibody and founder virus," Nature, vol. 496, No. 7446, No. 7446, pp. 469-476, Author Manuscript—25 total pages (Apr. 25, 2013).

Liao, H.-X., et al., "Initial antibodies binding to HIV-1 gp41 in acutely infected subjects are polyreactive and highly mutated," JEM, vol. 208, pp. 1-13 (Oct. 10, 2011).

Mascola, J. R. and Haynes, B. F., "HIV-1 neutralizing antibodies: understanding nature's pathways" Immunol. Rev., vol. 254, No. 1, pp. 225-244, Author Manuscript—29 total pages (Jul. 2013).

Meffre, E., et al., "Immunoglobulin heavy chain expression shapes the B cell receptor repertoire in human B cell development," The Journal of Clinical Investigation, vol. 108, No. 6, pp. 879-886 (Sep. 2001).

Perreau, M., et al., "DNA/NYVAC Vaccine Regimen Induces HIV-Specific CD4 and CD8 T-Cell Responses in Intestinal Mucosa," J. Virology, vol. 85, No. 19, pp. 9854-9862 (Oct. 2011).

Pissani, F., et al., "Improvement of Antibody Responses by HIV Envelope DNA and Protein Co-Immunization," Vaccine, vol. 32, No. 4, pp. 507-513, Author Manuscript—17 total pages (Jan. 16, 2014).

Santra, S., et al., "Mosaic Vaccines Elicit CD8+ T lymphocyte Responses in Monkeys that Confer Enhanced Immune Coverage of Diverse HIV Strains," Nature Med., vol. 16, No. 3, pp. 324-328, Authur Manuscript—13 total pages (Mar. 2010).

Shiokawa, S., et al., "IgM Heavy Chain Complementarity-Determining Region 3 Diversity Is Constrained by Genetic and Somatic Mechanisms Until Two Months After Birth," The Journal of Immunology, vol. 162, pp. 6060-6070 (1999).

Tomaras, G. D., et al., "Initial B-Cell Responses to Transmitted Human Immunodeficiency Virus Type 1: Virion-Binding Immunoglobulin M (IgM) and IgG Anitbodies Followed by Plasma Anti-gp41 Antibodies with Ineffective Control of Initial Viremia," J. Virol., vol. 82, No. 24, pp. 12449-12463 (Dec. 2008).

U.S. Appl. No. 61/972,531, filed Mar. 31, 2014, 102 total pages.

Verkoczy, L., et al., "Autoreactivity in an HIV-1 broadly reactive neutralizing antibody variable region heavy chain induces immunologic tolerance," PNAS, vol. 107, No. 1, pp. 181-186 (Jan. 5, 2010).

Verkoczy, L., et al., "Rescue of HIV-1 Broad Neutralizing Antibody-Expressing B Cells in 2F5 $V_H X V_L$ Knockin Mice Reveals Multiple Tolerance Controls," J. Immunol., vol. 187, pp. 3785-3797 (2011).

Yu, J.-S., et al., "Generation of Mucosal Anti-Human Immunodeficiency Virus Type 1 T-Cell Responses by Recombinant *Mycobacterium smegmatis*," Clin. Vaccine Immunol., vol. 13, No. 11, pp. 1204-1211 (Nov. 2006).

Yu, J.-S., et al., "Recombinant *Mycobacterium bovis* Bacillus Calmette-Guerin Elicits Human Immunodeficiency Virus Type 1 Envelope-Specific T Lymphocytes at Mucosal Sites," Clinical and Vaccine Immunology, vol. 14, No. 7, pp. 886-893 (Jul. 2007).

Zhang, J. and Shakhnovich, E. I., "Optimality of Mutation and Selection in Germinal Centers," PLoS Comp. Biol., vol. 6, Issue 6, e1000800, pp. 1-9 (Jun. 2010).

| Lane # | ug/lane (Coo/WB) | Study Group/ Specificity | PTID | Reagent ID | Plasmid/Heavy# | Light # | Lot# | conc. (mg/mL) | % Monomer | Yield (mg) | Date produced |
|---|---|---|---|---|---|---|---|---|---|---|---|
| 1 | N/A | | | Marker | | | | | | | |
| 2 | 1/0.25 | Alam | | CH505TFgp120GCN4 293iTrimer | | | 140826 | 4.92 | | | |
| 3 | 1/0.25 | Alam | | ConC_gp120 N332A 293F Monomer | | | 140818 | 3.56 | | | |
| 4 | 1/0.25 | Alam | | ConC_gp120 WT 293F Monomer | | | 140602 | 1.44 | | | |
| 5 | 1/0.25 | | | CH505.w4.26D8gp120/293F | HV1300777 | | 205JAH | 8.47 | 91.7 | 17.96 | 22-Aug-14 |
| 6 | 1/0.25 | | | CH505w020 4D8gp120/293F | HV1300550 | | 206JAH | 10.56 | 92.9 | 19.85 | 22-Aug-14 |
| 7 | 1/0.25 | | | CH505w030.11D8gp120 | HV1300567 | | 1543MI | 9.91 | 84.2 | 21.80 | 27-Aug-14 |
| 8 | 1/0.25 | | | CH505w030.17D8gp120 | HV1300570 | | 89DRP | 12.00 | 84.0 | 21.00 | 27-Aug-14 |
| 9 | 1/0.25 | | | CH505w030.18D8gp120 | HV1300571 | | 1555MI | 9.54 | 83.0 | 19.08 | 27-Aug-14 |
| 10 | 1/0.25 | | | CH505w030.508gp120 | HV1300568 | | 1979JA | 10.71 | 91.8 | 21.25 | 28-Aug-14 |
| 11 | 1/0.25 | | | CH505w030.908gp120 | HV1300565 | | 88DRP | 9.13 | 89.6 | 17.00 | 27-Aug-14 |
| 12 | 1/0.25 | | | M.CON-Sgp140CFI.avi | HV1300111.avi | | 280HC | 10.31 | N/A | 58.87 | 22-Aug-14 |
| 13 | 1/0.25 | | | CH505TFgp120GCN4-L11-hCD40L(E113-L261)/293F | HV1300760 | | 207JAH | 5.56 | 47.3 | 12.01 | 22-Aug-14 |
| 14 | 1/0.25 | | | CH505TFgp120GCN4-L11-hCD40L(E113-L281) Hs10 | HV1300761 | | 1985JA | 3.94 | 50.6 | 8.50 | 28-Aug-14 |

Figure 2B

| Lane # | ug/lane (Coo/WB) | Study Group/ Specificity | PTID | Reagent ID | Plasmid/Heavy# | Light # | Lot# | conc. (mg/mL) | % Monomer | Yield (mg) | Date produced |
|---|---|---|---|---|---|---|---|---|---|---|---|
| 1 | N/A | | | Marker | | | | | | | |
| 2 | 1/0.25 | Alam | | CH505TF.gp120.6CN4.293iTrimer | | | 140826 | 4.92 | | | |
| 3 | 1/0.25 | Alam | | ConC_gp120_N332A.293F Monomer | | | 140818 | 3.56 | | | |
| 4 | 1/0.15 | Alam | | ConC_gp120_WT 293F Monomer | | | 140602 | 1.44 | | | |
| 5 | 1/0.25 | | | CH505_w4.26D8gp120/293F | HV1300777 | | 2051AH | 8.47 | 91.7 | 17.96 | 22-Aug-14 |
| 6 | 1/0.25 | | | CH505w020.4D8gp120/293F | HV1300550 | | 2061AH | 10.56 | 92.9 | 19.85 | 27-Aug-14 |
| 7 | 1/0.25 | | | CH505w030.11D8gp120/293F | HV1300567 | | 1545M | 9.91 | 84.2 | 21.80 | 27-Aug-14 |
| 8 | 1/0.25 | | | CH505w030.17D8gp120 | HV1300570 | | 89DRP | 12.00 | 84.0 | 21.00 | 27-Aug-14 |
| 9 | 1/0.25 | | | CH505w030.18D8gp120 | HV1300571 | | 155SM | 9.54 | 88.0 | 19.08 | 27-Aug-13 |
| 10 | 1/0.25 | | | CH505w030.5D8gp120 | HV1300563 | | 197SJA | 10.71 | 91.8 | 21.25 | 28-Aug-14 |
| 11 | 1/0.25 | | | CH505w030.9D8gp120 | HV1300565 | | 68DRP | 9.13 | 89.6 | 17.02 | 27-Aug-14 |
| 12 | 1/0.25 | | | M.CON-Sgp140CF_avi | HV1300111_avi | | 280HC | 10.31 | N/A | 58.87 | 22-Aug-14 |
| 13 | 1/0.25 | | | CH505TFgp120GCN4-L11-hCD40L (E113-L261)/293F | HV1300760 | | 2071AH | 5.56 | 47.3 | 12.01 | 22-Aug-14 |
| 14 | 1/0.25 | | | CH505TFgp120GCN4-L11-hCD40L (E113-L261)_His10 | HV1300761 | | 1983JA | 3.94 | 50.6 | 8.50 | 28-Aug-14 |

Figure 3B

Antigenicity of CH505 gp120 and CH505 gp140
Dissociation Constant, Kd (nM)

| Antibody/Epitope | CH505TF gp120 Δ7 Monomer | CH505TF gp120 GCN4 Trimer | CH505TF gp140 Trimer |
|---|---|---|---|
| CD4 | +++ | +++ | +++ |
| 17b (CD4i) constitutive | ++ | + | + |
| 17b-CD4 induced | +++ | +++ | +++ |
| A32 (C1) | 0.1 | 2.9 | 3.0 |
| VRC01 (CD4 bs) | 8.4 | 2.5 | 2.4 |
| CH103_UCA (CD4 bs) | 179 | 14.6 | 36.1 |
| CH106 (CD4 bs) | 6.5 | 5.5 | 5.81 |
| F105 (CD4 bs) | 448 | 40.7 | 24.9 |
| 19b (V3) | 9.7 | 0.8 | 1.2 |
| PG9 (V1-V2) | 926 | 159 | 69.2 |
| CH01 (V1-V2) | >100 μM | >100 μM | NB |
| 697 D (V2) | 564 | 554 | 170 |
| CH58 (V2) | 278 | 104 | 60.5 |
| 2G12 (-CHO) | 656 | 169 | 6.5 |
| PGT128 (-CHO) | 154 | 53 | 20.3 |
| 35022 | NB | NB | NB |
| PGT145 | NB | NB | NB |
| PGT151 | NB | NB | NB |

Figure 5

"The Production 10" CH505 gp120, gp145 and gp160 Envs

| Env name | Plasmid ID | Unique bar code ID at the 3' end |
|---|---|---|
| CH505.M6D8gp120 | HV1300532_v2 | TAGTAAGgtcaccgaattcgggacccggatcc |
| CH505.M11D8gp120 | HV1300537_v2 | TAGTAAGgtgaccgaattcaggtcccggatcc |
| CH505w020.14D8gp120 | HV1300556_v2 | TAGTAAGggacccgaattcggtcaccggatcc |
| CH505w030.28D8gp120 | HV1300578_v2 | TAGTAAGggtcctgaattcggttaccggatcc |
| CH505w030.21D8gp120 | HV1300574_v2 | TAGTAAGggtcccgaattcggttaccggatcc |
| CH505w053.16D8gp120 | HV1300583 | TAGTAAGaattcggtgaccgggtcccggatcc |
| CH505w053.31D8gp120 | HV1300586 | TAGTAAGaattcggtgaccgggacctggatcc |
| CH505w078.33D8gp120 | HV1300595 | TAGTAAGaattcggtaaccaggtcccggatcc |
| CH505w078.15D8gp120 | HV1300592 | TAGTAAGaattcggtcaccgggtcctggatcc |
| CH505w100.B6D8gp120 | HV1300605 | TAGTAAGgtaaccgggacccgaattcggatcc |
| CH505.M6gp145 | HV1300657 | TGATGAGgtcaccgaattcgggacccggatcc |
| CH505.M11gp145 | HV1300662 | TGATGAGgtgaccgaattcaggtcccggatcc |
| CH505w020.14gp145 | HV1300635 | TGATGAGggacccgaattcggtcaccggatcc |
| CH505w030.28gp145 | HV1300636 | TGATGAGggtcctgaattcggttaccggatcc |
| CH505w30.21gp145 | HV1300689 | TGATGAGggtcccgaattcggttaccggatcc |
| CH505w53.16gp145 | HV1300696 | TGATGAGaattcggtgaccgggtcccggatcc |
| CH505w053.31gp145 | HV1300638 | TGATGAGaattcggtgaccgggacctggatcc |
| CH505w78.33gp145 | HV1300705 | TGATGAGaattcggtaaccaggtcccggatcc |
| CH505w078.15gp145 | HV1300639 | TGATGAGaattcggtcaccgggtcctggatcc |
| CH505w100.B6gp145 | HV1300714 | TGATGAGgtaaccgggacccgaattcggatcc |

CH505.M6 gp160

CH505.M11 gp160

CH505w020.14 gp160

CH505w030.28 gp160

CH505w030.21 gp160

CH505w053.16 gp160

CH505w053.31 gp160

CH505w078.33 gp160

CH505w078.15 gp160

CH505w100.B6 gp160

All CH505 gp120 and 145 gene inserts were cloned into VRC8400 plasmid at SalI-BamHI site.

GP120 DNA constructs:

>HV1300532_v2, CH505.M6D8gp120
gtcgacaagaaGCCACCATGCGCGTGATGGGCATCCAGCGCAACTACCCGCAGTGGTGGATCTGGTCGATGCTGGGCTTCTGG
ATGCTCATGATCTGCAACGGCgtgccggtgTGGAAGGAGGCCAAGACGACCCTGTTCTGCGCGTCGGACGCCAAGGCCTACGA
GAAGGAGGTGCACAACGTGTGGGCGACCCACGCCTGCGTGCCCACGGACCCCAACCCGCAGGAGATGGTGCTGAAGAACGTGA
CCGAGAACTTCAACATGTGGAAGAACGACATGGTGGACCAGATGCACGAGGACGTGATCTCCCTGTGGGACCAGTCCCTGAAG
CCCTGCGTGAAGCTGACCCCGCTGTGCGTGACCCTGAACTGCACCAACGCCGCGTCCAACTCCTCCATCATCGAGGGCAT
GAAGAACTGCTCCTTCAACATCACGACGGAGCTGCGCGACAAGCGCGAGAAGAAGAACGCCCTGTTCTACAAGCTGGACATCG
TGCAGCTGGACGGCAACTCCTCGCAGTACAGGCTGATCAACTGCAACACCTCCGTCATCACGCAGGGCGTGCCCCAAGGTGTCC
TTCGACCCCATCCCCATCCACTACTGCGCCCCCGCCGGCTACGCCATCCTGAAGTGCAACAACAAGACCTTCACCGGCACCGG
CCCGTGCAACAACGTGTCCACCGTGCAGTGCACGCACGGGATCAAGCCCGTGGTGTCCACGCAGCTGCTCCTGAACGGGTCGC

Figure 17

```
TGGCCGAGGGCGAGATCATCATCCGGTCCGAGAACATCACGAACAACGCGAAGACCATCATCGTGCACCTGAACGAGTCCGTG
AAGATCGAGTGCACCCGCCCGAACAACAAGACGCGCACCTCCATCCGGATCGGCCCTGGCCAGGCCTTCTACGCCACCGGCCA
GGTGATCGGCGACATCCGCGAGGCGTACTGCAACATCAACGAGTCCAAGTGGAACGAGACCCTGCAGCGCGTGTCCAAGAAGC
TGAAGGAGTACTTCCCCCACAAGAACATCACCTTCCAGCCGTCGTCCGGCGGCGACCTCGAGATCACCACGCACTCCTTCAAC
TGCGGTGGCGAGTTCTTCTACTGCAACACGTCGTCGCTGTTCAACCGCACCTACATGGCCAACTCCACCGACATGGCCAACTC
CACCGAGACCAACTCCACGCGCACCATCACGATCCACTGCCGCATCAAGCAGATCATCAACATGTGGCAGGAGGTGGGCCGCG
CCATGTACGCACCGCCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGA
GGTGAAGCCCCTGGGCGTGGCACCCACCAACGCCcgcGAGcgcgtcgtggagcgcgagaagGAGTAGTAAGgtcaccgaattc
gggacccggatcc
>HV1300537_v2, CH505.M11D8gp120
gtcgacaagaaGCCACCATGCGCGTGATGGGCATCCAGCGCAACTACCCGCAGTGGTGGATCTGGTCGATGCTGGGCTTCTGG
ATGCTCATGATCTGCAACGGCgtgccggtgTGGAAGGAGGCCAAGACGACCCTGTTCTGCGCGTCGGACGCCAAGGCCTACGA
GAAGGAGGTGCACAACGTGTGGGCGACCCACGCCTGCGTGCCCACGGACCCCAACCCGCAGGAGATGGTGCTGAAGAACGTGA
CCGAGAACTTCAACATGTGGAAGAACGACATGGTGGACCAGATGCACGAGGACGTGATCTCCCTGTGGGACCAGTCCCTGAAG
CCCTGCGTGAAGCTGACCCCGCTGTGCGTGACCCTGAACTGCACCAACGCCACCGCGTCCAACTCCTCCATCATCGAGGGCAT
GAAGAACTGCTCCTTCAACATCACGACGGAGCTGCGCGACAAGCGCGAGAAGAAGAACGCCCTGTTCTACAAGCTGGACATCG
TGCAGCTGGACGGCAACTCCTCGCAGTACAGGCTGATCAACTGCAACACCTCCGTCATCACGCAGGCGTGCCCCAAGGTGTCC
TTCGACCCCATCCCCATCCACTACTGCGCCCCCGCCGGCTACGCCATCCTGAAGTGCAACAACAAGACCTTCACCGGCACCGG
CCCGTCCAACAACGTGTCCACCGTGCAGTGCACGCACGGGATCAAGCCCGTGGTGTCCACCCAGCTGCTCCTGAACGGGTCGC
TGGCCGAGGGCGAGATCATCATCCGGTCCGAGAACATCACGGACAACGGGAAGACCATCATCGTGCACCTGAACGAGTCCGTG
AAGATCGAGTGCACCCGCCCGAACAACAAGACGCGCACCTCCATCCGGATCGGCCCTGGCCAGGCCTTCTACGCCACCGGCCA
GGTGATCGGCGACATCCGCGAGGCGTACTGCAACATCAACGAGTCCAAGTGGAACGAGACCCTGCAGCGCGTGTCCAAGAAGC
TGAAGGAGTACTTCCCCCACAAGAACATCACCTTCCAGCCGTCGTCCGGCGGCGACCTCGAGATCACCACGCACTCCTTCAAC
TGCGGTGGCGAGTTCTTCTACTGCAACACGTCGTCGCTGTTCAACCGCACCTACATGGCCAACTCCACCGACATGGCCAACTC
CACCGAGACCAACTCCACGCGCACCATCACGATCCACTGCCGCATCAAGCAGATCATCAACATGTGGCAGGAGGTGGGCCGCG
CCATGTACGCACCGCCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGA
GGTGAAGCCCCTGGGCGTGGCACCCACCAACGCCcgcGAGcgcgtcgtggagcgcgagaagGAGTAGTAAGgtcaccgaattc
aggtcccggatcc
>HV1300556_v2, CH505w020.14D8gp120
gtcgacaagaaGCCACCATGCGCGTGATGGGCATCCAGCGCAACTACCCGCAGTGGTGGATCTGGTCGATGCTGGGCTTCTGG
ATGCTCATGATCTGCAACGGCgtgccggtgTGGAAGGAGGCCAAGACGACCCTGTTCTGCGCGTCGGACGCCAAGGCCTACGA
GAAGGAGGTGCACAACGTGTGGGCGACCCACGCCTGCGTGCCCACGGACCCCAACCCGCAGGAGATGGTGCTGAAGAACGTGA
CCGAGAACTTCAACATGTGGAAGAACGACATGGTGGACCAGATGCACGAGGACGTGATCTCCCTGTGGGACCAGTCCCTGAAG
CCCTGCGTGAAGCTGACCCCGCTGTGCGTGACCCTGAACTGCACCAACGCCACCGCGTCCAACAACTCCATCATCGAGGGCAT
GAAGAACTGCTCCTTCAACATCACGACGGAGCTGCGCGACAAGCGCGAGAAGAAGAACGCCCTGTTCTACAAGCTGGACATCG
TGCAGCTGGACGGCAACTCCTCGCAGTACAGGCTGATCAACTGCAACACCTCCGTCATCACGCAGGCGTGCCCCAAGGTGTCC
TTCGACCCCATCCCCATCCACTACTGCGCCCCCGCCGGCTACGCCATCCTGAAGTGCAACAACAAGACCTTCACCGGCACCGG
CCCGTCCAACAACGTGTCCACCGTGCAGTGCACGCACGGGATCAAGCCCGTGGTGTCCACCCAGCTGCTCCTGAACGGGTCGC
TGGCCGAGGGCGAGATCATCATCCGGTCCGAGAACATCACGAACAACGCGAAGACCATCATCGTGCACCTGAACGAGTCCGTG
AAGATCGAGTGCACCCGCCCGAACAACAAGACGCGCACCGTCCATCCGGATCGGCCCTGGCCAGGCCTTCTACGCCACCGGCCA
GGTGATCGGCGACATCCGCGAGGCGTACTGCAACATCTCGGAGTCCAAGTGGAACGAGACCCTGCAGCGCGTGTCCAAGAAGC
TGAAGGAGTACTTCCCCCACAAGAACATCACCTTCCAGCCGTCGTCCGGCGGCGACCTCGAGATCACCACGCACTCCTTCAAC
TGCGGTGGCGAGTTCTTCTACTGCAACACGTCGTCGCTGTTCAACCGCACCTACATGGCCAACTCCACCGACATGGCCAACTC
CACCGAGACCAACTCCACGCGCACCATCACGCTCCACTGCCGCATCAAGCAGATCATCAACATGTGGCAGGAGGTGGGCCGCG
CCATGTACGCACCGCCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGA
GGTGAAGCCCCTGGGCGTGGCACCCACCAACGCCcgcGAGcgcgtcgtggagcgcgagaagGAGTAGTAAGggacccgaattc
ggtcaccggatcc
>HV1300578_v2, CH505w030.28D8gp120
gtcgacaagaaGCCACCATGCGCGTGATGGGCATCCAGCGCAACTACCCGCAGTGGTGGATCTGGTCGATGCTGGGCTTCTGG
ATGCTCATGATCTGCAACGGCgtgccggtgTGGAAGGAGGCCAAGACGACCCTGTTCTGCGCGTCGGACGCCAAGGCCTACGA
GAAGGAGGTGCACAACGTGTGGGCGACCCACGCCTGCGTGCCCACGGACCCCAACCCGCAGGAGATGGTGCTGAAGAACGTGA
CCGAGAACTTCAACATGTGGAAGAACGACATGGTGGACCAGATGCACGAGGACGTGATCTCCCTGTGGGACCAGTCCCTGAAG
CCCTGCGTGAAGATGACCCCGCTGTGCGTGACCCTGAACTGCACCAACGCCACCGCGATCAACTCCTCCATCATCGAGGGCAT
GAAGAACTGCTCCTTCAACATCACGACGGAGCTGCGCGACAAGCGCGAGAAGAAGAACGCCCTGTTCTACAAGCTGGACATCG
TGCAGCTGGACGGCAACTCCTCGCAGTACAGGCTGATCAACTGCAACACCTCCGTCATCACGCAGGCGTGCCCCAAGGTGTCC
TTCGACCCCATCCCCATCCACTACTGCGCCCCCGCCGGCTACGCCATCCTGAAGTGCAACAACAAGACCTTCACCGGCACCGG
CCCGTCCAACAACGTGTCCACCGTGCAGTGCACGCACGGGATCAAGCCCGTGGTGTCCACCCAGCTGCTCCTGAACGGGTCGC
TGGCCGAGGGCGAGATCATCATCCGGTCCGAGAACATCACGAACAACGACAAGACCATCATCGTGCACCTGAACGAGTCCGTG
AAGATCGAGTGCACCCGCCCGAACAACAAGACGCGCACCTCCATCCGGATCGGCCCTGGCCAGGCCTTCTACGCCACCGGCCA
GGTGATCGGCGACATCCGCGAGGCGCACTGCAACATCTCGGAGTCCAAGTGGAACGAGACCCTGCAGCGCGTGTCCAAGAAGC
TGAAGGAGTACTTCCCCCACAAGAACATCACCTTCCAGCCGTCGTCCGGCGGCGACCTCGAGATCACCACGCACTCCTTCAAC
TGCGGTGGCGAGTTCTTCTACTGCAACACGTCGTCGCTGTTCAACCGCACCTACATGGCCAACTCCACCGACATGGCCAACTC
CACCGAGACCAACTCCACGCGCACCATCACGATCCGCTGCCGCATCAAGCAGATCATCAACATGTGGCAGGAGGTGGGCCGCG
CCATGTACGCACCGCCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGA
GGTGAAGCCCCTGGGCGTGGCACCCACCAACGCCcgcGAGcgcgtcgtggagcgcgagaagGAGTAGTAAGgtcctgaattc
ggttaccggatcc
>HV1300574_v2, CH505w030.21D8gp120
```

Figure 17 (cont.)

```
gtcgacaagaaGCCACCATGCGCGTGATGGGCATCCAGCGCAACTACCCGCAGTGGTGGATCTGGTCGATGCTGGGCTTCTGG
ATGCTCATGATCTGCAACGGCgtgccggtgTGGAAGGAGGCCAAGACGACCCTGTTCTGCGCGTCGGACGCCAAGGCCTACGA
GAAGGAGGTGCACAACGTGTGGGCGACCCACGCCTGCGTGCCCACGGACCCCAACCCGCAGGAGATGGTGCTGAAGAACGTGA
CCGAGAACTTCAACATGTGGAAGAACGACATGGTGGACCAGATGCACGAGGACGTGATCTCCCTGTGGGACCAGTCCCTGAAG
CCCTGCGTGAAGCTGACCCCGCTGTGCGTGACCCTGAACTGCACCAACGCGACGACGAACGCCACCGCGTCCAACTCGTCCAT
CATCGAGGAGATGAAGAACTGCTCCTTCAACATCACGACGGAGCTGCGCGACAAGCGCGAGAAGAAGAACGCCCTGTTCTACA
AGCTGGACATCGTGCAGCTGGACGGCAACTCCTCGCAGTACAGGCTGATCAACTGCAACACCTCCGTCATCACGCAGGCGTGC
CCCAAGGTGTCCTTCGACCCCATCCCCATCCACTACTGCGCCCCCGCCGGCTACGCCATCCTGAAGTGCAACAACAAGACCTT
CACCGGCACCGGCCCGTGCAACAACGTGTCCACCGTGCAGTGCACGCACGGGATCAAGCCCGTGGTGTCCACGCAGCTGCTCC
TGAACGGGTCGCTGGCCGAGGGCGAGATCATCATCCGGTCCGAGAACATCACGAACACGGCGAAGACCATCATCGTGCACCTG
AACGAGTCCGTGAAGATCGAGTGCACCCGCCCGAACAACAAGACGCGCACCTCCATCCGGATCGGCCCTGGCCAGGCCTTCTA
CGCCACCGGCCAGGTGATCGGCGACATCCGCGAGGCGTACTGCAACATCTCGGAGTCCAAGTGGAACGAGACCCTGCAGCGCG
TGTCCAAGAAGCTGAAGGAGTACTTCCCCCACAAGAACATCACCTTCCAGCCGTCGTCCGGCGGCGACCTCGAGATCACCACG
CACTCCTTCAACTGCGGTGGCGAGTTCTTCTACTGCAACACGTCGTCGCTGTTCAACCGCACCTACATGGCCAACTCCACCGA
CATGGCCAACTCCACCGAGACCAACTCCACGCGCATCATCACGATCCGGTGCCGCATCAAGCAGATCATCAACATGTGGCAGG
AGGTGGGCCGCGCCATGTACGCACCGCCCATCGCCGGCAACATCACCTGCATCTCCAACATCACCGGCCTCCTGCTGACCCGC
GACGGCGGCGAGAACAACACGGAGACCTTCAGGCCAGGCGGAGGCAACATGAAGGACAACTGGCGCTCCGAGCTGTACAAGTA
CAAGGTGGTGGAGGTGAAGCCCCTGGGCGTGGCACCCACCAACGCCcgcGAGcgcgtcgtggagcgcgagaagGAGTAGTAAG
ggtcccgaattcggttaccggatcc
>HV1300583, CH505w053.16D8gp120
GgtcgacaagaaGCCACCATGCGCGTGATGGGCATCCAGCGCAACTACCCGCAGTGGTGGATCTGGTCGATGCTGGGCTTCTG
GATGCTCATGATCTGCAACGGCgtgccggtgTGGAAGGAGGCCAAGACGACCCTGTTCTGCGCGTCGGACGCCAAGGCCTACG
AGAAGGAGGTGCACAACGTGTGGGCGACCCACGCCTGCGTGCCCACGGACCCCAACCCGCAGGAGATGGTGCTGAAGAACGTG
ACCGAGAACTTCAACATGTGGAAGAACGACATGGTGGACCAGATGCACGAGGACGTGATCTCCCTGTGGGACCAGTCCCTGAA
GCCCTGCGTGAAGCTGACCCCGCTGTGCGTGACCCTGAACTGCACCAACGCGAACGCCACCGCGTCCAACTCCTCTATCATCG
AGGGGATGAACTCCTCCATCATCGAGGGCATGAAGAACTGCTCCTTCAACATCACGACGGAGCTGCGCGACAAGCGCGAGAAG
AAGAACGCCCTGTTCTACAAGCTGGACATCGTGCAGCTGGACGGCAACTCCTCGCAGTACAGGCTGATCAACTGCAACACCTC
CGTCATCACGCAGGCGTGCCCCAAGGTGTCCTTCGACCCCATCCCCATCCACTACTGCGCCCCCGCCGGCTACGCCATCCTGA
AGTGCAACAACAAGACCTTCAACGGCACCGGCCCGTGCAACAACGTGTCCACCGTGCAGTGCACGCACGGGATCAAGCCCGTG
GTGTCCACGCAGCTGCTCCTGAACGGGTCGCTGGCCGAGGGCGAGATCATCATCCGGTCCGAGAACATCACGGACAACGGGAA
GACCATCATCGTGCACCTGAACGAGTCCGTGAAGATCGAGTGCACCCGCCCGAGCAACAACACGCGCACCTCCATCCGGATCG
GCCCTGGCCAGGCCTTCTACGCCACCGGCCAGGTGATCGGCGACATCCGCGAGGCGCACTGCAACATCTCGGAGTCCAAGTGG
AACGAGACCCTGCAGCGCGTGTCCGAGAAGCTGAAGGAGTACTTCCCCCACAAGAACATCACCTTCCAGCCGTCGTCCGGCGG
CGACCTCGAGATCACCACGCACTCCTTCAACTGCGGTGGCGAGTTCTTCTACTGCAACACGTCGTCGCTGTTCAACCGCACCT
ACATGGCCACGTCACCGAGACATGGCCAACTCCACCGAGACCAACTCCACGCGCATCATCACGATCCGGTGCCGCATCAAGCAG
ATCATCAACATGTGGCAGGAGGTGGGCCGCGCCATGTACGCACCGCCCATCGCCGGCAACATCACCTGCATCTCCAACATCAC
CGGCCTCCTGCTGACCCGCGACGGCGGCGAGAACAACACGGAGACCTTCGAGACGTTCAGGCCAGGCGGAGGCAACATGAAGG
ACAACTGGCGCTCCGAGCTGTACAAGTACAAGGTGGTGGAGGTGAAGCCCCTGGGCGTGGCACCCACCAACGCCcgcGAGcgc
gtcgtggagcgcgagaagGAGTAGTAAGaattcggtgaccgggtccggatcc
>HV1300586, CH505w053.31D8gp120
GgtcgacaagaaGCCACCATGCGCGTGATGGGCATCCAGCGCAACTACCCGCAGTGGTGGATCTGGTCGATGCTGGGCTTCTG
GATGCTCATGATCTGCAACGGCgtgccggtgTGGAAGGAGGCCAAGACGACCCTGTTCTGCGCGTCGGACGCCAAGGCCTACG
AGAAGGAGGTGCACAACGTGTGGGCGACCCACGCCTGCGTGCCCACGGACCCCAACCCGCAGGAGATGGTGCTGAAGAACGTG
ACCGAGAACTTCAACATGTGGAAGAACGACATGGTGGACCAGATGCACGAGGACGTGATCTCCCTGTGGGACCAGTCCCTGAA
GCCCTGCGTGAAGCTGACCCCGCTGTGCGTGACCCTGAACTGCACCGACGCCACGCGTCCAACGCAACCGCGAGCAACGCCA
CGGCGTCGAACTCCTCCATCATCGAGGGCATGAAGAACTGCTCCTTCAACATCACGACGGAGCTGCGCGACAAGCGCGAGAAG
AAGAACGCCCTGTTCTACAAGCTGGACATCGTGCAGCTGGACGGCAACTCCTCGCAGTACAGGCTGATCAACTGCAACACCTC
CGTCATCACGCAGGCGTGCCCCCAAGGTGTCCTTCGACCCCATCCCATCCACTACTGCGCCCCCGCCGGCTACGCCATCCTGA
AGTGCAACAACAAGACCTTCAACGGCACCGGCCCGTGCAACAACGTGTCCACCGTGCAGTGCACGCACGGGATCAAGCCCGTG
GTGTCCACGCAGCTGCTCCTGAACGGGTCGCTGGCCGAGGGCGAGATCATCATCCGGTCCGAGAACATCACGGACAACGGGAA
GACCATCATCGTGCACCTGAACGAGTCCGTGAAGATCGAGTGCACCCGCCCGTCGAACAACACGCGCACCTCCATCCGGATCG
GCCCTGGCCAGGCCTTCTACGCCACCGGCCAGGTGATCGGCGACATCCGCGAGGCGCACTGCAACATCTCGGAGTCCAAGTGG
AACGAGACCCTGCAGCGCGTGTCCAAGAAGCTGAAGGAGTACTTCCCCCACAAGAACATCACCTTCCAGCCGTCGTCCGGCGG
CGACCTCGAGATCACCACGCACTCCTTCAACTGCGGTGGCGAGTTCTTCTACTGCAACACGTCGTCGCTGTTCAACCGCACCT
ACATGGCCAACTCCACCGAGACCAACTCCACGCGCATCATCACGATCCGCTGCCGCATCAAGCAGATCATCAACATGTGGCAG
GAGGTGGGCCGCGCCATGTACGCCCCATCGCCGGCAACATCACCTGCATCTCCAACATCACCGGCCTCCTGCTGACCCG
CGACGGCGGCAACAACACGGAGACCTTCAGGCCAGGCGGAGGCAACATGAAGGACAACTGGCGCTCCGAGCTGTACAAGT
ACAAGGTGGTGGAGGTGAAGCCCCTGGGCGTGGCACCCACCAACGCCcgcGAGcgcgtcgtggagcgcgagaagGAGTAGTAA
Gaattcggtgaccgggacctggatcc
>HV1300595, CH505w078.33D8gp120
GgtcgacaagaaGCCACCATGCGCGTGACGGGCATCCAGCGCAACTACCCGCAGTGGTGGATCTGGTCGATGCTGGGCTTCTG
GATGCTCATGATCTGCAACGGCgtgccggtgTGGAAGGAGGCCAAGACGACCCTGTTCTGCGCGTCGGACGCCAAGGCCTACG
AGAAGGAGGTGCACAACGTGTGGGCGACCCACGCCTGCGTGCCCACGGACCCCAACCCGCAGGAGATGGTGCTGAAGAACGTG
ACCGAGAACTTCAACATGTGGAAGAACGACATGGCGGACCAGATGCACGAGGACGTGATCTCCCTGTGGGACCAGTCCCTGAA
GCCCTGCGTGAAGCTGACCCCGCTGTGCGTGACCCTGAACTGCATCGACGTCCAACGCGACCGCGTCCAACGCGACGGCATCCA
ACTCGTCCATCATCGAGGGGATGAAGAACTGCTCCTTCAACATCACGACGGAGCTGCGCGACAAGATCGAGAAGAAGAACGCC
CTGTTCTACAAGCTGGACATCGTGCAGCTGGACGGCAACTCCTCGCAGTACAGGCTGATCAACTGCAACACCTCCGTCATCAC
GCAGGCGTGCCCCAAGGTGTCCTTCGACCCCATCCCCATCCACTACTGCGCCCCCGCCGGCTACGCCATCCTGAAGTGCAACA
ACAAGACCTTCAACGGCACCGGCCCGTGCAACAACGTGTCCACCGTGCAGTGCACGCACGGGATCAAGCCCGTGGTGTCCACG
CAGCTGCTCCTGAACGGGTCGCTGGCCGAGGGCGAGATCATCATCCGGTCGGAGAACATCACGAACAGCGCGAAGACCATCAT
CGTGCACCTGAACGAGTCCGTGAAGATCGAGTGCACCCGCCCGAGCAACAACACGCGCACCTCCATCCGGATCGGCCCTGGCC
```

Figure 17 (cont.)

```
AGGCCTTCTACGCCACCGGCCAGGTGATCGGCGACATCCGCAAGGCGCACTGCAACATCTCCGAGTCCAAGTGGAACGAGACC
CTGCAGCGCGTGTCCAAGAAGCTGAAGGAGTACTTCCCCCACAAGAACATCACCTTCCAGCCGTCGTCCGGCGGCGACCTCGA
GATCACCACGCACTCCTTCAACTGCGGTGGCGAGTTCTTCTACTGCAACACGTCGTCGCTGTTCAACCGCACCTACATGGCCA
ACTCCACCGAGACCAACTCCACGCGCACGATCACGCTCCACTGCCGCATCAAGCAGATCATCAACATGTGGCAGGAGGTGGGC
CGCGCCATGTACGCACCGCCCATCGCCGGCAACATCACCTGCATCTCCAACATCACCGGCCTCCTGCTGACCCGCGACGGCGG
CAACAACAACACCACGGAGACCTTCAGGCCAGGGGGAGGCAACATGAAGGACAACTGGCGCTCCGAGCTGTACAAGTACAAGG
TGGTGGAGATCAAGCCCCTGGGCGTGGCACCCACCAACGCCgcGAGcgcgtcgtggagcgcgagaagGAGTAGTAAGaattc
ggtaaccaggtccccgatcc
>HV1300592, CH505w078.15D8gp120
GgtcgacaagaaGCCACCATGCGCGTGATGGGCATCCAGCGCAACTACCCGCAGTGGTGGATCTGGTCGATGCTGGGCTTCTG
GATGCTCATGATCTGCAACGGCgtgccggtgTGGAAGGAGGCCAAGACGACCCTGTTCTGCGCGTCGGACGCCAAGGCCTACG
AGAAGGAGGTGCACAACGTGTGGGCGACCCACGCCTGCGTGCCCACGGACCCCAACCCGCAGGAGATGGTGCTGAAGAACGTG
ACCGAGAACTTCAACATGTGGAAGAACGACATGGTGGACCAGATGCACGAGGACGTGATCTCCCTGTGGGACCAGTCCCTGAA
GCCCTGCGTGAAGCTGACCCCGCTGTGCGTGACCCTGAACTGCACCAACGCCACCACCGCGTCGAACTCGTCCATCC
TCGAGGGGATGAAGAACTGCTCCTTCAACATCACGACGGAGCTGCGCGACAAGCGCGAGAAGAAGAACGCCCTGTTCTACAAG
CTGGACATCGTGCAGCTGGACGGCAACTCCTCGCAGTACAGGCTGATCAACTGCAACACCTCCGTCATCACGCAGGCGTGCCC
CAAGGTGTCCTTCGACCCCATCCCCATCCACTACTGCGCCCCCGCCGGCTACGCCATCCTGAAGTGCAACAACAAGACCTTCA
ACGGCACCGGCCCGTGCAACAACGTGTCCACCGTGCAGTGCACGCACGGGATCAAGCCCGTGGTGTCCACGCAGCTGCTCCTG
AACGGGTCGCTGGCCGAGGGCGAGATCATCATCCGGTCGAAGAACATCACGGACAACGGGAAGACCATCATCGTGCACCTGAA
CGAGTCCGTGAAGATCGAGTGCACCCGCCCGAGCAACAACACGCGCACCTCCATCCGGATCGGCCCTGGCCAGGCCTTCTACG
CCACCGGCCAGGTGATCGGCGACATCCGCGAGGCGCACTGCAACATCTCCGAGTCCAAGTGGAACGAGACCCTGCAGCGCGTG
TCCGAGAAGCTGAAGGAGTACTTCCCCCACAAGAACATCACCTTCCAGCCGTCCGGCGGCGACCTCGAGATCACCACGCA
CTCCTTCAACTGCGGTGGCGAGTTCTTCTACTGCAACACGTCGTCGCTGTTCAACCGCACCTACATGGCCAACTCCACCGAGA
CCAACTCCACGCGCATCATCACGATCCGCTGCCGCATCAAGCAGATCATCAACATGTGGCAGGAG
GTGGGCCGCGCCATGTACGCACCGCCCATCGCCGGCAACATCACCTGCATCTCCAACATCACCGGCCTCCTGCTGACCCGCGA
CGGCGGCAAGAACGACACGGACACCTTCAGGCCAGGGGAGGCAACATGAAGGACAACTGGCGCTCCGAGCTGTACAAGTACA
AGGTGGTGGAGGTGAAGCCCCTGGGCGTGGCACCCACCAACGCCgcGAGcgcgtcgtggagcgcgagaagGAGTAGTAAGaa
ttcggtcaccgggtcctggatcc
>HV1300605, CH505w100.B6D8gp120
GgtcgacaagaaGCCACCATGAAGGTGCGGGCATCCAGCGCAACTACCCGCAGTGGTGGATCTGGTCGATGCTGGGCCTCTG
GATGCTCATGATCTGCAACGGCgtgccggtgTGGAAGGAGGCCAAGACGACCCTGTTCTGCGCGTCGGACGCCAAGGCCTACG
AGAAGGAGGTGCACAACGTGTGGGCGACCCACGCCTGCGTGCCCACGGACCCCAACCCGCAGGAGATGGTGCTGGAGAACGTG
ACCGAGAACTTCAACATGTGGAAGAACGACATGGTGGACCAGATGCACGAGGACGTGATCTCCCTGTGGGACCAGTCCCTGAA
GCCCTGCGTGAAGCTGACCCCGCTGTGCGTGACCCTGAACTGCACCGGACGCCACCAACGCCACCAACGCGACCG
CAAGCAACATCAACGCGACGGCGTCGAAGTCCTCCATCATCGAGGAGATGAAGAACTGCTCCTTCAACATCACGACGGAGCTG
CGCGACAAGCGCGAGAAGAAGTACGCCCTGTTCTACAAGCTGGACATCGTGCAGCTGGACGGCAACTCCTCGCAGTACAGGCT
GATCAACTGCAACACCTCCGTCATCACGCAGGCGTGCCCCAAGGTGTCCTTCGACCCCATCCCCATCCACTACTGCGCCCCCG
CCGGCTACGCCATCCTGAAGTGCAACAACAAGACCTTCAACGGCACCGGCCCGTGCAACAACGTGTCCACCGTGCAGTGCACA
CACGGGATCAAGCCCGTGGTGTCCACGCAGCTGCTCCTGAACGGGTCGCTGGCCGAGGGCGAGATCATCATCCGGTCGGAGAA
CATCACGGACAACAGCAAGACCATCATCGTGCACCTGAACGAGTCCGTGAAGATCGAGTGCACCCGCCCGAGCAACAACACGC
GCACCTCCATCCGGATCGGCCCTGGCCAGGCCTTCTACGCCACCGGCCAAGTGATCGGCGACATCCGCGAGGCGCACTGCAAC
ATCTCCGAGTCCAAGTGGAACGAGACCCTGCAGCGCGTGTCCGAGAAGCTGAAGGAGTACTTCCCCCGACAAGAACATCACCTT
CCAGCCGTCGTCCGGCGGCGACCTCGAGATCACCACGCACTCCTTCAACTGCGGTGGCGAGTTCTTCTACTGCAACACGTCGT
CCCTGTTCAACCGCACCTACATGGCGAACTCCACCGAGACCAACTCCACGCGCACCATCACGCTGCACTGCCGCATCAAGCAG
ATCATCAACATGTGGCAGGAGGTGGGCCGCGCCATGTACGCACCGCCCATCGCCGGCAACATCACCTGCATCTCCAACATCAC
CGGCCTCCTGCTGACCCGCGACGGCGGCGAGAACAACACCGGGACGGAGGCAACAACAACACGGAGACCTTCAGGCCAGAGGGAG
GCAACATGAAGGACAACTGGCGCTCCGAGCTGTACAAGTACAAGGTGGTGGAGGTGAAGCCCCTGGGCGTGGCACCCACCAAG
GCCCgcGAGcgcgtcgtggagcgcgagaagGAGTAGTAAGgtaaccgggacccgaattcggatcc
```

Amino acid sequences of the production 10 CH505 Δ8gp120:

>HV1300532_v2, CH505.M6D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNATASNSSIIEGMKNCSFNITTELRDKREKKNALFYKLDI
VQLDGNSSQYRLINCNTSVITQACPKVSFDPIPIHYCAPAGYAILKCNNKTFTGTGPCNNVSTVQCTHGIKPVVSTQLLL
NGSLAEGEIIIRSENITNNAKTIIVHLNESVKIECTRPNNKTRTSIRIGPGQAFYATGQVIGDIREAYCNINESKWNETL
QRVSKKLKEYFPHKNITFQPSSGGDLEITTHSFNCGGEFFYCNTSSLFNRTYMANSTDMANSTETNSTRTITIHCRIKQI
INMWQEVGRAMYAPPIAGNITCISNITGLLLTRDGGKNNTETFRPGGGNMKDNWRSELYKYKVVEVKPLGVAPTNARERV
VEREKE*
>HV1300537_v2, CH505.M11D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNATASNSSIIEGMKNCSFNITTELRDKREKKNALFYKLDI
VQLDGNSSQYRLINCNTSVITQACPKVSFDPIPIHYCAPAGYAILKCNNKTFTGTGPCNNVSTVQCTHGIKPVVSTQLLL
NGSLAEGEIIIRSENITDNGKTIIVHLNESVKIECTRPNNKTRTSIRIGPGQAFYATGQVIGDIREAYCNINESKWNETL
QRVSKKLKEYFPHKNITFQPSSGGDLEITTHSFNCGGEFFYCNTSSLFNRTYMANSTDMANSTETNSTRTITIHCRIKQI
INMWQEVGRAMYAPPIAGNITCISNITGLLLTRDGGKNNTETFRPGGGNMKDNWRSELYKYKVVEVKPLGVAPTNARERV
VEREKE*
>HV1300556_v2, CH505w020.14D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNATASNSSIIEGMKNCSFNITTELRDKREKKNALFYKLDI

Figure 17 (cont.)

VQLDGNSSQYRLINCNTSVITQACPKVSFDPIPIHYCAPAGYAILKCNNKTFTGTGPCNNVSTVQCTHGIKPVVSTQLLL
NGSLAEGEIIIRSENITNNAKTIIVHLNESVKIECTRPNNKTRTSIRIGPGQAFYATGQVIGDIREAYCNISESKWNETL
QRVSKKLKEYFPHKNITFQPSSGGDLEITTHSFNCGGEFFYCNTSSLFNRTYMANSTDMANSTETNSTRTITLHCRIKQI
INMWQEVGRAMYAPPIAGNITCISNITGLLLTRDGGKNNTETFRPGGGNMKDNWRSELYKYKVVEVKPLGVAPTNARERV
VEREKE*
>HV1300578_v2, CH505w030.28D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKMTPLCVTLNCTNATAINSSIIEGMKNCSFNITTELRDKREKKNALFYKLDI
VQLDGNSSQYRLINCNTSVITQACPKVSFDPIPIHYCAPAGYAILKCNNKTFTGTGPCNNVSTVQCTHGIKPVVSTQLLL
NGSLAEGEIIIRSENITNNDKTIIVHLNESVKIECTRPNNKTRTSIRIGPGQAFYATGQVIGDIREAHCNISESKWNETL
QRVSKKLKEYFPHKNITFQPSSGGDLEITTHSFNCGGEFFYCNTSSLFNRTYMANSTDMANSTETNSTRTITIRCRIKQI
INMWQEVGRAMYAPPIAGNITCISNITGLLLTRDGGKNNTETFRPGGGNMKDNWRSELYKYKVVEVKPLGVAPTNARERV
VEREKE*
>HV1300574_v2, CH505w030.21D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNATTNATASNSSIIEEMKNCSFNITTELRDKREKKNALFY
KLDIVQLDGNSSQYRLINCNTSVITQACPKVSFDPIPIHYCAPAGYAILKCNNKTFCTGTGPCNNVSTVQCTHGIKPVVST
QLLLNGSLAEGEIIIRSENITNTAKTIIVHLNESVKIECTRPNNKTRTSIRIGPGQAFYATGQVIGDIREAYCNISESKW
NETLQRVSKKLKEYFPHKNITFQPSSGGDLEITTHSFNCGGEFFYCNTSSLFNRTYMANSTDMANSTETNSTRTITIRCR
IKQIINMWQEVGRAMYAPPIAGNITCISNITGLLLTRDGGENNTETFRPGGGNMKDNWRSELYKYKVVEVKPLGVAPTNA
RERVVEREKE*
>HV1300583, CH505w053.16D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNANATASNSSIIEGMNSSIIEGMKNCSFNITTELRDKREK
KNALFYKLDIVQLDGNSSQYRLINCNTSVITQACPKVSFDPIPIHYCAPAGYAILKCNNKTFNGTGPCNNVSTVQCTHGI
KPVVSTQLLLNGSLAEGEIIIRSENITDNGKTIIVHLNESVKIECTRPSNNTRTSIRIGPGQAFYATGQVIGDIREAHCN
ISESKWNETLQRVSEKLKEYFPHKNITFQPSSGGDLEITTHSFNCGGEFFYCNTSSLFNRTYMATSTDMANSTETNSTRI
ITIRCRIKQIINMWQEVGRAMYAPPIAGNITCISNITGLLLTRDGGKNNTETFETFRPGGGNMKDNWRSELYKYKVVEVK
PLGVAPTNARERVVEREKE*
>HV1300586, CH505w053.31D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLNCTDATASNATASNATASNSSIIEGMKNCSFNITTELRDKREK
KNALFYKLDIVQLDGNSSQYRLINCNTSVITQACPKVSFDPIPIHYCAPAGYAILKCNNKTFNGTGPCNNVSTVQCTHGI
KPVVSTQLLLNGSLAEGEIIIRSENITDNGKTIIVHLNESVKIECTRPSNNTRTSIRIGPGQAFYATGQVIGDIREAHCN
ISESKWNETLQRVSKKLKEYFPHKNITFQPSSGGDLEITTHSFNCGGEFFYCNTSSLFNRTYMANSTETNSTRIITIRCR
IKQIINMWQEVGRAMYAPPIAGNITCISNITGLLLTRDGGNNNTETFRPGGGNMKDNWRSELYKYKVVEVKPLGVAPTNA
RERVVEREKE*
>HV1300595, CH505w078.33D8gp120
MRVTGIQRNYPQWWIWSMLGLWMLMICNGVPVWKEAKTTLFCASDAKAYEKEVHNVWATHACVPTDPNPQEMVLKNVTEN
FNMWKNDMADQMHEDVISLWDQSLKPCVKLTPLCVTLNCIDANATASNATASNSSIIEGMKNCSFNITTELRDKIEKKNA
LFYKLDIVQLDGNSSQYRLINCNTSVITQACPKVSFDPIPIHYCAPAGYAILKCNNKTFNGTGPCNNVSTVQCTHGIKPV
VSTQLLLNGSLAEGEIIIRSENITNSAKTIIVHLNESVKIECTRPSNNTRTSIRIGPGQAFYATGQVIGDIRKAHCNISE
SKWNETLQRVSKKLKEYFPHKNITFQPSSGGDLEITTHSFNCGGEFFYCNTSSLFNRTYMANSTETNSTRTITLHCRIKQ
IINMWQEVGRAMYAPPIAGNITCISNITGLLLTRDGGNNNYTETFRPGGGNMKDNWRSELYKYKVVEIKPLGVAPTNARE
RVVEREKE*
>HV1300592, CH505w078.15D8gp120
MRVMGIQRNYPQWWIWSMLGFWMLMICNGVPVWKEAKTTLFCASDAKAYEKEVHNVWATHACVPTDPNPQEMVLKNVTEN
FNMWKNDMVDQMHEDVISLWDQSLKPCVKLTPLCVTLSCTNATNATASNSSIIEGMKNCSFNITTELRDKREKKNALFYK
LDIVQLDGNSSQYRLINCNTSVITQACPKVSFDPIPIHYCAPAGYAILKCNNKTFNGTGPCNNVSTVQCTHGIKPVVSTQ
LLLNGSLAEGEIIIRSKNITDNGKTIIVHLNESVKIECTRPSNNTRTSIRIGPGQAFYATGQVIGDIREAHCNISESKWN
ETLQRVSEKLKEYFPHKNITFQPSSGGDLEITTHSFNCGGEFFYCNTSSLFNRTYMATSTDMANSTETNSTRIITIRCRI
KQIINMWQEVGRAMYAPPIAGNITCISNITGLLLTRDGGKNDTDTFRPEGGNMKDNWRSELYKYKVVEVKPLGVAPTNAR
ERVVEREKE*
>HV1300605, CH505w100.B6D8gp120
MKVRGIQRNYPQWWIWSMLGLWMLMICNGVPVWKEAKTTLFCASDAKAYEKEVHNVWATHACVPTDPNPQEMVLENVTEN
FNMWKNDMADQMHEDVISLWDQSLKPCVKLTPLCVTLNCTDANATASNATASNINATASKSSIIEEMKNCSFNITTEL
RDKREKKYALFYKLDIVQLDGNSSQYRLINCNTSVITQACPKVSFDPIPIHYCAPAGYAILKCNNKTFNGTGPCNNVSTV
QCTHGIKPVVSTQLLLNGSLAEGEIIIRSENITDNSKTIIVHLNESVKIECTRPSNNTRTSIRIGPGQAFYATGQVIGDI
REAHCNISESKWNETLQRVSKKLKEYFPDKNITFQPSSGGDPEITTHSFNCGGEFFYCNTSSLFNRTYMANSTETNSTRT
ITLHCRIKQIINMWQEVGRAMYAPPIAGNITCISNITGLLLTRDGGENTRDGGNNNTETFRPEGGNMKDNWRSELYKYKV
VEVKPLGVAPTKARERVVEREKE*

Gp145 DNA constructs:

>HV1300657, CH505.M6gp145
gtcgacaagaaGCCACCATGCGCGTGATGGGCATCCAGCGCAACTACCCGCAGTGGTGGATCTGGTCGATGCTGGGCTTCTGGATGCTCATGATCTGCAACGGC
ATGTGGGTGACGGTGTACTACCGGCgtgccggtgTGGAAGGAGGCCAAGACGACCCTGTTCTGCGCGTCGGACGCCAAGGCCTACGAGAAGGAGGTGCACAACGT
GTGGGCGACCCACGCCTGCGTGCCCACGGACCCCAACCCGCAGGAGATGGTGCTGAAGAACGTGACCGAGAACTTCAACATGTGGAAGAACGACATGGTGGACC
AGATGCACGAGGACGTGATCTCCCTGTGGGACCAGTCCCTGAAGCCCTGCGTGAAGCTGACCCCGCTGTGCGTGACCCTGAACTGCACCAACGCCACCGCGTCC
AACTCCTCCATCATCGAGGGCATGAAGAACTGCTCCTTCAACATCACGACGGAGCTGCGCGACAAGCGCGAGAAGAAGAACGCCCTGTTCTACAAGCTGGACAT
CGTGCAGCTGGACGGCAACTCCTCGCAGTACAGGCTGATCAACTGCAACACCTCCGTCATCACGCAGGCGTGCCCCAAGGTGTCCTTCGACCCCATCCCCATCC

Figure 17 (cont.)

```
ACTACTGCGCCCCCGCCGGCTACGCCATCCTGAAGTGCAACAACAAGACCTTCACCGGCACCGGCCCGTGCAACAACGTGTCCACCGTGCAGTGCACGCACGGG
ATCAAGCCCGTGGTGTCCACGCAGCTGCTCCTGAACGGGTCGCTGGCCGAGGGCGAGATCATCATCCGGTCGAGAACATCACGAACAACGCGAAGACCATCAT
CGTGCACCTGAACGAGTCCGTGAAGATCGAGTGCACCCGCCCGAACAACAAGACGCGCACCTCCATCCGGATCGGCCCTGGCCAGGCCTTCTACGCCACCGGCC
AGGTGATCGGCGACATCCGCGAGGCGTACTGCAACATCAACGAGTCCAAGTGGAACGAGACCCTGCAGCGCGTGTCCAAGAAGCTGAAGGAGTACTTCCCCCAC
AAGAACATCACCTTCCAGCCGTCGTCCGGCGGCGACCTCGAGATCACCACGCACTCCTTCAACTGCGGTGGCGAGTTCTTCTACTGCAACACGTCGTCGCTGTT
CAACCGCACCTACATGGCCAACTCTCACCGACATGGCCAACTCCACCGAGACCAACTCCACGCGCACCATCACGATCCACTGCCGCATCAAGCAGATCATCAACA
TGTGGCAGGAGGTGGGCCGCGCCATGTACGCACCGCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGAGGTGAAGCCCCTGGGCGTGGCC
ACCCACCAACGCCcgcaggcgcgtcgtggagcgcgagaagcgcGCCGTGGGCATGGGCGCCGTGTTCCTGGGCTTCCTGGGCGCTGCGGGCTCCACCATGGGTG
CCGCGTCCATCACCCTGACCGTGCAGGCCCGCCAGCTGCTCTCCGGCATCGTGCAGCAGCAGTCCAACCTCCTGAAGGCCATCGAGGCCCAGCAGCACATGCTG
AAGCTGACCGTGTGGGGCATCAAGCAGCTGCAGGCCAGGGTGCTCGCGTCGAGCGCTACCTGAAGGACCAGCAGCTGCTCGGCATGTGGGGCTGCTCCGGCAA
GCTGATCTGCACCACCAACGTGTACTGGAACTCGTCCTGGTCCAACAAGACCTACGGCGACATCTGGGACAACATGACCTGGATGCAGTGGGAGCGCGAGATCT
CCAACTACACCGAGATCATCTACGAGCTCCTCGAGGAGTCCCAGAACCAGCAGGAGAAGAACGAGCAGGATCTGCTCGCGCTGGACCGCTGGAACTCCCCTGTGG
AACTGGTTCAACATCACCAACTGGCTGTGGTACATCAAGATCTTCATCATGATCGTGGGCGGCCTGATCGGCCTGCGCATCATCTTCGCCGTGCTGTCGCTGGT
GAACCGCGTGCGCCAGGGCTGATGAGgtcaccgaattcgggaccggatcc
>HV1300662, CH505.M11gp145
gtcgacaagaaGCCACCATGCGCGTGATGGGCATCCAGCGCAACTACCCGCAGTGGTGGATCTGGTCGATGCTGGGCTTCTGGATGCTCATGATCTGCAACGGC
ATGTGGGTGACGGTGTACTACGGCcgtgccggtgTGGAAGGAGGCCAAGACGACCCTGTTCTGCGCGTCGGACGCCAAGGCCTACGAGAAGGAGGTGCACAACGT
GTGGGCGACCCACGCCTGCGTGCCCACGGACCCCAACCCGCAGGAGATGGTGCTGAAGAACGTGACCGAGAACTTCAACATGTGGAAGAACGACATGGTGGACC
AGATGCAcGAGGACGTGATCTCCCTGTGGGACCAGTCCCTGAAGCCCTGCGTGAAGCTGACCCCGCTGTGCGTGACCCTGAACTGCACCAACCGCCACCGCGTCC
AACTCCTCCATCATCGAGGGCATGAAGAACTGCTCCTTCAACATCACGACGGAGCTGCGCGACAAGCGCGAGAAGAAGAACGCCCTGTTCTACAAGCTGGACAT
CGTGCAGCTGGACGGCAACTCCTCGCAGTACAGGCTGATCAACTGCAACACCTCCGTCATCACGCAGGCGTGCCCCAAGGTGTCCTTCGACCCCATCCCCATCC
ACTACTGCGCCCCCGCCGGCTACGCCATCCTGAAGTGCAACAACAAGACCTTCACCGGCACCGGCCCGTGCAACAACGTGTCCACCGTGCAGTGCACGCACGGG
ATCAAGCCCGTGGTGTCCACGCAGCTGCTCCTGAACGGGTCGCTGGCCGAGGGCGAGATCATCATCCGGTCGAGAACATCACGAACAACGCGAAGACCATCAT
CGTGCACCTGAACGAGTCCGTGAAGATCGAGTGCACCCGCCCGAACAACAAGACGCGCACCTCCATCCGGATCGGCCCTGGCCAGGCCTTCTACGCCACCGGCC
AGGTGATCGGCGACATCCGCGAGGCGTACTGCAACATCAACGAGTCCAAGTGGAACGAGACCCTGCAGCGCGTGTCCAAGAAGCTGAAGGAGTACTTCCCCCAC
AAGAACATCACCTTCCAGCCGTCGTCCGGCGGCGACCTCGAGATCACCACGCACTCCTTCAACTGCGGTGGCGAGTTCTTCTACTGCAACACGTCGTCGCTGTT
CAACCGCACCTACATGGCCAACTCTCACCGACATGGCCAACTCCACCGAGACCAACTCCACGCGCACCATCACGATCCACTGCCGCATCAAGCAGATCATCAACA
TGTGGCAGGAGGTGGGCCGCGCCATGTACGCACCGCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGAGGTGAAGCCCCTGGGCGTGGCC
ACCCACCAACGCCcgcaggcgcgtcgtggagcgcgagaagcgcGCCGTGGGCATGGGCGCCGTGTTCCTGGGCTTCCTGGGCGCTGCGGGCTCCACCATGGGTG
CCGCGTCCATCACCCTGACCGTGCAGGCCCGCCAGCTGCTCTCCGGCATCGTGCAGCAGCAGTCCAACCTCCTGAAGGCCATCGAGGCCCAGCAGCACATGCTG
AAGCTGACCGTGTGGGGCATCAAGCAGCTGCAGGCCAGGGTGCTCGCGTCGAGCGCTACCTGAAGGACCAGCAGCTGCTCGGCATGTGGGGCTGCTCCGGCAA
GCTGATCTGCACCACCAACGTGTACTGGAACTCGTCCTGGTCCAACAAGACCTACGGCGACATCTGGGACAACATGACCTGGATGCAGTGGGAGCGCGAGATCT
CCAACTACACCGAGATCATCTACGAGCTCCTCGAGGAGTCCCAGAACCAGCAGGAGAAGAACGAGCAGGATCTGCTCGCGCTGGACCGCTGGAACTCCCCTGTGG
AACTGGTTCAACATCACCAACTGGCTGTGGTACATCAAGATCTTCATCATGATCGTGGGCGGCCTGATCGGCCTGCGCATCATCTTCGCCGTGCTGTCGCTGGT
GAACCGCGTGCGCCAGGGCTGATGAGgtgaccgaattcaggtcccggatcc
>HV1300635, CH505w020.14gp145
gtcgacaagaaGCCACCATGCGCGTGATGGGCATCCAGCGCAACTACCCGCAGTGGTGGATCTGGTCGATGCTGGGCTTCTGGATGCTCATGATCTGCAACGGC
ATGTGGGTGACGGTGTACTACGGCcgtgccggtgTGGAAGGAGGCCAAGACGACCCTGTTCTGCGCGTCGGACGCCAAGGCCTACGAGAAGGAGGTGCACAACGT
GTGGGCGACCCACGCCTGCGTGCCCACGGACCCCAACCCGCAGGAGATGGTGCTGAAGAACGTGACCGAGAACTTCAACATGTGGAAGAACGACATGGTGGACC
AGATGCACGAGGACGTGATCTCCCTGTGGGACCAGTCCCTGAAGCCCTGCGTGAAGCTGACCCCGCTGTGCGTGACCCTGAACTGCACCAACCGCACCGCGTCC
AACAACTCCATCATCGAGGGCATGAAGAACTGCTCCTTCAACATCACGACGGAGCTGCGCGACAAGCGCGAGAAGAAGAACGCCCTGTTCTACAAGCTGGACAT
CGTGCAGCTGGACGGCAACTCCTCGCAGTACAGGCTGATCAACTGCAACACCTCCGTCATCACGCAGGCGTGCCCCAAGGTGTCCTTCGACCCCATCCCCATCC
ACTACTGCGCCCCCGCCGGCTACGCCATCCTGAAGTGCAACAACAAGACCTTCACCGGCACCGGCCCGTGCAACAACGTGTCCACCGTGCAGTGCACGCACGGG
ATCAAGCCCGTGGTGTCACGCAGCTGCTCCTGAACGGGTCGCTGGCCGAGGGCGAGATCATCATCCGGTCCGAGAACATCACGAACAACGCGAAGACCATCAT
CGTGCACCTGAACGAGTCCGTGAAGATCGAGTGCACCCGCCCGAACAACAAGACGCGCACGTCATCCGGATCGGCCCTGGCCAGGCCTTCTACGCCACCGGCC
AGGTGATCGGCGACATCCGCAAGGCGTACTGCAACATCTCGGAGTCCAAGTGGAACGAGACCCTGCAGCGCGTGTCCAAGAAGCTGAAGGAGTACTTCCCCCAC
AAGAACATCACCTTCCAGCCGTCGTCCGGCGGCGACCTCGAGATCACCACGCACTCCTTCAACTGCGGTGGCGAGTTCTTCTACTGCAACACGTCGTCGCTGTT
CAACCGCACCTACATGGCCAACTCCACCGACATGGCCAACTCCACCGAGACCAACTCCACGCGCACCATCACGTCCACTGCCGCATCAAGCAGATCATCAACA
TGTGGCAGGAGGTGGGCCGCGCCATGTACGCACCGCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGAGGTGAAGCCCCTGGGCGTGGCC
ACCCACCAACGCCcgcaggcgcgtcgtggagcgcgagaagcgcGCCGTGGGCATGGGCGCCGTGTTCCTGGGCTTCCTGGGCGCTGCGGGCTCCACCATGGGTG
CCGCGTCCATCACCCTGACCGTGCAGGCCCGCCAGCTGCTCTCCGGCATCGTGCAGCAGCAGTCCAACCTCCTGAAGGCCATCGAGGCCCAGCAGCACATGCTG
AAGCTGACCGTGTGGGGCATCAAGCAGCTGCAGGCCAGGGTGCTCGCGTCGAGCGCTACCTGAAGGACCAGCAGCTGCTCGGCATGTGGGGCTGCTCCGGCAA
GCTGATCTGCACCACCAACGTGTACTGGAACTCGTCCTGGTCCAACAAGACCTACGGCGACATCTGGGACAACATGACCTGGATGCAGTGGGAGCGCGAGATCT
CCAACTACACCGAGATCATCTACGAGCTCCTCGAGGAGTCCCAGAACCAGCAGGAGAAGAACGAGCAGGATCTGCTCGCGCTGGACCGCTGGAACTCCCCTGTGG
AACTGGTTCAACATCACCAACTGGCTGTGGTACATCAAGATCTTCATCATGATCGTGGGCGGCCTGATCGGCCTGCGCATCATCTTCGCCGTGCTGTCGCTGGT
GAACCGCGTGCGCCAGGGCTGATGAGggacccgaattcggtcaccgatcc
>HV1300636, CH505w030.28gp145
gtcgacaagaaGCCACCATGCGCGTGATGGGCATCCAGCGCAACTACCCGCAGTGGTGGATCTGGTCGATGCTGGGCTTCTGGATGCTCATGATCTGCAACGGC
ATGTGGGTGACGGTGTACTACGGCcgtgccggtgTGGAAGGAGGCCAAGACGACCCTGTTCTGCGCGTCGGACGCCAAGGCCTACGAGAAGGAGGTGCACAACGT
GTGGGCGACCCACGCCTGCGTGCCCACGGACCCCAACCCGCAGGAGATGGTGCTGAAGAACGTGACCGAGAACTTCAACATGTGGAAGAACGACATGGTGGACC
AGATGCACGAGGACGTGATCTCCCTGTGGGACCAGTCCCTGAAGCCCTGCGTGAAGATGACCCCGCTGTGCGTGACCCTGAACTGCACCAACCGCACCGCGATC
AACTCCTCCATCATCGAGGGCATGAAGAACTGCTCCTTCAACATCACGACGGAGCTGCGCGACAAGCGCGAGAAGAAGAACGCCCTGTTCTACAAGCTGGACAT
CGTGCAGCTGGACGGCAACTCCTCGCAGTACAGGCTGATCAACTGCAACACCTCCGTCATCACGCAGGCGTGCCCCAAGGTGTCCTTCGACCCCATCCCCATCC
ACTACTGCGCCCCCGCCGGCTACGCCATCCTGAAGTGCAACAACAAGACCTTCACCGGCACCGGCCCGTGCAACAACGTGTCCACCGTGCAGTGCACGCACGGG
ATCAAGCCCGTGGTGTCCACGCAGCTGCTGAACGGGTCGCTGGCCGAGGGCGAGATCATCATCCGGTCGAGAACATCACGAACAACGCGAAGAGACCATCAT
CGTGCACCTGAACGAGTCCGTGAAGATCGAGTGCACCCGCCCGAACAACAAGACGCGCACCTCCATCCGGATCGGCCCTGGCCAGGCCTTCTACGCCACCGGCC
AGGTGATCGGCGACATCCGCGAGGCGCACTGCAACATCTCGGAGTCCAAGTGGAACGAGACCCTGCAGCGCGTGTCCAAGAAGCTGAAGGAGTACTTCCCCCAC
AAGAACATCACCTTCCAGCCGTCGTCCGGCGGCGACCTCGAGATCACCACGCACTCCTTCAACTGCGGTGGCGAGTTCTTCTACTGCAACACGTCGTCGCTGTT
CAACCGCACCTACATGGCCAACTCCACCGACATGGCCAACTCCACCGAGACCAACTCCACGCGCACCATCACGATCCGCTGCCGCATCAAGCAGATCATCAACA
TGTGGCAGGAGGTGGGCCGCGCCATGTACGCACCGCCATCGCCGGCAACATCACCTGCATCTCCAACATCACCGGCCTCCTGCTGACCCGCGACGGCGGCAAG
AACAACACGGAGACCTTCAGGCCAGGCGGAGGCAACATGAAGGACAACTGGCGCTCCGAGCTGTACAAGTACAAGGTGGTGGAGGTGAAGCCCCTGGGCGTGGCC
ACCCACCAACGCCcgcaggcgcgtcgtggagcgcgagaagcgcGCCGTGGGCATGGGCGCCGTGTTCCTGGGCTTCCTGGGCGCTGCGGGCTCCACCATGGGTG
CCGCGTCCATCACCCTGACCGTGCAGGCCCGCCAGCTGCTCTCCGGCATCGTGCAGCAGCAGTCCAACCTCCTGAAGGCCATCGAGGCCCAGCAGCACATGCTG
AAGCTGACCGTGTGGGGCATCAAGCAGCTGCAGGCAGGGTGCTCGCGTCGAGCGCTACCTGAAGGACCAGCAGCTGCTCGGCATGTGGGGCTGCTCCGGCAA
GCTGATCTGCACCACCAACGTGTACTGGAACTCGTCCTGGTCCAACAAGACCTACGGCGACATCTGGGACAACATGACCTGGATGCAGTGGGAGCGCGAGATCT
CCAACTACACCGAGATCATCTACGAGCTCCTCGAGGAGTCCCAGAACCAGCAGGAGAAGAACGAGCAGGATCTGCTCGCGCTGGACCGCTGGAACTCCCCTGTGG
AACTGGTTCAACATCACCAACTGGCTGTGGTACATCAAGATCTTCATCATGATCGTGGGCGGCCTGATCGGCCTGCGCATCATCTTCGCCGTGCTGTCGCTGGT
GAACCGCGTGCGCCAGGGCTGATGAGggtcctgaattcggttaccgatcc
>HV1300689, CH505w30.21gp145
gtcgacaagaaGCCACCATGCGCGTGATGGGCATCCAGCGCAACTACCCGCAGTGGTGGATCTGGTCGATGCTGGGCTTCTGGATGCTCATGATCTGCAACGGC
ATGTGGGTGACGGTGTACTACGGCcgtgccggtgTGGAAGGAGGCCAAGACGACCCTGTTCTGCGCGTCGGACGCCAAGGCCTACGAGAAGGAGGTGCACAACGT
GTGGGCGACCCACGCCTGCGTGCCCACGGACCCCAACCCGCAGGAGATGGTGCTGAAGAACGTGACCGAGAACTTCAACATGTGGAAGAACGACATGGTGGACC
AGATGCACGAGGACGTGATCTCCCTGTGGGACCAGTCCCTGAAGCCCTGCGTGAAGCTGACCCCGCTGTGCGTGACCCTGAACTGCACCAACCGCGACGACGAAC
GCCACCGCGTCCAACTCGTCCATCATCGAGGAGATGAAGAACTGCTCCTTCAACATCACGACGGAGCTGCGCGACAAGCGCGAGAAGAAGAACGCCCTGTTCTA
CAAGCTGGACATCGTGCAGCTGGACGGCAACTCCTCGCAGTACAGGCTGATCAACTGCAACACCTCCGTCATCACGCAGGCGTGCCCCAAGGTGTCCTTCGACC
```

```
CH505.M6        IHCRIPQIIN  MWQEVGRAMY  APPIAGNITC  ISNITGLLLT  RDGGKNNTET  FRPGGGNMKD  NWRSELYKYK  VVEVKPLGVA
CH505.M11       ----------  ----------  ----------  ----------  ----------  ----------  ----------  ----------
CH505w020.14    L---------  ----------  ----------  ----------  ----------  ----------  ----------  ----------
CH505w030.28    -R--------  ----------  ----------  ----------  ----------  ----------  ----------  ----------
                    480

CH505.M6        PTNARRPVVE  REKRAVGMGA  VFLGPLGAAG  STMGAASITL  TVQARQLLSG  IVQQQSNLLK  AIEAQQHMLK  LTVWGIKQLQ
CH505.M11       ----------  ----------  ----------  ----------  ----------  ----------  ----------  ----------
CH505w020.14    ----------  ----------  ----------  ----------  ----------  ----------  ----------  ----------
CH505w030.28    ----------  ----------  ----------  ----------  ----------  ----------  ----------  ----------
                    560

CH505.M6        ARVLALERYL  KLQQLLGMWG  CSGKLICTTN  VYWNSSWSNK  TYGDIWDNMT  WMQWEREISN  YTEIIYELLE  ESQNQQEKNE
CH505.M11       ----------  ----------  ----------  ----------  ----------  ----------  ----------  ----------
CH505w020.14    ----------  ----------  ----------  ----------  ----------  ----------  ----------  ----------
CH505w030.28    ----------  ----------  ----------  ----------  S---------  ----------  ----------  ----------
                    640

CH505.M6        QDLLALDPWN  SLWNWFNITN  WLWYIKIFIM  IVGGLIGLRI  IFAVLSLVNR  VRQGYSPLSL  QTLIPSPRGP  DRPGGIEEEG
CH505.M11       ----------  ----------  ----------  ----------  ----------  ----------  ----------  ----------
CH505w020.14    ----------  ----------  ----------  ----------  ----------  ----------  ----------  ----------
CH505w030.28    ----------  ----------  ----------  ----------  ----------  ----------  ----------  ----------
                    720

CH505.M6        GEQDRNRSTR  LVSGFLALVW  DDLRSLCLFI  YHRLRDFILI  AARAGELLGR  SSLKGLRRGW  EALKYLGSLV  QYWGLELKRS
CH505.M11       ----------  ----------  ----------  ----------  ----------  ----------  ----------  ----------
CH505w020.14    ----------  ----------  ----------  ----------  ----------  ----------  ----------  ----------
CH505w030.28    ----------  ----------  ----------  ----------  ----------  ----------  ----------  ----------
                    800

CH505.M6        AISLLDTLAI  AVGEGTDRIL  EFVLGICRAI  RNIPTRIRQG  FETALL*
CH505.M11       ----------  ----------  ----------  ----------  -------
CH505w020.14    ----------  ----------  ----------  ----------  -------
CH505w030.28    ----------  ----------  ----------  ----------  ------- 800
```

>CH505.s.03gp160 (HV1300412)(SEQ ID NO 83)
MRVMGIQRNYPQWWIWSMLGFWMLMICNGMWVTVYYGVPVWKEAKTTLFCASDAKAYEKEVHNVWAT
HACVPTDPNPQEMVLKNVTENFNMWKNDMVDQMHEDVISLWDQSLKPCVKLTPLCVTLNCTNATASN
SSIIEGMKNCSFNITTELRDKREKKNALFYKLDIVQLDGNSSQYRLINCNTSVITQACPKVSFDPIP
IHYCAPAGYAILKCNNKTFTGTGPCNNVSTVQCTHGIKPVVSTQLLLNGSLAEGEIIIRSENITNNV
KTIIVHLNESVKIECTRPNNKTRTSIRIGPGQAFYATGQVIGDIREAYCNINESKWNETLQRVSKKL
KEYFPHKNITFQPSSGGDLEITTHSFNCGGEFFYCNTSSLFNRTYMANSTDMANSTETNSTRTITIH
CRIKQIINMWQEVGRAMYAPPIAGNITCISNITGLLLTRDGGKNNTETFRPGGGNMKDNWRSELYKY
KVVEVKPLGVAPTNARRRVVEREKRAVGMGAVFLGFLGAAGSTMGAASITLTVQARQLLSGIVQQQS
NLLKAIEAQQHMLKLTVWGIKQLQARVLALERYLKDQQLLGMWGCSGKLICTTNVYWNSSWSNKTYG
DIWDNMTWMQWEREISNYTEIIYELLEESQNQQEKNEQDLLALDRWNSLWNWFNITNWLGYIKIFIM
IVGGLIGLRIIFAVLSLVNRVRQGYSPLSLQTLIPSPRGPDRPGGIEEEGGEQDRNRSTRLVSGFLA
LVWDDLRSLCLFIYHRLRDFILIAARAGELLGRSSLKGLRRGWEALKYLGSLVQYWGLELKRSAISL
LDTLAIAVGEGTDRILEFVLGICRAIRNIPTRIRQGFETALL

>HV1300412, CH505.s.03gp160.opt (SEQ ID NO 84)
gtcgacgctagcaccATGCGCGTGATGGGCATCCAGCGCAACTACCCCCAGTGGTGGATCTGGTCCA
TGCTGGGCTTCTGGATGCTGATGATCTGCAACGGCATGTGGGTGACCGTGTACTACGGCGTGCCCGT
GTGGAAGGAGGCCAAGACCACCCTGTTCTGCGCCTCCGACGCCAAGGCCTACGAGAAGGAGGTGCAC
AACGTGTGGGCCACCCACGCCTGCGTGCCCACCGACCCCAACCCCCAGGAGATGGTGCTGAAGAACG
TGACCGAGAACTTCAACATGTGGAAGAACGACATGGTGGACCAGATGCACGAGGACGTGATCTCCCT
GTGGGACCAGTCCCTGAAGCCCTGCGTGAAGCTGACCCCCCTGTGCGTGACCCTGAACTGCACCAAC
GCCACCGCCTCCAACTCCTCCATCATCGAGGGCATGAAGAACTGCTCCTTCAACATCACCACCGAGC
TGCGCGACAAGCGCGAGAAGAAGAACGCCCTGTTCTACAAGCTGGACATCGTGCAGCTGGACGGCAA
CTCCTCCCAGTACCGCCTGATCAACTGCAACACCTCCGTGATCACCCAGGCCTGCCCCAAGGTGTCC
TTCGACCCCATCCCCATCCACTACTGCGCCCCCGCCGGCTACGCCATCCTGAAGTGCAACAACAAGA
CCTTCACCGGCACCGGCCCCTGCAACAACGTGTCCACCGTGCAGTGCACCCACGGCATCAAGCCCGT
GGTGTCCACCCAGCTGCTGCTGAACGGCTCCCTGGCCGAGGGCGAGATCATCATCCGCTCCGAGAAC
ATCACCAACAACGTGAAGACCATCATCGTGCACCTGAACGAGTCCGTGAAGATCGAGTGCACCCGCC
CCAACAACAAGACCCGCACCTCCATCCGCATCGGCCCCGGCCAGGCCTTCTACGCCACCGGCCAGGT
GATCGGCGACATCCGCGAGGCCTACTGCAACATCAACGAGTCCAAGTGGAACGAGACCCTGCAGCGC

Figure 17 (cont.)

```
GTGTCCAAGAAGCTGAAGGAGTACTTCCCCCACAAGAACATCACCTTCCAGCCCTCCTCCGGCGGCG
ACCTGGAGATCACCACCCACTCCTTCAACTGCGGCGGCGAGTTCTTCTACTGCAACACCTCCTCCCT
GTTCAACCGCACCTACATGGCCAACTCCACCGACATGGCCAACTCCACCGAGACCAACTCCACCCGC
ACCATCACCATCCACTGCCGCATCAAGCAGATCATCAACATGTGGCAGGAGGTGGGCCGCGCCATGT
ACGCCCCCCCCATCGCCGGCAACATCACCTGCATCTCCAACATCACCGGCCTGCTGCTGACCCGCGA
CGGCGGCAAGAACAACACCGAGACCTTCCGCCCCGGCGGCGGCAACATGAAGGACAACTGGCGCTCC
GAGCTGTACAAGTACAAGGTGGTGGAGGTGAAGCCCCTGGGCGTGGCCCCACCAACGCCCGCCGCC
GCGTGGTGGAGCGCGAGAAGCGCGCCGTGGGCATGGGCGCCGTGTTCCTGGGCTTCCTGGGCGCCGC
CGGCTCCACCATGGGCGCCGCCTCCATCACCCTGACCGTGCAGGCCCGCCAGCTGCTGTCCGGCATC
GTGCAGCAGCAGTCCAACCTGCTGAAGGCCATCGAGGCCAGCAGCACATGCTGAAGCTGACCGTGT
GGGGCATCAAGCAGCTGCAGGCCCGCGTGCTGGCCCTGGAGCGCTACCTGAAGGACCAGCAGCTGCT
GGGCATGTGGGGCTGCTCCGGCAAGCTGATCTGCACCACCAACGTGTACTGGAACTCCTCCTGGTCC
AACAAGACCTACGGCGACATCTGGGACAACATGACCTGGATGCAGTGGGAGCGCGAGATCTCCAACT
ACACCGAGATCATCTACGAGCTGCTGGAGGAGTCCCAGAACCAGCAGGAGAAGAACGAGCAGGACCT
GCTGGCCCTGGACCGCTGGAACTCCCTGTGGAACTGGTTCAACATCACCAACTGGCTGGGCTACATC
AAGATCTTCATCATGATCGTGGGCGGCCTGATCGGCCTGCGCATCATCTTCGCCGTGCTGTCCCTGG
TGAACCGCGTGCGCCAGGGCTACTCCCCCCTGTCCCTGCAGACCCTGATCCCCTCCCCCCGCGGCCC
CGACCGCCCCGGCGGCATCGAGGAGGAGGGCGGCGAGCAGGACCGCAACCGCTCCACCCGCCTGGTG
TCCGGCTTCCTGGCCCTGGTGTGGGACGACCTGCGCTCCCTGTGCCTGTTCATCTACCACCGCCTGC
GCGACTTCATCCTGATCGCCGCCCGCGCCGGCGAGCTGCTGGGCCGCTCCTCCCTGAAGGGCCTGCG
CCGCGGCTGGGAGGCCCTGAAGTACCTGGGCTCCCTGGTGCAGTACTGGGGCCTGGAGCTGAAGCGC
TCCGCCATCTCCCTGCTGGACACCCTGGCCATCGCCGTGGGCGAGGGCACCGACCGCATCCTGGAGT
TCGTGCTGGGCATCTGCCGCGCCATCCGCAACATCCCCACCCGCATCCGCCAGGGCTTCGAGACCGC
CCTGCTGtagggatcc
```

Figure 17 (cont.)

Binding of CH103 antibodies to the autologous Envs, log AUC

| mAbs | UCA | IA8 | IA7 | IA4 | IA3.1 | IA2 | IA1 | CH104 | CH106 | CH103 |
|---|---|---|---|---|---|---|---|---|---|---|
| M11 | 7.51 | 8.786 | 10.04 | 11.82 | | | | | | 8.966 |
| M6 | 6.849 | 8.581 | 8.569 | 10.916 | 11.859 | | | | | 9.26 |
| w20.14 | 0.688 | 3.114 | 6.308 | 7.423 | 9.344 | 9.529 | 9.694 | 9.002 | 10.355 | 8.543 |
| w30.28 | 0 | 1.374 | 2.299 | 4.875 | | 11.449 | | 8.723 | | 9.132 |
| w78.15 | 0 | 0.198 | 1.71 | 2.197 | 10.028 | 10.987 | 10.678 | 10.295 | 10.448 | 8.564 |
| w53.31 | 0 | 0 | 0 | 0 | | | | | | |
| w030.21 | 0 | 0 | 0 | 0 | | | | | 8.605 | |
| w78.env33 | 0 | 0 | 0 | 0 | 6.848 | 9.236 | 8.608 | 8.678 | 10.171 | 8.698 |
| w53.e16 | 0 | 0 | 0 | 0 | | | | | | |
| w100.B6 | 0 | 0 | 0 | 0 | | | | | | 5.162 |

Selection of 10 CH505 Envs (10PR) Based on Binding Intensity of Envs for The CH103 lineage Members. ELISA-Area Under The Curves. Humanized mice are immunized with this selection of HIV-1 envelopes.

>CH505w000.TFgp160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATASNSSIIEGM
KNCSFNITTELRDKREKKNALFYKLDIVQLDGNSSQYRLINCNTSVITQACPKVSFDPIPIHYCAPAGYAILKCNNKTFTGT
GPCNNVSTVQCTHGIKPVVSTQLLLNGSLAEGEIIRSENITNNVKTIIVHLNESVKIECTRPNNKTRTSIRIGPGQAFYATG
QVIGDIREAYCNINESKWNETLQRVSKKLKEYFPHKNITFQPSSGGDLEITTHSFNCGGEFFYCNTSSLFNRTYMANSTD
MANSTETNSTRTITIHCRIKQIINMWQEVGRAMYAPPIAGNTCISNITGLLLTRDGGKNNTETFRPGGGNMKDNWRS
ELYKYKVVEVKPLGVAPTNARRRVVEREKRAVGMGAVFLGFLGAAGSTMGAASITLTVQARQLLSGIVQQQSNLLKAIE
AQQHMLKLTVWGIKQLQARVLALERYLKDQQLLGMWGCSGKLICTTNVYWNSSWSNKTYGDIWDNMTWMQWE
REISNYTEIIYELLEESQNQQEKNEQDLLALDRWNSLWNWFNITNWLWYIKIFIMIVGGLIGLRIIFAVLSLVNRVRQGYS
PLSLQTLIPSPRGPDRPGGIEEEGGEQDRNRSTRLVSGFLALVWDDLRSLCLFIYHRLRDFILIAARAGELLGRSSLKGLRR
GWEALKYLGSLVQYWGLELKRSAISLLDTLAIAVGEGTDRILEFVLGICRAIRNIPTRIRQGFETALL*

>CH505w053.16gp160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNANATASNSSIIEG
MNSSIIEGMKNCSFNITTELRDKREKKNALFYKLDIVQLDGNSSQYRLINCNTSVITQACPKVSFDPIPIHYCAPAGYAILK
CNNKTFNGTGPCNNVSTVQCTHGIKPVVSTQLLLNGSLAEGEIIRSENITDNGKTIIVHLNESVKIECTRPSNNTRTSIRIG
PGQAFYATGQVIGDIREAHCNISESKWNETLQRVSEKLKEYFPHKNITFQPSSGGDLEITTHSFNCGGEFFYCNTSSLFNR
TYMATSTDMANSTETNSTRIITIRCRIKQIINMWQEVGRAMYAPPIAGNITCISNITGLLLTRDGGKNNTETFETFRPGG
GNMKDNWRSELYKYKVVEVKPLGVAPTNARRRVVEREKRAVGMGAVFLGFLGAAGSTMGAASITLTVQARQLLSGIV
QQQSNLLKAIEAQQHMLKLTVWGIKQLQARVLALERYLKDQQLLGMWGCSGKLICTTNVYWNSSWSNKTYGDIWD
NMTWMQWEREISNYTEIIYELLEESQNQQEKNEQDLLALDRWNSLWNWFNITNWLWYIKIFIMIVGGLIGLRIIFAVLS
LVNRVRQGYSPLSLQTLIPSPRGPDRPGGIEEEGGEQDRNRSTRLVSGFLALAWDDLRSLCLFIYHRLRDFILIAARAGELL
GRSSLKGLRRGWEALKYLGSLVQYWGLELKRSAISLLDTLAIAVGEGTDRILEFVLGICRAIRNIPTRIRQGFETALL*

>CH505w078.33gp160

MRVTGIQRNYPQWWIWSMLGLWMLMICNGMWVTVYYGVPVWKEAKTTLFCASDAKAYEKEVHNVWA
THACVPTDPNPQEMVLKNVTENFNMWKNDMADQMHEDVISLWDQSLKPCVKLTPLCVTLNCIDANATASNATASN
SSIIEGMKNCSFNITTELRDKIEKKNALFYKLDIVQLDGNSSQYRLINCNTSVITQACPKVSFDPIPIHYCAPAGYAILKCNN
KTFNGTGPCNNVSTVQCTHGIKPVVSTQLLLNGSLAEGEIIRSENITNSAKTIIVHLNESVKIECTRPSNNTRTSIRIGPGQ
AFYATGQVIGDIRKAHCNISESKWNETLQRVSKKLKEYFPHKNITFQPSSGGDLEITTHSFNCGGEFFYCNTSSLFNRTYM
ANSTETNSTRTITLHCRIKQIINMWQEVGRAMYAPPIAGNITCISNITGLLLTRDGGNNNTTETFRPGGGNMKDNWRS
ELYKYKVVEIKPLGVAPTNARRRVVEREKRAVGMGAVFLGFLGAAGSTMGAASITLTVQARQLLSGIVQQQSNLLKAIE
AQQHMLKLTVWGIKQLQARVLALERYLKDQQLLGMWGCSGKLICTTNVYWNSSWSNKTYGDIWDNMTWMQWE
REISDYTEIIYELLEESQNQQEKNEQDLLALDRWNSLWNWFNITNWLWYIKIFIMIVGGLIGLRIIFAVLSLVNRVRQGYS
PLSLQTLTPSPRGPDRPGGIEEEGGEQDRNRSTRLVSGFLALAWDDLRSLCLFIYHRLRDFILIAARAGELLGRSSLKGLRR
GWEALKYLGGLVQYWGLELKRSAISLLDTLAIAVGEGTDRILEFVLGICRAIRNIPTRIRQGFETALL*

MKVRGIQRNYPQWWIWSMLGLWMLMICNGMWVTVYYGVPVWKEAKTTLFCASDAKAYEKEVHNVWA
THACVPTDPNPQEMVLENVTENFNMWKNDMADQMHEDVISLWDQSLKPCVKLTPLCVTLNCTDANATASNTNAT
ASNINATASKSSIIEEMKNCSFNITTELRDKREKKYALFYKLDIVQLDGNSSQYRLINCNTSVITQACPKVSFDPIPIHYCAP
AGYAILKCNNKTFNGTGPCNNVSTVQCTHGIKPVVSTQLLLNGSLAEGEIIIRSENITDNSKTIIVHLNESVKIECTRPSNNT
RTSIRIGPGQAFYATGQVIGDIREAHCNISESKWNETLQRVSKKLKEYFPDKNITFQPSSGGDPEITTHSFNCGGEFFYCN
TSSLFNRTYMANSTETNSTRTITLHCRIKQIINMWQEVGRAMYAPPIAGNITCISNITGLLLTRDGGENTRDGGNNNTET
FRPEGGNMKDNWRSELYKYKVVEVKPLGVAPTKARRRVVEREKRAVGMGAVFLGFLGAAGSTMGAASITLTVQARQ
LLSGIVQQQSNLLKAIEAQQHMLKLTVWGIKQLQARVLALERYLKDQQLLGMWGCSGKLICTTNVYWNSSWSNKTYG
DIWDNMTWMQWEREISNYTDIIYDLLEESQNQQEKNEQDLLALDRWNSLWNWFNITKWLWYIKIFIMIVGGLIGLRII
FAVLSLVNRVRQGYSPLSLQTLIPSPRGPDRPGGIEEEGGEQDRNRSTRLVSGFLALAWDDLRSLCLFIYHRLRDFILIAAR
AGELLGRSSLKGLRRGWEALKYLGGLVQYWGLELKRSAISLLDTLAIAVGEGTDRILEFVLGICRAIRNIPTRIRQGFETALL
*

Figure 22 (cont.)

Sequences of CAP 206 env from 6months

>6mo_B6 (SEQ ID NO 85)

MRVRGIPRNWPQWWIWGILGFWVIITCRVVGQLWVTVYYGVPVWTEAKTTLFCASDAKAYDKEVHNVWATHACVPTD
PNPQEIVLGNITENFNMWENDMVDQMHEDIISLWDQSLKPCVKLTPLCVTLICTNANISVTSVSNDSRILNEEIKNC
SFNTTTEIRDKKQQVYALFYRSDVAPLSNSSEYILNCNTSTITQACPKVTFDPIPLHYCAPAGYAILKCNNKTFNG
TGPCLNVSTVQCTHGIKPVVSTQLLLNGSLAEEEIIIKSKNLTDDTNTIIVHLNKSIEIVCTRPGNNTRKSIRIGPG
QTFFATGDIIGDIREAHCNLSKDAWNTTLEQIKRKLKEHFSSKEIKFAPSSGGDPEVATHSFNCRGEFFYCNTTKLF
NENYTLSNNSNETIILPCRIKQIINMWQGVGRAMYAPPIAGNITCNSSITGLLLTRDKDSNTETFRPTGGNMKDNWR
NELYKYKVVEIKPLGVAPTNAKRRVVEREKRAVGIGAVLLGFLGAAGSTMGAASITLTVQARQLLSGIVQQQSNLLR
AIEAQQHMLQLTVWGIKQLQTRVLAIERYLKDQQLLGLWGCSGRLICTTNVPWNSSWSNKSQEDIWGNMTWMQWDRE
ISNYTSTIYRLLEDSQNQQEKNEKDLLALDSWKNLWNWFDITKWLWYIKIFIIIVGGLIGLRIVLGVLAIVKRVRQG
YSPLSFQTLIPSPRGLDRLGRIEEEGGEQDKDRSIRLVNGFLALAWEDLRNLCLFSYHQLRDFILIVARAVELLGRS
SLRGLQRGWEALKYLGALIQQGGLELKKSAISLLDTTAIAVAEGTDRILELIQRICRAIRNIPTRIRQGFEAALL*

>6mo_B6 (SEQ ID NO 86)

ATGAGAGTGAGGGGGATACCGAGGAATTGGCCACAATGGTGGATATGGGGCATCTTAGGCTTTTGGGTGATAATAAC
TTGTAGGGTGGTAGGGCAATTGTGGGTCACAGTCTATTATGGGGTACCTGTGTGGACAGAAGCAAAAACTACTCTAT
TCTGTGCATCAGATGCTAAAGCATATGACAAAGAAGTGCATAATGTCTGGGCTACACATGCCTGTGTACCCACAGAC
CCCAATCCACAAGAAATAGTCTTGGAAATATAACAGAAAATTTTAACATGTGGGAAAATGACATGGTGGATCAGAT
GCATGAGGATATAATCAGTTTATGGGATCAAAGTCTAAAACCATGTGTAAAGTTGACTCCACTCTGTGTCACTTTAA
TTTGTACAAATGCAAATATTAGTGTTACCAGTGTGAGTAATGATAGCAGGATTTTGAATGAAGAAATAAAAAATTGC
TCTTTCAATACAACCACAGAAATAAGAGATAAGAAACAGCAAGGTGTATGCACTTTTTTATAGATCTGATGTAGCACC
ACTTAGTAATTCTAGTGAGTATATATTAATAAATTGTAATACCTCAACCATAACACAAGCCTGTCCAAAGGTCACTT
TTGACCCAATTCCTTTGCATTATTGTGCTCCAGCTGGTTATGCGATTCTAAAATGCAACAATAAGACATTCAATGGG
ACAGGACCATGCCTTAATGTCAGCACAGTACAATGTACACATGGAATTAAGCCAGTGGTATCAACTCAATTACTGTT
AAATGGTAGCCTAGCAGAAGAGGAGATAATAATTAAATCTAAAAATCTGACAGATGATACCAATACAATAATAGTAC
ACCTTAATAAATCTATAGAAATTGTGTGTACAAGACCTGGCAATAATACAAGAAAAAGTATAAGGATAGGACCAGGA
CAAACATTCTTTGCAACAGGTGACATAATAGGAGACATAAGAGAAGCCCATTGTAACCTTAGTAAAGATGCATGGAA
CACAACTCTAGAACAGATAAAAAGAAAACTCAAAGAACACTTCTCTAGTAAAGAAATAAAATTTGCTCCAAGCTCAG
GAGGAGATCCAGAAGTTGCGACACATAGTTTTAATTGTAGAGGAGAATTTTTCTATTGCAATACAACAAAACTGTTT
AATGAGAATTATACACTGAGCAATAACAGTAATGAAACAATCATACTCCCATGTAGAATAAAACAAATTATAAATAT
GTGGCAGGGGGTAGGACGAGCAATGTATGCCCCTCCCATTGCAGGAAACATAACATGTAACTCAAGTATCACAGGAC
TGTTATTGACGCGTGACAAAGACAGCAACACAGAGACATTCAGACCTACAGGAGGAAATATGAAGGACAATTGGAGA
AATGAATTATACAAATATAAAGTGGTAGAAATTAAACCATTAGGAGTAGCACCCACTAATGCAAAAGGAGAGTGGT
GGAGAGAGAAAAAGAGCAGTAGGAATAGGAGCTGTGCTCCTTGGGTTCTTGGGAGCAGCAGGAAGCACTATGGGCG
CGGCGTCAATAACGCTGACGGTACAGGCCAGACAACTGTTATCTGGTATAGTGCAACAGCAAAGTAATTTGCTGAGA
GCTATAGAGGCGCAACAGCACATGTTGCAACTCACAGTCTGGGGCATTAAACAGCTCCAGACAAGAGTCTTGGCTAT
AGAAAGATACCTAAAGGATCAACAGCTCCTAGGACTTTGGGGCTGCTCTGGAAGACTCATCTGCACCACTAATGTGC
CTTGGAACTCGAGTTGGAGTAATAAATCTCAAGAAGATATTTGGGGGAACATGACCTGGATGCAGTGGGATAGAGAA
ATTAGTAATTACACAAGCACAATATACAGGTTACTTGAAGACTCGCAAAACCAGCAGGAGAAAAATGAAAAGGATTT
GTTAGCATTGGACAGTTGGAAAAATCTGTGGAATTGGTTTGACATAACAAAATGGCTGTGGTATATAAAAATATTCA
TCATAATAGTAGGAGGTTTAATAGGTTTGAGAATAGTTTTGGGTGTGCTTGCTATAGTAAAAAGAGTTAGGCAGGGA
TACTCACCTTTGTCGTTTCAGACCCTTATCCCAAGTCCGAGGGGACTCGACAGGCTCGGAAGAATCGAAGAAGAAGG
TGGAGAGCAAGACAAAGACAGATCCATTCGATTAGTGAACGGATTCTTAGCACTTGCTTGGGAAGATCTGCGGAATC
TGTGCCTCTTCAGCTACCACCAATTGAGAGACTTTATATTGATTGTAGCGAGAGCAGTGGAACTTCTGGGACGCAGC

Figure 23

```
AGCCTCAGGGGACTACAGAGGGGGTGGGAAGCTCTTAAGTATCTGGGAGCTCTTATACAGCAGGGGGGTCTGGAACT
AAAGAAGAGTGCTATTAGTCTGCTTGATACCACAGCAATAGCAGTAGCTGAAGGAACAGATAGGATTCTAGAATTAA
TACAAAGAATTTGTAGAGCTATCCGCAACATACCTACAAGAATAAGACAAGGCTTTGAAGCAGCTTTGCTATAA
```

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATASNSSIIEGM
KNCSFNITTELRDKREKKNALFYKLDIVQLDGNSSQYRLINCNTSVITQACPKVSFDPIPIHYCAPAGYAILKCNNKTFTGT
GPCNNVSTVQCTHGIKPVVSTQLLLNGSLAEGEIIRSENITDNGKTIIVHLNESVKIECTRPNNKTRTSIRIGPGQAFYATG
QVIGDIREAYCNINESKWNETLQRVSKKLKEYFPHKNITFQPSSGGDLEITTHSFNCGGEFFYCNTSSLFNRTYMANSTD
MANSTETNSTRTITIHCRIKQIINMWQEVGRAMYAPPIAGNITCISNITGLLLTRDGGKNNTETFRPGGGNMKDNWRS
ELYKYKVVEVKPLGVAPTNARRRVVEREKRAVGMGAVFLGFLGAAGSTMGAASITLTVQARQLLSGIVQQQSNLLKAIE
AQQHMLKLTVWGIKQLQARVLALERYLKDQQLLGMWGCSGKLICTTNVYWNSSWSNKTYGDIWDNMTWMQWE
REISNYTEIIYELLEESQNQQEKNEQDLLALDRWNSLWNWFNITNWLWYIKIFIMIVGGLIGLRIIFAVLSLVNRVRQGYS
PLSLQTLIPSPRGPDRPGGIEEEGGEQDRNRSTRLVSGFLALVWDDLRSLCLFIYHRLRDFILIAARAGELLGRSSLKGLRR
GWEALKYLGSLVQYWGLELKRSAISLLDTLAIAVGEGTDRILEFVLGICRAIRNIPTRIRQGFETALL*

>CH505w004.03gp160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATASNSSIIEGM
KNCSFNITTELRDKREKKNALFYKLDIVQLDGNSSQYRLINCNTSVITQACPKVSFDPIPIHYCAPAGYAILKCNNKTFTGT
GPCNNVSTVQCTHGIKPVVSTQLLLNGSLAEGEIIRSENITNNVKTIIVHLNESVKIECTRPNNKTRTSIRIGPGQAFYATG
QVIGDIREAYCNINESKWNETLQRVSKKLKEYFPHKNITFQPSSGGDLEITTHSFNCGGEFFYCNTSSLFNRTYMANSTD
MANSTETNSTRTITIHCRIKQIINMWQEVGRAMYAPPIAGNITCISNITGLLLTRDGGKNNTETFRPGGGNMKDNWRS
ELYKYKVVEVKPLGVAPTNARRRVVEREKRAVGMGAVFLGFLGAAGSTMGAASITLTVQARQLLSGIVQQQSNLLKAIE
AQQHMLKLTVWGIKQLQARVLALERYLKDQQLLGMWGCSGKLICTTNVYWNSSWSNKTYGDIWDNMTWMQWE
REISNYTEIIYELLEESQNQQEKNEQDLLALDRWNSLWNWFNITNWLGYIKIFIMIVGGLIGLRIIFAVLSLVNRVRQGYSP
LSLQTLIPSPRGPDRPGGIEEEGGEQDRNRSTRLVSGFLALVWDDLRSLCLFIYHRLRDFILIAARAGELLGRSSLKGLRRG
WEALKYLGSLVQYWGLELKRSAISLLDTLAIAVGEGTDRILEFVLGICRAIRNIPTRIRQGFETALL*

>CH505w020.14gp160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATASNNSIIEGM
KNCSFNITTELRDKREKKNALFYKLDIVQLDGNSSQYRLINCNTSVITQACPKVSFDPIPIHYCAPAGYAILKCNNKTFTGT
GPCNNVSTVQCTHGIKPVVSTQLLLNGSLAEGEIIRSENITNNAKTIIVHLNESVKIECTRPNNKTRTSIRIGPGQAFYATG
QVIGDIRKAYCNISESKWNETLQRVSKKLKEYFPHKNITFQPSSGGDLEITTHSFNCGGEFFYCNTSSLFNRTYMANSTD
MANSTETNSTRTITLHCRIKQIINMWQEVGRAMYAPPIAGNITCISNITGLLLTRDGGKNNTETFRPGGGNMKDNWRS
ELYKYKVVEVKPLGVAPTNARRRVVEREKRAVGMGAVFLGFLGAAGSTMGAASITLTVQARQLLSGIVQQQSNLLKAIE
AQQHMLKLTVWGIKQLQARVLALERYLKDQQLLGMWGCSGKLICTTNVYWNSSWSNKTYGDIWDNMTWMQWE
REISNYTEIIYELLEESQNQQEKNEQDLLALDRWNSLWNWFNITNWLWYIKIFIMIVGGLIGLRIIFAVLSLVNRVRQGYS
PLSLQTLIPSPRGPDRPGGIEEEGGEQDRNRSTRLVSGFLALVWDDLRSLCLFIYHRLRDFILIAARAGELLGRSSLKGLRR
GWEALKYLGSLVQYWGLELKRSAISLLDTLAIAVGEGTDRILEFVLGICRAIRNIPTRIRQGFETALL*

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKMTPLCVTLNCTNATAINSSIIEGM
KNCSFNITTELRDKREKKNALFYKLDIVQLDGNSSQYRLINCNTSVITQACPKVSFDPIPIHYCAPAGYAILKCNNKTFTGT
GPCNNVSTVQCTHGIKPVVSTQLLLNGSLAEGEIIRSENITNNDKTIIVHLNESVKIECTRPNNKTRTSIRIGPGQAFYATG
QVIGDIREAHCNISESKWNETLQRVSKKLKEYFPHKNITFQPSSGGDLEITTHSFNCGGEFFYCNTSSLFNRTYMANSTD
MANSTETNSTRTITIRCRIKQIINMWQEVGRAMYAPPIAGNITCISNITGLLLTRDGGKNNTETFRPGGGNMKDNWRS
ELYKYKVVEVKPLGVAPTNARRRVVEREKRAVGMGAVFLGFLGAAGSTMGAASITLTVQARQLLSGIVQQQSNLLKAIE
AQQQHMLKLTVWGIKQLQARVLALERYLKDQQLLGMWGCSGKLICTTNVYWNSSWSNKSYGDIWDNMTWMQWER
EISNYTEIIYELLEESQNQQEKNEQDLLALDRWNSLWNWFNITNWLWYIKIFIMIVGGLIGLRIIFAVLSLVNRVRQGYSP
LSLQTLIPSPRGPDRPGGIEEEGGEQDRNRSTRLVSGFLALVWDDLRSLCLFIYHRLRDFILIAARAGELLGRSSLKGLRRG
WEALKYLGSLVQYWGLELKRSAISLLDTLAIAVGEGTDRILEFVLGICRAIRNIPTRIRQGFETALL*

>CH505w30.12pg160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATNATASNSSIIE
GMKNCSFNITTELRDKREKKNALFYKLDIVQLDGNSSQYRLINCNTSVITQACPKVSFDPIPIHYCAPAGYAILKCNNKTFT
GTGPCNNVSTVQCTHGIKPVVSTQLLLNGSLAEGEIIRSENITNNDKTIIVHLNESVKIECTRPSNKTRTSIRIGPGQAFYA
TGQVIGDIREAYCNISESKWNETLQRVSKKLKEYFPHKNITFQPSSGGDLEITTHSFNCGGEFFYCNTSSLFNRTYMANST
DMANSTETNSTRNITIHCRIKQIINMWQEVGRAMYAPPIAGNITCISNITGLLLTRDGGKNDTETFRPGGGNMKDNWR
SELYKYKVVEVKPLGVAPTNARRRVVEREKRAVGMGAVFLGFLGAAGSTMGAASITLTVQARQLLSGIVQQQSNLLKAI
EAQQHMLKLTVWGIKQLQARVLALERYLKDQQLLGMWGCSGKLICTTNVYWNSSWSNKTYGDIWDNMTWMQWE
REISNYTEIIYELLEESQNQQEKNEQDLLALDRWNSLWNWFNITNWLWYIKIFIMIVGGLIGLRIIFAVLSLVNRVRQGYS
PLSLQTLIPSPRGPDRPGGIEEEGGEQDRNRSTRLVSGFLALVWDDLRSLCLFIYHRLRDFILIAARAGELLGRSSLKGLRR
GWEALKYLGSLVQYWGLELKRSAISLLDTLAIAVGEGTDRILEFILGICRAIRNIPTRIRQGFETALL*

>CH505w020.2pg160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATANNSNIIEEM
KNCSFNITTELRDKREKKNALFYKLDIVQLDGNSSQYRLINCNTSVITQACPKVSFDPIPIHYCAPAGYAILKCNNKTFTGT
GPCNNVSTVQCTHGIKPVVSTQLLLNGSLAEGEIIRSENITNNVKTIIVHLNESVKIECTRPNNKTRTSIRIGPGQAFYATG
QVIGDIREAYCNINESKWNETLQRVSKKLKEYFPHKNITFQPSSGGDLEITTHSFNCGGEFFYCNTSSLFNRTDMANSTET
NNTRTITIHCRIKQIINMWQEVGRAMYAPPIAGNITCISNITGLLLTRDGGKNNTETFRPGGGNMKDNWRSELYKYKVV
EVKPLGVAPTNARRRVVEREKRAVGMGAVFLGFLGAAGSTMGAASITLTVQARQLLSGIVQQQSNLLKAIEAQQHML
KLTVWGIKQLQARVLALERYLKDQQLLGMWGCSGKLICTTNVYWNSSWSNKTYGDIWDNMTWMQWEREISNYTEII
YELLEESQNQQEKNEQDLLALDRWNSLWNWFNITNWLWYIKIFIMIVGGLIGLRIIFAVLSLVNRVRQGYSPLSLQTLIPS
PRGPDRPGGIEEEGGEQDRNRSTRLVSGFLALVWDDLRSLCLFIYHRLRDFILIAARAGELLGRSSLKGLRRGWEALKYLG
SLVQYWGLELKRSAISLLDTLAIAVGEGTDRILEFVLGICRAIRNIPTRIRQGFETALL*

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATTSNSSIIEGMK
NCSFNITTELRDKREKKNALFYKLDIVQLDGNSSQYRLINCNTSVITQACPKVSFDPIPIHYCAPAGYAILKCNNKTFTGTG
PCNNVSTVQCTHGIKPVVSTQLLLNGSLAEGEIIRSENITNNDKTIIVHLNESVKIECTRPNNNTRTSIRIGPGQAFYATGQ
VIGDIREAYCNISESKWNETLQRVSKKLKEYFPHKNITFQPSSGGDLEITTHSFNCGGEFFYCNTSSLFNRTYMANSTDM
ANSTETNSTRIITIHCRIKQIINMWQEVGRAMYAPPIAGNITCISNITGLLLTRDGGKNNTETFRPGGGNMKDNWRSELY
KYKVVEVKPLGVAPTNARRRVVEREKRAVGMGAVFLGFLGAAGSTMGAASITLTVQARQLLSGIVQQQSNLLKAIEAQ
QHMLKLTVWGIKQLQARVLALERYLKDQQLLGMWGCSGKLICTTNVYWNSSWSNKTYGDIWDNMTWMQWEREIS
NYTEIIYELLEESQNQQEKNEQDLLALDRWNSLWNWFNITNWLWYIKIFIMIVGGLIGLRIIFAVLSLVNRVRQGYSPLSL
QTLIPSPRGPDRPGGIEEEGGEQDRNRSTRLVSGFLALVWDDLRSLCLFIYHRLRDFILIAARAGELLGRSSLKGLRRGWE
ALKYLGSLVQYWGLELKRSAISLLDTLAIAVGEGTDRILEFVLGICRAIRNIPTRIRQGFETALL*

>CH505w078.15gp160

MRVMGIQRNYPQWWIWSMLGFWMLMICNGMWVTVYYGVPVWKEAKTTLFCASDAKAYEKEVHNVWATHACVP
TDPNPQEMVLKNVTENFNMWKNDMVDQMHEDVISLWDQSLKPCVKLTPLCVTLSCTNATNATASNSSILEGMKNCSFN
ITTELRDKREKKNALFYKLDIVQLDGNSSQYRLINCNTSVITQACPKVSFDPIPIHYCAPAGYAILKCNNKTFNGTGP
CNNVSTVQCTHGIKPVVSTQLLLNGSLAEGEIIIRSKNITDNGKTIIVHLNESVKIECTRPSNNTRTSIRIGPGQAFY
ATGQVIGDIREAHCNISESKWNETLQRVSEKLKEYFPHKNITFQPSSGGDLEITTHSFNCGGEFFYCNTSSLFNRTYM
ATSTDMANSTETNSTRIITIRCRIKQIINMWQEVGRAMYAPPIAGNITCISNITGLLLTRDGGKNDTDTFRPEGGNMK
DNWRSELYKYKVVEVKPLGVAPTNARRRVVEREKRAVGMGAVFLGFLGAAGSTMGAASITLTVQARQLLSGIVQQQSN
LLKAIEAQQHMLKLTVWGIKQLQARVLALERYLKDQQLLGMWGCSGKLICTTNVYWNSSWSNKTYGDIWDNMTWMQWE
REISNYTELIYELLEESQNQQEKNEQDLLALDRWNSLWNWFNITNWLWYIKIFIMIVGGLIGLRIIFAVLSLVNRVRQ
GYSPLSLQTLIPSPRGPDRPGGIEEEGGEQDRNRSTRLVSGFLALAWDDLRSLCLFIYHRLRDFILIAARAGELLGRS
SLKGLRRGWEALKYLGNLVQYWGLELKRSAISLLDTLAIAVGEGTDRILEFVLGICRAIRNIPTRIRQGFETALL*

>CH505w030.19gp160

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATARNCTNATA
SNSSIIEGMKNCSFNITTELRDKREKKNALFYKLDIVQLDGNSSQYRLINCNTSVITQACPKVSFDPIPIHYCAPAGYAILKC
NNKTFTGTGPCNNVSTVQCTHGIKPVVSTQLLLNGSLAEGEIIRSENITNSGKTIIVHLNESVKIECTRPNNNTRTSIRIGP
GQAFYATGQVIGDIREAYCNISESKWNETLQRVSKKLKEYFPHKNITFQPSSGGDLEITTHSFNCGGEFFYCNTSSLFNRT
YMANSTDMANSTETNSTRIITIHCRIKQIINMWQEVGRAMYAPPIAGNITCISSITGLLLTRDGGENNTETFRPGGGNM
KDNWRSELYKYKVVEVKPLGVAPTNARRRVVEREKRAVGMGAVFLGFLGAAGSTMGAASITLTVQARQLLSGIVQQQ
SNLLKAIEAQQHMLKLTVWGIKQLQARVLALERYLKDQQLLGMWGCSGKLICTTNVYWNSSWSNKTYGDIWDNMT
WMQWEREISNYTEIIYELLEESQNQQEKNEQDLLALDRWNSLWNWFNITNWLWYIKIFIMIVGGLIGLRIIFAVFSLVN
RVRQGYSPLSLQTLIPSPRGPDRPGGIEEEGGEQDRNRSTRLVSGFLALVWDDLRSLCLFIYHRLRDFILIAARAGELLGRS
SLKGLRRGWEALKYLGSLVQYWGLELKRSAISLLDTLAIAVGEGTDRILEFVLGICRAIRNIPTRIRQGFETALL*

MRVMGIQRNYPQWWIWSMLGFWMLMICNGMWVTVYYGVPVWKEAKTTLFCASDAKAYEKEVHNVWA
THACVPTDPNPQEMVLKNVTENFNMWKNDMVDQMHEDVISLWDQSLKPCVKLTPLCVTLNCTNATTNATASNSSII
EEMKNCSFNITTELRDKREKKNALFYKLDIVQLDGNSSQYRLINCNTSVITQACPKVSFDPIPIHYCAPAGYAILKCNNKTF
TGTGPCNNVSTVQCTHGIKPVVSTQLLLNGSLAEGEIIRSENITNTAKTIIVHLNESVKIECTRPNNKTRTSIRIGPGQAFY
ATGQVIGDIREAYCNISESKWNETLQRVSKKLKEYFPHKNITFQPSSGGDLEITTHSFNCGGEFFYCNTSSLFNRTYMANS
TDMANSTETNSTRTITIRCRIKQIINMWQEVGRAMYAPPIAGNITCISNITGLLLTRDGGENNTETFRPGGGNMKDNW
RSELYKYKVVEVKPLGVAPTNARRRVVEREKRAVGMGAVFLGFLGAAGSTMGAASITLTVQARQLLSGIVQQQSNLLK
AIEAQQHMLKLTVWGIKQLQARVLALERYLKDQQLLGMWGCSGKLICTTNVYWNSSWSNKTYGDIWDNMTWMQ
WEREISNYTEIIYELLEESQNQQEKNEQDLLALDRWNSLWNWFNITNWLWYIKIFIMIVGGLIGLRIIFAVLSLVNRVRQ
GYSPLSLQTLIPSPRGPDRPGGIEEEGGEQDRNRSTRLVSGFLALVWDDLRSLCLFIYHRLRDFILIAARAGELLGRSSLKGL
RRGWEALKYLGSLVQYWGLELKRSAISLLDTLAIAVGEGTDRILEFVLGICRAIRNIPTRIRQGFETALL*

Figure 24 (cont.)

COMPOSITIONS COMPRISING CH505 ENVELOPES, AND TRIMERS

CROSS-REFERENCE TO RELATED APPLICATIONS

This application is the National Stage of International Application No. PCT/US2015/052346, filed Sep. 25, 2015, which claims the benefit of and priority to the U.S. Provisional Patent Application No. 62/056,602, entitled "Compositions Comprising CH505 Envelopes, and Trimers" filed on Sep. 28, 2014, the contents of each of which are hereby incorporated by reference in their entirety.

STATEMENT OF FEDERALLY FUNDED RESEARCH

This invention was made with government support under Center for HIV/AIDS Vaccine Immunology-Immunogen Design grant UM1-AI100645 from the NIH, NIAID, Division of AIDS. The government has certain rights in the invention.

SEQUENCE LISTING

The instant application contains a Sequence Listing which has been submitted electronically in ASCII format and is hereby incorporated by reference in its entirety. Said ASCII copy, created on Dec. 29, 2015, is named 1324300.00254US1_SL.txt and is 339,527 bytes in size.

FIELD OF THE INVENTION

The present invention relates in general, to a composition suitable for use in inducing anti-HIV-1 antibodies, and, in particular, to immunogenic compositions comprising envelope proteins and nucleic acids to induce cross-reactive neutralizing antibodies and increase their breadth of coverage. The invention also relates to methods of inducing such broadly neutralizing anti-HIV-1 antibodies using such compositions.

BACKGROUND

The development of a safe and effective HIV-1 vaccine is one of the highest priorities of the scientific community working on the HIV-1 epidemic. While anti-retroviral treatment (ART) has dramatically prolonged the lives of HIV-1 infected patients, ART is not routinely available in developing countries.

SUMMARY OF THE INVENTION

In certain aspects the invention is directed to HIV-1 envelopes which are designed as fusion molecules comprising a portion of an envelope protein and a trimerization domain so as to trimerize. In certain aspects the invention is directed towards methods of using such HIV-1 envelopes for immunization so as to induce immune response, which comprises humoral immune response. In certain embodiments, the methods of immunization comprise administering an agent which transiently modulates the immune response.

In certain aspects, the invention provides a composition comprising any one of the HIV-1 envelope polypeptides corresponding to the HIV-1 envelopes CH505.M6, CH505.M11, CH505w020.14, CH505w030.28, CH505w-078.15, CH505w053.31, CH505w030.21, CH505w078.33, CH505w053.16, CH505w100.B6 or a combination thereof, or polynucleotide encoding the same.

In certain aspects, the invention provides a composition comprising any one of the HIV-1 envelope polypeptides corresponding to the HIV-1 envelopes CH505.T/F; CH505.M11; CH505w020.14; CH505w030.28; CH505w-030.21; CH505w053.16; CH505w053.31; CH505w078.33; CH505w078.15; CH505w100.B6 or a combination thereof, or a polynucleotide encoding the same.

In certain aspects, the invention provides a composition comprising any one of the HIV-1 envelope polypeptides corresponding to the HIV-1 envelopes CH505.M11, CH505.w004.03, CH505.w020.14, CH505.w030.28, CH505.w030.12, CH505.w020.2, CH505.w030.10, CH505.w078.15, CH505.w030.19 CH505.w030.21 or a combination thereof, or polynucleotide encoding the same.

In certain aspects the invention provides, a composition comprising any one of the polynucleotides in Table 4 or Table 5 or a combination thereof. In some embodiments the compositions comprises envelope proteins. In some embodiments, the composition comprises polynucleotides encoding the envelope proteins.

In certain embodiments, the proteins or polynucleotides comprise a trimerization domain. In certain embodiments the trimerziation domain is GCN4. In certain embodiments the trimerization domain is CD40L. In certain embodiments the trimerization domain is linked to the envelope sequence via a linker. In certain embodiments the linker is about 6 amino acids. In other embodiments the linker is about 3-20 amino acids. In certain embodiments, the linker is 3, 4, 5, 6, 7, 8, 9, 10, 11, 12, 13, 14, 15, 16, 17, 18, 19, 20 amino acids.

In certain embodiments, the proteins or polynucleotides further comprises a CD40L sequence.

In certain aspects the invention provides a composition comprising MPER-peptide-liposome-CD40L conjugate.

In certain embodiments, the compositions of the invention further comprise an adjuvant.

In one aspect the invention provides methods of inducing an immune response in a subject comprising administering the composition of any one of the compositions in an amount sufficient to induce an immune response.

In certain embodiments, the methods comprise administering any suitable agent or transient immune modulation which could modulate mechanisms of host immune tolerance and release of the induced antibodies. In certain embodiments, the methods of the invention comprise administering chloloquine before each immunization. In certain embodiments, chloloquine is administered for about 10 days before each immunization.

In certain embodiments, the methods of the invention comprise administering anti-CD25 antibody prior or after each immunization. In certain embodiments, anti-CD25 antibody is administered for about 5 days before each immunization.

In certain embodiments, the methods of the invention comprise compositions which comprise a nucleic acid, a protein or any combination thereof. In certain embodiments, the nucleic acid encoding the envelope is operably linked to a promoter inserted in an expression vector. In certain embodiments, the protein is recombinant.

In certain aspects, the invention provides a composition comprising any one of the HIV-1 envelope polypeptides corresponding to the HIV-1 envelopes 703010505.TF, 703010505.W53.16, 703010505.W78.33, 703010505. W100.B6 or a combination thereof, or polynucleotide encoding the same.

In certain aspects, the invention provides a composition comprising any one of the HIV-1 envelope polypeptides corresponding to the HIV-1 envelopes 703010505.TF, 703010505.W4.03, 703010505.W4.26, 703010505.W14.21, 703010505.W20.14, 703010505.W30.28, 703010505.W-30.13, 703010505.W53.31, 703010505.W78.15, 703010-505.W100.B4 or a combination thereof, or polynucleotide encoding the same.

In certain aspects, the invention provides a composition comprising any one of the HIV-1 envelope polypeptides corresponding to the HIV-1 envelopes 703010505.TF, 703010505.W4.03, 703010505.W4.26, 703010505.W14.3, 703010505.W14.8, 703010505.W14.21, 703010505.W20.7, 703010505.W20.26, 703010505.W20.9, 703010505.W-20.14, 703010505.W30.28, 703010505.W30.12, 703010-505.W30.19, 703010505.W30.13, 703010505.W53.19, 703010505.W53.13, 703010505.W53.31, 703010505.W-78.1, 703010505.W78.15, 703010505.W100.B4 or a combination thereof, or polynucleotide encoding the same.

Also disclosed are compositions wherein each HIV-1 envelope polypeptide comprises polypeptide or polynucleotide which is a gp 41, gp 120, gp 145, gp140, gp 150 or gp 160 variant.

In certain embodiments, the HIV-1 envelopes are administered as a nucleic acid, a protein or any combination thereof. In certain embodiments, the nucleic acid encoding the envelope is operably linked to a promoter inserted in an expression vector. In certain embodiments, the protein is recombinant.

In certain embodiments, the envelopes are administered as a prime, a boost, or both. In certain embodiments, the envelopes, or any combinations thereof are administered as a multiple boosts. In certain embodiments, the compositions and method further comprise an adjuvant. In certain embodiments, the HIV-1 envelopes are provided as nucleic acid sequences, including but not limited to nucleic acids optimized for expression in the desired vector and/or host cell. In other embodiments, the HIV-1 envelopes are provided as recombinantly expressed protein.

In certain embodiments, the invention provides compositions and method for induction of immune response, for example cross-reactive (broadly) neutralizing Ab induction. In certain embodiments, the methods use compositions comprising "swarms" of sequentially evolved envelope viruses that occur in the setting of bnAb generation in vivo in HIV-1 infection.

In certain aspects the invention provides compositions comprising a selection of HIV-1 envelopes or nucleic acids encoding these envelopes, for example but not limited to, as described herein. In certain embodiments, these compositions are used in immunization methods as a prime and/or boost, for example but not limited to, as described herein.

In certain embodiments, the compositions contemplate nucleic acid, as DNA and/or RNA, or protein immunogens either alone or in any combination. In certain embodiments, the methods contemplate genetic, as DNA and/or RNA, immunization either alone or in combination with envelope protein(s).

In certain embodiments, the nucleic acid encoding an envelope is operably linked to a promoter inserted in an expression vector. In certain aspects the compositions comprise a suitable carrier. In certain aspects, the compositions comprise a suitable adjuvant.

In certain embodiments, the induced immune response includes induction of antibodies, including, but not limited to autologous and/or cross-reactive (broadly) neutralizing antibodies against HIV-1 envelope. Various assays that analyze whether an immunogenic composition induces an immune response, and the type of antibodies induced are known in the art and are also described herein.

In certain aspects, the invention provides an expression vector comprising any of the nucleic acid sequences of the invention, wherein the nucleic acid is operably linked to a promoter. In certain aspects the invention provides an expression vector comprising a nucleic acid sequence encoding any of the polypeptides of the invention, wherein the nucleic acid is operably linked to a promoter. In certain embodiments, the nucleic acids are codon optimized for expression in a mammalian cell, in vivo or in vitro. In certain aspects, the invention provides nucleic acid comprising any one of the nucleic acid sequences of invention. Also provided is a nucleic acid consisting essentially of any one of the nucleic acid sequences of invention. Also provided is a nucleic acid consisting of any one of the nucleic acid sequences of invention. In certain embodiments, the nucleic acid of invention, is operably linked to a promoter and is inserted in an expression vector. In certain aspects the invention provides an immunogenic composition comprising the expression vector.

In certain aspects, the invention provides a composition comprising at least one of the nucleic acid sequences of the invention. In certain aspects, the invention provides a composition comprising any one of the nucleic acid sequences of invention. In certain aspects, the invention provides a composition comprising a combination of one nucleic acid sequence encoding any one of the polypeptides of the invention. In certain embodiments, combining DNA and protein gives higher magnitude of ab responses. See Pissani F. Vaccine 32: 507-13, 2013; Jalah R et al PLoS One 9: e91550, 2014.

In certain embodiments, the compositions and methods employ an HIV-1 envelope as polypeptide instead of a nucleic acid sequence encoding the HIV-1 envelope. In certain embodiments, the compositions and methods employ an HIV-1 envelope as polypeptide, a nucleic acid sequence encoding the HIV-1 envelope, or a combination thereof. The envelope can be a gp160, gp150, gp145, gp140, gp120, gp41, N-terminal deletion variants as described herein, cleavage resistant variants as described herein, or codon optimized sequences thereof. The polypeptide of the inventions can be a trimer. The polypeptide contemplated by the invention can be a polypeptide comprising any one of the polypeptides described herein. The polypeptide contemplated by the invention can be a polypeptide consisting essentially of any one of the polypeptides described herein. The polypeptide contemplated by the invention can be a polypeptide consisting of any one of the polypeptides described herein. In certain embodiments, the polypeptide is recombinantly produced. In certain embodiments, the polypeptides and nucleic acids of the invention are suitable for use as an immunogen, for example to be administered in a human subject.

BRIEF DESCRIPTION OF THE DRAWINGS

FIGS. 2A and 2B show Envelope monomer timer QC—Non-reducing conditions.

FIGS. 3A and 3B show Envelope monomer timer QC—reducing conditions.

FIG. 5 shows a summary of the data in FIGS. 6-11. FIG. 5 shows that CH505TF gp120 GCN4 Trimer binds to CH103 UCA (CD4bs) with a lower Kd (nm) compared to the CH505TF gp120 D7 Monomer.

FIG. 17 shows sequence of a selection of ten envelopes ("P10" derived from CH505). FIG. 17 discloses SEQ ID NOS 91-110, 10, 15, 20, 25, 49, 60, 44, 55, 30, 65, 9, 14, 19, 24, 48, 59, 43, 54, 29, 64, 11, 16, 21, 26, 50, 61, 45, 56, 40, 66, 13, 18, 23, 28, 52, 63, 47, 58, 42, 68, 12, 17, 22, 27, 51, 62, 46, 57, 41, 67, 12, 17, 22, 27, 83 and 84, respectively, in order of appearance. See Tables 4 and 5 for detailed assignment of SEQ ID NOS.

FIG. 18A shows binding of CH103 antibodies to the autologous Envs of FIG. 17, log AUC.

FIG. 22 show the sequences of four envelopes, grouped as HIV-1 Envelopes Selection C. FIG. 22 discloses SEQ ID NOS 79-82, respectively, in order of appearance.

FIG. 23 shows the sequences of CAP 206 envelopes from 6 months. FIG. 23 discloses SEQ ID NOS 85-86, respectively, in order of appearance.

FIG. 24 shows the sequence of ten early envelopes, grouped as HIV-1 Envelopes Selection E. FIG. 24 discloses SEQ ID NOS 69-78, respectively, in order of appearance.

DETAILED DESCRIPTION

Figure 1:
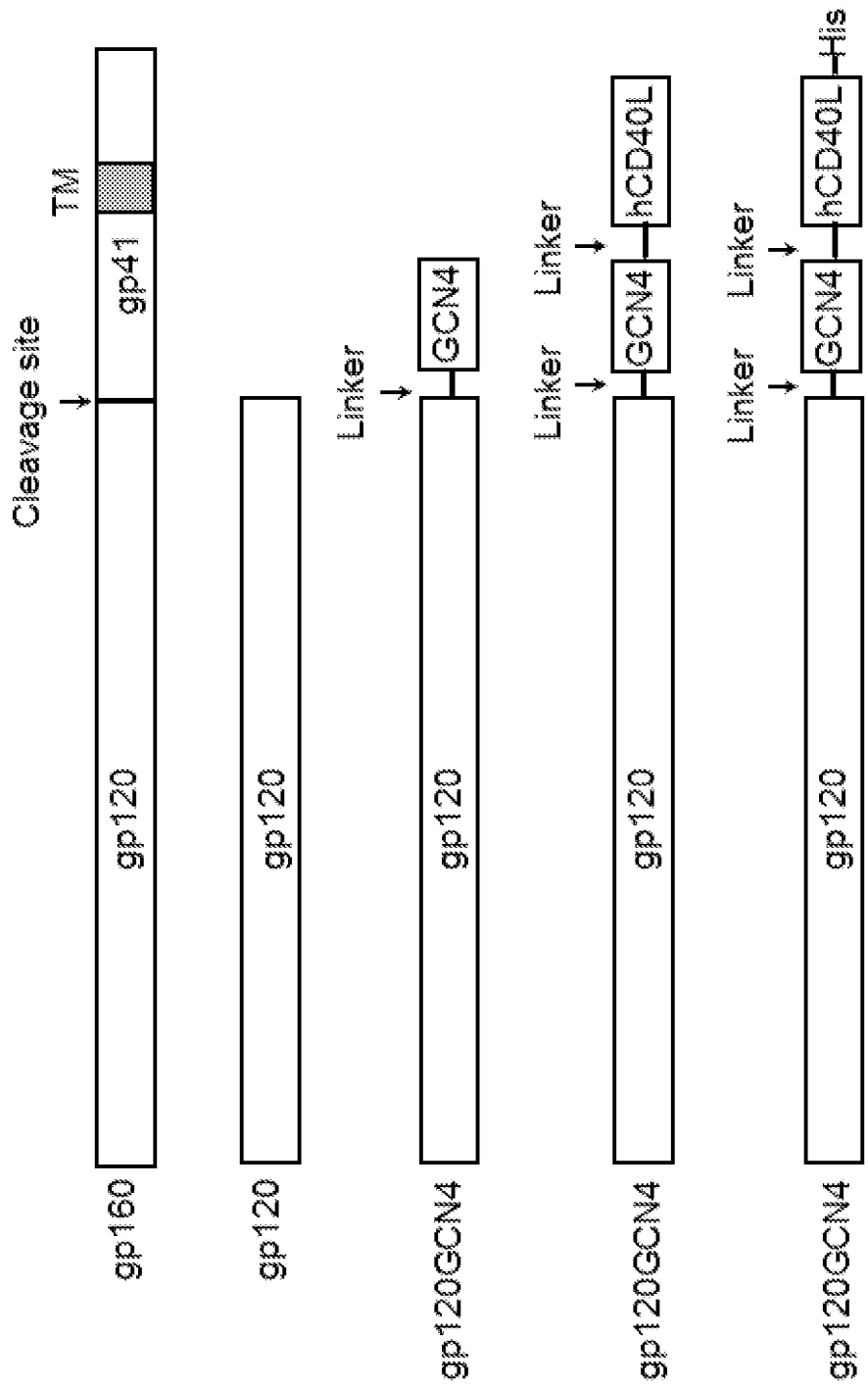
FIG. 1 shows designs of HIV-1 envelopes with trimerization domain, and immune modulating (e.g. CD40L) domain.

The development of a safe, highly efficacious prophylactic HIV-1 vaccine is of paramount importance for the control and prevention of HIV-1 infection. A major goal of HIV-1 vaccine development is the induction of broadly neutralizing antibodies (bnAbs) (Immunol. Rev. 254: 225-244, 2013). BnAbs are protective in rhesus macaques against SHIV challenge, but as yet, are not induced by current vaccines.

For the past 25 years, the HIV vaccine development field has used single or prime boost heterologous Envs as immunogens, but to date has not found a regimen to induce high levels of bnAbs.

Recently, a new paradigm for design of strategies for induction of broadly neutralizing antibodies was introduced, that of B cell lineage immunogen design (Nature Biotech. 30: 423, 2012) in which the induction of bnAb lineages is recreated. It was recently demonstrated the power of mapping the co-evolution of bnAbs and founder virus for elucidating the Env evolution pathways that lead to bnAb induction (Nature 496: 469, 2013). From this type of work has come the hypothesis that bnAb induction will require a selection of antigens to recreate the "swarms" of sequentially evolved viruses that occur in the setting of bnAb generation in vivo in HIV infection (Nature 496: 469, 2013).

A critical question is why the CH505 immunogens are better than other immunogens. This rationale comes from three recent observations. First, a series of immunizations of single putatively "optimized" or "native" trimers when used as an immunogen have not induced bnAbs as single immunogens. Second, in all the chronically infected individuals who do develop bnAbs, they develop them in plasma after ~2 years. When these individuals have been studied at the time soon after transmission, they do not make bnAbs immediately.

Two other considerations are important. The first is that for the CH103 bnAb CD4 binding site lineage, the VH4-59 and Vλ3-1 genes are common as are the VDJ, VJ recombinations of the lineage (Liao, Nature 496: 469, 2013). In addition, the bnAb sites are so unusual, we are finding that the same VH and VL usage is recurring in multiple individuals. Thus, we can expect the CH505 Envs to induce CD4 binding site antibodies in many different individuals.

Finally, one needs to make a choice regarding gp120 vs. gp160 for the genetic immunization However, in acute infection, gp41 non-neutralizing antibodies are dominant and overwhelm gp120 responses (Tomaras, G et al. J. Virol. 82: 12449, 2008; Liao, H X et al. JEM 208: 2237, 2011). Recently we have found that the HVTN 505 DNA prime, rAd5 vaccine trial that utilized gp140 as an immunogen, also had the dominant response of non-neutralizing gp41 antibodies. Thus, the use of gp160 vs gp120 for gp41 dominance needs to be evaluated.

In certain aspects, the invention provides a strategy for induction of bnAbs, which involves selecting and developing immunogens designed to recreate the antigenic evolution of Envs that occur when bnAbs develop in the context of infection.

That broadly neutralizing antibodies (bnAbs) occur in nearly all sera from chronically infected HIV-1 subjects suggests anyone can develop some bnAb response if exposed to immunogens via vaccination. Working back from mature bnAbs through intermediates enabled understanding their development from the unmutated ancestor, and showed that antigenic diversity preceded the development of population breadth. See Liao et al. (2013) Nature 496, 469-476. In this study, an individual "CH505" was followed from HIV-1 transmission to development of broadly neutralizing antibodies. This individual developed antibodies targeted to CD4 binding site on gp120. In this individual the virus was sequenced over time, and broadly neutralizing antibody clonal lineage ("CH103") was isolated by antigen-specific B cell sorts, memory B cell culture, and amplified by VH/VL next generation pyrosequencing. See Liao et al. (2013) Nature 496, 469-476.

Further analysis of envelopes and antibodies from the CH505 individual indicated that a non-CH103 Lineage participates in driving CH103-BnAb induction. For example V1 loop, V5 loop and CD4 binding site loop mutations escape from CH103 and are driven by CH103 lineage. Loop D mutations enhanced neutralization by CH103 lineage and are driven by another lineage. Transmitted/founder Env, or another early envelope for example W004.03, and/or W004.26, triggers naïve B cell with CH103 Unmutated Common Ancestor (UCA) which develop in to intermediate antibodies. Transmitted/founder Env, or another early envelope for example W004.03, and/or W004.26, also triggers non-CH103 autologous neutralizing Abs that drive loop D mutations in Env that have enhanced binding to intermediate and mature CH103 antibodies and drive remainder of the lineage.

The invention provides various methods to choose a subset of viral variants, including but not limited to envelopes, to investigate the role of antigenic diversity in serial samples. In other aspects, the invention provides compositions comprising viral variants, for example but not limited to envelopes, selected based on various criteria as described herein to be used as immunogens.

In other aspects, the invention provides immunization strategies using the selections of immunogens to induce cross-reactive neutralizing antibodies. In certain aspects, the immunization strategies as described herein are referred to as "swarm" immunizations to reflect that multiple envelopes are used to induce immune responses. The multiple envelopes in a swarm could be combined in various immunization protocols of priming and boosting.

Sequences/Clones

Described herein are nucleic and amino acids sequences of HIV-1 envelopes. In certain embodiments, the described HIV-1 envelope sequences are gp160s. In certain embodiments, the described HIV-1 envelope sequences are gp120s. Other sequences, for example but not limited to gp140s, both cleaved and uncleaved, gp140 Envs with the deletion of the cleavage (C) site, fusion (F) and immunodominant (I) region in gp41—named as gp140ΔCFI, gp140 Envs with the deletion of only the cleavage (C) site and fusion (F) domain—named as gp140ΔCF, gp140 Envs with the deletion of only the cleavage (C)—named gp140ΔC (See e.g. Liao et al. Virology 2006, 353, 268-282), gp145s, gp150s, gp41s, which are readily derived from the nucleic acid and amino acid gp160 sequences. In certain embodiments the nucleic acid sequences are codon optimized for optimal expression in a host cell, for example a mammalian cell, a rBCG cell or any other suitable expression system.

In certain embodiments, the envelope design in accordance with the present invention involves deletion of residues (e.g., 5-11, 5, 6, 7, 8, 9, 10, or 11 amino acids) at the N-terminus. For delta N-terminal design, amino acid residues ranging from 4 residues or even fewer to 14 residues or even more are deleted. These residues are between the maturation (signal peptide, usually ending with CX, X can be any amino acid) and "VPVXXXX . . . ". In case of CH505 T/F Env as an example, 8 amino acids (italicized and underlined in the below sequence) were deleted: MRVMGIQRNYPQWWIWSMLGFWMLMICNGMWVT-VYYGVPVWKEAKTTLFCASDAKA YEKEVHN-VWATHACVPTDPNPQE . . . (rest of envelope sequence is indicated as " . . . ") (SEQ ID NO: 87). CH505 Envelopes with delta N-terminal design are referred to as D8 or ΔN8 or deltaN8. In other embodiments, the delta N-design described for CH505 T/F envelope can be used to make delta N-designs of other CH505 envelopes. In certain embodiments, the invention relates generally to an immunogen, gp160, gp120 or gp140, without an N-terminal Herpes Simplex gD tag substituted for amino acids of the N-terminus of gp120, with an HIV leader sequence (or other leader sequence), and without the original about 4 to about 25, for example 11, amino acids of the N-terminus of the envelope (e.g. gp120). See WO2013/006688, e.g. at pages 10-12, the contents of which publication is hereby incorporated by reference in its entirety.

The general strategy of deletion of N-terminal amino acids of envelopes results in proteins, for example gp120s, expressed in mammalian cells that are primarily monomeric, as opposed to dimeric, and, therefore, solves the production and scalability problem of commercial gp120 Env vaccine production. In other embodiments, the amino acid deletions at the N-terminus result in increased immunogenicity of the envelopes.

In certain embodiments, the invention provides envelope sequences, amino acid sequences and the corresponding nucleic acids, and in which the V3 loop is substituted with the following V3 loop sequence TRPNNNTRKSIRIG-PGQTFY ATGDIIGNIRQAH (SEQ. ID NO. 1). This substitution of the V3 loop reduced product cleavage and improves protein yield during recombinant protein production in CHO cells.

In certain embodiments, the CH505 envelopes will have added certain amino acids to enhance binding of various broad neutralizing antibodies. Such modifications could include but not limited to, mutations at W680G or modification of glycan sites for enhanced neutralization.

In certain aspects, the invention provides composition and methods which use a selection of sequential CH505 Envs, as gp120s, gp 140s cleaved and uncleaved and gp160s, as proteins, DNAs, RNAs, or any combination thereof, administered as primes and boosts to elicit immune response. Sequential CH505 Envs as proteins would be co-administered with nucleic acid vectors containing Envs to amplify antibody induction.

Figure 2A:
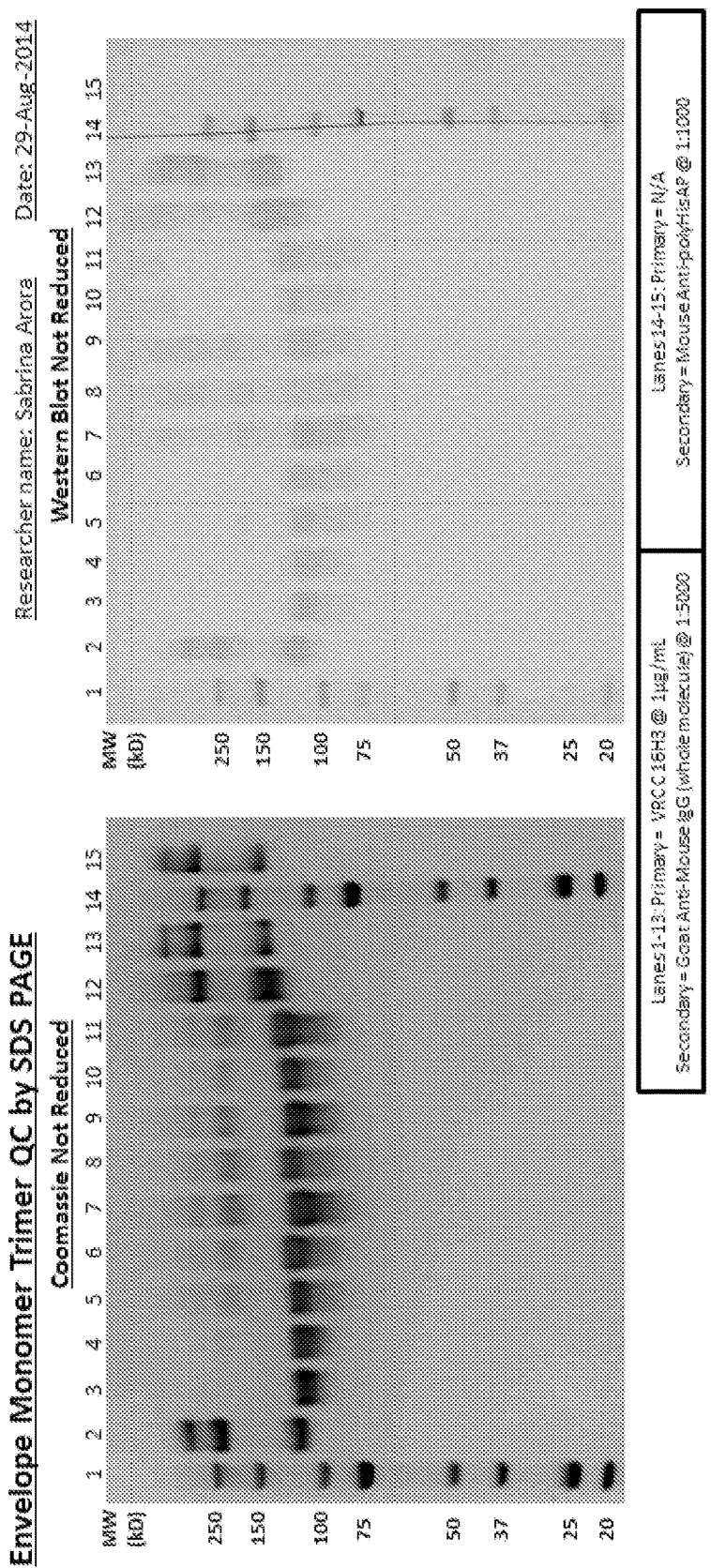
Figure 3A:
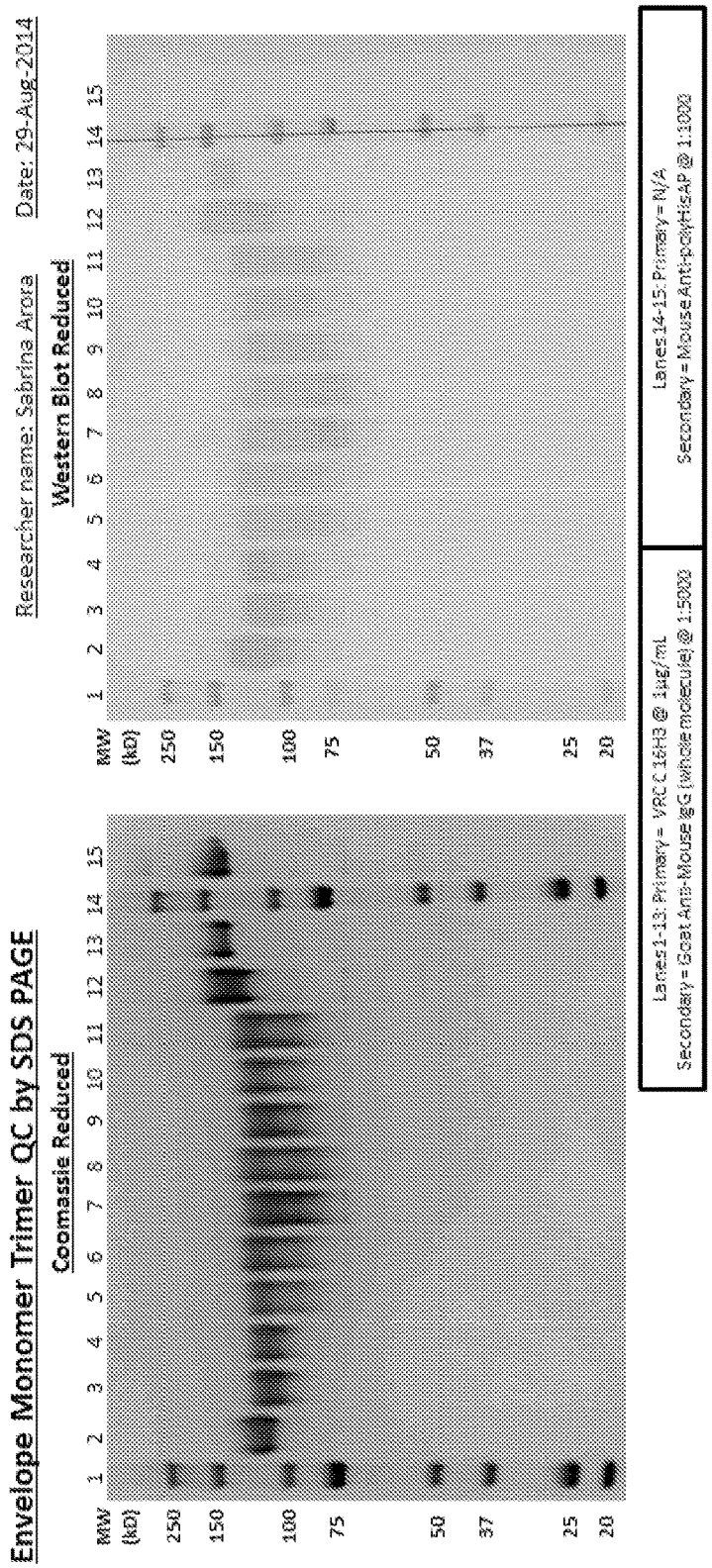
Figure 4:
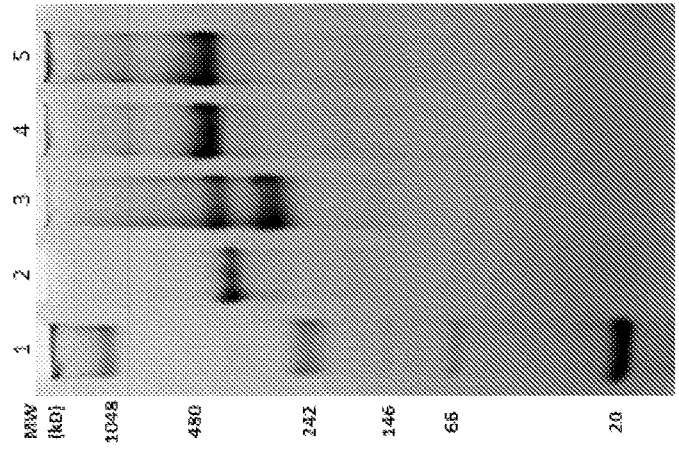
FIG. 4 shows Envelope trimer by Blue Native PAGE.
Figure 6:
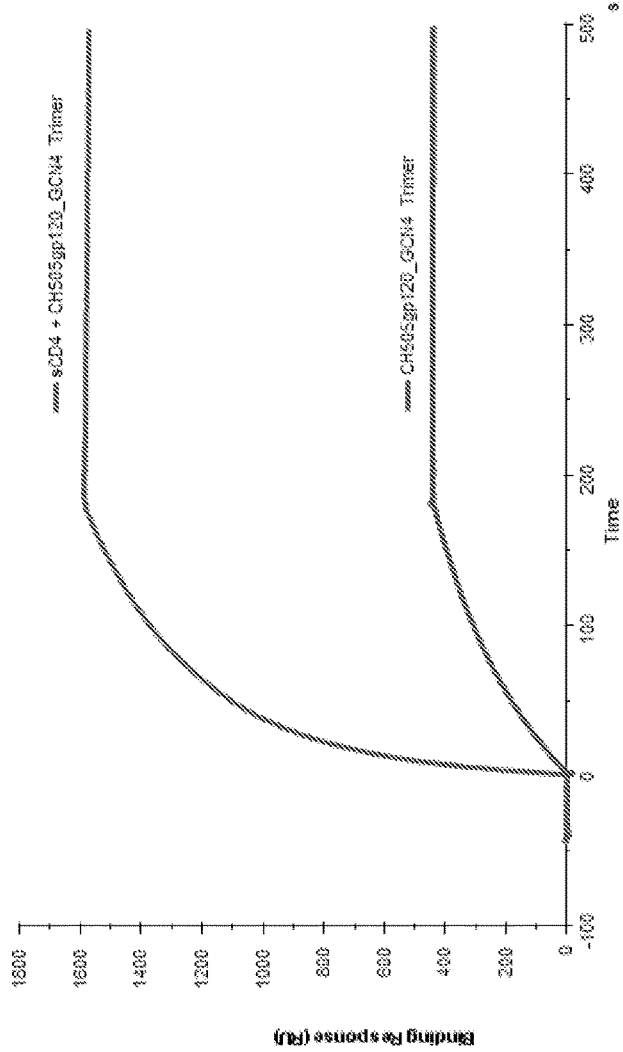
FIG. 6 shows gp120 trimers antigenicity.
Figure 7:
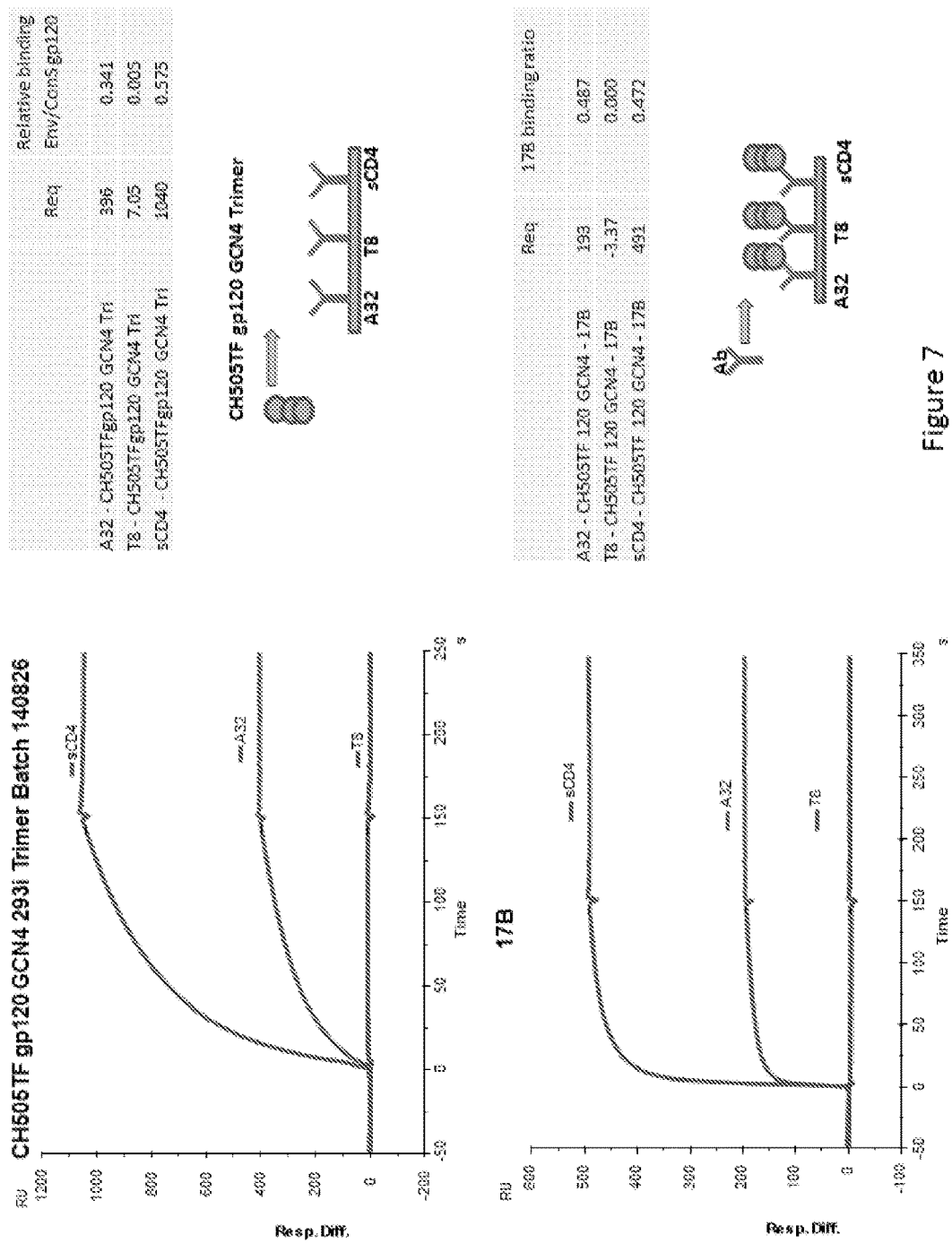
FIG. 7 shows gp120 trimers antigenicity.
Figure 8:
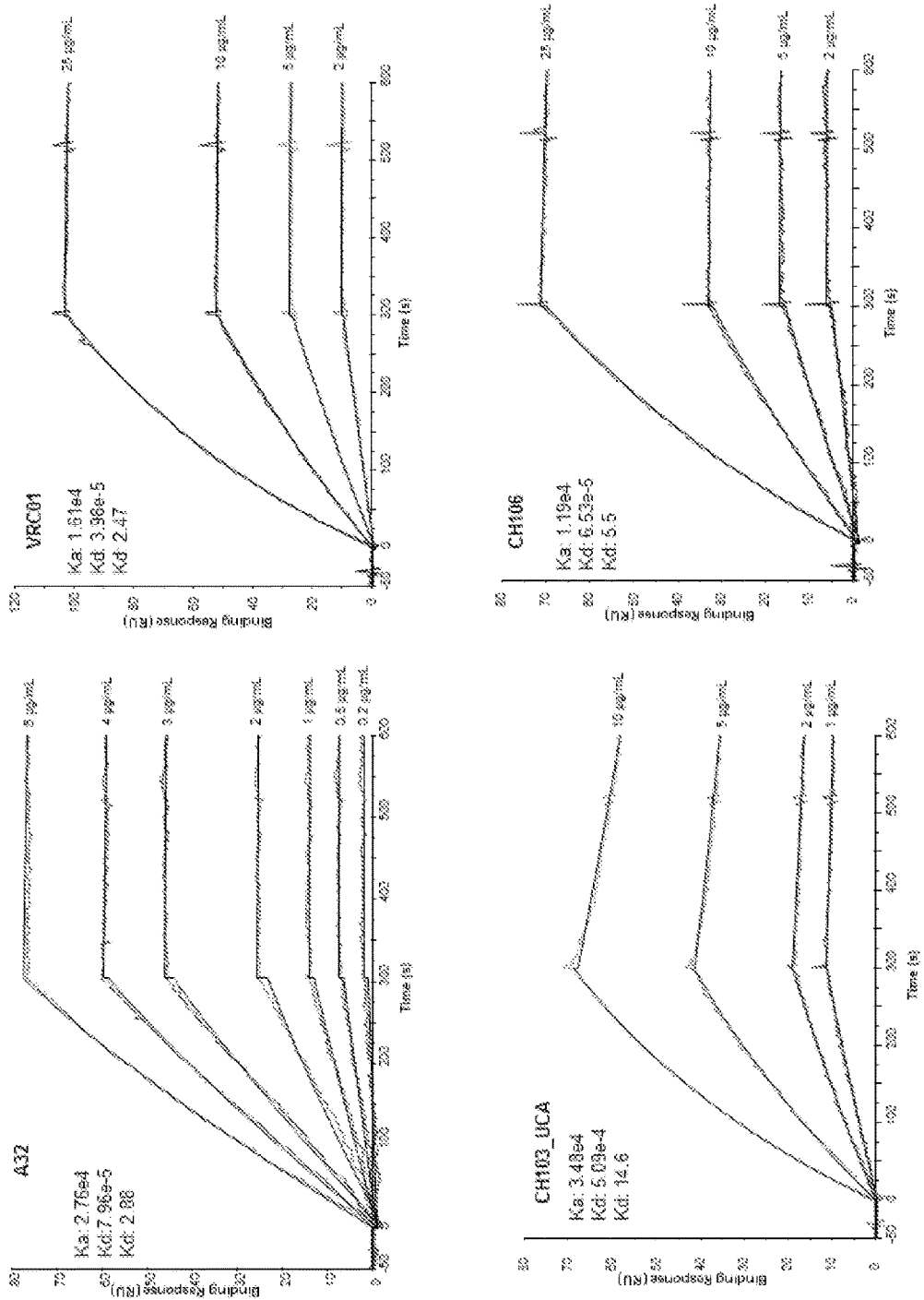
FIG. 8 shows gp120 trimers antigenicity.
Figure 9:
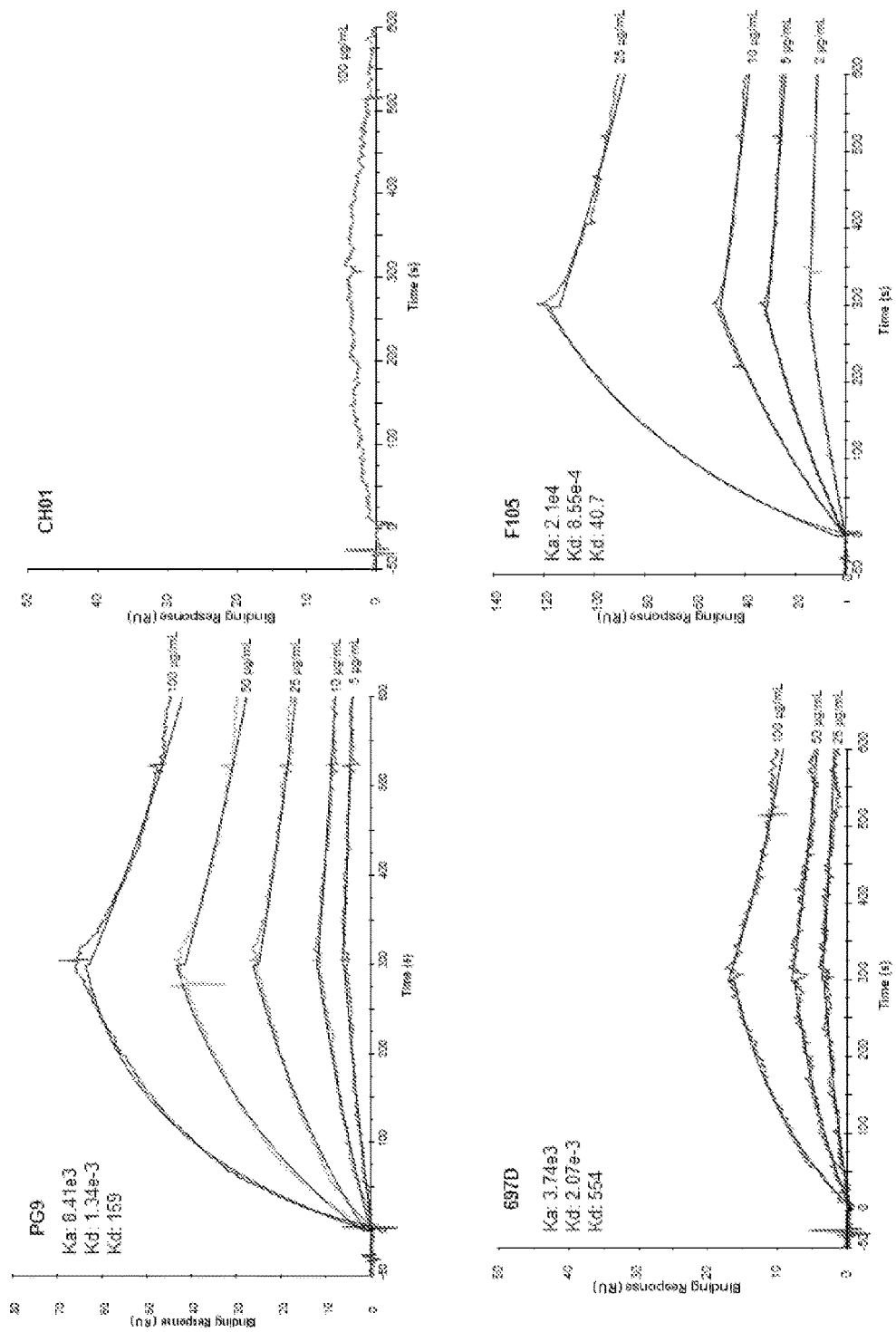
FIG. 9 shows gp120 trimers antigenicity.
Figure 10:
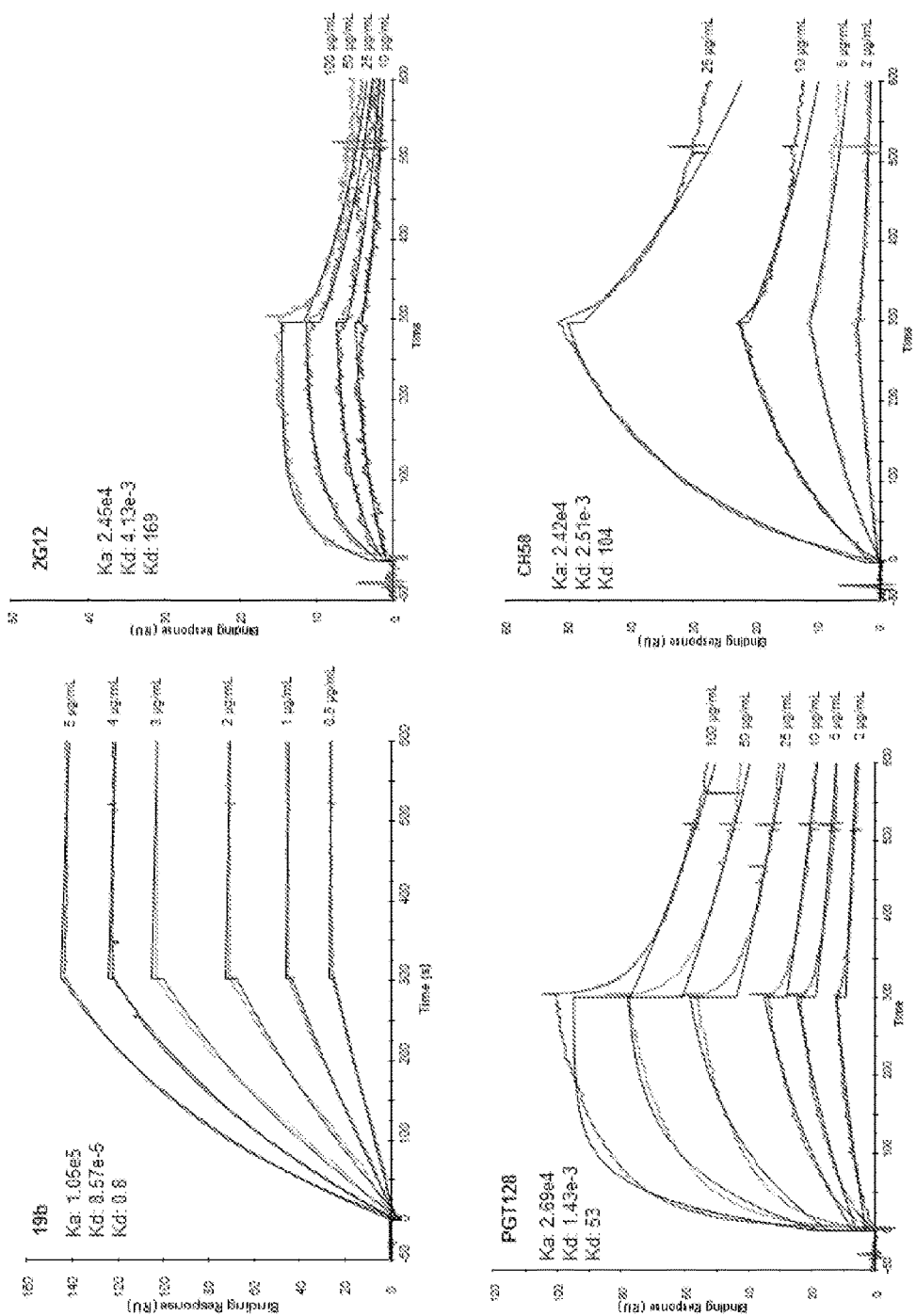
FIG. 10 shows gp120 trimers antigenicity.
Figure 11:
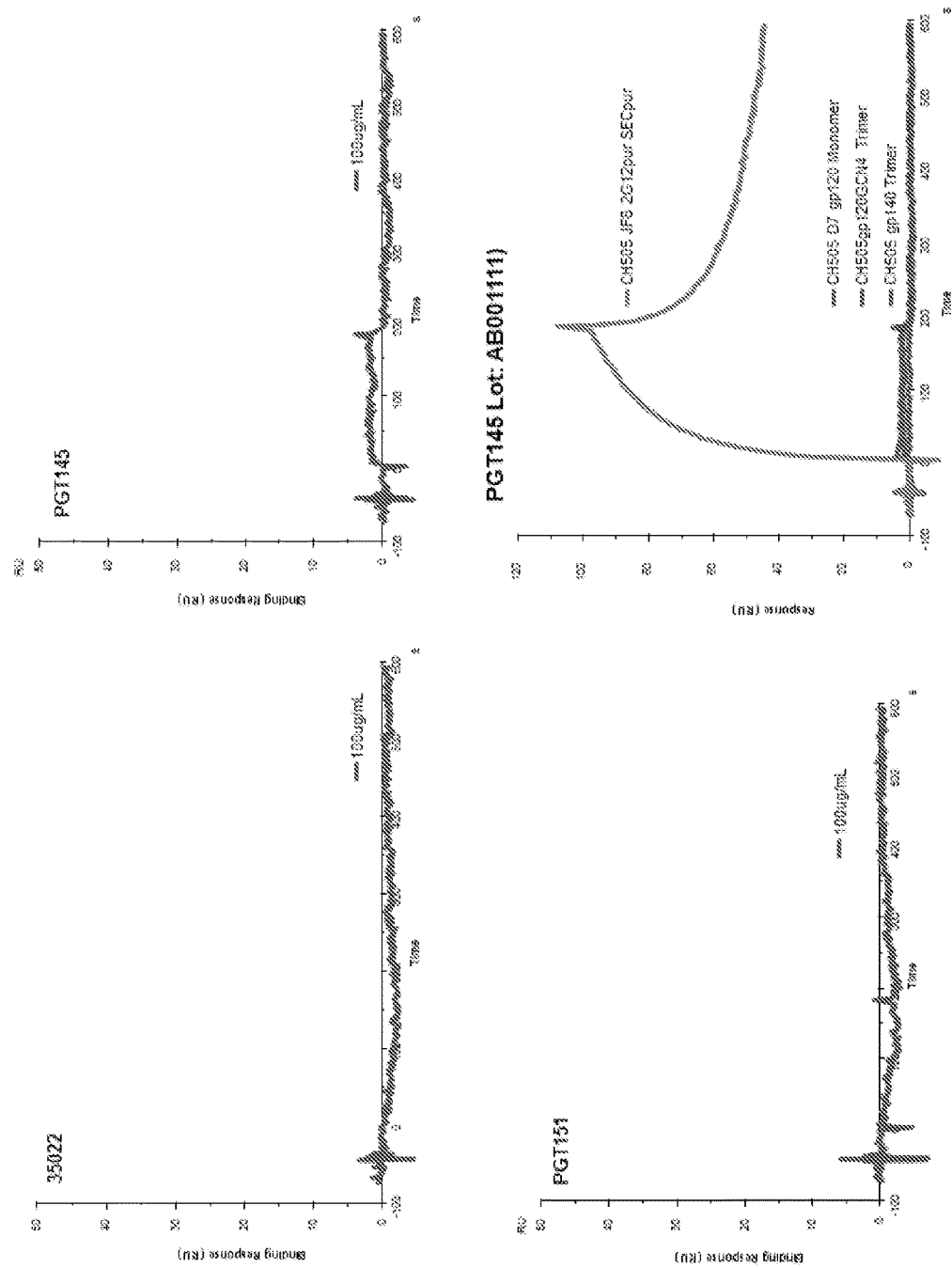
FIG. 11 shows gp120 trimers antigenicity.

In certain embodiments the invention provides immunogens and compositions which include immunogens as trimers. In certain embodiments, the immunogens include a trimerization domain which is not derived from the HIV-1 envelope. In certain embodiments, the trimerization domain is GCN4 (See FIGS. 1 and 2B). In other embodiments the trimerization domain is CD40L. In other embodiments, the immunogens include CD40L domain (See FIGS. 1 and 2B).

HIV-1 gp120 Trimer Vaccine Immunogens (FIG. 1):

HIV-1 Env gp120 GCN4 Trimer

HIV-1 Env gp120 GCN4 trimer is designed to be expressed as soluble recombinant trimeric HIV-1 gp120 protein. HIV-1 Env gp120 is mutated from residue R to E at the cleavage site of HIV-1 gp120 at the residue positions R503 and R511 (or any mutations at this region) to destroyed the cleavage site, a 6-residue linker (GSGSGS) (SEQ. ID. NO. 2) (the linker can be variations of 3-20 residues in length) is added to the C-terminal end of HIV-1 gp120 followed by addition of 33 amino acid residues of GCN4 sequence (RMKQIEDKIEEILSKIYHIENEIARIK-KLIGER) (SEQ ID NO. 3).

HIV-1 Env gp120 GCN4 CD40L Trimer:

In certain embodiments the trimer design includes an immune co-stimulator. HIV-1 Env gp120 GCN4 CD40L trimer is designed to be expressed as soluble recombinant trimeric HIV-1 gp120 protein co-expressed with functional CD40L as immune co-stimulator. HIV-1 Env gp120 is mutated from residue R to E at the cleavage site of HIV-1 gp120 at the residue positions R503 and R511 (or any mutations at this region) to destroyed the cleavage site, a 6-residue linker (GSGSGS) (SEQ.

adeno-associated virus, Venezuelan equine encephalitis (VEE) replicons, Herpes Simplex Virus vectors, and other suitable vectors.

In certain aspects the invention contemplates using immunogenic compositions wherein immunogens are delivered as DNA or RNA in suitable formulations. Various technologies which contemplate using DNA or RNA, or may use complexes of nucleic acid molecules and other entities to be used in immunization. In certain embodiments, DNA or RNA is administered as nanoparticles consisting of low dose antigen-encoding DNA formulated with a block copolymer (amphiphilic block copolymer 704). See Cany et al., Journal of Hepatology 2011 vol. 54 j 115-121; Arnaoty et al., Chapter 17 in Yves Bigot (ed.), Mobile Genetic Elements: Protocols and Genomic Applications, Methods in Molecular Biology, vol. 859, pp 293-305 (2012); Arnaoty et al. (2013) Mol Genet Genomics. 2013 August; 288(7-8):347-63. Nanocarrier technologies called Nanotaxi® for immunogenic macromolecules (DNA, RNA, Protein) delivery are under development. See www.incellart.com/en/research-and-development/technologies.html.

In certain aspects the invention contemplates using immunogenic compositions wherein immunogens are delivered as recombinant proteins. Various methods for production and purification of recombinant proteins suitable for use in immunization are known in the art.

The immunogenic envelopes can also be administered as a protein boost in combination with a variety of nucleic acid envelope primes (e.g., HIV-1 Envs delivered as DNA expressed in viral or bacterial vectors).

Dosing of proteins and nucleic acids can be readily determined by a skilled artisan. A single dose of nucleic acid can range from a few nanograms (ng) to a few micrograms (μg) or milligram of a single immunogenic nucleic acid. Recombinant protein dose can range from a few μg micrograms to a few hundred micrograms, or milligrams of a single immunogenic polypeptide.

Administration: The compositions can be formulated with appropriate carriers using known techniques to yield compositions suitable for various routes of administration. In certain embodiments the compositions are delivered via intramascular (IM), via subcutaneous, via intravenous, via nasal, via mucosal routes.

The compositions can be formulated with appropriate carriers and adjuvants using techniques to yield compositions suitable for immunization. The compositions can include an adjuvant, such as, for example but not limited to, alum, poly IC, MF-59 or other squalene-based adjuvant, ASOIB, or other liposomal based adjuvant suitable for protein or nucleic acid immunization. In certain embodiments, the adjuvant is GSK AS01E adjuvant containing MPL and QS21. This adjuvant has been shown by GSK to be as potent as the similar adjuvant AS01B but to be less reactogenic using HBsAg as vaccine antigen [Leroux-Roels et al., IABS Conference, April 2013, 9]. In certain embodiments, TLR agonists are used as adjuvants. In some embodiments, the TLR agonist is a TLR4 agonist, such as but not limited to GLA/SE. In other embodiment, adjuvants which break immune tolerance are included in the immunogenic compositions. In some embodiments the adjuvant is TLR7 or a TLR7/8 agonist, or a TLR-9 agonist, or a combination thereof. See PCT/US2013/029164.

There are various host mechanisms that control bNAbs. For example highly somatically mutated antibodies become autoreactive and/or less fit (Immunity 8: 751, 1998; PloS Comp. Biol. 6 e1000800, 2010; J. Thoret. Biol. 164:37, 1993); Polyreactive/autoreactive naïve B cell receptors (unmutated common ancestors of clonal lineages) can lead to deletion of Ab precursors (Nature 373: 252, 1995; PNAS 107: 181, 2010; J. Immunol. 187: 3785, 2011); Abs with long HCDR3 can be limited by tolerance deletion (JI 162: 6060, 1999; JCI 108: 879, 2001). BnAb knock-in mouse models are providing insights into the various mechanisms of tolerance control of MPER BnAb induction (deletion, anergy, receptor editing). Other variations of tolerance control likely will be operative in limiting BnAbs with long HCDR3s, high levels of somatic hypermutations. 2F5 and 4E10 BnAbs were induced in mature antibody knock-in mouse models with MPER peptide-liposome-TLR immunogens. Next step is immunization of germline mouse models and humans with the same immunogens.

In certain embodiments the immunogens and compositions of the invention comprise immunostimulatory components. In a non-limiting embodiment, the immunogen comprises a CD40L.

In certain embodiments, the compositions and methods comprise any suitable agent or immune modulation which could modulate mechanisms of host immune tolerance and release of the induced antibodies. In non-limiting embodiments modulation includes PD-1 blockade; T regulatory cell depletion; CD40L hyperstimulation; soluble antigen administration, wherein the soluble antigen is designed such that the soluble agent eliminates B cells targeting dominant epitopes, or a combination thereof. In certain embodiments, an immunomodulatory agent is administered in at time and in an amount sufficient for transient modulation of the subject's immune response so as to induce an immune response which comprises broad neutralizing antibodies against HIV-1 envelope. Non-limiting examples of such agents is any one of the agents described herein: e.g. chloroquine (CQ), PTP1B Inhibitor-CAS 765317-72-4-Calbiochem or MSI 1436 clodronate or any other bisphosphonate; a Foxo1 inhibitor, e.g. 344355|Foxo1 Inhibitor, AS1842856-Calbiochem; Gleevac, anti-CD25 antibody, anti-CCR4 Ab, an agent which binds to a B cell receptor for a dominant HIV-1 envelope epitope, or any combination thereof. In certain embodiments, the methods comprise administering a second immunomodulatory agent, wherein the second and first immunomodulatory agents are different.

EXAMPLES

Example 1: GCN4 Envelope Trimers and CD40L Containing Immunogens Bind HIV-1 Envelope Antibodies and are Functionally Active Provided is one example of the design and formulation of liposomes that present immune-modulating CD40 ligand (CD40L) and HIV-1 gp41 neutralizing antigen. CD40L, the ligand for CD40 expressed on B-cell surface is anchored on the liposomes that had HIV-1 gp41 MPER peptide immunogen conjugated in them. Two broadly neutralizing gp41 membrane proximal external region (MPER) antibodies (2F5, 4E10) bound strongly to CD40L conjugated MPER peptide liposomes. This construct has important application as an experimental AIDS vaccine in providing immune-modulating effect to stimulate proliferation of B-cells capable of producing neutralizing antibodies targeting HIV-1 gp41 MPER region.

CD40L-gp41 MPER peptide-liposome conjugates: Recombinant CD40L with an N-terminal Histidine Tag (SEQ ID NO 8)
(MGSSHHHHHH SSGLVPRGSH MQKGDQNPQI

AAHVISEASS KTTSVLQWAE KGYYTMSNNL VTLENGKQLT

VKRQGLYYIY AQVTFCSNRE ASSQAPFIAS LCLKSPGRFE

RILLRAANTH SSAKPCGQQS IHLGGVFELQ PGASVFVNVT

Figure 12:
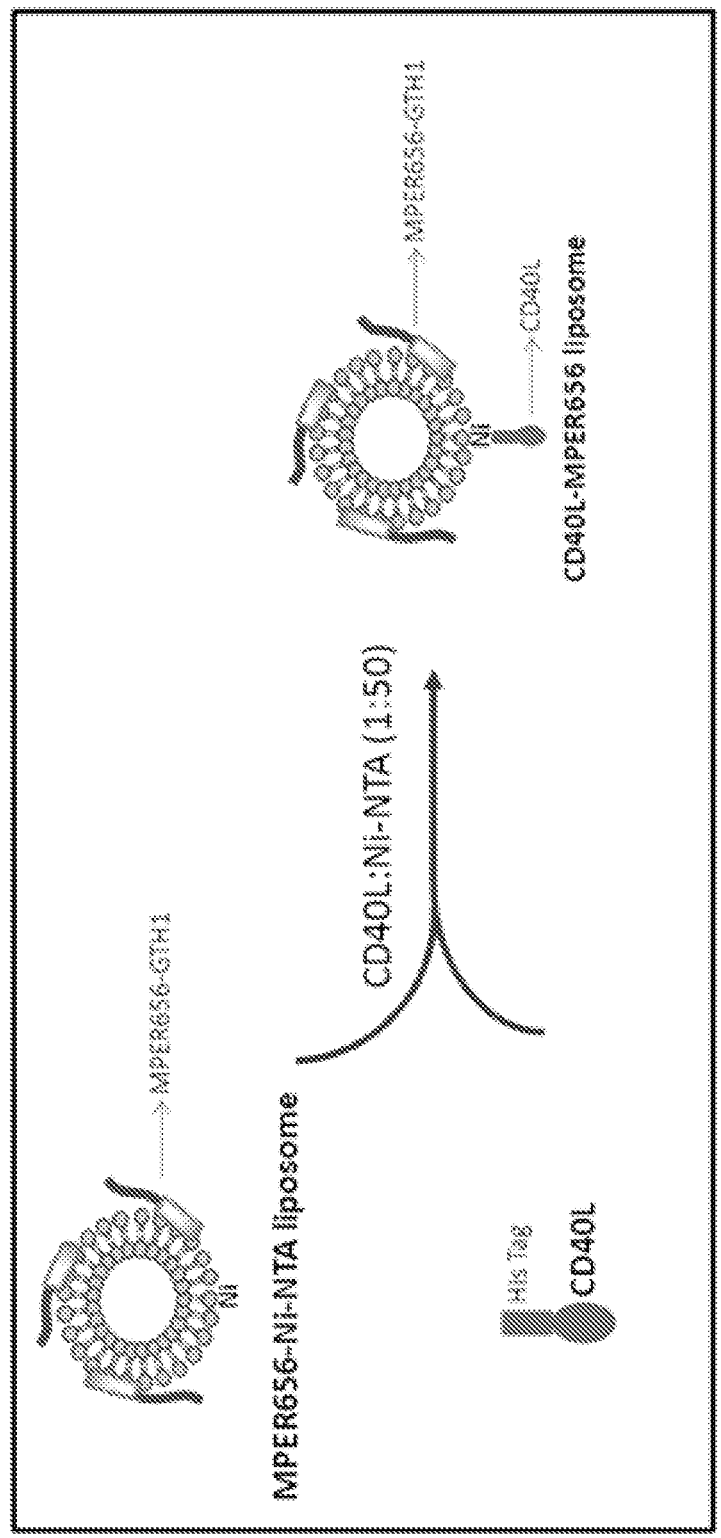
FIG. 12 shows the design of CD40L-MPER656 peptide-liposome conjugate.

DPSQVSHGTG FTSFGLLKL)

was anchored to MPER peptide liposomes via His-Ni-NTA chelation by mixing CD40L with MPER656-Ni-NTA liposomes at 1:50 CD40L and Ni-NTA molar ratio (Figure-12).

The construction of MPER peptide Ni-NTA liposomes utilized the method of co-solubilization of MPER peptide having a membrane anchoring amino acid sequence and synthetic lipids 1-Palmitoyl-2-Oleoyl-sn-Glycero-3-Phosphocholine (POPC), 1-Palmitoyl-2-Oleoyl-sn-Glycero-3-Phosphoethanolamine (POPE), 1,2-Dimyristoyl-sn-Glycero-3-Phosphate (DMPA), Cholesterol and 1,2-dioleoyl-sn-Glycero-3-[(N-(5-amino-1-carboxypentyl) iminodiacetic acid)succinyl] (nickel salt) (DGS-NTA(Ni) at mole fractions 0.216, 35.00, 25.00, 20.00, 1.33 and 10 respectively. Appropriate amount of MPER peptide dissolved in chloroform-methanol mixture (7:3 v/v), appropriate amounts of chloroform stocks of phospholipids were dried in a stream of nitrogen followed by overnight vacuum drying. Liposomes were made from the dried peptide-lipid film in phosphate buffered saline (pH 7.4) using extrusion technology.

Figure 13:
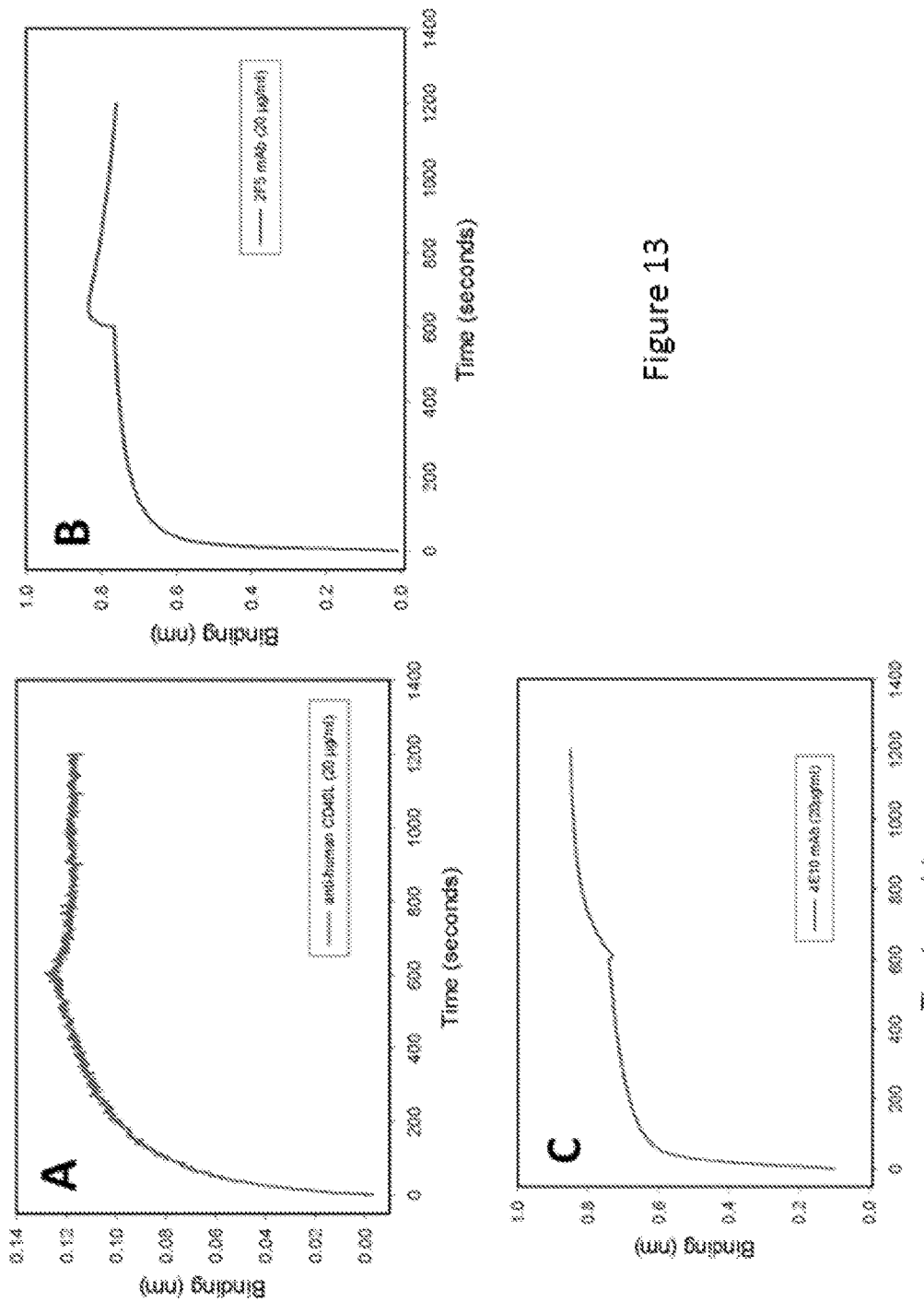
FIG. 13 shows antigenicity of the MPER-liposome of FIG. 12. Biolayer interferometry assay of binding of mouse anti-human CD40L mAb (A) and broadly neutralizing HIV-1 gp41 MPER mAbs 2F5 (B) and 4E10 mAbs (C) at 20 μg/ml to CD40L-MPER656 liposomes loaded onto Aminopropyl silane sensors are shown. The binding of antibodies to appropriate control liposomes were subtracted to obtain the specific binding shown in panel A-C.

Biolayer interferometry (BLI) assay showed the binding of anti-human CD40L antibody to CD40L-MPER656 liposomes and confirmed the correct presentation of CD40 L on liposome surface (FIG. 13A). The broadly neutralizing HIV-1 gp41 MPER antibodies 2F5 and 4E10 bound strongly to CD40L-MPER656 liposomes (FIGS. 13B-C) and demonstrated that the CD40L co-display did not impede the presentation of the epitopes of 2F5 and 4E10 mAbs.

Figure 14:
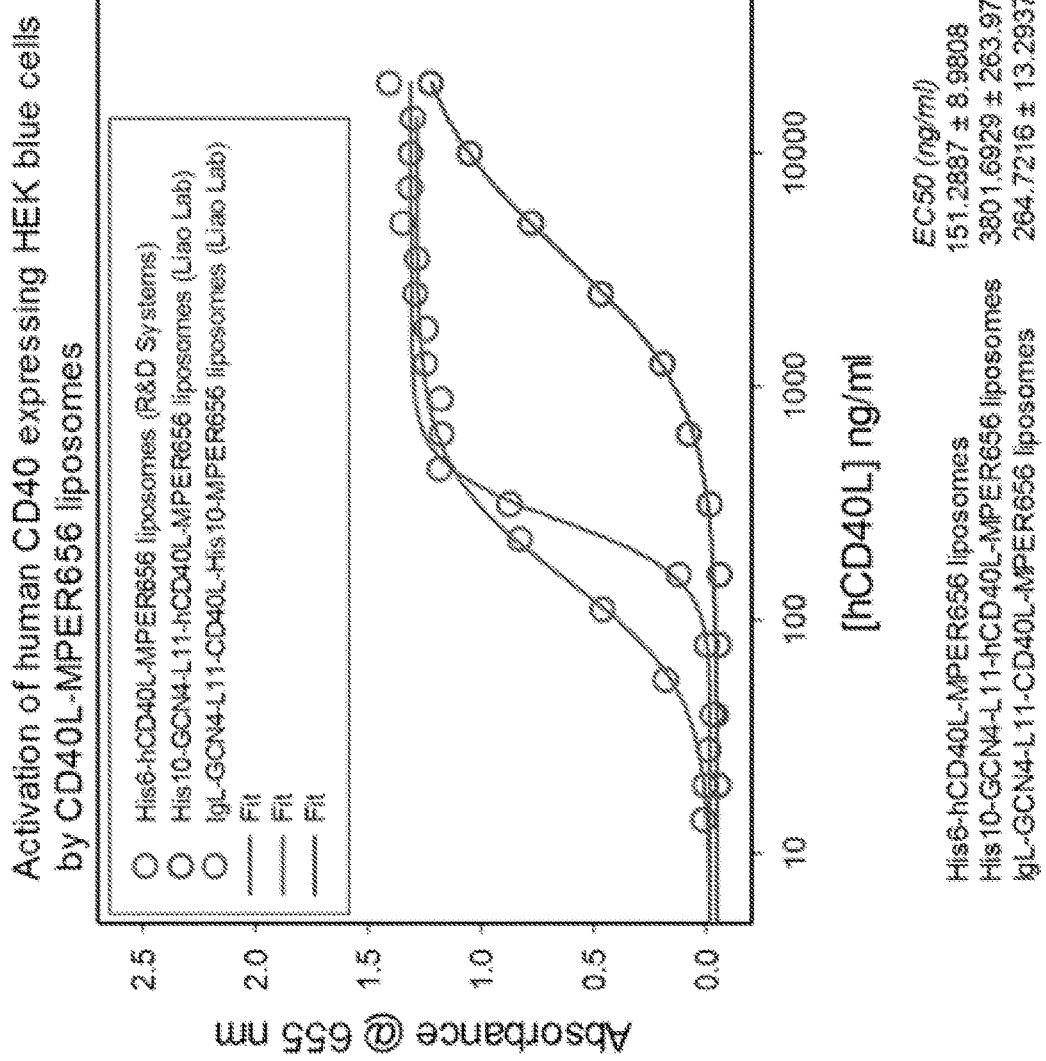
FIG. 14 show that the CD40L-MPER656 peptide-liposome conjugate is functional.
Figure 15:
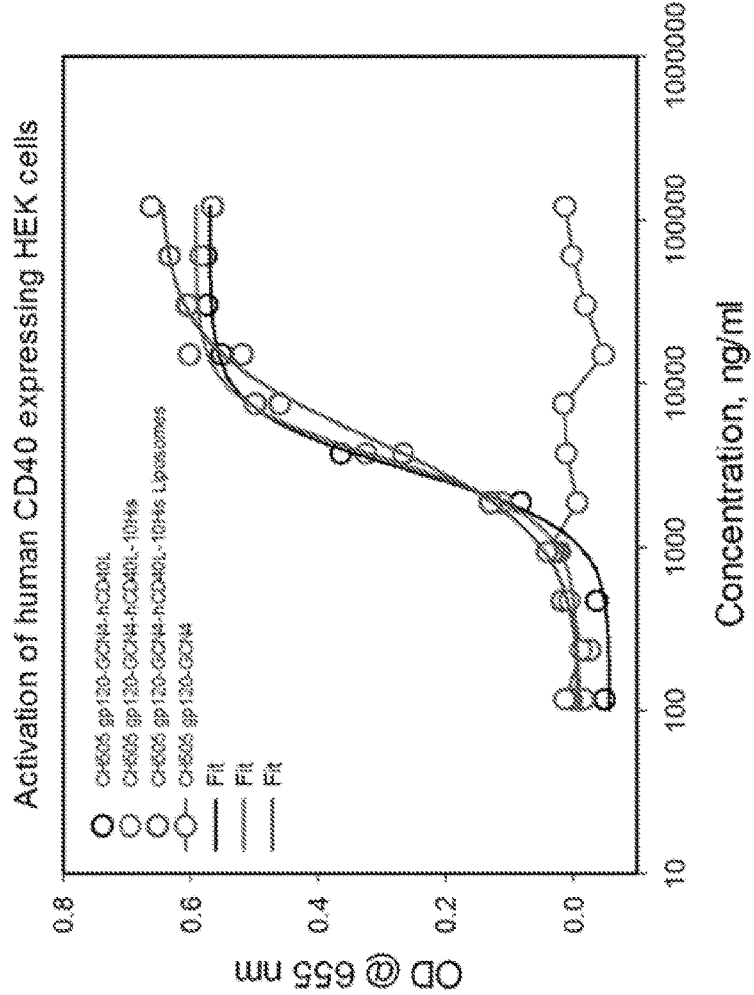
FIG. 15 shows that CH505 gp120-GCN4-CD40L activates human CD40 expressing HEK cells.
Figure 16:
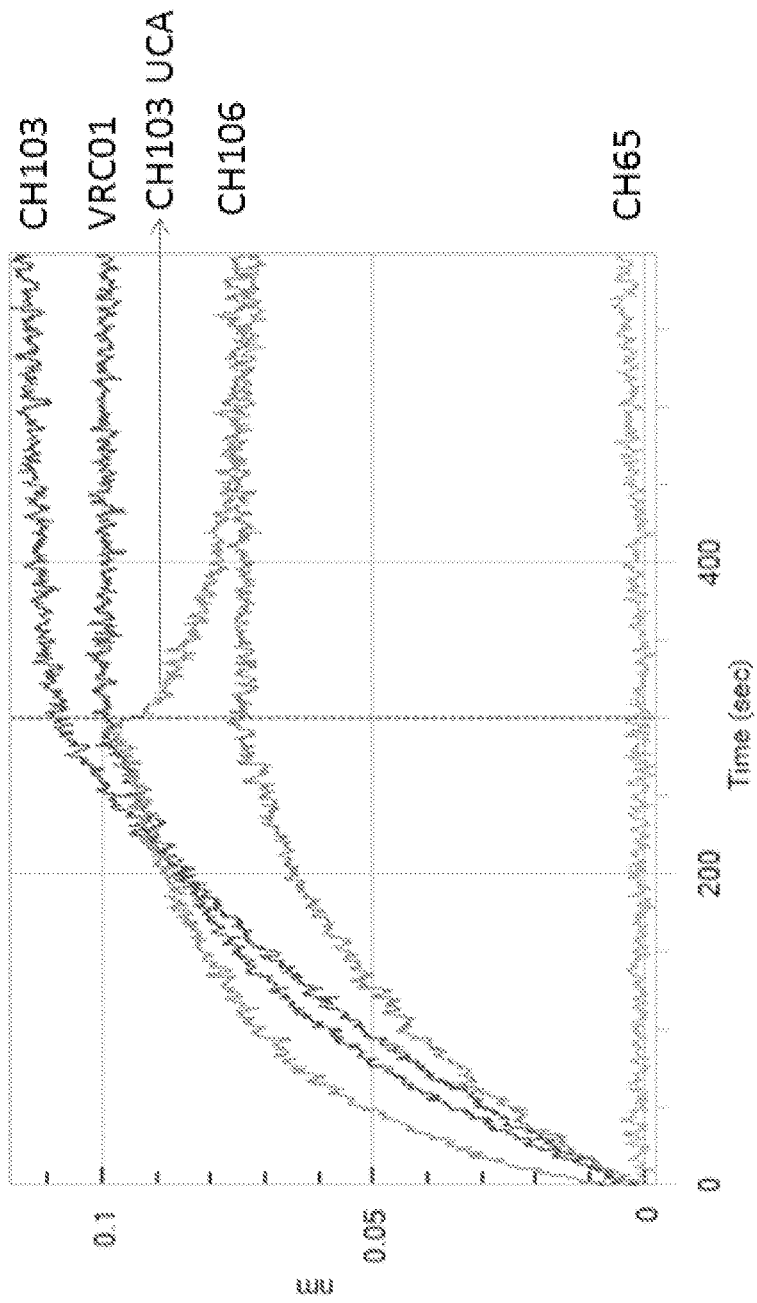
FIG. 16 shows antigenicity of CH505 gp120-GCN4-CD40L. SPR binding assay essentially as described in FIG. 13.

FIGS. 14 and 15 show that CD40L containing immunogens activate human CD40 expressing HEK cells.

Example 2—Combination of Antigens from CH505 Envelope Sequences for Immunization Provided herein are non-limiting examples of combinations of antigens derived from CH505 envelope sequences for a swarm immunization. The selection includes priming with a virus which binds to the UCA, for example a T/F virus or another early (e.g. but not limited to week 004.3, or 004.26) virus envelope. In certain embodiments the prime could include D-loop variants. In certain embodiments the boost could include D-loop variants.

Non-limiting embodiments of envelopes selected for swarm vaccination are shown as the selections described below. A skilled artisan would appreciate that a vaccination protocol can include a sequential immunization starting with the "prime" envelope(s) and followed by sequential boosts, which include individual envelopes or combination of envelopes. In another vaccination protocol, the sequential immunization starts with the "prime" envelope(s) and is followed with boosts of cumulative prime and/or boost envelopes. In certain embodiments, the prime does not include T/F sequence (W000.TF). In certain embodiments, the prime includes w004.03 envelope. In certain embodiments, the prime includes w004.26 envelope. In certain embodiments, the immunization methods do not include immunization with HIV-1 envelope T/F. In other embodiments for example the T/F envelope may not be included when w004.03 or w004.26 envelope is included. In certain embodiments, there is some variance in the immunization regimen; in some embodiments, the selection of HIV-1 envelopes may be grouped in various combinations of primes and boosts, either as nucleic acids, proteins, or combinations thereof.

In certain embodiments the immunization includes a prime administered as DNA, and MVA boosts. See Goepfert, et al. 2014; "Specificity and 6-Month Durability of Immune Responses Induced by DNA and Recombinant Modified Vaccinia Ankara Vaccines Expressing HIV-1 Virus-Like Particles" J Infect Dis. 2014 Feb. 9. [Epub ahead of print].

HIV-1 Envelope selection A (ten envelopes: sensitive envelopes): 703010505.TF, 703010505.W4.03, 703010-505.W4.26, 703010505.W14.21, 703010505.W20.14, 703010505.W30.28, 703010505.W30.13, 703010505.W-53.31, 703010505.W78.15, 703010505.W100.B4, optionally in certain embodiments designed as trimers. See U.S. Provisional Application No. 62/027,427 incorporated by reference.

HIV-1 Envelope selection B (twenty envelopes: sensitive envelopes): 703010505.TF, 703010505.W4.03, 703010-505.W4.26, 703010505.W14.3, 703010505.W14.8, 703010505.W14.21, 703010505.W20.7, 703010505.W-20.26, 703010505.W20.9, 703010505.W20.14, 703010-505.W30.28, 703010505.W30.12, 703010505.W30.19, 703010505.W30.13, 703010505.W53.19, 703010505.W-53.13, 703010505.W53.31, 703010505.W78.1, 703010-505.W78.15, 703010505.W100.B4, optionally in certain embodiments designed as trimers. See U.S. Provisional Application No. 62/027,427 incorporated by reference.

HIV-1 Envelope selection C (four envelopes): 703010505.TF, 703010505.W53.16, 703010505.W78. 33, 703010505.W100.B6, optionally in certain embodiments designed as trimers. See WO2014042669.

HIV-1 Envelope selection D (ten production envelopes): CH505.M6; CH505.M11; CH505w020.14; CH505w030.28; CH505w030.21; CH505w053.16; CH505w053.31; CH505-w078.33; CH505w078.15; CH505w100.B6, optionally in certain embodiments designed as trimers. See FIG. 17.

HIV-1 Envelopes selection E (ten early envelopes): optionally in certain embodiments designed as trimers. CH505.M11; CH505.w004.03; CH505.w020.14; CH505.-w030.28; CH505.w030.12; CH505.w020.2; CH505.-w030.10; CH505.w078.15; CH505.w030.19; CH505.-w030.21, optionally in certain embodiments designed as trimers. See FIG. 24.

Figure 18B:
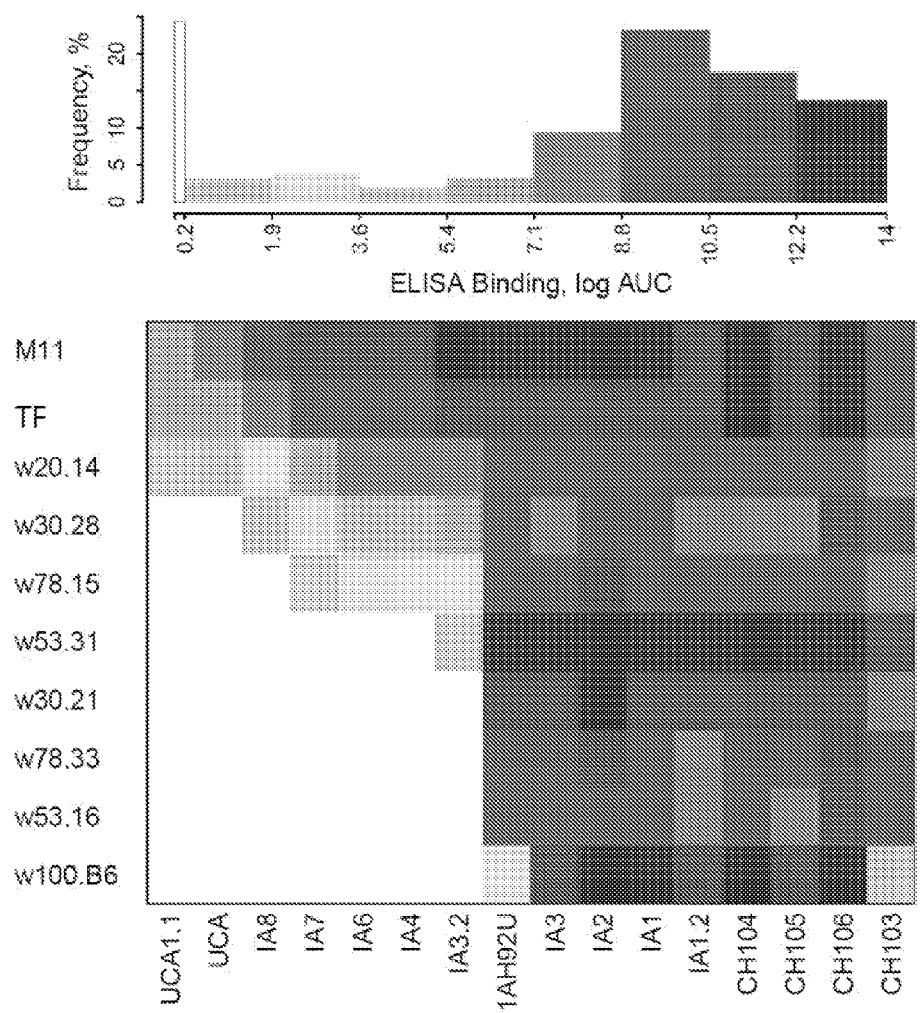
FIG. 18B shows the selection of 10 CH505 Envs (10 PR) based on the binding intensity for the CH103 members. Humanized mice are immunized with this selection of HIV-1 envelopes.

HIV-1 Envelope selection F (ten production envelopes (10PR)): CH505.T/F; CH505.M11; CH505w020.14; CH-505w030.28; CH505w030.21; CH505w053.16; CH505-w053.31; CH505w078.33; CH505w078.15; CH505w-100.B6, optionally in certain embodiments designed as trimers. See FIG. 18B.

Example 3: Examples of Immunization Protocols in Subjects with Swarms of HIV-1 Envelopes Immunization protocols contemplated by the invention include envelope sequences as described herein including but not limited to nucleic acids and/or amino acid sequences of gp160s, gp150s, cleaved and uncleaved gp140s, gp120s, gp41s, N-terminal deletion variants as described herein, cleavage resistant variants as described herein, or codon optimized sequences thereof. A skilled artisan can readily modify the gp160 and gp120 sequences described herein to obtain these envelope variants. The swarm immunization protocols can be administered in any subject, for example monkeys, mice, guinea pigs, or human subjects. The swarm immunization protocols include additive and/or sequential immunization with the selections of HIV envelopes.

In non-limiting embodiments, the immunization includes a nucleic acid is administered as DNA, for example in a modified vaccinia vector (MVA). In non-limiting embodiments, the nucleic acids encode gp160 envelopes. In other embodiments, the nucleic acids encode gp120 envelopes. In other embodiments, the boost comprises a recombinant gp120 envelope. The vaccination protocols include envelopes formulated in a suitable carrier and/or adjuvant, for example but not limited to alum. In certain embodiments the immunizations include a prime, as a nucleic acid or a recombinant protein, followed by a boost, as a nucleic acid or a recombinant protein. A skilled artisan can readily determine the number of boosts and intervals between boosts.

In non-limiting embodiments, the prime includes a 703010505.TF envelope and a loop D variant as described herein. In non-limiting embodiments, the prime includes a 703010505.TF envelope and/or 703010505.W4.03, 703010505.W4.26 envelope, and a loop D variant as described herein. In certain embodiments, the loop D variant is M6. In certain embodiments, the loop D variant is M5. In certain embodiments, the loop D variant is M10. In certain embodiments, the loop D variant is M19. In certain embodiments, the loop D variant is M11. In certain embodiments, the loop D variant is M20. In certain embodiments, the loop D variant is M21. In certain embodiments, the loop D variant is M9. In certain embodiments, the loop D variant is M8. In certain embodiments, the loop D variant is M7.

Table 1 shows a non-limiting example of a sequential immunization protocol using a swarm of HIV1 envelopes (703010505.TF, 703010505.W4.03, 703010505.W4.26, 703010505.W14.21, 703010505.W20.14, 703010505.W30.28, 703010505.W30.13, 703010505.W53.31, 703010505.W78.15, 703010505.W100.B4, optionally in certain embodiments designed as trimers. In a non-limiting embodiment, a suggested grouping for prime and boost is to begin with the CH505 TF+W4.03, then boost with a mixture of w4.26+14.21+20.14, then boost with a mixture of w30.28+30.13+53.31, then boost with a mixture of w78.15+100.B4.

| Envelope | Prime | Boost(s) | Boost(s) | Boost(s) |
|---|---|---|---|---|
| CH505 TF + W4.03 | CH505 TF + W4.03 as a nucleic acid e.g. DNA/MVA vector and/or protein | | | |
| w4.26 + 14.21 + 20.14 | | w4.26 + 14.21 + 20.14 as a nucleic acid e.g. DNA/MVA vector and/or protein | | |
| w30.28 + 30.13 + 53.31 | | | w30.28 + 30.13 + 53.31 as a nucleic acid e.g. DNA/MVA vector and/or protein | |
| w78.15 + 100.B4 | | | | w78.15 + 100.B4 as a nucleic acid e.g. DNA/MVA vector and/or protein |

A skilled artisan can readily determine the number and interval between boosts.

Table 2 shows a non-limiting example of a sequential immunization protocol using a swarm of HIV1 envelopes optionally in certain embodiments designed as trimers.

| Envelope | Prime | Boost(s) |
|---|---|---|
| 703010505.TF, 703010505.W4.03, 703010505.W4.26, 703010505.W14.21, 703010505.W20.14, 703010505.W30.28, 703010505.W30.13, 703010505.W53.31, 703010505.W78.15, 703010505.W100.B4. | 703010505.TF (optionally 703010505.W4.03, 703010505.W4.26) as a nucleic acid e.g. DNA/MVA vector and/or protein | 703010505.TF, 703010505.W4.03, 703010505.W4.26, 703010505.W14.21, 703010505.W20.14, 703010505.W30.28, 703010505.W30.13, 703010505.W53.31, 703010505.W78.15, 703010505.W100.B4 as a nucleic acid e.g. DNA/MVA vector and/or protein |

A skilled artisan can readily determine the number and interval between boosts.

For a 20mer immunization regimen (envelopes (703010505.TF, 703010505.W4.03, 703010505.W4.26, 703010505.W14.3, 703010505.W14.8, 703010505.W14.21, 703010505.W20.7, 703010505.W20.26, 703010505.W20.9, 703010505.W20.14, 703010505.W30.28, 703010505.W30.12, 703010505.W30.19, 703010505.W30.13, 703010505.W53.19, 703010505.W53.13, 703010505.W53.31, 703010505.W78.1, 703010505.W78.15, 703010505.W100.B4), in a non-limiting embodiment, one can prime with CH505 TF+W4.03, then boost with a mixture of w4.26+14.21+20.14+14.3+14.8+20.7, then boost with a mixture of w 20.26+20.9+30.12+w30.28+30.13+53.31, then boost with a mixture of w78.15+100.B4+30.19+53.19+53.13+78.1. Other combinations of envelopes are contemplated for boosts.

Table 3 shows a non-limiting example of a sequential immunization protocol using a swarm of HIV1 envelopes optionally in certain embodiments designed as trimers

| Envelope | Prime | Boost(s) |
|---|---|---|
| 703010505.TF, 703010505.W4.03, 703010505.W4.26, 703010505.W14.3, 703010505.W14.8, 703010505.W14.21, 703010505.W20.7, | 703010505.TF (optionally 703010505.W4.03, 703010505.W4.26, 703010505.W14.3, 703010505.W14.8, 703010505.W14.21), | 703010505.TF, 703010505.W4.03, 703010505.W4.26, 703010505.W14.3, 703010505.W14.8, 703010505.W14.21, 703010505.W20.7, |

-continued

| Envelope | Prime | Boost(s) |
|---|---|---|
| 703010505.W20.26, 703010505.W20.9, 703010505.W20.14, 703010505.W30.28, 703010505.W30.12, 703010505.W30.19, 703010505.W30.13, 703010505.W53.19, 703010505.W53.13, 703010505.W53.31, 703010505.W78.1, | as a nucleic acid e.g. DNA/MVA vector and/or protein | 703010505.W20.26, 703010505.W20.9, 703010505.W20.14, 703010505.W30.28, 703010505.W30.12, 703010505.W30.19, 703010505.W30.13, 703010505.W53.19, 703010505.W53.13, 703010505.W53.31, 703010505.W78.1, |
| 703010505.W78.15, 703010505.W100.B4. | | 703010505.W78.15, 703010505.W100.B4. as a nucleic acid e.g. DNA/MVA vector and/or protein |

A skilled artisan can readily determine the number and interval between boosts.

Table 4 shows a non-limiting example of a sequential immunization protocol using a swarm of HIV1 envelopes optionally in certain embodiments designed as trimers.

| Envelope | Prime | Boost(s) | Boost(s) | Boost(s) |
|---|---|---|---|---|
| CH505.M6 CH505.M11 | CH505.M6 CH505.M11 as a nucleic acid e.g. DNA/MVA vector and/or protein | | | |
| CH505w020.14 CH505w030.28 | | CH505w020.14 CH505w030.28 as a nucleic acid e.g. DNA/MVA vector and/or protein | | |
| CH505w078.15 CH505w053.31 CH505w030.21 | | | CH505w078.15 CH505w053.31 CH505w030.21as a nucleic acid e.g. DNA/MVA vector and/or protein | |
| CH505w078.33 CH505w053.16 CH505w100.B6 | | | | CH505w078.33 CH505w053.16 CH505w100.B6 as a nucleic acid e.g. DNA/MVA vector and/or protein |

A skilled artisan can readily determine the number and interval between boosts.

Table 5 shows a non-limiting example of a sequential immunization protocol using a swarm of HIV1 envelopes optionally in certain embodiments designed as trimers.

| Envelope | Prime | Boost(s) | Boost(s) | Boost(s) |
|---|---|---|---|---|
| CH505.T/F CH505.M11 | CH505.T/F CH505.M11 as a nucleic acid e.g. DNA/MVA vector and/or protein | | | |
| CH505w020.14 CH505w030.28 | | CH505w020.14 CH505w030.28 as a nucleic acid e.g. DNA/MVA vector and/or protein | | |
| CH505w078.15 CH505w053.31 CH505w030.21 | | | CH505w078.15 CH505w053.31 CH505w030.21as | |

-continued

| Envelope | Prime | Boost(s) | Boost(s) | Boost(s) |
|---|---|---|---|---|
| | | | a nucleic acid e.g. DNA/MVA vector and/or protein | |
| CH505w078.33 CH505w053.16 CH505w100.B6 | | | | CH505w078.33 CH505w051.36 CH505w100.B6 as a nucleic acid e.g. DNA/MVA vector and/or protein |

A skilled artisan can readily determine the number and interval between boosts.

Example 4: Selection of Ten Early Envelopes

Provided is the approach to selecting a 10-immunogen set from CH505 (See FIG. 24). Here we choose 10 low-diversity variants from the subject early on, rather than down-selecting from a short list of 18, (which you are already making) to represent diversity that appeared through week 160, and includes samples after escape from the mature CH103 mAb.

Without being bound by theory, the hypothesis is that affinity maturation in the presence of antigenic diversity helps select for breadth, allowing it to evolve gradually from a population of Envs selected by clonal autologous neutralization response. But here we would test whether modest variation in the antigen might better stimulate responses that allow the clonal lineage to interact and adapt, while the full range of variation might introduce too much diversity for the developing lineage. For example, a set of Envs with 1 or 2 substitutions in an epitope might reduce affinity, but still allow binding, and the evolving B cell population would be able to adapt. Such variants might allow more "generalists" to evolve. Env variants fully escaped from early lineage clones might be immunologically silent, and less able to draw increased breadth from the B cell clones.

This is essentially like trying a serial version of the swarm vaccine of 100, where we plan on starting with the low-diversity forms, and increase diversity as we vaccinate, but by making these 10 we could try other delivery strategies.

We selected a set of 10 gp120s for use as candidate immunogens. The focus here is on Env diversity at week 30, which coincides with an expansion in heterologous neutralization seen also by antigenic cartography. Unlike the TF and earlier forms, all week 30 sequences contain the V3 glycan shift from 334 to 332.

We identified Env sites to use as criteria for Env selection. The sites were determined by TF loss, neutralization signatures, and contact with the CD4bs and CH103 bnAb (Table 6): (a) At least 80% TF loss through week 160 yielded 36 sites, as described previously. (b) Neutralization signatures for single or PNG sites with q<0.1 for tree-corrected signatures of IC50s below 20 µg/ml, as described previously. (c) The list of contact sites was expanded by one amino acid up- and downstream of each known contact, to include a slightly larger neighborhood of contact sites. These 66 HXB2 sites grew to 71 sites when mapped onto the CH505 Env alignment. When reviewed for polymorphisms, 28 of these sites vary in CH505 over the sampling period.

CTL responses were mapped and found one ELISpot positive peptide on the C-terminus of the V4 loop, sites 409-418, EGSDTITLPC in HXB2 (SEQ ID NO: 89), NSTRTITIHC in CH505 (SEQ ID NO: 90). CTL epitope variants are identified among selected sites in Table 5.

Figure 19:
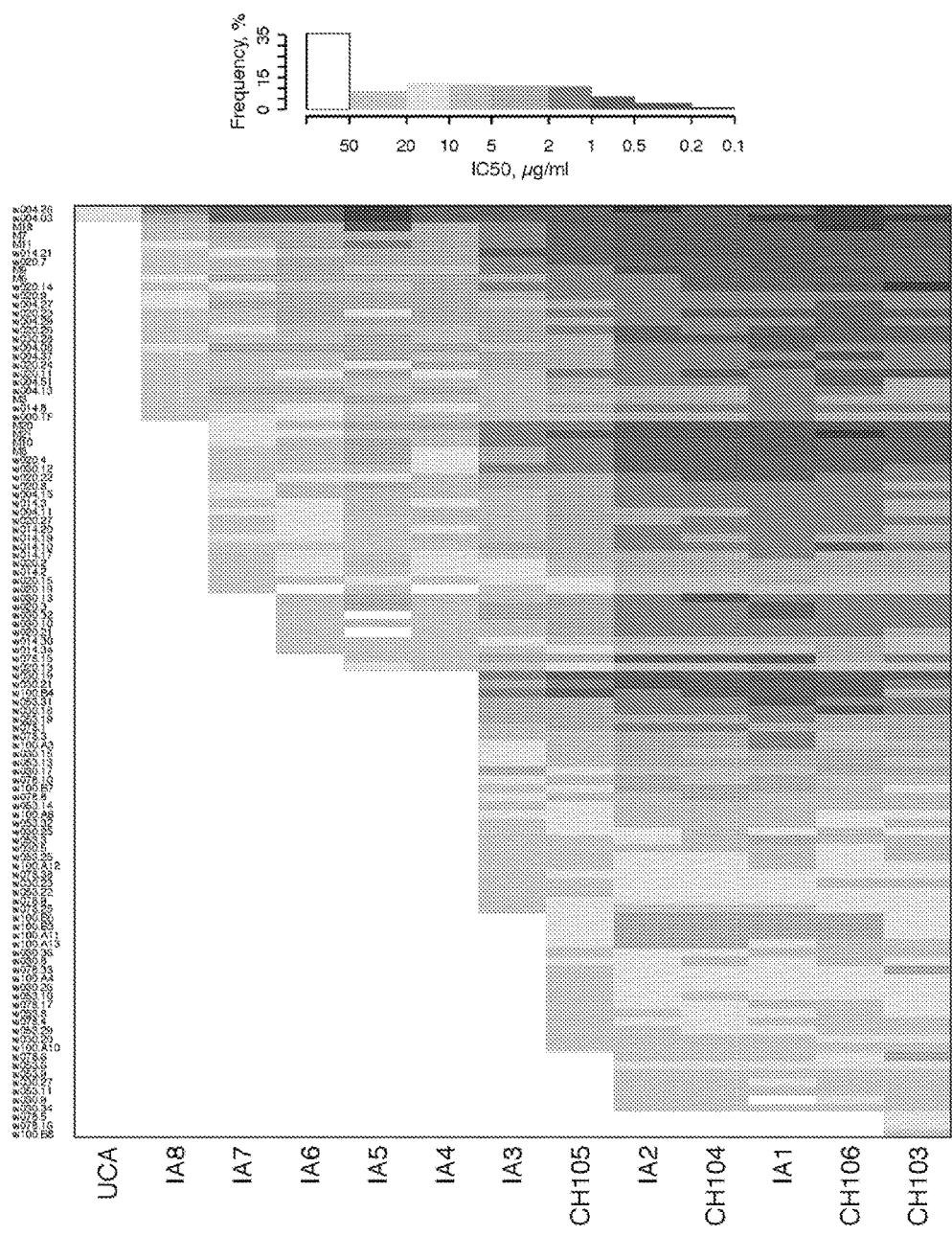
FIG. 19 shows neutralization IC50s of CH103 lineage mAbs against autologous CH505 Envs. Pseudoviruses are sorted by sensitivity to CH103-lineage mAbs, then geometric mean IC50. Here only 108 viruses with distinct gp120s are shown, not the full set of 135 Envs assayed.
Figure 20:
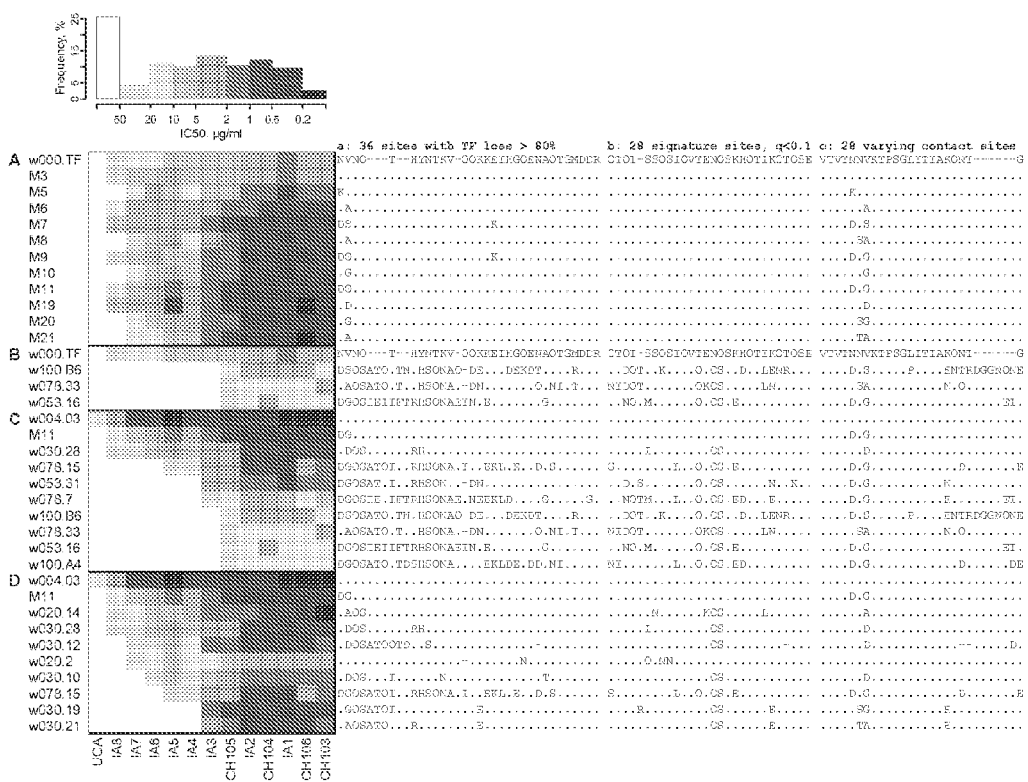
FIG. 20 shows autologous neutralization profiles for (A) mutated TF viruses, (B) 4-Env immunogen set, (C) previously identified 10-Env immunogen set, and (D) currently identified 10-Env immunogen set. Concatenated sites listed in Table 1 are shown for each candidate immunogen FIG. 21 CH505 (A) Env Mutations, (B) CH103 lineage MAb IC50s, and (C) Env phylogeny. Env immunogens proposed in alternative vaccination regimes are shown by colored diamonds. Unlike earlier phylogenies of these Envs, insertions and deletions here are treated as distinct characters, rather than missing data.

Neutralization sensitivity of autologous Envs to mAbs in the CH103 lineage further informs selection of 10 Envs (FIG. 19). Comparing selected Envs with concatenated sites (FIG. 20) allows selection for incremental progression of mAb sensitivities (FIG. 20D). An abrupt transition between neutralization sensitivity to IA7 and IA3 limits available Envs from week 30 (FIG. 19), perhaps because of the mAb discontinuity induced by a shift in light-chain usage from UCA to IA2 light chain associations with IA4 and IA3 heavy chains, respectively (i.e. IA4 mAb is I4 VH and UCA VL; IA3 mAb is VH I3 with VL I2).

Figure 21:
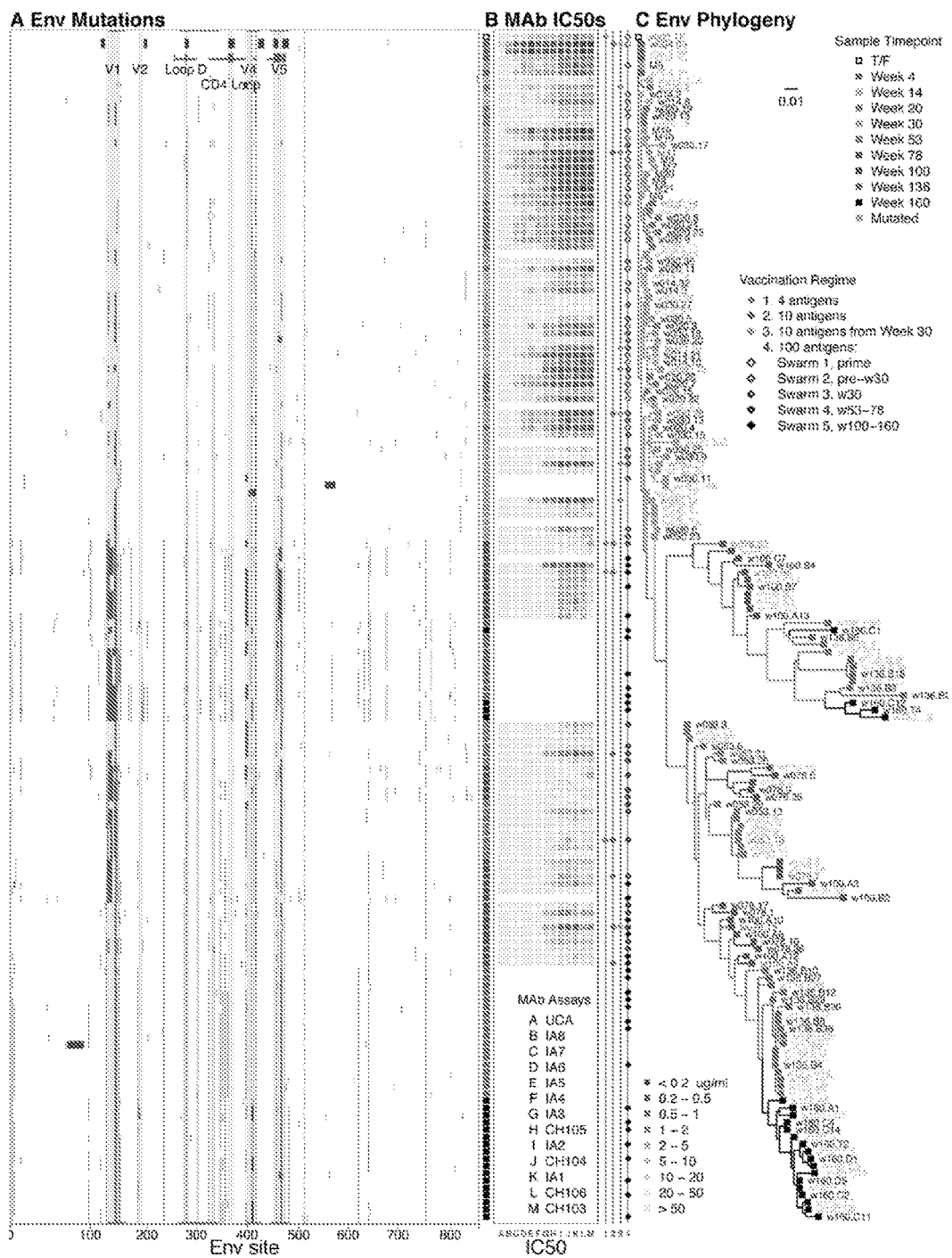

CH505 Env diversity and neutralization to the CH103 lineage mAbs, together with the distributions of proposed sets of 4, 10 (new and in preparation), and 100 antigens are all compared by established methods in FIG. 21.

TABLE 6

Alignment columns in Env "hot-spot" concatamer summaries.

| Col | HXB2 | AA | CH505 | Feature |
|---|---|---|---|---|
| a: 36 sites with TF loss >80% | | | | |
| 1 | 279 | D | N | Loop D |
| 2 | 281 | A | V | Loop D |
| 3 | 332 | O | N | PGT121 |
| 4 | 334 | S | O | 2G12 |
| 5 | 144+ | — | — | V1 |
| 6 | 144+ | — | — | V1 |
| 7 | 144+ | — | — | V1 |
| 8 | 413 | T | T | V4/CTL |
| 9 | 465 | S | — | V5 |
| 10 | 464 | E | — | V5 |
| 11 | 417 | P | H | V4/CTL |
| 12 | 330 | H | Y | V3 |
| 13 | 300 | N | N | V3 |
| 14 | 234 | O | T | 8ANC195 |
| 15 | 302 | N | K | V3 |
| 16 | 756 | I | V | gp41 |
| 17 | 463+ | — | — | V5 |
| 18 | 398 | S | O | V4 |
| 19 | 133 | D | O | V1 |
| 20 | 460 | N | K | V5 |
| 21 | 347 | S | K | |
| 22 | 275 | V | E | Loop D |
| 23 | 151 | K | I | V1 |
| 24 | 356 | O | H | |
| 25 | 471 | G | G | beta24 |
| 26 | 147 | M | O | V1 |
| 27 | 640 | S | E | gp41 |

TABLE 6-continued

Alignment columns in Env "hot-spot" concatamer summaries.

| Col | HXB2 | AA | CH505 | Feature |
|---|---|---|---|---|
| 28 | 462 | N | N | V5 |
| 29 | 145 | G | A | V1 |
| 30 | 130 | K | O | |
| 31 | 132 | T | T | V1 |
| 32 | 620 | E | G | gp41 |
| 33 | 4 | K | M | SignalPep |
| 34 | 325 | N | D | V3 |
| 35 | 185 | D | D | V2 |
| 36 | 412 | D | R | V4/CTL |
| b: 28 signature sites, q < 0.1 | | | | |
| 1 | 130 | K | O | |
| 2 | 132 | T | T | V1 |
| 3 | 133 | D | O | V1 |
| 4 | 135 | K | T | V1 |
| 5 | 137 | D | — | V1 |
| 6 | 146 | R | S | V1 |
| 7 | 148 | I | S | V1 |
| 8 | 147 | M | O | V1 |
| 9 | 149 | M | S | V1 |
| 10 | 151 | K | I | V1 |
| 11 | 160 | O | O | PG9 |
| 12 | 200 | V | V | |
| 13 | 234 | O | T | 8ANC195 |
| 14 | 328 | Q | E | V3 |
| 15 | 332 | O | N | PGT121 |
| 16 | 334 | S | O | 2G12 |
| 17 | 336 | A | S | |
| 18 | 347 | S | K | |
| 19 | 356 | O | H | |
| 20 | 358 | T | O | |
| 21 | 360 | I | T | |
| 22 | 416 | L | I | V4/CTL |
| 23 | 460 | N | K | V5 |
| 24 | 461 | S | O | V5 |
| 25 | 463 | O | T | V5 |
| 26 | 743 | D | O | Kennedy |
| 27 | 745 | S | S | Epitope |
| 28 | 831 | E | E | LLP-1 |
| c: 28 varying contacts | | | | |
| 1 | 127 | V | V | CD4 |
| 2 | 128 | S | T | CD4 |
| 3 | 255 | V | V | |
| 4 | 278 | T | T | |
| 5 | 279 | D | N | Loop D |
| 6 | 280 | N | N | Loop D |
| 7 | 281 | A | V | Loop D |
| 8 | 282 | K | K | Loop D |
| 9 | 283 | T | T | Loop D |
| 10 | 363 | Q | P | |
| 11 | 365 | S | S | |
| 12 | 367 | G | G | |
| 13 | 369 | P | L | CD4 |
| 14 | 371 | I | I | CD4 |
| 15 | 372 | V | T | |
| 16 | 424 | I | I | |
| 17 | 433 | A | A | |
| 18 | 460 | N | K | V5 |
| 19 | 461 | S | O | V5 |
| 20 | 462 | N | N | V5 |
| 21 | 463 | N | T | V5 |
| 22 | 463+ | — | — | V5 |
| 23 | 463+ | — | — | V5 |
| 24 | 463+ | — | — | V5 |
| 25 | 463+ | — | — | V5 |
| 26 | 463+ | — | — | V5 |
| 27 | 464+ | E | — | V5 |
| 28 | 471 | G | G | Beta24 |

Example 5: Non-Human Primate Studies

NHP 79: CH505T/F gp120 envelope in GLA/SE. NHP 85: CH505T/F gp140 envelope in GLA/SE. This compares gp140 with gp120 induced antibodies.

NHP study of CH505T/F gp120 with GCN4 CH505 T/F in GLA/SE.

NHP study of CH505T/F gp120 with GCN4 CD40L CH505 T/F in GLA/SE.

NHP study of CH505T/F gp120 with GCN4 CD40L CH505 T/F in ALUM.

NHP study of CH505 T/F gp120 with GCN4 CD40L CH505 T/F=-HIS tag with liposomes in ALUM.

NHP study of M6 then rest of production 10 (Table 4) gp120 in sequence gp120 GNC4 CD40L CH505 trimers with ALUM or GLA/SE (depends on antigenicity).

NHP study of M6 then rest of production 10 (Table 4) gp120 in sequence gp120 GNC4 CD40L CH505 trimers in ALUM or GLA/SE (depends on antigenicity), with a dose of chloloquine orally each day 10 days before each immunization and then a dose of CD25 Ab 5 days after each immunization. See U.S. Application Ser. No. 62/056,583 ("Tolerance" filed concurrently), which contents is herein incorporated by reference in its entirety.

The contents of all documents and other information sources cited herein are herein incorporated by reference in their entirety.

Provided below are examples of sequences and HIV-1 envelopes disclosed in this application.

HIV-1 Envelope Selection D: Ten Production Envelopes

TABLE 4

FIG. 17

| | |
|---|---|
| CH505.M6 | CH505.M6D8gp120 (aa SEQ ID NO 9; nt SEQ ID NO: 10), CH505.M6gp145 (nt SEQ ID NO 11), CH505.M6 gp160 (aa SEQ ID NO: 12; nt SEQ ID NO 13) |
| CH505.M11 | CH505.M11D8gp120 (aa SEQ ID NO 14; nt SEQ ID NO 15), CH505.M11gp145 (nt SEQ ID NO 16), CH505.M11 gp160 (aa SEQ ID NO 17; nt SEQ ID NO 18) |
| CH505w020.14 | CH505w020.14D8gp120 (aa SEQ ID NO 19; nt SEQ ID NO: 20), CH505w020.14gp145 (nt SEQ ID NO 21), CH505w020.14 gp160 (aa SEQ ID NO 22; nt SEQ ID NO 23) |
| CH505w030.28 | CH505w030.28D8gp120 (aa SEQ ID NO 24; nt SEQ ID NO 25), CH505w030.28gp145(nt SEQ ID NO 26),, CH505w030.28 gp160 (aa SEQ ID NO 27; nt SEQ ID NO 28) |
| CH505w078.15 | CH505w078.15D8gp120 (aa SEQ ID NO 29; nt SEQ ID NO 30), CH505w078.15gp145 (nt SEQ ID NO 40), CH505w078.15 gp160 (aa SEQ ID NO 41; nt SEQ ID NO 42) |
| CH505w053.31 | CH505w053.31D8gp120 (aa SEQ ID NO 43; nt SEQ ID NO 44), CH505w053.31gp145 (nt SEQ ID NO 45), CH505w053.31 gp160 (aa SEQ ID NO 46; nt SEQ ID NO 47) |
| CH505w030.21 | CH505w030.21D8gp120 (aa SEQ ID NO 48; nt SEQ ID NO 49), CH505w30.21gp145 (nt SEQ ID NO 50), CH505w030.21 gp160 (aa SEQ ID NO 51 nt SEQ ID NO 52) |
| CH505w078.33 | CH505w78.33gp120 (aa SEQ ID NO 54; nt SEQ ID NO 55), CH505w78.33gp145 (nt SEQ ID NO 56), CH505w078.33 gp160 (aa SEQ ID NO 57; nt SEQ ID NO 58) |
| CH505w053.16 | CH505w053.16D8gp120 (aa SEQ ID NO 59; nt SEQ ID NO 60), CH505w53.16gp145 (nt SEQ ID NO 61), CH505w053.16 gp160 (aa SEQ ID NO 62; nt SEQ ID NO 63) |
| CH505w100.B6 | CH505w100.B6D8gp120 (aa SEQ ID NO 64; nt SEQ ID NO 65), CH505w100.B6gp145 (nt SEQ ID NO 66), CH505w100.B6 gp160 (aa SEQ ID NO 67; nt SEQ ID NO 68) |

HIV-1 Envelopes Selection E: Ten Early Envelopes (FIG. 24)

| FIG. 24 | HIV-1 Envelopes Selection E |
|---|---|
| CH505M11gp160 (aa SEQ ID NO 69) | CH505.M11 |
| CH505w004.03gp160 (aa SEQ ID NO 70) | CH505.w004.03 |
| CH505w020.14gp160 (aa SEQ ID NO 71) | CH505.w020.14 |
| CH505w030.28gp160 (aa SEQ ID NO 72) | CH505.w030.28 |
| CH505w30.12gp160 (aa SEQ ID NO 73) | CH505.w030.12 |
| CH505w020.2gp160 (aa SEQ ID NO 74) | CH505.w020.2 |
| CH505w030.10gp160 (aa SEQ ID NO 75) | CH505.w030.10 |
| CH505w078.15gp160 (aa SEQ ID NO 76) | CH505.w078.15 |
| CH505w030.19gp160 (aa SEQ ID NO 77) | CH505.w030.19 |
| CH505w030.21gp160 (aa SEQ ID NO 78) | CH505.w030.21 |

HIV-1 Envelopes Selection C: Four Envelopes (FIG. 22)

| FIG. 22 | HIV-1 Envelopes Selection C |
|---|---|
| CH505w000.TFgp160 (aa SEQ ID NO 79) | 703010505.TF, |
| CH505w053.16gp160 (aa SEQ ID NO 80) | 703010505.W53.16 |
| CH505w078.33gp160 (aa SEQ ID NO 81) | 703010505.W78.33 |
| CH505w100.B6gp160 (aa SEQ ID NO 82) | 703010505.W100.B6 |

HIV-1 Envelopes Selection F: Ten Production Envelopes (10PR)

TABLE 5

Figure 17:
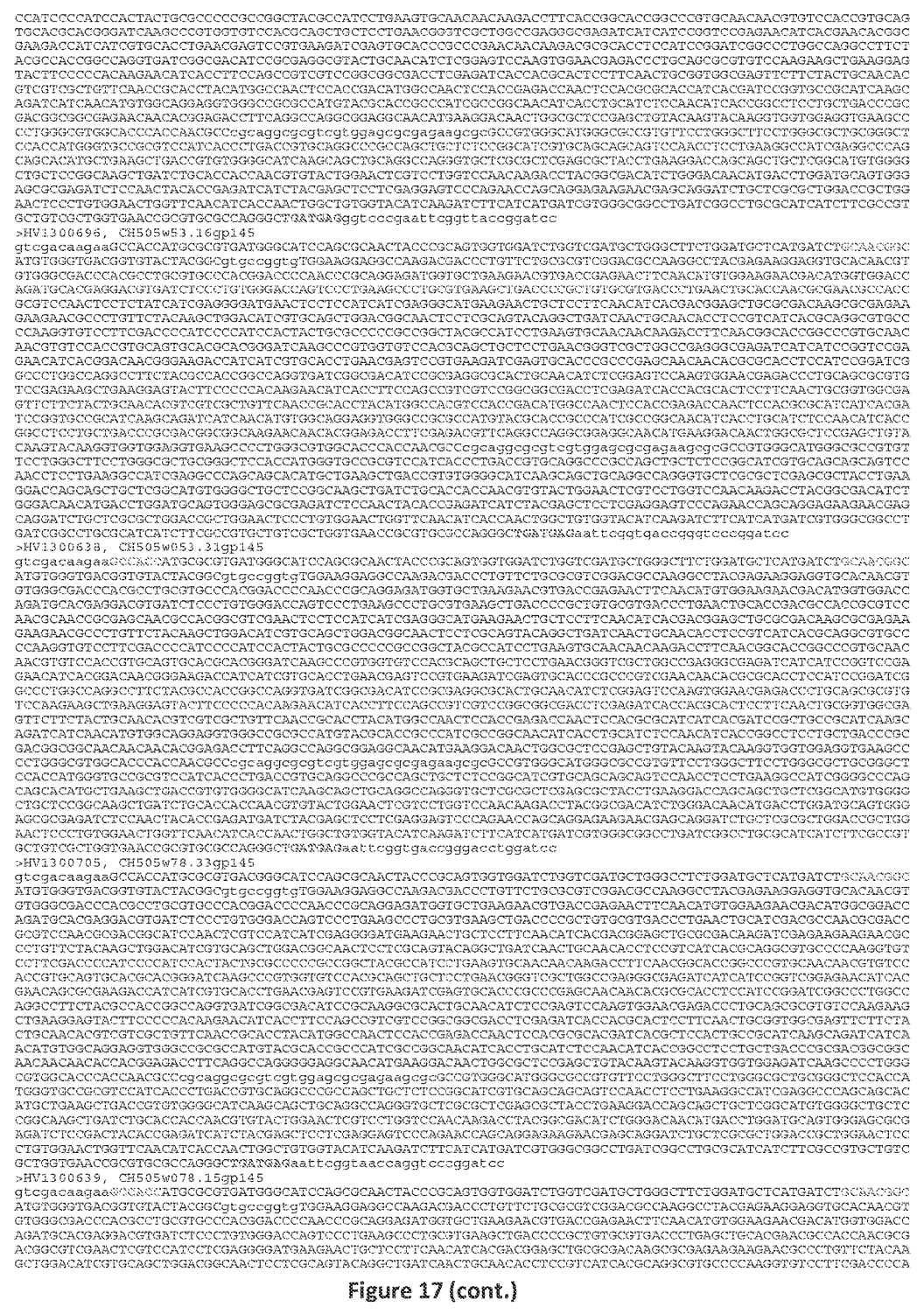
Figure 17:
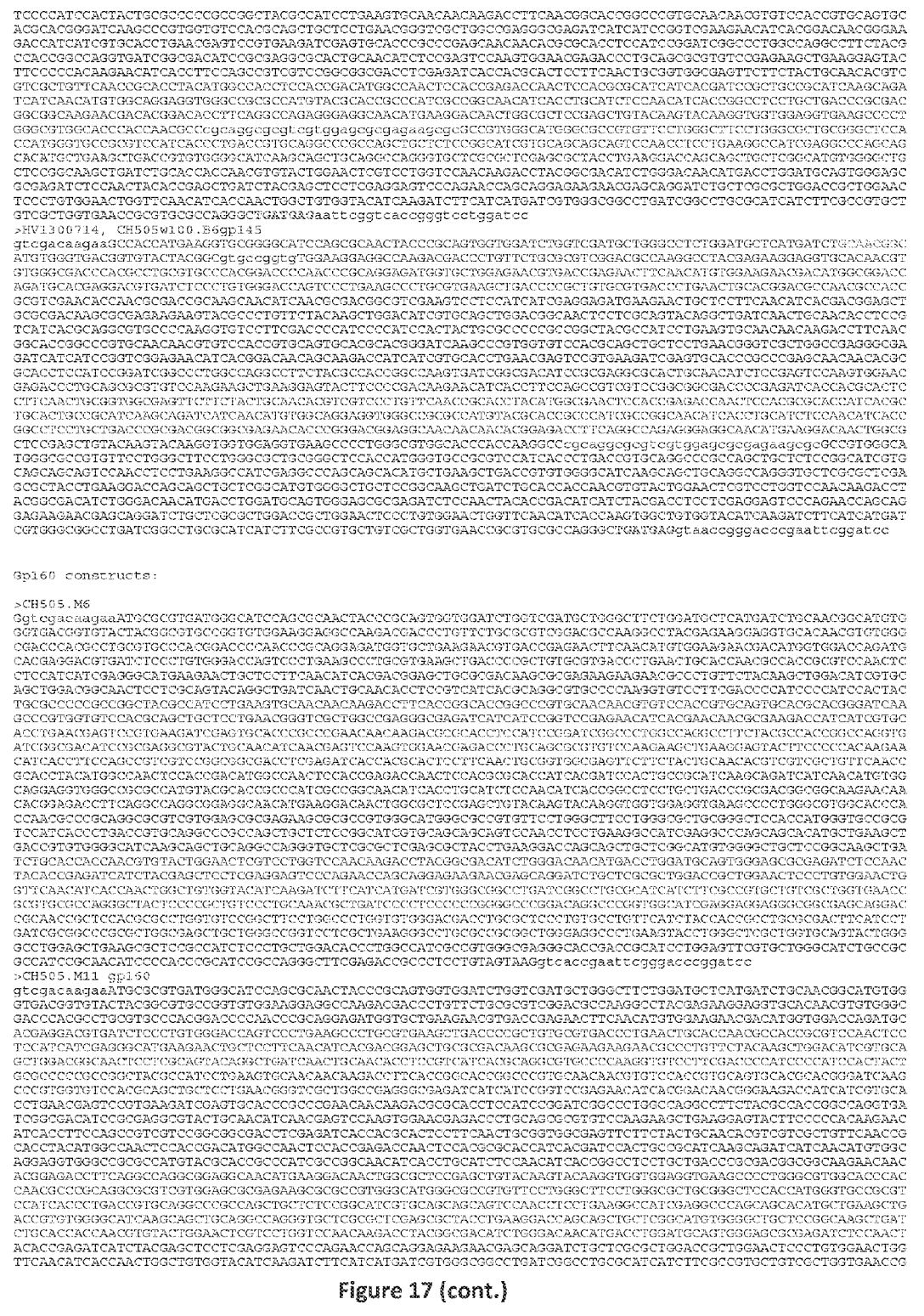
Figure 17:
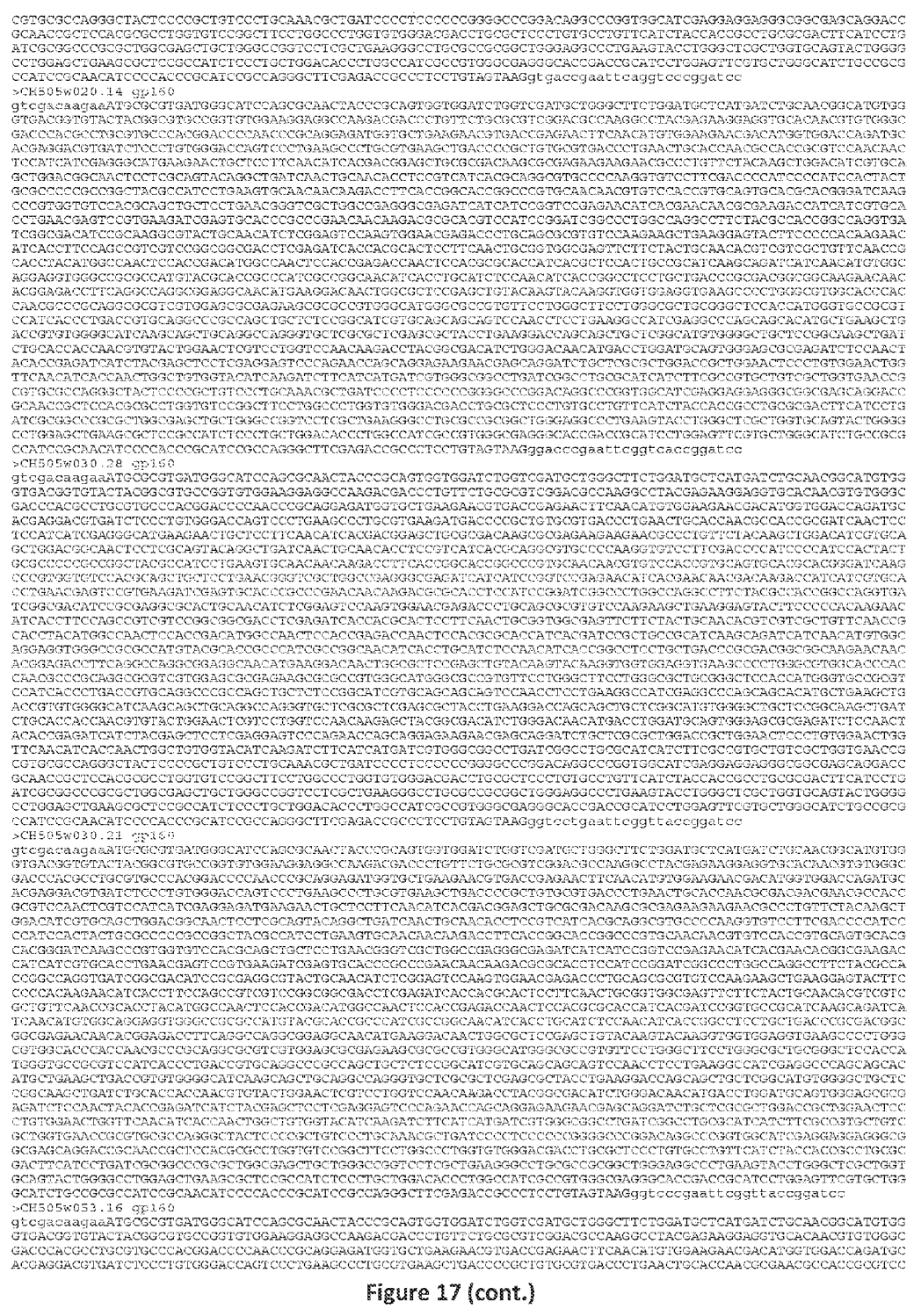
Figure 17:
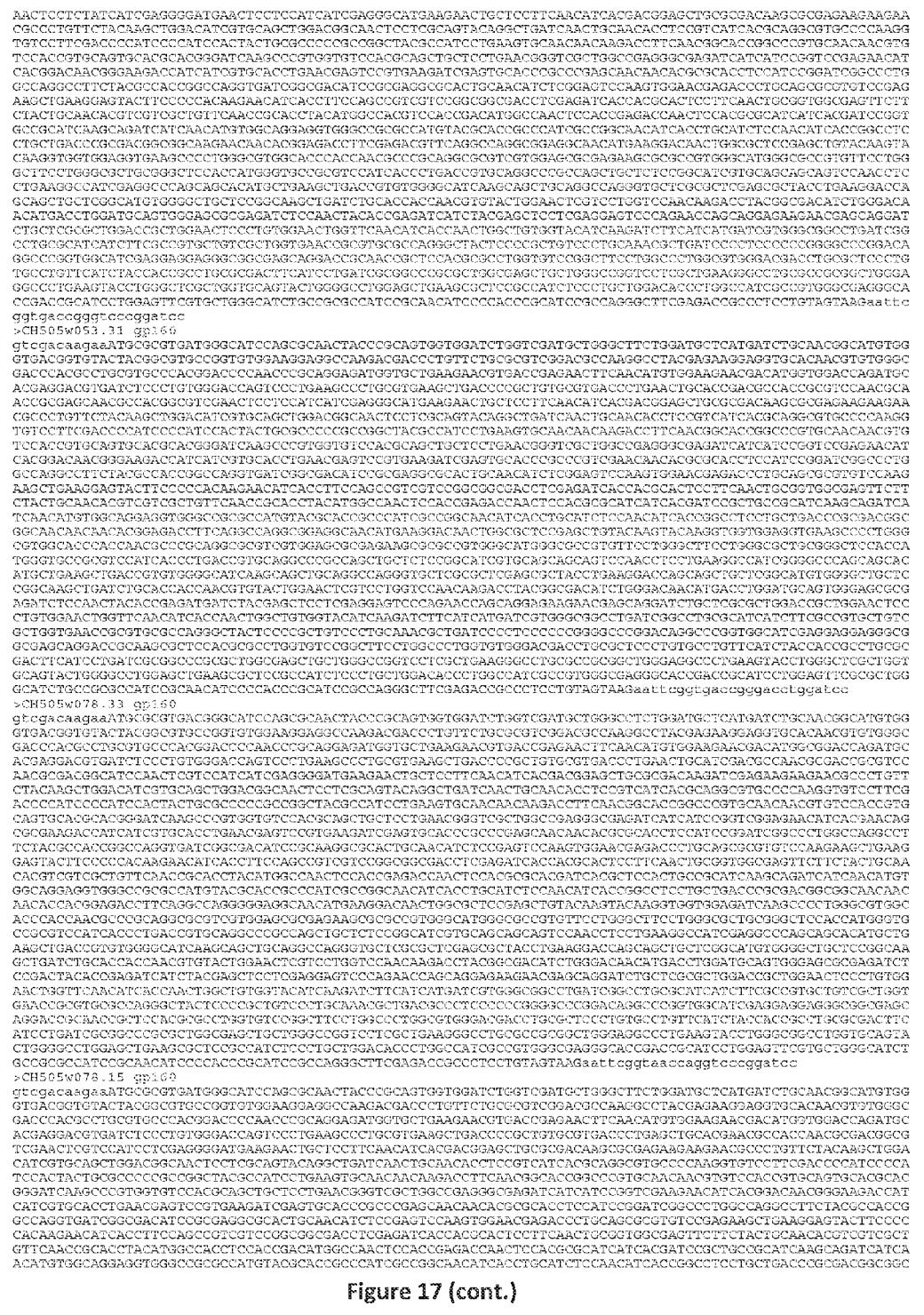
Figure 17:
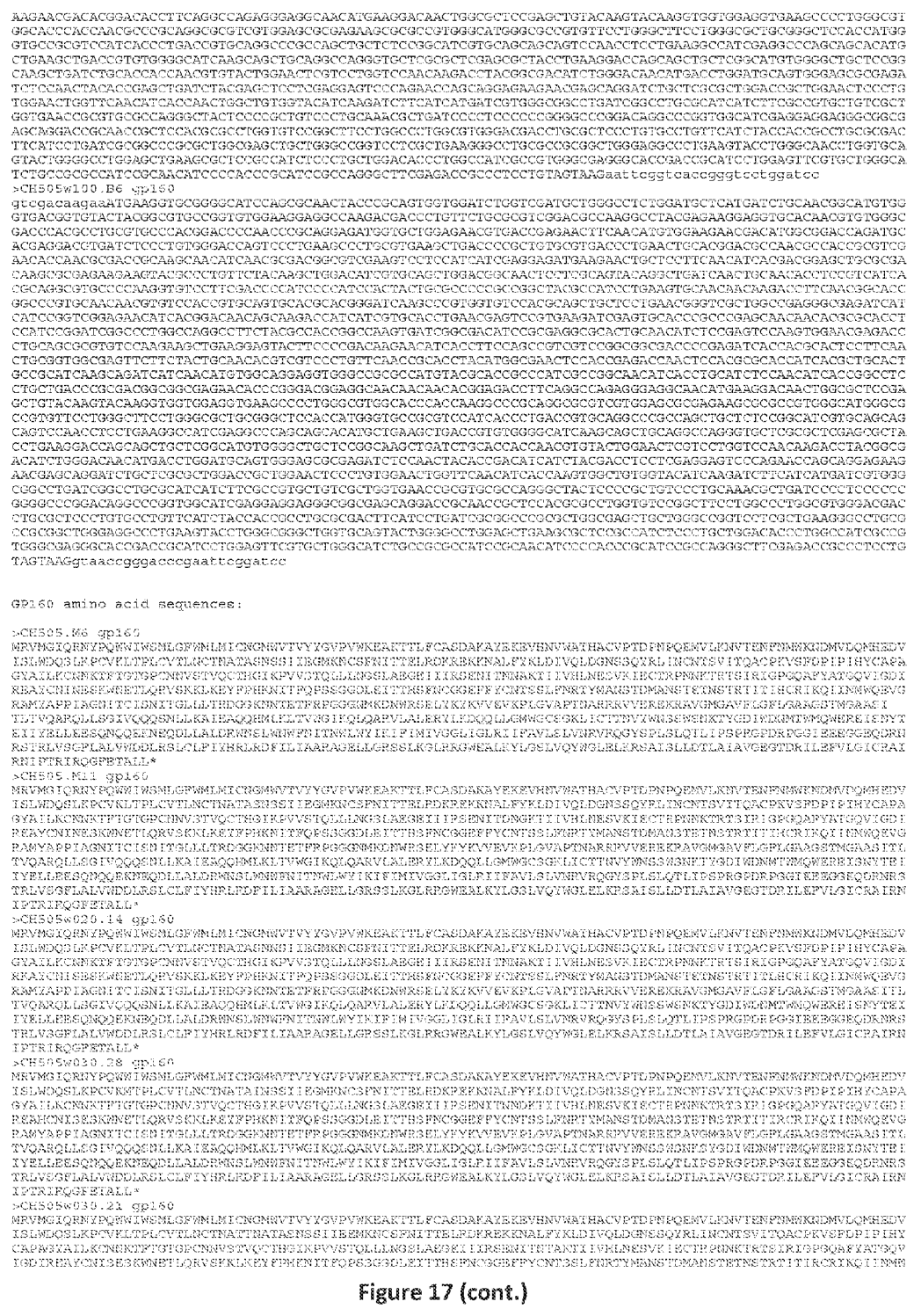

| FIG. 17 | |
|---|---|
| CH505.T/F | CH505w000.TFgp160 (aa SEQ ID NO 79) from FIG. 22 |
| CH505.M11 | CH505.M11D8gp120 (aa SEQ ID NO 14; nt SEQ ID NO 15), CH505.M11gp145 (nt SEQ ID NO 16), CH505.M11 gp160 (aa SEQ ID NO 17; nt SEQ ID NO 18) |
| CH505w020.14 | CH505w020.14D8gp120 (aa SEQ ID NO 19; nt SEQ ID NO: 20), CH505w020.14gp145 (nt SEQ ID NO 21), CH505w020.14 gp160 (aa SEQ ID NO 22; nt SEQ ID NO 23) |
| CH505w030.28 | CH505w030.28D8gp120 (aa SEQ ID NO 24; nt SEQ ID NO 25), CH505w030.28gp145(nt SEQ ID NO 26),, CH505w030.28 gp160 (aa SEQ ID NO 27; nt SEQ ID NO 28) |
| CH505w078.15 | CH505w078.15D8gp120 (aa SEQ ID NO 29; nt SEQ ID NO 30), CH505w078.15gp145 (nt SEQ ID NO 40), CH505w078.15 gp160 (aa SEQ ID NO 41; nt SEQ ID NO 42) |
| CH505w053.31 | CH505w053.31D8gp120 (aa SEQ ID NO 43; nt SEQ ID NO 44), CH505w053.31gp145 (nt SEQ ID NO 45), CH505w053.31 gp160 (aa SEQ ID NO 46; nt SEQ ID NO 47) |
| CH505w030.21 | CH505w030.21D8gp120 (aa SEQ ID NO 48; nt SEQ ID NO 49), CH505w30.21gp145 (nt SEQ ID NO 50), CH505w030.21 gp160 (aa SEQ ID NO 51; nt SEQ ID NO 52) |
| CH505w078.33 | CH505w78.33gp120 (aa SEQ ID NO 54; nt SEQ ID NO 55), CH505w78.33gp145 (nt SEQ ID NO 56), CH505w078.33 gp160 (aa SEQ ID NO 57; nt SEQ ID NO 58) |
| CH505w053.16 | CH505w053.16D8gp120 (aa SEQ ID NO 59; nt SEQ ID NO 60), CH505w53.16gp145 (nt SEQ ID NO 61), CH505w053.16 gp160 (aa SEQ ID NO 62; nt SEQ ID NO 63) |
| CH505w100.B6 | CH505w100.B6D8gp120 (aa SEQ ID NO 64; nt SEQ ID NO 65), CH505w100.B6gp145 (nt SEQ ID NO 66), CH505w100.B6 gp160 (aa SEQ ID NO 67; nt SEQ ID NO 68) |

What is claimed is:

1. A composition comprising polynucleotides encoding HIV-1 envelope polypeptides CH505.M6 and CH505.M11, wherein CH505.M6 is a gp120d8 CH505.M6 envelope comprising SEQ ID NO:9, a gp145 CH505.M6 envelope derived from SEQ ID NO:12, a gp150 CH505.M6 envelope derived from SEQ ID NO:12, or a gp160 CH505.M6 envelope comprising SEQ ID NO:12, and wherein CH505.M11 is a gp120d8 CH505.M11 envelope comprising SEQ ID NO:14, a gp145 CH505.M11 envelope derived from SEQ ID NO:17, a gp150 CH505.M11 envelope derived from SEQ ID NO:17, or a gp160 CH505.M11 envelope comprising SEQ ID NO:17.

2. The composition of claim 1 further comprising polynucleotides encoding HIV-1 envelope polypeptides CH505w020.14 and CH505w030.28, wherein CH505w020.14 is a gp120d8 CH505w020.14 envelope comprising SEQ ID NO:19, a gp145 CH505w020.14 envelope derived from SEQ ID NO:22, a gp150 CH505w020.14 envelope derived from SEQ ID NO:22, or a gp160 CH505w020.14 envelope comprising SEQ ID NO:22, and wherein CH505w030.28 is a gp120d8 CH505w030.28 envelope comprising SEQ ID NO:24, a gp145 CH505w030.28 envelope derived from SEQ ID NO:27, a gp150 CH505w030.28 envelope derived from SEQ ID NO:27, or a gp160 CH505w030.28 envelope comprising SEQ ID NO:27.

3. The composition of claim 2 further comprising polynucleotides encoding HIV-1 envelope polypeptides CH505.w078.15, CH505w053.31, and CH505.w030.21, wherein CH505.w078.15 is a gp120d8 CH505.w078.15 envelope comprising SEQ ID NO:29, a gp145 CH505.w078.15 envelope derived from SEQ ID NO:41, a gp150 CH505.w078.15 envelope derived from SEQ ID NO:41, or a gp160 CH505.w078.15 envelope comprising SEQ ID NO:41, and wherein CH505w053.31 is a gp120d8 CH505w053.31 envelope comprising SEQ ID NO:43, a gp145 CH505w053.31 envelope derived from SEQ ID NO:46, a gp150 CH505w053.31 envelope derived from SEQ ID NO:46, or a gp160 CH505w053.31 envelope comprising SEQ ID NO:46, and wherein CH505.w030.21 is a gp120d8 CH505.w030.21 envelope comprising SEQ ID NO:48, a gp145 CH505.w030.21 envelope derived from SEQ ID NO:51, a gp150 CH505.w030.21 envelope derived from SEQ ID NO:51, or a gp160 CH505.w030.21 envelope comprising SEQ ID NO:51.

4. The composition of claim 1, wherein each polynucleotide further comprises polynucleotides corresponding to a trimerization domain selected from a group consisting of GCN4 (SEQ ID NO: 3) and CD40L (amino acids 21 to 169 of SEQ ID NO:8).

5. The composition of claim 1 further comprising an adjuvant.

6. A method of inducing an immune response in a subject comprising administering the composition of claim 5 in an amount sufficient to induce an immune response.

7. The method of claim 6, further comprising administering chloloquine before each immunization.

8. The method of claim 6, further comprising administering anti-CD25 antibody before each immunization.

9. The method of claim 6, further comprising administering anti-CD25 antibody after each immunization.

10. The method of claim 6, wherein the method further comprises administering a composition comprising a protein corresponding to a polynucleotide in the composition.

11. The method of claim 10, wherein the polynucleotide encoding the envelope is operably linked to a promoter inserted in an expression vector.

12. The method of claim 10, wherein the protein is recombinant.

13. The method of claim 10, wherein the composition is administered as a prime, a boost, or both.

14. The method of claim 13, wherein the prime comprises polynucleotides encoding HIV-1 envelope polypeptides CH505.M6 and CH505.M11.

15. The composition of claim 3 further comprising polynucleotides encoding HIV-1 envelope polypeptides CH505w030.21, CH505w078.33, CH505w053.16, and CH505w100.B6, wherein CH505.w030.21 is a gp120d8 CH505.w030.21 envelope comprising SEQ ID NO:48, a gp145 CH505.w030.21 envelope derived from SEQ ID NO:51, a gp150 CH505.w030.21 envelope derived from SEQ ID NO:51, or a gp160 CH505.w030.21 envelope comprising SEQ ID NO:51, wherein CH505w078.33 is a gp120d8 CH505w078.33 envelope comprising SEQ ID NO:54, a gp145 CH505w078.33 envelope derived from SEQ ID NO:57, a gp150 CH505w078.33 envelope derived from SEQ ID NO:57, or a gp160 CH505w078.33 envelope comprising SEQ ID NO:57, and wherein CH505w053.16 is a gp120d8 CH505w053.16 envelope comprising SEQ ID NO:59, a gp145 CH505w053.16 envelope derived from SEQ ID NO:62, a gp150 CH505w053.16 envelope derived from SEQ ID NO:62, or a gp160 CH505w053.16 envelope comprising SEQ ID NO:62, and wherein CH505w100.B6 is a gp120d8 CH505w100.B6 envelope comprising SEQ ID NO:64, a gp145 CH505w100.B6 envelope derived from SEQ ID NO:67, a gp150 CH505w100.B6 envelope derived from SEQ ID NO:67, or a gp160 CH505w100.B6 envelope comprising SEQ ID NO:67.

16. The composition of claim 2, wherein each polynucleotide further comprises polynucleotides corresponding to a trimerization domain selected from a group consisting of GCN4 (SEQ ID NO:3) and CD40L (amino acids 21 to 169 of SEQ ID NO:8).

17. The composition of claim 3, wherein each polynucleotide further comprises polynucleotides corresponding to a trimerization domain selected from a group consisting of GCN4 (SEQ ID NO:3) and CD40L (amino acids 21 to 169 of SEQ ID NO:8).

18. The composition of claim 15, wherein each polynucleotide further comprises polynucleotides corresponding to a trimerization domain selected from a group consisting of GCN4 (SEQ ID NO:3) and CD40L (amino acids 21 to 169 of SEQ ID NO:8).

19. The composition of claim 2, further comprising an adjuvant.

20. The composition of claim 3, further comprising an adjuvant.

21. The composition of claim 15, further comprising an adjuvant.

22. The compositions of claim 1, wherein the polynucleotide encoding the envelope is operably linked to a promoter inserted in an expression vector.

23. The compositions of claim 2, wherein the polynucleotide encoding the envelope is operably linked to a promoter inserted in an expression vector.

24. The compositions of claim 3, wherein the polynucleotide encoding the envelope is operably linked to a promoter inserted in an expression vector.

25. The compositions of claim 15, wherein the polynucleotide encoding the envelope is operably linked to a promoter inserted in an expression vector.

* * * * *

UNITED STATES PATENT AND TRADEMARK OFFICE
CERTIFICATE OF CORRECTION

PATENT NO. : 10,232,034 B2
APPLICATION NO. : 15/513539
DATED : March 19, 2019
INVENTOR(S) : Haynes et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Seventeenth Day of March, 2020

Andrei Iancu
*Director of the United States Patent and Trademark Office*

```
SEQUENCE LISTING

<160> NUMBER OF SEQ ID NOS: 110

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Thr Arg Pro Asn Asn Asn Thr Arg Lys Ser Ile Arg Ile Gly Pro Gly
1               5                   10                  15

Gln Thr Phe Tyr Ala Thr Gly Asp Ile Ile Gly Asn Ile Arg Gln Ala
            20                  25                  30

His

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ser Gly Ser Gly Ser
1               5

<210> SEQ ID NO 3
```

```
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Arg Met Lys Gln Ile Glu Asp Lys Ile Glu Glu Ile Leu Ser Lys Ile
 1               5                  10                  15

Tyr His Ile Glu Asn Glu Ile Ala Arg Ile Lys Lys Leu Ile Gly Glu
            20                  25                  30

Arg

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Met Lys Gln Ile Glu Asp Lys Ile Glu Glu Ile Leu Ser Lys Ile
 1               5                  10                  15

Tyr His Ile Glu Asn Glu Ile Ala Arg Ile Lys Lys Leu Ile Gly Glu
            20                  25                  30

Arg

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Ser Gly Gly Ser Gly Gly Ser Gly Gly
 1               5                  10

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Met Lys Gln Ile Glu Asp Lys Ile Glu Glu Ile Leu Ser Lys Ile
 1               5                  10                  15

Tyr His Ile Glu Asn Glu Ile Ala Arg Ile Lys Lys Leu Ile Gly Glu
            20                  25                  30

Arg

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

```
Gly Gly Ser Gly Gly Ser Gly Gly Ser Gly Gly
1               5                   10
```

<210> SEQ ID NO 8
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Gly Ser Ser His His His His His Ser Gly Leu Val Pro
1               5                   10                  15

Arg Gly Ser His Met Gln Lys Gly Asp Gln Asn Pro Gln Ile Ala Ala
                20                  25                  30

His Val Ile Ser Glu Ala Ser Ser Lys Thr Thr Ser Val Leu Gln Trp
            35                  40                  45

Ala Glu Lys Gly Tyr Tyr Thr Met Ser Asn Asn Leu Val Thr Leu Glu
        50                  55                  60

Asn Gly Lys Gln Leu Thr Val Lys Arg Gln Gly Leu Tyr Tyr Ile Tyr
65                  70                  75                  80

Ala Gln Val Thr Phe Cys Ser Asn Arg Glu Ala Ser Ser Gln Ala Pro
                85                  90                  95

Phe Ile Ala Ser Leu Cys Leu Lys Ser Pro Gly Arg Phe Glu Arg Ile
            100                 105                 110

Leu Leu Arg Ala Ala Asn Thr His Ser Ser Ala Lys Pro Cys Gly Gln
        115                 120                 125

Gln Ser Ile His Leu Gly Gly Val Phe Glu Leu Gln Pro Gly Ala Ser
    130                 135                 140

Val Phe Val Asn Val Thr Asp Pro Ser Gln Val Ser His Gly Thr Gly
145                 150                 155                 160

Phe Thr Ser Phe Gly Leu Leu Lys Leu
                165
```

<210> SEQ ID NO 9
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
                20                  25                  30

Trp Lys Glu Ala Lys Thr Thr Leu Phe Cys Ala Ser Asp Ala Lys Ala
            35                  40                  45

Tyr Glu Lys Glu Val His Asn Val Trp Ala Thr His Ala Cys Val Pro
        50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110
```

```
Leu Cys Val Thr Leu Asn Cys Thr Asn Ala Thr Ala Ser Asn Ser Ser
            115                 120                 125

Ile Ile Glu Gly Met Lys Asn Cys Ser Phe Asn Ile Thr Thr Glu Leu
130                 135                 140

Arg Asp Lys Arg Glu Lys Lys Asn Ala Leu Phe Tyr Lys Leu Asp Ile
145                 150                 155                 160

Val Gln Leu Asp Gly Asn Ser Ser Gln Tyr Arg Leu Ile Asn Cys Asn
                165                 170                 175

Thr Ser Val Ile Thr Gln Ala Cys Pro Lys Val Ser Phe Asp Pro Ile
            180                 185                 190

Pro Ile His Tyr Cys Ala Pro Ala Gly Tyr Ala Ile Leu Lys Cys Asn
            195                 200                 205

Asn Lys Thr Phe Thr Gly Thr Gly Pro Cys Asn Asn Val Ser Thr Val
        210                 215                 220

Gln Cys Thr His Gly Ile Lys Pro Val Val Ser Thr Gln Leu Leu Leu
225                 230                 235                 240

Asn Gly Ser Leu Ala Glu Gly Glu Ile Ile Arg Ser Glu Asn Ile
                245                 250                 255

Thr Asn Asn Ala Lys Thr Ile Ile Val His Leu Asn Glu Ser Val Lys
        260                 265                 270

Ile Glu Cys Thr Arg Pro Asn Asn Lys Thr Arg Thr Ser Ile Arg Ile
            275                 280                 285

Gly Pro Gly Gln Ala Phe Tyr Ala Thr Gly Gln Val Ile Gly Asp Ile
        290                 295                 300

Arg Glu Ala Tyr Cys Asn Ile Asn Glu Ser Lys Trp Asn Glu Thr Leu
305                 310                 315                 320

Gln Arg Val Ser Lys Lys Leu Lys Glu Tyr Phe Pro His Lys Asn Ile
                325                 330                 335

Thr Phe Gln Pro Ser Ser Gly Gly Asp Leu Glu Ile Thr Thr His Ser
            340                 345                 350

Phe Asn Cys Gly Gly Glu Phe Phe Tyr Cys Asn Thr Ser Ser Leu Phe
        355                 360                 365

Asn Arg Thr Tyr Met Ala Asn Ser Thr Asp Met Ala Asn Ser Thr Glu
        370                 375                 380

Thr Asn Ser Thr Arg Thr Ile Thr Ile His Cys Arg Ile Lys Gln Ile
385                 390                 395                 400

Ile Asn Met Trp Gln Glu Val Gly Arg Ala Met Tyr Ala Pro Pro Ile
                405                 410                 415

Ala Gly Asn Ile Thr Cys Ile Ser Asn Ile Thr Gly Leu Leu Leu Thr
            420                 425                 430

Arg Asp Gly Gly Lys Asn Asn Thr Glu Thr Phe Arg Pro Gly Gly Gly
        435                 440                 445

Asn Met Lys Asp Asn Trp Arg Ser Glu Leu Tyr Lys Tyr Lys Val Val
450                 455                 460

Glu Val Lys Pro Leu Gly Val Ala Pro Thr Asn Ala Arg Glu Arg Val
465                 470                 475                 480

Val Glu Arg Glu Lys Glu
                485

<210> SEQ ID NO 10
<211> LENGTH: 1507
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 10

| | | |
|---|---|---|
| gtcgacaaga agccaccatg cgcgtgatgg gcatccagcg caactacccg cagtggtgga | 60 |
| tctggtcgat gctgggcttc tggatgctca tgatctgcaa cggcgtgccg gtgtggaagg | 120 |
| aggccaagac gaccctgttc tgcgcgtcgg acgccaaggc ctacgagaag gaggtgcaca | 180 |
| acgtgtgggc gacccacgcc tgcgtgccca cggaccccaa cccgcaggag atggtgctga | 240 |
| agaacgtgac cgagaacttc aacatgtgga agaacgacat ggtggaccag atgcacgagg | 300 |
| acgtgatctc cctgtgggac cagtccctga gccctgcgt gaagctgacc ccgctgtgcg | 360 |
| tgaccctgaa ctgcaccaac gccaccgcgt ccaactcctc catcatcgag ggcatgaaga | 420 |
| actgctcctt caacatcacg acggagctgc gcgacaagcg cgagaagaag aacgccctgt | 480 |
| tctacaagct ggacatcgtg cagctggacg gcaactcctc gcagtacagg ctgatcaact | 540 |
| gcaacacctc cgtcatcacg caggcgtgcc ccaaggtgtc cttcgacccc atccccatcc | 600 |
| actactgcgc ccccgccggc tacgccatcc tgaagtgcaa caacaagacc ttcaccggca | 660 |
| ccggcccgtg caacaacgtg tccaccgtgc agtgcacgca cggatcaag cccgtggtgt | 720 |
| ccacgcagct gctcctgaac gggtcgctgg ccgagggcga gatcatcatc cggtccgaga | 780 |
| acatcacgaa caacgcgaag accatcatcg tgcacctgaa cgagtccgtg aagatcgagt | 840 |
| gcacccgccc gaacaacaag acgcgcacct ccatccggat cggccctggc caggccttct | 900 |
| acgccaccgg ccaggtgatc ggcgacatcc gcgaggcgta ctgcaacatc aacgagtcca | 960 |
| agtggaacga gaccctgcag cgcgtgtcca agaagctgaa ggagtacttc ccccacaaga | 1020 |
| acatcacctt ccagccgtcg tccggcggcg acctcgagat caccacgcac tccttcaact | 1080 |
| gcggtggcga gttcttctac tgcaacacgt cgtcgctgtt caaccgcacc tacatggcca | 1140 |
| actccaccga catggccaac tccaccgaga ccaactccac gcgcaccatc acgatccact | 1200 |
| gccgcatcaa gcagatcatc aacatgtggc aggaggtggg ccgcgccatg tacgcaccgc | 1260 |
| ccatcgccgg caacatcacc tgcatctcca acatcaccgg cctcctgctg acccgcgacg | 1320 |
| gcggcaagaa caacacggag accttcaggc caggcggagg caacatgaag gacaactggc | 1380 |
| gctccgagct gtacaagtac aaggtggtgg aggtgaagcc cctgggcgtg cacccacca | 1440 |
| acgcccgcga gcgcgtcgtg gagcgcgaga aggagtagta aggtcaccga attcgggacc | 1500 |
| cggatcc | 1507 |

<210> SEQ ID NO 11
<211> LENGTH: 2131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | | |
|---|---|---|
| gtcgacaaga agccaccatg cgcgtgatgg gcatccagcg caactacccg cagtggtgga | 60 |
| tctggtcgat gctgggcttc tggatgctca tgatctgcaa cggcatgtgg gtgacggtgt | 120 |
| actacggcgt gccggtgtgg aaggaggcca agacgaccct gttctgcgcg tcggacgcca | 180 |
| aggcctacga gaaggaggtg cacaacgtgt gggcgaccca cgcctgcgtg cccacggacc | 240 |
| ccaacccgca ggagatggtg ctgaagaacg tgaccgagaa cttcaacatg tggaagaacg | 300 |
| acatggtgga ccagatgcac gaggacgtga tctccctgtg ggaccagtcc ctgaagccct | 360 |

```
gcgtgaagct gaccccgctg tgcgtgaccc tgaactgcac caacgccacc gcgtccaact    420
cctccatcat cgagggcatg aagaactgct ccttcaacat cacgacggag ctgcgcgaca    480
agcgcgagaa gaagaacgcc ctgttctaca agctggacat cgtgcagctg acggcaact    540
cctcgcagta caggctgatc aactgcaaca cctccgtcat cacgcaggcg tgccccaagg    600
tgtccttcga ccccatcccc atccactact gcgcccccgc cggctacgcc atcctgaagt    660
gcaacaacaa gaccttcacc ggcaccggcc gtgcaacaa cgtgtccacc gtgcagtgca    720
cgcacgggat caagcccgtg gtgtccacgc agctgctcct gaacgggtcg ctggccgagg    780
gcgagatcat catccggtcc gagaacatca cgaacaacgc gaagaccatc atcgtgcacc    840
tgaacgagtc cgtgaagatc gagtgcaccc gcccgaacaa caagacgcgc acctccatcc    900
ggatcggccc tggccaggcc ttctacgcca ccggccaggt gatcggcgac atccgcgagg    960
cgtactgcaa catcaacgag tccaagtgga cgagaccct gcagcgcgtg tccaagaagc   1020
tgaaggagta cttcccccac aagaacatca ccttccagcc gtcgtccggc ggcgacctcg   1080
agatcaccac gcactccttc aactgcggtg gcgagttctt ctactgcaac acgtcgtcgc   1140
tgttcaaccg cacctacatg gccaactcca ccgacatggc caactccacc gagaccaact   1200
ccacgcgcac catcacgatc cactgccgca tcaagcagat catcaacatg tggcaggagg   1260
tgggccgcgc catgtacgca ccgcccatcg ccggcaacat cacctgcatc tccaacatca   1320
ccggcctcct gctgacccgc gacggcggca agaacaacac ggagaccttc aggccaggcg   1380
gaggcaacat gaaggacaac tggcgctccg agctgtacaa gtacaaggtg gtggaggtga   1440
agcccctggg cgtggcaccc accaacgccc gcaggcgcgt cgtggagcgc gagaagcgcg   1500
ccgtgggcat gggcgccgtg ttcctgggct tcctgggcgc tgcgggctcc accatgggtg   1560
ccgcgtccat caccctgacc gtgcaggccc gccagctgct ctccggcatc gtgcagcagc   1620
agtccaacct cctgaaggcc atcgaggccc agcagcacat gctgaagctg accgtgtggg   1680
gcatcaagca gctgcaggcc agggtgctcg cgctcgagcg ctacctgaag gaccagcagc   1740
tgctcggcat gtggggctgc tccggcaagc tgatctgcac caccaacgtg tactggaact   1800
cgtcctggtc caacaagacc tacggcgaca tctgggacaa catgacctgg atgcagtggg   1860
agcgcgagat ctccaactac accgagatca tctacgagct cctcgaggag tcccagaacc   1920
agcaggagaa gaacgagcag atctgctcg cgctggaccg ctggaactcc ctgtggaact   1980
ggttcaacat caccaactgg ctgtggtaca tcaagatctt catcatgatc gtgggcggcc   2040
tgatcggcct gcgcatcatc ttcgccgtgc tgtcgctggt gaaccgcgtg cgccagggct   2100
gatgaggtca ccgaattcgg gacccggatc                                   2131
```

<210> SEQ ID NO 12
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu

```
             35                  40                  45
    Phe Cys Ala Ser Asp Ala Lys Ala Tyr Glu Lys Glu Val His Asn Val
                         55                  60
     50
    Trp Ala Thr His Ala Cys Val Pro Thr Asp Pro Asn Pro Gln Glu Met
     65                  70                  75                  80
    Val Leu Lys Asn Val Thr Glu Asn Phe Asn Met Trp Lys Asn Asp Met
                     85                  90                  95
    Val Asp Gln Met His Glu Asp Val Ile Ser Leu Trp Asp Gln Ser Leu
                100                 105                 110
    Lys Pro Cys Val Lys Leu Thr Pro Leu Cys Val Thr Leu Asn Cys Thr
                115                 120                 125
    Asn Ala Thr Ala Ser Asn Ser Ser Ile Ile Glu Gly Met Lys Asn Cys
                130                 135                 140
    Ser Phe Asn Ile Thr Thr Glu Leu Arg Asp Lys Arg Glu Lys Lys Asn
    145                 150                 155                 160
    Ala Leu Phe Tyr Lys Leu Asp Ile Val Gln Leu Asp Gly Asn Ser Ser
                    165                 170                 175
    Gln Tyr Arg Leu Ile Asn Cys Asn Thr Ser Val Ile Thr Gln Ala Cys
                180                 185                 190
    Pro Lys Val Ser Phe Asp Pro Ile Pro Ile His Tyr Cys Ala Pro Ala
                195                 200                 205
    Gly Tyr Ala Ile Leu Lys Cys Asn Asn Lys Thr Phe Thr Gly Thr Gly
    210                 215                 220
    Pro Cys Asn Asn Val Ser Thr Val Gln Cys Thr His Gly Ile Lys Pro
    225                 230                 235                 240
    Val Val Ser Thr Gln Leu Leu Leu Asn Gly Ser Leu Ala Glu Gly Glu
                    245                 250                 255
    Ile Ile Ile Arg Ser Glu Asn Ile Thr Asn Asn Ala Lys Thr Ile Ile
                260                 265                 270
    Val His Leu Asn Glu Ser Val Lys Ile Glu Cys Thr Arg Pro Asn Asn
                275                 280                 285
    Lys Thr Arg Thr Ser Ile Arg Ile Gly Pro Gly Gln Ala Phe Tyr Ala
    290                 295                 300
    Thr Gly Gln Val Ile Gly Asp Ile Arg Glu Ala Tyr Cys Asn Ile Asn
    305                 310                 315                 320
    Glu Ser Lys Trp Asn Glu Thr Leu Gln Arg Val Ser Lys Lys Leu Lys
                    325                 330                 335
    Glu Tyr Phe Pro His Lys Asn Ile Thr Phe Gln Pro Ser Ser Gly Gly
                340                 345                 350
    Asp Leu Glu Ile Thr Thr His Ser Phe Asn Cys Gly Gly Glu Phe Phe
                355                 360                 365
    Tyr Cys Asn Thr Ser Ser Leu Phe Asn Arg Thr Tyr Met Ala Asn Ser
                370                 375                 380
    Thr Asp Met Ala Asn Ser Thr Glu Thr Asn Ser Thr Arg Thr Ile Thr
    385                 390                 395                 400
    Ile His Cys Arg Ile Lys Gln Ile Ile Asn Met Trp Gln Glu Val Gly
                    405                 410                 415
    Arg Ala Met Tyr Ala Pro Pro Ile Ala Gly Asn Ile Thr Cys Ile Ser
                420                 425                 430
    Asn Ile Thr Gly Leu Leu Leu Thr Arg Asp Gly Gly Lys Asn Asn Thr
                435                 440                 445
    Glu Thr Phe Arg Pro Gly Gly Gly Asn Met Lys Asp Asn Trp Arg Ser
    450                 455                 460
```

Glu Leu Tyr Lys Tyr Lys Val Val Glu Val Lys Pro Leu Gly Val Ala
465                 470                 475                 480

Pro Thr Asn Ala Arg Arg Val Val Glu Arg Lys Arg Ala Val
            485                 490                 495

Gly Met Gly Ala Val Phe Leu Gly Phe Leu Gly Ala Ala Gly Ser Thr
            500                 505                 510

Met Gly Ala Ala Ser Ile Thr Leu Thr Val Gln Ala Arg Gln Leu Leu
            515                 520                 525

Ser Gly Ile Val Gln Gln Gln Ser Asn Leu Leu Lys Ala Ile Glu Ala
530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
            580                 585                 590

Trp Asn Ser Ser Trp Ser Asn Lys Thr Tyr Gly Asp Ile Trp Asp Asn
        595                 600                 605

Met Thr Trp Met Gln Trp Glu Arg Glu Ile Ser Asn Tyr Thr Glu Ile
            610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                645                 650                 655

Asn Ile Thr Asn Trp Leu Trp Tyr Ile Lys Ile Phe Ile Met Ile Val
            660                 665                 670

Gly Gly Leu Ile Gly Leu Arg Ile Ile Phe Ala Val Leu Ser Leu Val
            675                 680                 685

Asn Arg Val Arg Gln Gly Tyr Ser Pro Leu Ser Leu Gln Thr Leu Ile
690                 695                 700

Pro Ser Pro Arg Gly Pro Asp Arg Pro Gly Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
            740                 745                 750

Arg Leu Arg Asp Phe Ile Leu Ile Ala Ala Arg Ala Gly Glu Leu Leu
            755                 760                 765

Gly Arg Ser Ser Leu Lys Gly Leu Arg Arg Gly Trp Glu Ala Leu Lys
            770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
            835                 840                 845

<210> SEQ ID NO 13
<211> LENGTH: 2582
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 13

```
ggtcgacaag aaatgcgcgt gatgggcatc cagcgcaact acccgcagtg gtggatctgg       60
tcgatgctgg gcttctggat gctcatgatc tgcaacggca tgtgggtgac ggtgtactac      120
ggcgtgccgg tgtggaagga ggccaagacg accctgttct gcgcgtcgga cgccaaggcc      180
tacgagaagg aggtgcacaa cgtgtgggcg acccacgcct gcgtgccac ggaccccaac       240
ccgcaggaga tggtgctgaa gaacgtgacc gagaacttca acatgtggaa gaacgacatg      300
gtggaccaga tgcacgagga cgtgatctcc ctgtgggacc agtccctgaa gccctgcgtg      360
aagctgaccc cgctgtgcgt gaccctgaac tgcaccaacg ccaccgcgtc caactcctcc      420
atcatcgagg gcatgaagaa ctgctccttc aacatcacga cggagctgcg cgacaagcgc      480
gagaagaaga acgccctgtt ctacaagctg gacatcgtgc agctggacgg caactcctcg      540
cagtacaggt tgatcaactg caacacctcc gtcatcacgc aggcgtgccc caaggtgtcc      600
ttcgacccca tccccatcca ctactgcgcc ccgcgcggct acgccatcct gaagtgcaac      660
aacaagacct tcaccggcac cggcccgtgc aacaacgtgt ccaccgtgca gtgcacgcac      720
gggatcaagc ccgtggtgtc cacgcagctg ctcctgaacg gtcgctggc cgagggcgag       780
atcatcatcc ggtccgagaa catcacgaac aacgcgaaga ccatcatcgt gcacctgaac      840
gagtccgtga agatcgagtg cacccgcccg aacaacaaga cgcgcacctc catccggatc      900
ggccctggcc aggccttcta cgccaccggc caggtgatcg cgacatccg cgaggcgtac       960
tgcaacatca acgagtccaa gtggaacgag accctgcagc gcgtgtccaa gaagctgaag     1020
gagtacttcc cccacaagaa catcaccttc agccgtcgt ccggcggcga cctcgagatc      1080
accacgcact ccttcaactg cggtggcgag ttcttctact gcaacacgtc gtcgctgttc     1140
aaccgcacct acatggccaa ctccaccgac atggccaact ccaccgagac caactccacg     1200
cgcaccatca cgatccactg ccgcatcaag cagatcatca catgtggca ggaggtgggc      1260
cgcgccatgt acgcaccgcc catcgccggc aacatcacct gcatctccaa catcaccggc     1320
ctcctgctga cccgcgacgg cggcaagaac aacacggaga ccttcaggcc aggcggaggc     1380
aacatgaagg acaactggcg ctccgagctg tacaagtaca aggtggtgga ggtgaagccc     1440
ctgggcgtgg cacccaccaa cgcccgcagg cgcgtcgtgg agcgcgagaa gcgcgccgtg     1500
ggcatgggcg ccgtgttcct gggcttcctg ggcgctgcgg gctccaccat gggtgccgcg     1560
tccatcaccc tgaccgtgca ggcccgccag ctgctctccg gcatcgtgca gcagcagtcc     1620
aacctcctga aggccatcga ggcccagcag cacatgctga agctgaccgt gtggggcatc     1680
aagcagctgc aggccagggt gctcgcgctc gagcgctacc tgaaggacca gcagctgctc     1740
ggcatgtggg gctgctccgg caagctgatc tgcaccacca acgtgtactg gaactcgtcc     1800
tggtccaaca gacctacgg cgacatctgg gacaacatga cctggatgca gtgggagcgc      1860
gagatctcca actacaccga gatcatctac gagctcctcg aggagtccca gaaccagcag     1920
gagaagaacg agcaggatct gctcgcgctg gaccgctgga actccctgtg gaactggttc     1980
aacatcacca actggctgtg gtacatcaag atcttcatca tgatcgtggg cggcctgatc     2040
ggcctgcgca tcatcttcgc cgtgctgtcg ctggtgaacc gcgtgcgcca gggctactcc     2100
ccgctgtccc tgcaaacgct gatccctcc ccccggggcc cggacaggcc cggtggcatc      2160
gaggaggagg gcggcgagca ggaccgcaac cgctccacgc gcctggtgtc cggcttcctg     2220
```

-continued

```
gccctggtgt gggacgacct gcgctccctg tgcctgttca tctaccaccg cctgcgcgac    2280
ttcatcctga tcgcggcccg cgctggcgag ctgctgggcc ggtcctcgct gaagggcctg    2340
cgccgcggct gggaggccct gaagtacctg ggctcgctgg tgcagtactg gggcctggag    2400
ctgaagcgct ccgccatctc cctgctggac accctggcca tcgccgtggg cgagggcacc    2460
gaccgcatcc tggagttcgt gctgggcatc tgccgcgcca tccgcaacat ccccacccgc    2520
atccgccagg gcttcgagac cgccctcctg tagtaaggtc accgaattcg ggacccggat    2580
cc                                                                   2582
```

<210> SEQ ID NO 14
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Arg Val Met Gly Ile Gln Arg Asn Tyr Pro Gln Trp Trp Ile Trp
 1               5                  10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Thr Ala Ser Asn Ser Ser
        115                 120                 125

Ile Ile Glu Gly Met Lys Asn Cys Ser Phe Asn Ile Thr Thr Glu Leu
    130                 135                 140

Arg Asp Lys Arg Glu Lys Lys Asn Ala Leu Phe Tyr Lys Leu Asp Ile
145                 150                 155                 160

Val Gln Leu Asp Gly Asn Ser Ser Gln Tyr Arg Leu Ile Asn Cys Asn
                165                 170                 175

Thr Ser Val Ile Thr Gln Ala Cys Pro Lys Val Ser Phe Asp Pro Ile
            180                 185                 190

Pro Ile His Tyr Cys Ala Pro Ala Gly Tyr Ala Ile Leu Lys Cys Asn
        195                 200                 205

Asn Lys Thr Phe Thr Gly Thr Gly Pro Cys Asn Asn Val Ser Thr Val
    210                 215                 220

Gln Cys Thr His Gly Ile Lys Pro Val Val Ser Thr Gln Leu Leu Leu
225                 230                 235                 240

Asn Gly Ser Leu Ala Glu Gly Glu Ile Ile Ile Arg Ser Glu Asn Ile
                245                 250                 255

Thr Asp Asn Gly Lys Thr Ile Ile Val His Leu Asn Glu Ser Val Lys
            260                 265                 270

Ile Glu Cys Thr Arg Pro Asn Asn Lys Thr Arg Thr Ser Ile Arg Ile
        275                 280                 285
```

```
Gly Pro Gly Gln Ala Phe Tyr Ala Thr Gly Gln Val Ile Gly Asp Ile
            290                 295                 300

Arg Glu Ala Tyr Cys Asn Ile Asn Glu Ser Lys Trp Asn Glu Thr Leu
305                 310                 315                 320

Gln Arg Val Ser Lys Lys Leu Lys Glu Tyr Phe Pro His Lys Asn Ile
                325                 330                 335

Thr Phe Gln Pro Ser Ser Gly Gly Asp Leu Glu Ile Thr Thr His Ser
            340                 345                 350

Phe Asn Cys Gly Gly Glu Phe Phe Tyr Cys Asn Thr Ser Ser Leu Phe
        355                 360                 365

Asn Arg Thr Tyr Met Ala Asn Ser Thr Asp Met Ala Asn Ser Thr Glu
370                 375                 380

Thr Asn Ser Thr Arg Thr Ile Thr Ile His Cys Arg Ile Lys Gln Ile
385                 390                 395                 400

Ile Asn Met Trp Gln Glu Val Gly Arg Ala Met Tyr Ala Pro Pro Ile
                405                 410                 415

Ala Gly Asn Ile Thr Cys Ile Ser Asn Ile Thr Gly Leu Leu Leu Thr
            420                 425                 430

Arg Asp Gly Gly Lys Asn Asn Thr Glu Thr Phe Arg Pro Gly Gly Gly
        435                 440                 445

Asn Met Lys Asp Asn Trp Arg Ser Glu Leu Tyr Lys Tyr Lys Val Val
450                 455                 460

Glu Val Lys Pro Leu Gly Val Ala Pro Thr Asn Ala Arg Glu Arg Val
465                 470                 475                 480

Val Glu Arg Glu Lys Glu
            485

<210> SEQ ID NO 15
<211> LENGTH: 1507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gtcgacaaga agccaccatg cgcgtgatgg gcatccagcg caactacccg cagtggtgga       60
tctggtcgat gctgggcttc tggatgctca tgatctgcaa cggcgtgccg gtgtggaagg      120
aggccaagac gaccctgttc tgcgcgtcgg acgccaaggc ctacgagaag gaggtgcaca      180
acgtgtgggc gacccacgcc tgcgtgccca cggaccccaa cccgcaggag atggtgctga      240
agaacgtgac cgagaacttc aacatgtgga agaacgacat ggtggaccag atgcacgagg      300
acgtgatctc cctgtgggac cagtccctga gccctgcgt gaagctgacc ccgctgtgcg       360
tgaccctgaa ctgcaccaac gccaccgcgt ccaactcctc catcatcgag ggcatgaaga      420
actgctcctt caacatcacg acggagctgc gcgacaagcg cgagaagaag aacgccctgt      480
tctacaagct ggacatcgtg cagctggacg gcaactcctc gcagtacagg ctgatcaact      540
gcaacaccct cgtcatcacg caggcgtgcc ccaaggtgtc cttcgacccc atccccatcc      600
actactgcgc cccgccggc tacgccatcc tgaagtgcaa caacaagacc ttcaccggca       660 ccggccgtg caacaacgtg tccaccgtgc agtgcacgca cgggatcaag cccgtggtgt       720
ccacgcagct gctcctgaac gggtcgctgg ccgagggcga gatcatcatc cggtccgaga      780
acatcacgga caacgggaag accatcatcg tgcacctgaa cgagtccgtg aagatcgagt      840
gcacccgccc gaacaacaag acgcgcacct ccatccggat cggccctggc caggccttct      900
```

-continued

```
acgccaccgg ccaggtgatc ggcgacatcc gcgaggcgta ctgcaacatc aacgagtcca      960
agtggaacga gaccctgcag cgcgtgtcca agaagctgaa ggagtacttc ccccacaaga     1020
acatcacctt ccagccgtcg tccggcggcg acctcgagat caccacgcac tccttcaact     1080
gcggtggcga gttcttctac tgcaacacgt cgtcgctgtt caaccgcacc tacatggcca     1140
actccaccga catggccaac tccaccgaga ccaactccac gcgcaccatc acgatccact     1200
gccgcatcaa gcagatcatc aacatgtggc aggaggtggg ccgcgccatg tacgcaccgc     1260
ccatcgccgg caacatcacc tgcatctcca acatcaccgg cctcctgctg acccgcgacg     1320
gcggcaagaa caacacggag accttcaggc caggcggagg caacatgaag gacaactggc     1380
gctccgagct gtacaagtac aaggtggtgg aggtgaagcc cctgggcgtg cacccacca      1440 acgcccgcga gcgcgtcgtg gagcgcgaga aggagtagta aggtgaccga attcaggtcc     1500
cggatcc                                                               1507
```

<210> SEQ ID NO 16
<211> LENGTH: 2131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gtcgacaaga agccaccatg cgcgtgatgg gcatccagcg caactacccg cagtggtgga      60
tctggtcgat gctgggcttc tggatgctca tgatctgcaa cggcatgtgg gtgacggtgt     120
actacggcgt gccggtgtgg aaggaggcca agacgaccct gttctgcgcg tcggacgcca     180
aggcctacga gaaggaggtg cacaacgtgt gggcgaccca cgcctgcgtg cccacggacc     240
ccaacccgca ggagatggtg ctgaagaacg tgaccgagaa cttcaacatg tggaagaacg     300
acatggtgga ccagatgcac gaggacgtga tctccctgtg ggaccagtcc ctgaagccct     360
gcgtgaagct gaccccgctg tgcgtgaccc tgaactgcac caacgccacc gcgtccaact     420
cctccatcat cgagggcatg aagaactgct ccttcaacat cacgacggag ctgcgcgaca     480
agcgcgagaa gaagaacgcc ctgttctaca agctggacat cgtgcagctg acggcaact      540 cctcgcagta caggctgatc aactgcaaca cctccgtcat cacgcaggcg tgccccaagg     600
tgtccttcga ccccatcccc atccactact gcgccccgc cggctacgcc atcctgaagt      660
gcaacaacaa gaccttcacc ggcaccggcc cgtgcaacaa cgtgtccacc gtgcagtgca     720
cgcacgggat caagcccgtg gtgtccacgc agctgctcct gaacgggtcg ctggccgagg     780
gcgagatcat catccggtcc gagaacatca cggacaacgg gaagaccatc atcgtgcacc     840
tgaacgagtc cgtgaagatc gagtgcaccc gcccgaacaa caagacgcgc acctccatcc     900
ggatcggccc tggccaggcc ttctacgcca ccggccaggt gatcggcgac atccgcgagg     960
cgtactgcaa catcaacgag tccaagtgga acgagaccct gcagcgcgtg tccaagaagc    1020
tgaaggagta cttccccca aagaacatca ccttccagcc gtcgtccggc ggcgacctcg    1080
agatcaccac gcactccttc aactgcggtg gcgagttctt ctactgcaac acgtcgtcgc    1140
tgttcaaccg cacctacatg gccaactcca ccgacatggc caactccacc gagaccaact    1200
ccacgcgcac catcacgatc cactgccgca tcaagcagat catcaacatg tggcaggagg    1260
tgggccgcgc catgtacgca ccgcccatcg ccggcaacat caccctgcatc tccaacatca    1320 ccggcctcct gctgacccgc gacggcggca agaacaacac ggagaccttc aggccaggcg    1380
```

```
gaggcaacat gaaggacaac tggcgctccg agctgtacaa gtacaaggtg gtggaggtga   1440
agccccgggg cgtggcaccc accaacgccc gcaggcgcgt cgtggagcgc gagaagcgcg   1500
ccgtgggcat gggcgccgtg ttcctgggct tcctgggcgc tgcgggctcc accatgggtg   1560
ccgcgtccat caccctgacc gtgcaggccc gccagctgct ctccggcatc gtgcagcagc   1620
agtccaacct cctgaaggcc atcgaggccc agcagcacat gctgaagctg accgtgtggg   1680
gcatcaagca gctgcaggcc agggtgctcg cgctcgagcg ctacctgaag gaccagcagc   1740
tgctcggcat gtgggctgc tccggcaagc tgatctgcac caccaacgtg tactggaact   1800
cgtcctggtc caacaagacc tacggcgaca tctgggacaa catgaccgg atgcagtggg   1860 agcgcgagat ctccaactac accgagatca tctacgagct cctcgaggag tcccagaacc   1920
agcaggagaa gaacgagcag gatctgctcg cgctggaccg ctggaactcc ctgtggaact   1980
ggttcaacat caccaactgg ctgtggtaca tcaagatctt catcatgatc gtgggcggcc   2040
tgatcggcct gcgcatcatc ttcgccgtgc tgtcgctggt gaaccgcgtg cgccagggct   2100
gatgaggtga ccgaattcag gtcccggatc c                                 2131
```

<210> SEQ ID NO 17
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Ala Ser Asn Ser Ser Ile Ile Glu Gly Met Lys Asn Cys
    130                 135                 140

Ser Phe Asn Ile Thr Thr Glu Leu Arg Asp Lys Arg Glu Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
        195                 200                 205

Gly Tyr Ala Ile Leu Lys Cys Asn Asn Lys Thr Phe Thr Gly Thr Gly
    210                 215                 220
```

```
Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
            245                 250                 255

Ile Ile Ile Arg Ser Glu Asn Ile Thr Asp Asn Gly Lys Thr Ile Ile
            260                 265                 270

Val His Leu Asn Glu Ser Val Lys Ile Glu Cys Thr Arg Pro Asn Asn
        275                 280                 285

Lys Thr Arg Thr Ser Ile Arg Ile Gly Pro Gly Gln Ala Phe Tyr Ala
    290                 295                 300

Thr Gly Gln Val Ile Gly Asp Ile Arg Glu Ala Tyr Cys Asn Ile Asn
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
            340                 345                 350

Asp Leu Glu Ile Thr Thr His Ser Phe Asn Cys Gly Gly Glu Phe Phe
        355                 360                 365

Tyr Cys Asn Thr Ser Ser Leu Phe Asn Arg Thr Tyr Met Ala Asn Ser
370                 375                 380

Thr Asp Met Ala Asn Ser Thr Glu Thr Asn Ser Thr Arg Thr Ile Thr
385                 390                 395                 400

Ile His Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Ile Ser
            420                 425                 430

Asn Ile Thr Gly Leu Leu Leu Thr Arg Asp Gly Gly Lys Asn Asn Thr
        435                 440                 445

Glu Thr Phe Arg Pro Gly Gly Gly Asn Met Lys Asp Asn Trp Arg Ser
    450                 455                 460

Glu Leu Tyr Lys Tyr Lys Val Val Glu Val Lys Pro Leu Gly Val Ala
465                 470                 475                 480

Pro Thr Asn Ala Arg Arg Arg Val Val Glu Arg Glu Lys Arg Ala Val
                485                 490                 495

Gly Met Gly Ala Val Phe Leu Gly Phe Leu Gly Ala Ala Gly Ser Thr
            500                 505                 510

Met Gly Ala Ala Ser Ile Thr Leu Thr Val Gln Ala Arg Gln Leu Leu
        515                 520                 525

Ser Gly Ile Val Gln Gln Gln Ser Asn Leu Leu Lys Ala Ile Glu Ala
    530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
            580                 585                 590

Trp Asn Ser Ser Trp Ser Asn Lys Thr Tyr Gly Asp Ile Trp Asp Asn
        595                 600                 605

Met Thr Trp Met Gln Trp Glu Arg Glu Ile Ser Asn Tyr Thr Glu Ile
    610                 615                 620

Ile Tyr Glu Leu Leu Glu Glu Ser Gln Asn Gln Gln Glu Lys Asn Glu
625                 630                 635                 640
```

| | | | | | | | | | | | |
|---|---|---|---|---|---|---|---|---|---|---|---|
|Gln|Asp|Leu|Leu|Ala|Leu|Asp|Arg|Trp|Asn|Ser|Leu|Trp|Asn|Trp|Phe|
| | | |645| | | |650| | | |655|

Asn Ile Thr Asn Trp Leu Trp Tyr Ile Lys Ile Phe Ile Met Ile Val
            660                 665                 670

Gly Gly Leu Ile Gly Leu Arg Ile Ile Phe Ala Val Leu Ser Leu Val
            675                 680                 685

Asn Arg Val Arg Gln Gly Tyr Ser Pro Leu Ser Leu Gln Thr Leu Ile
        690                 695                 700

Pro Ser Pro Arg Gly Pro Asp Arg Pro Gly Ile Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
            740                 745                 750

Arg Leu Arg Asp Phe Ile Leu Ile Ala Ala Arg Ala Gly Glu Leu Leu
            755                 760                 765

Gly Arg Ser Ser Leu Lys Gly Leu Arg Arg Gly Trp Glu Ala Leu Lys
    770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
            835                 840                 845

<210> SEQ ID NO 18
<211> LENGTH: 2581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gtcgacaaga aatgcgcgtg atgggcatcc agcgcaacta cccgcagtgg tggatctggt    60
cgatgctggg cttctggatg ctcatgatct gcaacggcat gtgggtgacg gtgtactacg   120
gcgtgccggt gtggaaggag gccaagacga ccctgttctg cgcgtcggac gccaaggcct   180
acgagaagga ggtgcacaac gtgtgggcga cccacgcctg cgtgcccacg accccaacc    240 cgcaggagat ggtgctgaag aacgtgaccg agaacttcaa catgtggaag aacgacatgg   300
tggaccagat gcacgaggac gtgatctccc tgtgggacca gtccctgaag ccctgcgtga   360
agctgacccc gctgtgcgtg accctgaact gcaccaacgc caccgcgtcc aactcctcca   420
tcatcgaggg catgaagaac tgctccttca catcacgac ggagctgcgc gacaagcgcg   480
agaagaagaa cgccctgttc tacaagctgg acatcgtgca gctggacggc aactcctcgc   540
agtacaggct gatcaactgc aacacctccg tcatcacgca ggcgtgcccc aaggtgtcct   600
tcgaccccat ccccatccac tactgcgccc ccgccggcta cgccatcctg aagtgcaaca   660
acaagacctt caccggcacc ggcccgtgca acaacgtgtc caccgtgcag tgcacgcacg   720
ggatcaagcc cgtggtgtcc acgcagctgc tcctgaacgg tcgctggccc gagggcgaga   780
tcatcatccg gtccgagaac atcacggaca acggaagca catcatcgtg cacctgaacg   840
agtccgtgaa gatcgagtgc acccgcccga acaacaagac gcgcacctcc atccggatcg   900
```

```
gccctggcca ggccttctac gccaccggcc aggtgatcgg cgacatccgc gaggcgtact    960
gcaacatcaa cgagtccaag tggaacgaga ccctgcagcg cgtgtccaag aagctgaagg   1020
agtacttccc ccacaagaac atcaccttcc agccgtcgtc cggcggcgac ctcgagatca   1080
ccacgcactc cttcaactgc ggtggcgagt tcttctactg caaacacgtcg tcgctgttca   1140 accgcaccta catggccaac tccaccgaca tggccaactc caccgagacc aactccacgc   1200
gcaccatcac gatccactgc cgcatcaagc agatcatcaa catgtggcag gaggtggggcc   1260 gcgccatgta cgcaccgccc atcgccggca acatcacctg catctccaac atcaccggcc   1320
tcctgctgac ccgcgacggc ggcaagaaca cacggagac cttcaggcca ggcggaggca   1380
acatgaagga caactggcgc tccgagctgt acaagtacaa ggtggtggag gtgaagcccc   1440
tgggcgtggc acccaccaac gcccgcaggc cgtcgtgga gcgcgagaag cgcgccgtgg   1500
gcatgggcgc cgtgttcctg ggcttcctgg gcgctgcggg ctccaccatg ggtgccgcgt   1560
ccatcaccct gaccgtgcag gcccgccagc tgctctccgg catcgtgcag cagcagtcca   1620
acctcctgaa ggccatcgag gcccagcagc acatgctgaa gctgaccgtg tgggcatca   1680 agcagctgca ggccagggtg ctcgcgctcg agcgctacct gaaggaccag cagctgctcg   1740
gcatgtgggg ctgctccggc aagctgatct gcaccaccaa cgtgtactgg aactcgtcct   1800
ggtccaacaa gacctacggc gacatctggg acaacatgac ctggatgcag tgggagcgcg   1860
agatctccaa ctacaccgag atcatctacg agctcctcga ggagtcccag aaccagcagg   1920
agaagaacga gcaggatctg ctcgcgctgg accgctggaa ctccctgtgg aactggttca   1980
acatcaccaa ctggctgtgg tacatcaaga tcttcatcat gatcgtgggc ggcctgatcg   2040
gcctgcgcat catcttcgcc gtgctgtcgc tggtgaaccg cgtgcgccag ggctactccc   2100
cgctgtccct gcaaacgctg atccctccc cccggggccc ggacaggccc ggtggcatcg   2160
aggaggaggg cggcgagcag gaccgcaacc gctccacgcg cctggtgtcc ggcttcctgg   2220
ccctggtgtg ggacgacctg cgctccctgt gcctgttcat ctaccaccgc ctgcgcgact   2280
tcatcctgat cgcggcccgc gctggcgagc tgctgggccg gtcctcgctg aagggcctgc   2340
gccgcggctg ggaggccctg aagtacctgg gctcgctggt gcagtactgg ggcctggagc   2400
tgaagcgctc cgccatctcc ctgctggaca ccctggccat cgccgtgggc gagggcaccg   2460
accgcatcct ggagttcgtg ctgggcatct gccgcgccc ccgcaacatc cccacccgca   2520
tccgccaggg cttcgagacc gccctcctgt agtaaggtga ccgaattcag gtcccggatc   2580
c                                                                  2581
```

<210> SEQ ID NO 19
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

-continued

```
Tyr Glu Lys Glu Val His Asn Val Trp Ala Thr His Ala Cys Val Pro
 50                  55                  60
Thr Asp Pro Asn Pro Gln Glu Met Val Leu Lys Asn Val Thr Glu Asn
 65                  70                  75                  80
Phe Asn Met Trp Lys Asn Asp Met Val Asp Gln Met His Glu Asp Val
                     85                  90                  95
Ile Ser Leu Trp Asp Gln Ser Leu Lys Pro Cys Val Lys Leu Thr Pro
                100                 105                 110
Leu Cys Val Thr Leu Asn Cys Thr Asn Ala Thr Ala Ser Asn Asn Ser
            115                 120                 125
Ile Ile Glu Gly Met Lys Asn Cys Ser Phe Asn Ile Thr Thr Glu Leu
130                 135                 140
Arg Asp Lys Arg Glu Lys Lys Asn Ala Leu Phe Tyr Lys Leu Asp Ile
145                 150                 155                 160
Val Gln Leu Asp Gly Asn Ser Ser Gln Tyr Arg Leu Ile Asn Cys Asn
                165                 170                 175
Thr Ser Val Ile Thr Gln Ala Cys Pro Lys Val Ser Phe Asp Pro Ile
            180                 185                 190
Pro Ile His Tyr Cys Ala Pro Ala Gly Tyr Ala Ile Leu Lys Cys Asn
        195                 200                 205
Asn Lys Thr Phe Thr Gly Thr Gly Pro Cys Asn Asn Val Ser Thr Val
210                 215                 220
Gln Cys Thr His Gly Ile Lys Pro Val Val Ser Thr Gln Leu Leu Leu
225                 230                 235                 240
Asn Gly Ser Leu Ala Glu Gly Glu Ile Ile Ile Arg Ser Glu Asn Ile
                245                 250                 255
Thr Asn Asn Ala Lys Thr Ile Ile Val His Leu Asn Glu Ser Val Lys
            260                 265                 270
Ile Glu Cys Thr Arg Pro Asn Asn Lys Thr Arg Thr Ser Ile Arg Ile
        275                 280                 285
Gly Pro Gly Gln Ala Phe Tyr Ala Thr Gly Gln Val Ile Gly Asp Ile
290                 295                 300
Arg Lys Ala Tyr Cys Asn Ile Ser Glu Ser Lys Trp Asn Glu Thr Leu
305                 310                 315                 320
Gln Arg Val Ser Lys Lys Leu Lys Glu Tyr Phe Pro His Lys Asn Ile
                325                 330                 335
Thr Phe Gln Pro Ser Ser Gly Gly Asp Leu Glu Ile Thr Thr His Ser
            340                 345                 350
Phe Asn Cys Gly Gly Glu Phe Phe Tyr Cys Asn Thr Ser Ser Leu Phe
        355                 360                 365
Asn Arg Thr Tyr Met Ala Asn Ser Thr Asp Met Ala Asn Ser Thr Glu
370                 375                 380
Thr Asn Ser Thr Arg Thr Ile Thr Leu His Cys Arg Ile Lys Gln Ile
385                 390                 395                 400
Ile Asn Met Trp Gln Glu Val Gly Arg Ala Met Tyr Ala Pro Pro Ile
                405                 410                 415
Ala Gly Asn Ile Thr Cys Ile Ser Asn Ile Thr Gly Leu Leu Leu Thr
            420                 425                 430
Arg Asp Gly Gly Lys Asn Asn Thr Glu Thr Phe Arg Pro Gly Gly Gly
        435                 440                 445
Asn Met Lys Asp Asn Trp Arg Ser Glu Leu Tyr Lys Tyr Lys Val Val
450                 455                 460
Glu Val Lys Pro Leu Gly Val Ala Pro Thr Asn Ala Arg Glu Arg Val
```

```
                465                 470                 475                 480
                Val Glu Arg Glu Lys Glu
                                485

<210> SEQ ID NO 20
<211> LENGTH: 1507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gtcgacaaga agccaccatg cgcgtgatgg gcatccagcg caactacccg cagtggtgga      60
tctggtcgat gctgggcttc tggatgctca tgatctgcaa cggcgtgccg gtgtggaagg     120
aggccaagac gaccctgttc tgcgcgtcgg acgccaaggc ctacgagaag gaggtgcaca     180
acgtgtgggc gacccacgcc tgcgtgccca cggaccccaa cccgcaggag atggtgctga     240
agaacgtgac cgagaacttc aacatgtgga agaacgacat ggtggaccag atgcacgagg     300
acgtgatctc cctgtgggac cagtccctga agccctgcgt gaagctgacc ccgctgtgcg     360
tgaccctgaa ctgcaccaac gccaccgcgt ccaacaactc catcatcgag ggcatgaaga     420
actgctcctt caacatcacg acggagctgc gcgacaagcg cgagaagaag aacgccctgt     480
tctacaagct ggacatcgtg cagctggacg gcaactcctc gcagtacagg ctgatcaact     540
gcaacacctc cgtcatcacg caggcgtgcc ccaaggtgtc cttcgacccc atccccatcc     600
actactgcgc ccccgccggc tacgccatcc tgaagtgcaa caacaagacc ttcaccggca     660
ccggcccgtg caacaacgtg tccaccgtgc agtgcacgca cgggatcaag cccgtggtgt     720
ccacgcagct gctcctgaac gggtcgctgg ccgagggcga gatcatcatc cggtccgaga     780
acatcacgaa caacgcgaag accatcatcg tgcacctgaa cgagtccgtg aagatcgagt     840
gcacccgccc gaacaacaag acgcgcacgt ccatccggat cggccctggc caggccttct     900
acgccaccgg ccaggtgatc ggcgacatcc gcaaggcgta ctgcaacatc tcggagtcca     960
agtggaacga gaccctgcag cgcgtgtcca gaagctgaa ggagtacttc ccccacaaga    1020
acatcacctt ccagccgtcg tccggcggcg acctcgagat caccacgcac tccttcaact    1080
gcggtggcga gttcttctac tgcaacacgt cgtcgctgtt caaccgcacc tacatggcca    1140
actccaccga catggccaac tccaccgaga ccaactccac gcgcaccatc acgctccact    1200
gccgcatcaa gcagatcatc aacatgtggc aggaggtggg ccgcgccatg tacgcaccgc    1260
ccatcgccgg caacatcacc tgcatctcca acatcaccgg cctcctgctg acccgcgacg    1320
gcggcaagaa caacacggag accttcaggc caggcggagg caacatgaag gacaactggc    1380
gctccgagct gtacaagtac aaggtggtgg aggtgaagcc cctgggcgtg gcacccacca    1440
acgcccgcga gcgcgtcgtg gagcgcgaga aggagtagta agggacccga attcggtcac    1500
cggatcc                                                             1507

<210> SEQ ID NO 21
<211> LENGTH: 2131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
```

```
gtcgacaaga agccaccatg cgcgtgatgg gcatccagcg caactacccg cagtggtgga      60
tctggtcgat gctgggcttc tggatgctca tgatctgcaa cggcatgtgg gtgacggtgt     120
actacggcgt gccggtgtgg aaggaggcca agacgaccct gttctgcgcg tcggacgcca     180
aggcctacga gaaggaggtg cacaacgtgt gggcgaccca cgcctgcgtg cccacggacc     240
ccaacccgca ggagatggtg ctgaagaacg tgaccgagaa cttcaacatg tggaagaacg     300
acatggtgga ccagatgcac gaggacgtga tctccctgtg ggaccagtcc ctgaagccct     360
gcgtgaagct gaccccgctg tgcgtgaccc tgaactgcac caacgccacc gcgtccaaca     420
actccatcat cgagggcatg aagaactgct ccttcaacat cacgacggag ctgcgcgaca     480
agcgcgagaa gaagaacgcc ctgttctaca agctggacat cgtgcagctg gacggcaact     540
cctcgcagta caggctgatc aactgcaaca cctccgtcat cacgcaggcg tgccccaagg     600
tgtccttcga ccccatcccc atccactact gcgcccccgc cggctacgcc atcctgaagt     660
gcaacaacaa gaccttcacc ggcaccggcc cgtgcaacaa cgtgtccacc gtgcagtgca     720
cgcacgggat caagcccgtg tgtccacgc agctgctcct gaacgggtcg ctggccgagg     780
gcgagatcat catccggtcc gagaacatca cgaacaacgc gaagaccatc atcgtgcacc     840
tgaacgagtc cgtgaagatc gagtgcaccc gcccgaacaa caagacgcgc acgtccatcc     900
ggatcggccc tggccaggcc ttctacgcca ccggccaggt gatcggcgac atccgcaagg     960
cgtactgcaa catctcggag tccaagtgga cgagaccct gcagcgcgtg tccaagaagc    1020
tgaaggagta cttccccac aagaacatca ccttccagcc gtcgtccggc ggcgacctcg    1080
agatcaccac gcactccttc aactgcggtg gcgagttctt ctactgcaac acgtcgtcgc    1140
tgttcaaccg cacctacatg gccaactcca ccgacatggc caactccacc gagaccaact    1200
ccacgcgcac catcacgctc cactgccgca tcaagcagat catcaacatg tggcaggagg    1260
tgggccgcgc catgtacgca ccgcccatcg ccggcaacat cacctgcatc tccaacatca    1320
ccggcctcct gctgacccgc gacggcggca gaacaacac ggagaccttc aggccaggcg    1380
gaggcaacat gaaggacaac tggcgctccg agctgtacaa gtacaaggtg gtggaggtga    1440 agccctggg cgtggcaccc accaacgccc gcaggcgcgt cgtggagcgc gagaagcgcg    1500
ccgtgggcat gggcgccgtg ttcctgggct tcctgggcgc tgcgggctcc accatgggtg    1560
ccgcgtccat caccctgacc gtgcaggccg ccagctgct ctccggcatc gtgcagcagc    1620
agtccaacct cctgaaggcc atcgaggccc agcagcacat gctgaagctg accgtgtggg    1680
gcatcaagca gctgcaggcc agggtgctcg cgctcgagcg ctacctgaag gaccagcagc    1740
tgctcggcat gtggggctgc tccggcaagc tgatctgcac caccaacgtg tactggaact    1800
cgtcctggtc caacaagacc tacgcgaca tctgggacaa catgacctgg atgcagtggg    1860
agcgcgagat ctccaactac accgagatca tctacgagct cctcgaggag tcccagaacc    1920
agcaggagaa gaacgagcag gatctgctcg cgctggaccg ctggaactcc ctgtggaact    1980
ggttcaacat caccaactgg ctgtggtaca tcaagatctt catcatgatc gtgggcggcc    2040
tgatcggcct gcgcatcatc ttcgccgtgc tgtcgctggt gaaccgcgtg cgccagggct    2100
gatgagggac ccgaattcgg tcaccggatc c                                  2131
```

<210> SEQ ID NO 22
<211> LENGTH: 846
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Ala Ser Asn Asn Ser Ile Ile Glu Gly Met Lys Asn Cys
    130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
        195                 200                 205

Gly Tyr Ala Ile Leu Lys Cys Asn Asn Lys Thr Phe Thr Gly Thr Gly
    210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Ala Lys Thr Ile Ile
            260                 265                 270

Val His Leu Asn Glu Ser Val Lys Ile Glu Cys Thr Arg Pro Asn Asn
        275                 280                 285

Lys Thr Arg Thr Ser Ile Arg Ile Gly Pro Gly Gln Ala Phe Tyr Ala
    290                 295                 300

Thr Gly Gln Val Ile Gly Asp Ile Arg Lys Ala Tyr Cys Asn Ile Ser
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
            340                 345                 350

Asp Leu Glu Ile Thr Thr His Ser Phe Asn Cys Gly Gly Glu Phe Phe
        355                 360                 365

Tyr Cys Asn Thr Ser Ser Leu Phe Asn Arg Thr Tyr Met Ala Asn Ser
    370                 375                 380

Thr Asp Met Ala Asn Ser Thr Glu Thr Asn Ser Thr Arg Thr Ile Thr
385                 390                 395                 400
```

```
Leu His Cys Arg Ile Lys Gln Ile Ile Asn Met Trp Gln Glu Val Gly
                405                 410                 415
Arg Ala Met Tyr Ala Pro Pro Ile Ala Gly Asn Ile Thr Cys Ile Ser
            420                 425                 430
Asn Ile Thr Gly Leu Leu Thr Arg Asp Gly Gly Lys Asn Asn Thr
        435                 440                 445
Glu Thr Phe Arg Pro Gly Gly Asn Met Lys Asp Asn Trp Arg Ser
    450                 455                 460
Glu Leu Tyr Lys Tyr Lys Val Val Glu Val Lys Pro Leu Gly Val Ala
465                 470                 475                 480
Pro Thr Asn Ala Arg Arg Val Val Glu Arg Glu Lys Arg Ala Val
            485                 490                 495
Gly Met Gly Ala Val Phe Leu Gly Phe Leu Gly Ala Ala Gly Ser Thr
            500                 505                 510
Met Gly Ala Ala Ser Ile Thr Leu Thr Val Gln Ala Arg Gln Leu Leu
            515                 520                 525
Ser Gly Ile Val Gln Gln Gln Ser Asn Leu Leu Lys Ala Ile Glu Ala
        530                 535                 540
Gln Gln His Met Leu Lys Leu Thr Val Trp Gly Ile Lys Gln Leu Gln
545                 550                 555                 560
Ala Arg Val Leu Ala Leu Glu Arg Tyr Leu Lys Asp Gln Gln Leu Leu
                565                 570                 575
Gly Met Trp Gly Cys Ser Gly Lys Leu Ile Cys Thr Thr Asn Val Tyr
            580                 585                 590
Trp Asn Ser Ser Trp Ser Asn Lys Thr Tyr Gly Asp Ile Trp Asp Asn
        595                 600                 605
Met Thr Trp Met Gln Trp Glu Arg Glu Ile Ser Asn Tyr Thr Glu Ile
        610                 615                 620
Ile Tyr Glu Leu Leu Glu Glu Ser Gln Asn Gln Gln Glu Lys Asn Glu
625                 630                 635                 640
Gln Asp Leu Leu Ala Leu Asp Arg Trp Asn Ser Leu Trp Asn Trp Phe
                645                 650                 655
Asn Ile Thr Asn Trp Leu Trp Tyr Ile Lys Ile Phe Ile Met Ile Val
            660                 665                 670
Gly Gly Leu Ile Gly Leu Arg Ile Ile Phe Ala Val Leu Ser Leu Val
        675                 680                 685
Asn Arg Val Arg Gln Gly Tyr Ser Pro Leu Ser Leu Gln Thr Leu Ile
        690                 695                 700
Pro Ser Pro Arg Gly Pro Asp Arg Pro Gly Ile Glu Glu Glu Gly
705                 710                 715                 720
Gly Glu Gln Asp Arg Asn Arg Ser Thr Arg Leu Val Ser Gly Phe Leu
                725                 730                 735
Ala Leu Val Trp Asp Asp Leu Arg Ser Leu Cys Leu Phe Ile Tyr His
            740                 745                 750
Arg Leu Arg Asp Phe Ile Leu Ile Ala Ala Arg Ala Gly Glu Leu Leu
        755                 760                 765
Gly Arg Ser Ser Leu Lys Gly Leu Arg Arg Gly Trp Glu Ala Leu Lys
    770                 775                 780
Tyr Leu Gly Ser Leu Val Gln Tyr Trp Gly Leu Glu Leu Lys Arg Ser
785                 790                 795                 800
Ala Ile Ser Leu Leu Asp Thr Leu Ala Ile Ala Val Gly Glu Gly Thr
                805                 810                 815
Asp Arg Ile Leu Glu Phe Val Leu Gly Ile Cys Arg Ala Ile Arg Asn
```

```
                 820                 825                 830
Ile Pro Thr Arg Ile Arg Gln Gly Phe Glu Thr Ala Leu Leu
            835                 840                 845

<210> SEQ ID NO 23
<211> LENGTH: 2581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gtcgacaaga aatgcgcgtg atgggcatcc agcgcaacta cccgcagtgg tggatctggt      60
cgatgctggg cttctggatg ctcatgatct gcaacggcat gtgggtgacg gtgtactacg     120
gcgtgccggt gtggaaggag gccaagacga ccctgttctg cgcgtcggac gccaaggcct     180
acgagaagga ggtgcacaac gtgtgggcga cccacgcctg cgtgcccacg accccaaacc     240
cgcaggagat ggtgctgaag aacgtgaccg agaacttcaa catgtggaag aacgacatgg     300
tggaccagat gcacgaggac gtgatctccc tgtgggacca gtccctgaag ccctgcgtga     360
agctgacccc gctgtgcgtg accctgaact gcaccaacgc caccgcgtcc aacaactcca     420
tcatcgaggg catgaagaac tgctccttca catcacgac ggagctgcgc gacaagcgcg     480
agaagaagaa cgcccctgttc tacaagctgg acatcgtgca gctggacggc aactcctcgc     540
agtacaggct gatcaactgc aacacctccg tcatcacgca ggcgtgcccc aaggtgtcct     600
tcgaccccat ccccatccac tactgcgccc cgccggcta cgccatcctg aagtgcaaca     660
acaagacctt caccggcacc ggcccgtgca caacgtgtc caccgtgcag tgcacgcacg     720
ggatcaagcc cgtggtgtcc acgcagctgc tcctgaacgg tcgctggcc gagggcgaga     780 tcatcatccg gtccgagaac atcacgaaca cgcgaagac catcatcgtg cacctgaacg     840
agtccgtgaa gatcgagtgc acccgcccga caacaagc gcgcacgtcc atccggatcg     900
gccctggcca ggccttctac gccaccggcc aggtgatcgg cgacatccgc aaggcgtact     960
gcaacatctc ggagtccaag tggaacgaga ccctgcagcg cgtgtccaag aagctgaagg    1020
agtacttccc ccacaagaac atcaccttcc agccgtcgtc cggcggcgac ctcgagatca    1080
ccacgcactc cttcaactgc ggtggcgagt tcttctactg caacacgtcg tcgctgttca    1140
accgcaccta catggccaac tccaccgaca tggccaactc caccgagacc aactccacgc    1200
gcaccatcac gctccactgc cgcatcaagc agatcatcaa catgtggcag gaggtgggcc    1260
gcgccatgta cgcaccgccc atcgccggca acatcacctg catctccaac atcaccggcc    1320
tcctgctgac ccgcgacggc ggcaagaaca cacggagac cttcaggcca ggcgaggca    1380 acatgaagga caactggcgc tccgagctgt acaagtacaa ggtggtggag gtgaagcccc    1440
tgggcgtggc acccaccaac gcccgcaggc gcgtcgtgga gcgcgagaag cgcgccgtgg    1500
gcatgggcgc cgtgttcctg ggcttcctgg gcgctgcggg ctccaccatg ggtgccgcgt    1560 ccatcacccct gaccgtgcag gcccgccagc tgctctccgg catcgtgcag cagcagtcca    1620
acctcctgaa ggccatcgag gcccagcagc acatgctgaa gctgaccgtg tggggcatca    1680
agcagctgca ggccagggtg ctcgcgctcg agcgctacct gaaggaccag cagctgctcg    1740
gcatgtgggg ctgctccggc aagctgatct gcaccaccaa cgtgtactgg aactcgtcct    1800
ggtccaacaa gacctacggc gacatctggg acaaatgagc ctggatgcag tgggagcgcg    1860
agatctccaa ctacaccgag atcatctacg agctcctcga ggagtcccag aaccagcagg    1920
```

```
agaagaacga gcaggatctg ctcgcgctgg accgctggaa ctccctgtgg aactggttca    1980
acatcaccaa ctggctgtgg tacatcaaga tcttcatcat gatcgtgggc ggcctgatcg    2040
gcctgcgcat catcttcgcc gtgctgtcgc tggtgaaccg cgtgcgccag ggctactccc    2100
cgctgtccct gcaaacgctg atcccctccc ccggggccc ggacaggccc ggtggcatcg     2160
aggaggaggg cggcgagcag accgcaacc gctccacgcg cctggtgtcc ggcttcctgg     2220
ccctggtgtg ggacgacctg cgctcccgt gcctgttcat ctaccaccgc ctgcgcgact     2280
tcatcctgat cgcggcccgc gctggcgagc tgctgggccg gtcctcgctg aagggcctgc    2340
gccgcggctg ggaggccctg aagtacctgg gtcgctggt gcagtactgg ggcctggagc     2400
tgaagcgctc cgccatctcc ctgctggaca ccctggccat cgccgtgggc gagggcaccg    2460
accgcatcct ggagttcgtg ctgggcatct gccgcgccat ccgcaacatc cccacccgca    2520
tccgccaggg cttcgagacc gccctcctgt agtaagggac ccgaattcgg tcaccggatc    2580
c                                                                    2581
```

<210> SEQ ID NO 24
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Met Thr Pro
            100                 105                 110

Leu Cys Val Thr Leu Asn Cys Thr Asn Ala Thr Ala Ile Asn Ser Ser
        115                 120                 125

Ile Ile Glu Gly Met Lys Asn Cys Ser Phe Asn Ile Thr Thr Glu Leu
    130                 135                 140

Arg Asp Lys Arg Glu Lys Lys Asn Ala Leu Phe Tyr Lys Leu Asp Ile
145                 150                 155                 160

Val Gln Leu Asp Gly Asn Ser Ser Gln Tyr Arg Leu Ile Asn Cys Asn
                165                 170                 175

Thr Ser Val Ile Thr Gln Ala Cys Pro Lys Val Ser Phe Asp Pro Ile
            180                 185                 190

Pro Ile His Tyr Cys Ala Pro Ala Gly Tyr Ala Ile Leu Lys Cys Asn
        195                 200                 205

Asn Lys Thr Phe Thr Gly Thr Gly Pro Cys Asn Asn Val Ser Thr Val
    210                 215                 220

Gln Cys Thr His Gly Ile Lys Pro Val Val Ser Thr Gln Leu Leu Leu
```

```
                225                 230                 235                 240

Asn Gly Ser Leu Ala Glu Gly Glu Ile Ile Arg Ser Glu Asn Ile
                245                 250                 255

Thr Asn Asp Lys Thr Ile Ile Val His Leu Asn Glu Ser Val Lys
                260                 265                 270

Ile Glu Cys Thr Arg Pro Asn Asn Lys Thr Arg Thr Ser Ile Arg Ile
                275                 280                 285

Gly Pro Gly Gln Ala Phe Tyr Ala Thr Gly Gln Val Ile Gly Asp Ile
            290                 295                 300

Arg Glu Ala His Cys Asn Ile Ser Glu Ser Lys Trp Asn Glu Thr Leu
305                 310                 315                 320

Gln Arg Val Ser Lys Lys Leu Lys Glu Tyr Phe Pro His Lys Asn Ile
                325                 330                 335

Thr Phe Gln Pro Ser Ser Gly Gly Asp Leu Glu Ile Thr Thr His Ser
                340                 345                 350

Phe Asn Cys Gly Gly Glu Phe Phe Tyr Cys Asn Thr Ser Ser Leu Phe
                355                 360                 365

Asn Arg Thr Tyr Met Ala Asn Ser Thr Asp Met Ala Asn Ser Thr Glu
                370                 375                 380

Thr Asn Ser Thr Arg Thr Ile Thr Ile Arg Cys Arg Ile Lys Gln Ile
385                 390                 395                 400

Ile Asn Met Trp Gln Glu Val Gly Arg Ala Met Tyr Ala Pro Pro Ile
                405                 410                 415

Ala Gly Asn Ile Thr Cys Ile Ser Asn Ile Thr Gly Leu Leu Leu Thr
                420                 425                 430

Arg Asp Gly Gly Lys Asn Asn Thr Glu Thr Phe Arg Pro Gly Gly Gly
                435                 440                 445

Asn Met Lys Asp Asn Trp Arg Ser Glu Leu Tyr Lys Tyr Lys Val Val
                450                 455                 460

Glu Val Lys Pro Leu Gly Val Ala Pro Thr Asn Ala Arg Glu Arg Val
465                 470                 475                 480

Val Glu Arg Glu Lys Glu
                485

<210> SEQ ID NO 25
<211> LENGTH: 1507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gtcgacaaga agccaccatg cgcgtgatgg catccagcg caactacccg cagtggtgga       60
tctggtcgat gctgggcttc tggatgctca tgatctgcaa cggcgtgccg gtgtggaagg    120
aggccaagac gaccctgttc tgcgcgtcgg acgccaaggc ctacgagaag gaggtgcaca    180
acgtgtgggc gacccacgcc tgcgtgccca ggacccccaa cccgcaggag atggtgctga    240
agaacgtgac cgagaacttc aacatgtgga agaacgacat ggtggaccag atgcacgagg    300
acgtgatctc cctgtgggac cagtccctga gccctgcgt gaagatgacc ccgctgtgcg    360
tgaccctgaa ctgcaccaac gccaccgcga tcaactcctc catcatcgag ggcatgaaga    420
actgctcctt caacatcacg acggagctgc gcgacaagcg cgagaagaag aacgccctgt    480
tctacaagct ggacatcgtg cagctggacg gcaactcctc gcagtacagg ctgatcaact    540
```

```
gcaacacctc cgtcatcacg caggcgtgcc ccaaggtgtc cttcgacccc atccccatcc      600
actactgcgc ccccgccggc tacgccatcc tgaagtgcaa caacaagacc ttcaccggca      660
ccggcccgtg caacaacgtg tccaccgtgc agtgcacgca cgggatcaag cccgtggtgt      720
ccacgcagct gctcctgaac gggtcgctgg ccgagggcga gatcatcatc cggtccgaga      780
acatcacgaa caacgacaag accatcatcg tgcacctgaa cgagtccgtg aagatcgagt      840 gcaccgccc gaacaacaag acgcgcacct ccatccggat cggccctggc caggccttct      900
acgccaccgg ccaggtgatc ggcgacatcc gcgaggcgca ctgcaacatc tcggagtcca      960
agtggaacga gaccctgcag cgcgtgtcca agaagctgaa ggagtacttc ccccacaaga     1020
acatcacctt ccagccgtcg tccggcggcg acctcgagat caccacgcac tccttcaact     1080
gcggtggcga gttcttctac tgcaacacgt cgtcgctgtt caaccgcacc tacatggcca     1140
actccaccga catggccaac tccaccgaga ccaactccac gcgcaccatc acgatccgct     1200
gccgcatcaa gcagatcatc aacatgtggc aggaggtggg ccgcgccatg tacgcaccgc     1260
ccatcgccgg caacatcacc tgcatctcca acatcaccgg cctcctgctg acccgcgacg     1320
gcggcaagaa caacacggag accttcaggc caggcggagg caacatgaag acaactggc      1380 gctccgagct gtacaagtac aaggtggtgg aggtgaagcc cctgggcgtg cacccacca      1440 acgcccgcga gcgcgtcgtg gagcgcgaga aggagtagta agggtcctga attcggttac     1500
cggatcc                                                                 1507

<210> SEQ ID NO 26
<211> LENGTH: 2131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gtcgacaaga agccaccatg cgcgtgatgg gcatccagcg caactacccg cagtggtgga       60
tctggtcgat gctgggcttc tggatgctca tgatctgcaa cggcatgtgg gtgacggtgt      120
actacggcgt gccggtgtgg aaggaggcca agacgaccct gttctgcgcg tcggacgcca      180
aggcctacga gaaggaggtg cacaacgtgt gggcgaccca cgcctgcgtg cccacggacc      240
ccaacccgca ggagatggtg ctgaagaacg tgaccgagaa cttcaacatg tggaagaacg      300
acatggtgga ccagatgcac gaggacgtga tctccctgtg ggaccagtcc ctgaagccct      360
gcgtgaagat gaccccgctg tgcgtgaccc tgaactgcac caacgccacc gcgatcaact      420
cctccatcat cgagggcatg aagaactgct ccttcaacat cacgacggag ctgcgcgaca      480
agcgcgagaa gaagaacgcc ctgttctaca gctggacatc gtgcagctg acggcaact       540 cctcgcagta caggctgatc aactgcaaca cctccgtcat cacgcaggcg tgccccaagg      600
tgtccttcga ccccatcccc atccactact gcgccccgc cggctacgcc atcctgaagt      660
gcaacaacaa gaccttcacc ggcaccggcc cgtgcaacaa cgtgtccacc gtgcagtgca      720
cgcacgggat caagcccgtg gtgtccacgc agctgctcct gaacgggtcg ctggccgagg      780
gcgagatcat catccggtcc gagaacatca cgaacaacga caagaccatc atcgtgcacc      840
tgaacgagtc cgtgaagatc gagtgcaccc gcccgaacaa caagacgcgc acctccatcc      900
ggatcggccc tggccaggcc ttctacgcca ccggccaggt gatcggcgac atccgcgagg      960
cgcactgcaa catctcggag tccaagtgga acgagaccct gcagcgcgtg tccaagaagc     1020
```

```
tgaaggagta cttcccccac aagaacatca ccttccagcc gtcgtccggc ggcgacctcg    1080
agatcaccac gcactccttc aactgcggtg gcgagttctt ctactgcaac acgtcgtcgc    1140
tgttcaaccg cacctacatg gccaactcca ccgacatggc caactccacc gagaccaact    1200
ccacgcgcac catcacgatc cgctgccgca tcaagcagat catcaacatg tggcaggagg    1260
tgggccgcgc catgtacgca ccgcccatcg ccggcaacat cacctgcatc tccaacatca    1320
ccggcctcct gctgacccgc gacggcggca agaacaacac ggagaccttc aggccaggcg    1380
gaggcaacat gaaggacaac tggcgctccg agctgtacaa gtacaaggtg gtggaggtga    1440
agcccctggg cgtggcaccc accaacgccc gcaggcgcgt cgtggagcgc gagaagcgcg    1500
ccgtgggcat gggcgccgtg ttcctgggct tcctgggcgc tgcgggctcc accatgggtg    1560
ccgcgtccat caccctgacc gtgcaggccg ccagctgct ctccggcatc gtgcagcagc    1620
agtccaacct cctgaaggcc atcgaggccc agcagcacat gctgaagctg accgtgtggg    1680
gcatcaagca gctgcaggcc agggtgctcg cgctcgagcg ctacctgaag gaccagcagc    1740
tgctcggcat gtggggctgc tccggcaagc tgatctgcac caccaacgtg tactggaact    1800
cgtcctggtc caacaagagc tacggcgaca tctgggacaa catgacctgg atgcagtggg    1860
agcgcgagat ctccaactac accgagatca tctacgagct cctcgaggag tcccagaacc    1920
agcaggagaa gaacgagcag gatctgctcg cgctggaccg ctggaactcc ctgtggaact    1980
ggttcaacat caccaactgg ctgtggtaca tcaagatctt catcatgatc gtgggcggcc    2040
tgatcggcct gcgcatcatc ttcgccgtgc tgtcgctggt gaaccgcgtg cgccagggct    2100
gatgagggtc ctgaattcgg ttaccggatc c                                  2131
```

<210> SEQ ID NO 27
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Met Thr Pro Leu Cys Val Thr Leu Asn Cys Thr
        115                 120                 125

Asn Ala Thr Ala Ile Asn Ser Ser Ile Ile Glu Gly Met Lys Asn Cys
    130                 135                 140

Ser Phe Asn Ile Thr Thr Glu Leu Arg Asp Lys Arg Glu Lys Lys Asn
145                 150                 155                 160
```

```
Ala Leu Phe Tyr Lys Leu Asp Ile Val Gln Leu Asp Gly Asn Ser Ser
            165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
            195                 200                 205

Gly Tyr Ala Ile Leu Lys Cys Asn Asn Lys Thr Phe Thr Gly Thr Gly
            210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
            245                 250                 255

Ile Ile Ile Arg Ser Glu Asn Ile Thr Asn Asn Asp Lys Thr Ile Ile
            260                 265                 270

Val His Leu Asn Glu Ser Val Lys Ile Glu Cys Thr Arg Pro Asn Asn
            275                 280                 285

Lys Thr Arg Thr Ser Ile Arg Ile Gly Pro Gly Gln Ala Phe Tyr Ala
            290                 295                 300

Thr Gly Gln Val Ile Gly Asp Ile Arg Glu Ala His Cys Asn Ile Ser
305                 310                 315                 320

Glu Ser Lys Trp Asn Glu Thr Leu Gln Arg Val Ser Lys Lys Leu Lys
            325                 330                 335

Glu Tyr Phe Pro His Lys Asn Ile Thr Phe Gln Pro Ser Ser Gly Gly
            340                 345                 350

Asp Leu Glu Ile Thr Thr His Ser Phe Asn Cys Gly Gly Glu Phe Phe
            355                 360                 365

Tyr Cys Asn Thr Ser Ser Leu Phe Asn Arg Thr Tyr Met Ala Asn Ser
            370                 375                 380

Thr Asp Met Ala Asn Ser Thr Glu Thr Asn Ser Thr Arg Thr Ile Thr
385                 390                 395                 400

Ile Arg Cys Arg Ile Lys Gln Ile Ile Asn Met Trp Gln Glu Val Gly
            405                 410                 415

Arg Ala Met Tyr Ala Pro Pro Ile Ala Gly Asn Ile Thr Cys Ile Ser
            420                 425                 430

Asn Ile Thr Gly Leu Leu Leu Thr Arg Asp Gly Gly Lys Asn Asn Thr
            435                 440                 445

Glu Thr Phe Arg Pro Gly Gly Gly Asn Met Lys Asp Asn Trp Arg Ser
            450                 455                 460

Glu Leu Tyr Lys Tyr Lys Val Val Glu Val Lys Pro Leu Gly Val Ala
465                 470                 475                 480

Pro Thr Asn Ala Arg Arg Arg Val Val Glu Arg Glu Lys Arg Ala Val
            485                 490                 495

Gly Met Gly Ala Val Phe Leu Gly Phe Leu Gly Ala Ala Gly Ser Thr
            500                 505                 510

Met Gly Ala Ala Ser Ile Thr Leu Thr Val Gln Ala Arg Gln Leu Leu
            515                 520                 525

Ser Gly Ile Val Gln Gln Ser Asn Leu Leu Lys Ala Ile Glu Ala
            530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
            565                 570                 575

Gly Met Trp Gly Cys Ser Gly Lys Leu Ile Cys Thr Thr Asn Val Tyr
```

```
                     580                 585                 590
Trp Asn Ser Ser Trp Ser Asn Lys Ser Tyr Gly Asp Ile Trp Asp Asn
             595                 600                 605

Met Thr Trp Met Gln Trp Glu Arg Glu Ile Ser Asn Tyr Thr Glu Ile
         610                 615                 620

Ile Tyr Glu Leu Leu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                 645                 650                 655

Asn Ile Thr Asn Trp Leu Trp Tyr Ile Lys Ile Phe Ile Met Ile Val
             660                 665                 670

Gly Gly Leu Ile Gly Leu Arg Ile Ile Phe Ala Val Leu Ser Leu Val
         675                 680                 685

Asn Arg Val Arg Gln Gly Tyr Ser Pro Leu Ser Leu Gln Thr Leu Ile
690                 695                 700

Pro Ser Pro Arg Gly Pro Asp Arg Pro Gly Gly Ile Glu Glu Glu Gly
705                 710                 715                 720

Gly Glu Gln Asp Arg Asn Arg Ser Thr Arg Leu Val Ser Gly Phe Leu
                 725                 730                 735

Ala Leu Val Trp Asp Asp Leu Arg Ser Leu Cys Leu Phe Ile Tyr His
             740                 745                 750

Arg Leu Arg Asp Phe Ile Leu Ile Ala Ala Arg Ala Gly Glu Leu Leu
         755                 760                 765

Gly Arg Ser Ser Leu Lys Gly Leu Arg Arg Gly Trp Glu Ala Leu Lys
770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                 805                 810                 815

Asp Arg Ile Leu Glu Phe Val Leu Gly Ile Cys Arg Ala Ile Arg Asn
             820                 825                 830

Ile Pro Thr Arg Ile Arg Gln Gly Phe Glu Thr Ala Leu Leu
         835                 840                 845

<210> SEQ ID NO 28
<211> LENGTH: 2581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gtcgacaaga aatgcgcgtg atgggcatcc agcgcaacta cccgcagtgg tggatctggt      60
cgatgctggg cttctggatg ctcatgatct gcaacggcat gtgggtgacg gtgtactacg     120
gcgtgccggt gtgaaggag gccaagacga ccctgttctg cgcgtcggac gccaaggcct     180
acgagaagga ggtgcacaac gtgtgggcga cccacgcctg cgtgcccacg accccaacc     240 cgcaggagat ggtgctgaag aacgtgaccg agaacttcaa catgtggaag aacgacatgg     300
tggaccagat gcacgaggac gtgatctccc tgtgggacca gtccctgaag ccctgcgtga     360
agatgacccc gctgtgcgtg accctgaact gcaccaacgc caccgcgatc aactcctcca     420
tcatcgaggg catgaagaac tgctccttca acatcacgac ggagctgcgc gacaagcgcg     480
agaagaagaa cgccctgttc tacaagctgg acatcgtgca gctggacggc aactcctcgc     540
```

| | |
|---|---|
| agtacaggct gatcaactgc aacacctccg tcatcacgca ggcgtgcccc aaggtgtcct | 600 |
| tcgaccccat ccccatccac tactgcgccc ccgccggcta cgccatcctg aagtgcaaca | 660 |
| acaagacctt caccggcacc ggcccgtgca caacgtgtc caccgtgcag tgcacgcacg | 720 |
| ggatcaagcc cgtggtgtcc acgcagctgc tcctgaacgg gtcgctggcc gagggcgaga | 780 |
| tcatcatccg gtccgagaac atcacgaaca cgacaagac catcatcgtg cacctgaacg | 840 |
| agtccgtgaa gatcgagtgc acccgcccga caacaagac gcgcacctcc atccggatcg | 900 |
| gccctggcca ggccttctac gccaccggcc aggtgatcgg cgacatccgc gaggcgcact | 960 |
| gcaacatctc ggagtccaag tggaacgaga ccctgcagcg cgtgtccaag aagctgaagg | 1020 |
| agtacttccc ccacaagaac atcaccttcc agccgtcgtc cggcggcgac ctcgagatca | 1080 |
| ccacgcactc cttcaactgc ggtggcgagt tcttctactg caacacgtcg tcgctgttca | 1140 |
| accgcaccta catggccaac tccaccgaca tggccaactc caccgagacc aactccacgc | 1200 |
| gcaccatcac gatccgctgc cgcatcaagc agatcatcaa catgtggcag gaggtgggcc | 1260 |
| gcgccatgta cgcaccgccc atccgccgca acatcacctg catctccaac atcaccggcc | 1320 |
| tcctgctgac ccgcgacggc ggcaagaaca cacggagac cttcaggcca ggcggaggca | 1380 |
| acatgaagga caactggcgc tccgagctgt acaagtacaa ggtggtggag gtgaagcccc | 1440 |
| tgggcgtggc acccaccaac gcccgcaggc gcgtcgtgga gcgcgagaag cgcgccgtgg | 1500 |
| gcatgggcgc cgtgttcctg ggcttcctgg gcgctgcggg ctccaccatg ggtgccgcgt | 1560 |
| ccatcaccct gaccgtgcag gcccgccagc tgctctccgg catcgtgcag cagcagtcca | 1620 |
| acctcctgaa ggccatcgag gcccagcagc acatgctgaa gctgaccgtg tggggcatca | 1680 |
| agcagctgca ggccagggtg ctcgcgctcg agcgctacct gaaggaccag cagctgctcg | 1740 |
| gcatgtgggg ctgctccggc aagctgatct gcaccaccaa cgtgtactgg aactcgtcct | 1800 |
| ggtccaacaa gagctacggc gacatctggg acaacatgac ctggatgcag tgggagcgcg | 1860 |
| agatctccaa ctacaccgag atcatctacg agctcctcga ggagtcccag aaccagcagg | 1920 |
| agaagaacga gcaggatctg ctcgcgctgg accgctggaa ctccctgtgg aactggttca | 1980 |
| acatcaccaa ctggctgtgg tacatcaaga tcttcatcat gatcgtgggc ggcctgatcg | 2040 |
| gcctgcgcat catcttcgcc gtgctgtcgc tggtgaaccg cgtgcgccag ggctactccc | 2100 |
| cgctgtccct gcaaacgctg atccctccc ccggggccc ggacaggccc ggtggcatcg | 2160 |
| aggaggaggg cggcgagcag gaccgcaacc gctccacgcg cctggtgtcc ggcttcctgg | 2220 |
| ccctggtgtg ggacgacctg cgctcccgt gcctgttcat ctaccaccgc ctgcgcgact | 2280 |
| tcatcctgat cgcggcccgc gctggcgagc tgctgggccg gtcctcgctg aagggcctgc | 2340 |
| gccgcggctg ggaggccctg aagtacctgg gctcgctggt gcagtactgg ggcctggagc | 2400 |
| tgaagcgctc cgccatctcc ctgctggaca ccctggccat cgccgtgggc gagggcaccg | 2460 |
| accgcatcct ggagttcgtg ctgggcatct gccgcgccat ccgcaacatc cccacccgca | 2520 |
| tccgccaggg cttcgagacc gccctcctgt agtaagggtc tgaattcgg ttaccggatc | 2580 |
| c | 2581 |

<210> SEQ ID NO 29
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 29

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Ser Cys Thr Asn Ala Thr Asn Ala Thr Ala Ser
        115                 120                 125

Asn Ser Ser Ile Leu Glu Gly Met Lys Asn Cys Ser Phe Asn Ile Thr
    130                 135                 140

Thr Glu Leu Arg Asp Lys Arg Glu Lys Lys Asn Ala Leu Phe Tyr Lys
145                 150                 155                 160

Leu Asp Ile Val Gln Leu Asp Gly Asn Ser Ser Gln Tyr Arg Leu Ile
                165                 170                 175

Asn Cys Asn Thr Ser Val Ile Thr Gln Ala Cys Pro Lys Val Ser Phe
            180                 185                 190

Asp Pro Ile Pro Ile His Tyr Cys Ala Pro Ala Gly Tyr Ala Ile Leu
        195                 200                 205

Lys Cys Asn Asn Lys Thr Phe Asn Gly Thr Gly Pro Cys Asn Asn Val
    210                 215                 220

Ser Thr Val Gln Cys Thr His Gly Ile Lys Pro Val Val Ser Thr Gln
225                 230                 235                 240

Leu Leu Leu Asn Gly Ser Leu Ala Glu Gly Glu Ile Ile Ile Arg Ser
                245                 250                 255

Lys Asn Ile Thr Asp Asn Gly Lys Thr Ile Ile Val His Leu Asn Glu
            260                 265                 270

Ser Val Lys Ile Glu Cys Thr Arg Pro Ser Asn Asn Thr Arg Thr Ser
        275                 280                 285

Ile Arg Ile Gly Pro Gly Gln Ala Phe Tyr Ala Thr Gly Gln Val Ile
    290                 295                 300

Gly Asp Ile Arg Glu Ala His Cys Asn Ile Ser Glu Ser Lys Trp Asn
305                 310                 315                 320

Glu Thr Leu Gln Arg Val Ser Glu Lys Leu Lys Glu Tyr Phe Pro His
                325                 330                 335

Lys Asn Ile Thr Phe Gln Pro Ser Ser Gly Gly Asp Leu Glu Ile Thr
            340                 345                 350

Thr His Ser Phe Asn Cys Gly Gly Glu Phe Phe Tyr Cys Asn Thr Ser
        355                 360                 365

Ser Leu Phe Asn Arg Thr Tyr Met Ala Thr Ser Thr Asp Met Ala Asn
    370                 375                 380

Ser Thr Glu Thr Asn Ser Thr Arg Ile Ile Thr Ile Arg Cys Arg Ile
385                 390                 395                 400

Lys Gln Ile Ile Asn Met Trp Gln Glu Val Gly Arg Ala Met Tyr Ala
                405                 410                 415
```

Pro Pro Ile Ala Gly Asn Ile Thr Cys Ile Ser Asn Ile Thr Gly Leu
              420                 425                 430

Leu Leu Thr Arg Asp Gly Gly Lys Asn Asp Thr Asp Thr Phe Arg Pro
          435                 440                 445

Glu Gly Gly Asn Met Lys Asp Asn Trp Arg Ser Glu Leu Tyr Lys Tyr
450                 455                 460

Lys Val Glu Val Lys Pro Leu Gly Val Ala Pro Thr Asn Ala Arg
465                 470                 475                 480

Glu Arg Val Val Glu Arg Glu Lys Glu
              485

<210> SEQ ID NO 30
<211> LENGTH: 1517
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ggtcgacaag aagccaccat gcgcgtgatg ggcatccagc gcaactaccc gcagtggtgg      60
atctggtcga tgctgggctt ctggatgctc atgatctgca acggcgtgcc ggtgtggaag     120
gaggccaaga cgaccctgtt ctgcgcgtcg gacgccaagg cctacgagaa ggaggtgcac     180
aacgtgtggg cgacccacgc ctgcgtgccc acggacccca acccgcagga gatggtgctg     240
aagaacgtga ccgagaactt caacatgtgg aagaacgaca tggtggacca gatgcacgag     300
gacgtgatct ccctgtggga ccagtccctg aagccctgcg tgaagctgac cccgctgtgc     360
gtgaccctga gctgcacgaa cgccaccaac gcgacggcgt cgaactcgtc catcctcgag     420
gggatgaaga actgctcctt caacatcacg acggagctgc gcgacaagcg cgagaagaag     480
aacgccctgt tctacaagct ggacatcgtg cagctggacg gcaactcctc gcagtacagg     540
ctgatcaact gcaacacctc cgtcatcacg caggcgtgcc ccaaggtgtc cttcgacccc     600
atccccatcc actactgcgc ccccgccggc tacgccatcc tgaagtgcaa caacaagacc     660
ttcaacggca ccggcccgtg caacaacgtg tccaccgtgc agtgcacgca cgggatcaag     720
cccgtggtgt ccacgcagct gctcctgaac gggtcgctgg ccgagggcga gatcatcatc     780
cggtcgaaga acatcacgga caacgggaag accatcatcg tgcacctgaa cgagtccgtg     840
aagatcgagt gcacccgccc gagcaacaac acgcgcacct ccatccggat cggccctggc     900
caggccttct acgccaccgg ccaggtgatc ggcgacatcc gcgaggcgca ctgcaacatc     960
tccgagtcca gtggaacga ccctgcag cgcgtgtccg agaagctgaa ggagtacttc    1020
ccccacaaga acatcacctt ccagccgtcg tccggcggcg acctcgagat caccacgcac    1080
tccttcaact gcggtggcga gttcttctac tgcaacacgt cgtcgctgtt caaccgcacc    1140
tacatggcca cctccaccga catggccaac tccaccgaga ccaactccac gcgcatcatc    1200
acgatccgct gccgcatcaa gcagatcatc aacatgtggc aggaggtggg ccgcgccatg    1260
tacgcaccgc ccatcgccgg caacatcacc tgcatctcca acatcaccgg cctcctgctg    1320
acccgcgacg gcggcaagaa cgacacggac accttcaggc cagagggagg caacatgaag    1380
gacaactggc gctccgagct gtacaagtac aaggtggtgg aggtgaagcc cctgggcgtg    1440
gcacccacca acgcccgcga gcgcgtcgtg gagcgcgaga aggagtagta agaattcggt    1500
caccgggtcc tggatcc                                                   1517

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<211> LENGTH: 2140
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
gtcgacaaga agccaccatg cgcgtgatgg gcatccagcg caactacccg cagtggtgga     60
tctggtcgat gctgggcttc tgatgctca tgatctgcaa cggcatgtgg gtgacggtgt    120
actacggcgt gccggtgtgg aaggaggcca agacgaccct gttctgcgcg tcggacgcca    180

```
aggcctacga  gaaggaggtg  cacaacgtgt  gggcgaccca  cgcctgcgtg  cccacggacc       240
ccaacccgca  ggagatggtg  ctgaagaacg  tgaccgagaa  cttcaacatg  tggaagaacg       300
acatggtgga  ccagatgcac  gaggacgtga  tctccctgtg  ggaccagtcc  ctgaagccct       360
gcgtgaagct  gaccccgctg  tgcgtgaccc  tgagctgcac  gaacgccacc  aacgcgacgg       420
cgtcgaactc  gtccatcctc  gagggatga   agaactgctc  cttcaacatc  acgacggagc       480
tgcgcgacaa  cgcgagaag   aagaacgccc  tgttctacaa  gctggacatc  gtgcagctgg       540
acggcaactc  ctcgcagtac  aggctgatca  actgcaacac  ctccgtcatc  acgcaggcgt       600
gccccaaggt  gtccttcgac  ccatccccca  tccactactg  cgcccccgcc  ggctacgcca       660
tcctgaagtg  caacaacaag  accttcaacg  gcaccggccc  gtgcaacaac  gtgtccaccg       720
tgcagtgcac  gcacgggatc  aagcccgtgg  tgtccacgca  gctgctcctg  aacgggtcgc       780
tggccgaggg  cgagatcatc  atccggtcga  agaacatcac  ggacaacggg  aagaccatca       840
tcgtgcacct  gaacgagtcc  gtgaagatcg  agtgcacccg  cccgagcaac  aacacgcgca       900
cctccatccg  gatcggccct  ggccaggcct  tctacgccac  cggccaggtg  atcggcgaca       960
tccgcgaggc  gcactgcaac  atctccgagt  ccaagtggaa  cgagaccctg  cagcgcgtgt      1020
ccgagaagct  gaaggagtac  ttcccccaca  gaacatcac   cttccagccg  tcgtccggcg      1080
gcgacctcga  gatcaccacg  cactccttca  actgcggtgg  cgagttcttc  tactgcaaca      1140
cgtcgtcgct  gttcaaccgc  acctacatgg  ccacctccac  cgacatggcc  aactccaccg      1200
agaccaactc  cacgcgcatc  atcacgatcc  gctgccgcat  caagcagatc  atcaacatgt      1260
ggcaggaggt  gggccgcgcc  atgtacgcac  cgcccatcgc  cggcaacatc  acctgcatct      1320
ccaacatcac  cggcctcctg  ctgacccgcg  acggcggcaa  gaacgacacg  gacaccttca      1380
ggccagaggg  aggcaacatg  aaggacaact  ggcgctccga  gctgtacaag  tacaaggtgg      1440
tggaggtgaa  gccctgggc   gtggcaccca  ccaacgcccg  caggcgcgtc  gtggagcgcg      1500
agaagcgcgc  cgtgggcatg  ggcgccgtgt  tcctgggctt  cctgggcgct  gcgggctcca      1560
ccatgggtgc  cgcgtccatc  accctgaccg  tgcaggcccg  ccagctgctc  tccggcatcg      1620
tgcagcagca  gtccaacctc  ctgaaggcca  tcgaggccca  gcagcacatg  ctgaagctga      1680
ccgtgtgggg  catcaagcag  ctgcaggcca  gggtgctcgc  gctcgagcgc  tacctgaagg      1740
accagcagct  gctcggcatg  tggggctgct  ccggcaagct  gatctgcacc  accaacgtgt      1800
actggaactc  gtcctggtcc  aacaagacct  acggcgacat  ctgggacaac  atgacctgga      1860
tgcagtggga  gcgcgagatc  tccaactaca  ccgagctgat  ctacgagctc  ctcgaggagt      1920
cccagaacca  gcaggagaag  aacgagcagg  atctgctcgc  gctggaccgc  tggaactccc      1980 tgtgaactg   gttcaacatc  accaactggc  tgtggtacat  caagatcttc  atcatgatcg      2040
tgggcggcct  gatcggcctg  cgcatcatct  tcgccgtgct  gtcgctggtg  aaccgcgtgc      2100
gccagggctg  atgagaattc  ggtcaccggg  tcctggatcc                              2140
```

<210> SEQ ID NO 41
<211> LENGTH: 849
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Met Arg Val Met Gly Ile Gln Arg Asn Tyr Pro Gln Trp Trp Ile Trp

-continued

```
1               5                   10                  15
Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
                35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
                100                 105                 110

Lys Pro Cys Val Lys Leu Thr Pro Leu Cys Val Thr Leu Ser Cys Thr
                115                 120                 125

Asn Ala Thr Asn Ala Thr Ala Ser Asn Ser Ser Ile Leu Glu Gly Met
    130                 135                 140

Lys Asn Cys Ser Phe Asn Ile Thr Thr Glu Leu Arg Asp Lys Arg Glu
145                 150                 155                 160

Lys Lys Asn Ala Leu Phe Tyr Lys Leu Asp Ile Val Gln Leu Asp Gly
                165                 170                 175

Asn Ser Ser Gln Tyr Arg Leu Ile Asn Cys Asn Thr Ser Val Ile Thr
                180                 185                 190

Gln Ala Cys Pro Lys Val Ser Phe Asp Pro Ile Pro Ile His Tyr Cys
                195                 200                 205

Ala Pro Ala Gly Tyr Ala Ile Leu Lys Cys Asn Asn Lys Thr Phe Asn
    210                 215                 220

Gly Thr Gly Pro Cys Asn Asn Val Ser Thr Val Gln Cys Thr His Gly
225                 230                 235                 240

Ile Lys Pro Val Val Ser Thr Gln Leu Leu Leu Asn Gly Ser Leu Ala
                245                 250                 255

Glu Gly Glu Ile Ile Ile Arg Ser Lys Asn Ile Thr Asp Asn Gly Lys
                260                 265                 270

Thr Ile Ile Val His Leu Asn Glu Ser Val Lys Ile Glu Cys Thr Arg
                275                 280                 285

Pro Ser Asn Asn Thr Arg Thr Ser Ile Arg Ile Gly Pro Gly Gln Ala
    290                 295                 300

Phe Tyr Ala Thr Gly Gln Val Ile Gly Asp Ile Arg Glu Ala His Cys
305                 310                 315                 320

Asn Ile Ser Glu Ser Lys Trp Asn Glu Thr Leu Gln Arg Val Ser Glu
                325                 330                 335

Lys Leu Lys Glu Tyr Phe Pro His Lys Asn Ile Thr Phe Gln Pro Ser
                340                 345                 350

Ser Gly Gly Asp Leu Glu Ile Thr Thr His Ser Phe Asn Cys Gly Gly
                355                 360                 365

Glu Phe Phe Tyr Cys Asn Thr Ser Ser Leu Phe Asn Arg Thr Tyr Met
    370                 375                 380

Ala Thr Ser Thr Asp Met Ala Asn Ser Thr Glu Thr Asn Ser Thr Arg
385                 390                 395                 400

Ile Ile Thr Ile Arg Cys Arg Ile Lys Gln Ile Ile Asn Met Trp Gln
                405                 410                 415

Glu Val Gly Arg Ala Met Tyr Ala Pro Pro Ile Ala Gly Asn Ile Thr
                420                 425                 430
```

```
Cys Ile Ser Asn Ile Thr Gly Leu Leu Leu Thr Arg Asp Gly Gly Lys
            435                 440                 445

Asn Asp Thr Asp Thr Phe Arg Pro Glu Gly Gly Asn Met Lys Asp Asn
450                 455                 460

Trp Arg Ser Glu Leu Tyr Lys Tyr Lys Val Val Glu Val Lys Pro Leu
465                 470                 475                 480

Gly Val Ala Pro Thr Asn Ala Arg Arg Val Val Glu Arg Glu Lys
                485                 490                 495

Arg Ala Val Gly Met Gly Ala Val Phe Leu Gly Phe Leu Gly Ala Ala
                500                 505                 510

Gly Ser Thr Met Gly Ala Ala Ser Ile Thr Leu Thr Val Gln Ala Arg
                515                 520                 525

Gln Leu Leu Ser Gly Ile Val Gln Gln Gln Ser Asn Leu Leu Lys Ala
            530                 535                 540

Ile Glu Ala Gln Gln His Met Leu Lys Leu Thr Val Trp Gly Ile Lys
545                 550                 555                 560

Gln Leu Gln Ala Arg Val Leu Ala Leu Glu Arg Tyr Leu Lys Asp Gln
                565                 570                 575

Gln Leu Leu Gly Met Trp Gly Cys Ser Gly Lys Leu Ile Cys Thr Thr
            580                 585                 590

Asn Val Tyr Trp Asn Ser Ser Trp Ser Asn Lys Thr Tyr Gly Asp Ile
            595                 600                 605

Trp Asp Asn Met Thr Trp Met Gln Trp Glu Arg Glu Ile Ser Asn Tyr
        610                 615                 620

Thr Glu Leu Ile Tyr Glu Leu Leu Glu Glu Ser Gln Asn Gln Gln Glu
625                 630                 635                 640

Lys Asn Glu Gln Asp Leu Leu Ala Leu Asp Arg Trp Asn Ser Leu Trp
                645                 650                 655

Asn Trp Phe Asn Ile Thr Asn Trp Leu Trp Tyr Ile Lys Ile Phe Ile
                660                 665                 670

Met Ile Val Gly Gly Leu Ile Gly Leu Arg Ile Ile Phe Ala Val Leu
        675                 680                 685

Ser Leu Val Asn Arg Val Arg Gln Gly Tyr Ser Pro Leu Ser Leu Gln
        690                 695                 700

Thr Leu Ile Pro Ser Pro Arg Gly Pro Asp Arg Pro Gly Gly Ile Glu
705                 710                 715                 720

Glu Glu Gly Gly Glu Gln Asp Arg Asn Arg Ser Thr Arg Leu Val Ser
                725                 730                 735

Gly Phe Leu Ala Leu Ala Trp Asp Asp Leu Arg Ser Leu Cys Leu Phe
                740                 745                 750

Ile Tyr His Arg Leu Arg Asp Phe Ile Leu Ile Ala Ala Arg Ala Gly
        755                 760                 765

Glu Leu Leu Gly Arg Ser Ser Leu Lys Gly Leu Arg Arg Gly Trp Glu
        770                 775                 780

Ala Leu Lys Tyr Leu Gly Asn Leu Val Gln Tyr Trp Gly Leu Glu Leu
785                 790                 795                 800

Lys Arg Ser Ala Ile Ser Leu Leu Asp Thr Leu Ala Ile Ala Val Gly
                805                 810                 815

Glu Gly Thr Asp Arg Ile Leu Glu Phe Val Leu Gly Ile Cys Arg Ala
                820                 825                 830

Ile Arg Asn Ile Pro Thr Arg Ile Arg Gln Gly Phe Glu Thr Ala Leu
                835                 840                 845
```

Leu

<210> SEQ ID NO 42
<211> LENGTH: 2590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| | | | | | |
|---|---|---|---|---|---|
| gtcgacaaga | aatgcgcgtg | atgggcatcc | agcgcaacta | cccgcagtgg | tggatctggt | 60 |
| cgatgctggg | cttctggatg | ctcatgatct | gcaacggcat | gtgggtgacg | gtgtactacg | 120 |
| gcgtgccggt | gtggaaggag | gccaagacga | ccctgttctg | cgcgtcggac | gccaaggcct | 180 |
| acgagaagga | ggtgcacaac | gtgtgggcga | cccacgcctg | cgtgcccacg | accccaacc | 240 |
| cgcaggagat | ggtgctgaag | aacgtgaccg | agaacttcaa | catgtggaag | aacgacatgg | 300 |
| tggaccagat | gcacgaggac | gtgatctccc | tgtgggacca | gtccctgaag | ccctgcgtga | 360 |
| agctgacccc | gctgtgcgtg | accctgagct | gcacgaacgc | caccaacgcg | acggcgtcga | 420 |
| actcgtccat | cctcgagggg | atgaagaact | gctccttcaa | catcacgacg | gagctgcgcg | 480 |
| acaagcgcga | gaagaagaac | gccctgttct | acaagctgga | catcgtgcag | ctggacggca | 540 |
| actcctcgca | gtacaggctg | atcaactgca | acacctccgt | catcacgcag | gcgtgcccca | 600 |
| aggtgtcctt | cgaccccatc | cccatccact | actgcgcccc | cgccggctac | gccatcctga | 660 |
| agtgcaacaa | caagaccttc | aacggcaccg | gcccgtgcaa | caacgtgtcc | accgtgcagt | 720 |
| gcacgcacgg | gatcaagccc | gtggtgtcca | cgcagctgct | cctgaacggg | tcgctggccg | 780 |
| agggcgagat | catcatccgg | tcgaagaaca | tcacggacaa | cgggaagacc | atcatcgtgc | 840 |
| acctgaacga | gtccgtgaag | atcgagtgca | cccgcccgag | caacaacacg | cgcacctcca | 900 |
| tccggatcgg | ccctggccag | gccttctacg | ccaccggcca | ggtgatcggc | gacatccgcg | 960 |
| aggcgcactg | caacatctcc | gagtccaagt | ggaacgagac | cctgcagcgc | gtgtccgaga | 1020 |
| agctgaagga | gtacttcccc | cacaagaaca | tcaccttcca | gccgtcgtcc | ggcggcgacc | 1080 |
| tcgagatcac | cacgcactcc | ttcaactgcg | gtggcgagtt | cttctactgc | aacacgtcgt | 1140 |
| cgctgttcaa | ccgcacctac | atggccacct | ccaccgacat | ggccaactcc | accgagacca | 1200 |
| actccacgcg | catcatcacg | atccgctgcc | gcatcaagca | gatcatcaac | atgtggcagg | 1260 |
| aggtgggccg | cgccatgtac | gcaccgccca | tcgccggcaa | catcacctgc | atctccaaca | 1320 |
| tcaccggcct | cctgctgacc | cgcgacgcg | gcaagaacga | cacggacacc | ttcaggccag | 1380 |
| agggaggcaa | catgaaggac | aactggcgct | ccgagctgta | caagtacaag | gtggtggagg | 1440 |
| tgaagcccct | gggcgtggca | cccaccaacg | cccgcaggcg | cgtcgtggag | cgcgagaagc | 1500 |
| gcgccgtggg | catgggcgcc | gtgttcctgg | gcttcctggg | cgctgcgggc | tccaccatgg | 1560 |
| gtgccgcgtc | catcacccctg | accgtgcagg | cccgccagct | gctctccggc | atcgtgcagc | 1620 |
| agcagtccaa | cctcctgaag | gccatcgagg | cccagcagca | catgctgaag | ctgaccgtgt | 1680 |
| ggggcatcaa | gcagctgcag | gccagggtgc | tcgcgctcga | gcgctacctg | aaggaccagc | 1740 |
| agctgctcgg | catgtgggc | tgctccggca | agctgatctg | caccaccaac | gtgtactgga | 1800 |
| actcgtcctg | gtccaacaag | acctacggcg | acatctggga | caacatgacc | tggatgcagt | 1860 |
| gggagcgcga | gatctccaac | tacaccgagc | tgatctacga | gctcctcgag | gagtcccaga | 1920 |
| accagcagga | gaagaacgag | caggatctgc | tcgcgctgga | ccgctggaac | tccctgtgga | 1980 |

```
actggttcaa catcaccaac tggctgtggt acatcaagat cttcatcatg atcgtgggcg    2040
gcctgatcgg cctgcgcatc atcttcgccg tgctgtcgct ggtgaaccgc gtgcgccagg    2100
gctactcccc gctgtccctg caaacgctga tccctccccc ccggggcccg gacaggcccg    2160
gtggcatcga ggaggagggc ggcgagcagg accgcaaccg ctccacgcgc ctggtgtccg    2220
gcttcctggc cctggcgtgg gacgacctgc gctccctgtg cctgttcatc taccaccgcc    2280
tgcgcgactt catcctgatc gcggcccgcg ctggcgagct gctgggccgg tcctcgctga    2340
agggcctgcg ccgcggctgg gaggccctga agtacctggg caacctggtg cagtactggg    2400
gcctggagct gaagcgctcc gccatctccc tgctggacac cctggccatc gccgtgggcg    2460
agggcaccga ccgcatcctg gagttcgtgc tgggcatctg ccgcgccatc cgcaacatcc    2520
ccacccgcat ccgccagggc ttcgagaccg ccctcctgta gtaagaattc ggtcaccggg    2580
tcctggatcc                                                          2590
```

<210> SEQ ID NO 43
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asp Ala Thr Ala Ser Asn Ala Thr
        115                 120                 125

Ala Ser Asn Ala Thr Ala Ser Asn Ser Ile Ile Glu Gly Met Lys
    130                 135                 140

Asn Cys Ser Phe Asn Ile Thr Thr Glu Leu Arg Asp Lys Arg Glu Lys
145                 150                 155                 160

Lys Asn Ala Leu Phe Tyr Lys Leu Asp Ile Val Gln Leu Asp Gly Asn
                165                 170                 175

Ser Ser Gln Tyr Arg Leu Ile Asn Cys Asn Thr Ser Val Ile Thr Gln
            180                 185                 190

Ala Cys Pro Lys Val Ser Phe Asp Pro Ile Pro Ile His Tyr Cys Ala
        195                 200                 205

Pro Ala Gly Tyr Ala Ile Leu Lys Cys Asn Asn Lys Thr Phe Asn Gly
    210                 215                 220

Thr Gly Pro Cys Asn Asn Val Ser Thr Val Gln Cys Thr His Gly Ile
225                 230                 235                 240

Lys Pro Val Val Ser Thr Gln Leu Leu Leu Asn Gly Ser Leu Ala Glu

```
                  245                 250                 255
Gly Glu Ile Ile Ile Arg Ser Glu Asn Ile Thr Asp Asn Gly Lys Thr
            260                 265                 270
Ile Ile Val His Leu Asn Glu Ser Val Lys Ile Glu Cys Thr Arg Pro
        275                 280                 285
Ser Asn Asn Thr Arg Thr Ser Ile Arg Ile Gly Pro Gly Gln Ala Phe
    290                 295                 300
Tyr Ala Thr Gly Gln Val Ile Gly Asp Ile Arg Glu Ala His Cys Asn
305                 310                 315                 320
Ile Ser Glu Ser Lys Trp Asn Glu Thr Leu Gln Arg Val Ser Lys Lys
                325                 330                 335
Leu Lys Glu Tyr Phe Pro His Lys Asn Ile Thr Phe Gln Pro Ser Ser
            340                 345                 350
Gly Gly Asp Leu Glu Ile Thr Thr His Ser Phe Asn Cys Gly Gly Glu
        355                 360                 365
Phe Phe Tyr Cys Asn Thr Ser Ser Leu Phe Asn Arg Thr Tyr Met Ala
    370                 375                 380
Asn Ser Thr Glu Thr Asn Ser Thr Arg Ile Ile Thr Ile Arg Cys Arg
385                 390                 395                 400
Ile Lys Gln Ile Ile Asn Met Trp Gln Glu Val Gly Arg Ala Met Tyr
                405                 410                 415
Ala Pro Pro Ile Ala Gly Asn Ile Thr Cys Ile Ser Asn Ile Thr Gly
            420                 425                 430
Leu Leu Leu Thr Arg Asp Gly Gly Asn Asn Asn Thr Glu Thr Phe Arg
        435                 440                 445
Pro Gly Gly Gly Asn Met Lys Asp Asn Trp Arg Ser Glu Leu Tyr Lys
    450                 455                 460
Tyr Lys Val Val Glu Val Lys Pro Leu Gly Val Ala Pro Thr Asn Ala
465                 470                 475                 480
Arg Glu Arg Val Val Glu Arg Glu Lys Glu
                485                 490
```

<210> SEQ ID NO 44
<211> LENGTH: 1520
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
ggtcgacaag aagccaccat gcgcgtgatg ggcatccagc gcaactaccc gcagtggtgg    60
atctggtcga tgctgggctt ctggatgctc atgatctgca acggcgtgcc ggtgtggaag   120
gaggccaaga cgaccctgtt ctgcgcgtcg acgccaagg cctacgagaa ggaggtgcac    180
aacgtgtggg cgacccacgc ctgcgtgccc acggacccca cccgcaggga gatggtgctg   240
aagaacgtga ccgagaactt caacatgtgg aagaacgaca tggtggacca gatgcacgag   300
gacgtgatct ccctgtggga ccagtccctg aagccctgcg tgaagctgac cccgctgtgc   360
gtgacgctga actgcaccga cgccaccgcg tccaacgcaa ccgcgagcaa cgccacggcg   420
tcgaactcct ccatcatcga gggcatgaag aactgctcct tcaacatcac gacggagctg   480
cgcgacaagc gcgagaagaa gaacgccctg ttctacaagc tggacatcgt gcagctggac   540
ggcaactcct cgcagtacag gctgatcaac tgcaacacct ccgtcatcac gcaggcgtgc   600
cccaaggtgt ccttcgaccc catccccatc cactactgcg ccccccgccgg ctacgccatc   660
```

```
ctgaagtgca acaacaagac cttcaacggc accggcccgt gcaacaacgt gtccaccgtg      720
cagtgcacgc acgggatcaa gcccgtggtg tccacgcagc tgctcctgaa cgggtcgctg      780
gccgagggcg agatcatcat ccggtccgag aacatcacgg acaacgggaa gaccatcatc      840
gtgcacctga cgagtccgt gaagatcgag tgcacccgcc cgtcgaacaa cacgcgcacc       900
tccatccgga tcggccctgg ccaggccttc tacgccaccg gccaggtgat cggcgacatc      960
cgcgaggcgc actgcaacat ctcggagtcc aagtggaacg agaccctgca gcgcgtgtcc     1020
aagaagctga aggagtactt ccccacaag aacatcacct tccagccgtc gtccggcggc      1080
gacctcgaga tcaccacgca ctccttcaac tgcggtggcg agttcttcta ctgcaacacg     1140
tcgtcgctgt tcaaccgcac ctacatggcc aactccaccg agaccaactc cacgcgcatc     1200
atcacgatcc gctgccgcat caagcagatc atcaacatgt ggcaggaggt gggccgcgcc     1260
atgtacgcac cgcccatcgc cggcaacatc acctgcatct ccaacatcac cggcctcctg     1320
ctgacccgcg acgcggcaa caacaacacg gagaccttca ggccaggcgg aggcaacatg      1380
aaggacaact ggcgctccga gctgtacaag tacaaggtgg tggaggtgaa gcccctgggc     1440
gtggcaccca ccaacgcccg cgagcgcgtc gtggagcgcg agaaggagta gtaagaattc     1500
ggtgaccggg acctggatcc                                                 1520

<210> SEQ ID NO 45
<211> LENGTH: 2143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gtcgacaaga agccaccatg cgcgtgatgg gcatccagcg caactacccg cagtggtgga       60
tctggtcgat gctgggcttc tggatgctca tgatctgcaa cggcatgtgg gtgacggtgt      120
actacggcgt gccggtgtgg aaggaggcca agacgaccct gttctgcgcg tcggacgcca      180
aggcctacga gaaggaggtg cacaacgtgt gggcgaccca cgcctgcgtg cccacggacc      240
ccaacccgca ggagatggtg ctgaagaacg tgaccgagaa cttcaacatg tggaagaacg      300
acatggtgga ccagatgcac gaggacgtga tctccctgtg ggaccagtcc ctgaagccct      360
gcgtgaagct gaccccgctg tgcgtgaccc tgaactgcac cgacgccacc gcgtccaacg      420
caaccgcgag caacgccacg gcgtcgaact cctccatcat cgagggcatg aagaactgct      480
ccttcaacat cacgacggag ctgcgcgaca agcgcgagaa gaagaacgcc ctgttctaca      540
agctggacat cgtgcagctg acggcaact cctcgcagta caggctgatc aactgcaaca      600
cctccgtcat cacgcaggcg tgccccaagg tgtccttcga ccccatcccc atccactact      660
gcgcccccgc cggctacgcc atcctgaagt gcaacaacaa gaccttcaac ggcaccggcc      720
cgtgcaacaa cgtgtccacc gtgcagtgca cgcacgggat caagcccgtg gtgtccacgc      780
agctgctcct gaacgggtcg ctggccgagg gcgagatcat catccggtcc gagaacatca      840
cggacaacgg gaagaccatc atcgtgcacc tgaacgagtc cgtgaagatc gagtgcaccc      900
gcccgtcgaa caacacgcgc acctccatcc ggatcggccc tggccaggcc ttctacgcca      960
ccggccaggt gatcggcgac atcgcgagg cgcactgcaa catctcggag tccaagtgga     1020
acgagaccct gcagcgcgtg tccaagaagc tgaaggagta cttcccccac aagaacatca     1080
ccttccagcc gtcgtccggc ggcgacctcg agatcaccac gcactccttc aactgcggtg     1140
```

```
gcgagttctt ctactgcaac acgtcgtcgc tgttcaaccg cacctacatg gccaactcca    1200
ccgagaccaa ctccacgcgc atcatcacga tccgctgccg catcaagcag atcatcaaca    1260
tgtggcagga ggtgggccgc gccatgtacg caccgcccat cgccggcaac atcacctgca    1320
tctccaacat caccggcctc ctgctgaccc gcgacggcgg caacaacaac acggagacct    1380
tcaggccagg cggaggcaac atgaaggaca actggcgctc cgagctgtac aagtacaagg    1440
tggtggaggt gaagcccctg gcgtggcac ccaccaacgc ccgcaggcgc gtcgtggagc    1500
gcgagaagcg cgccgtgggc atgggcgccg tgttcctggg cttcctgggc gctgcgggct    1560
ccaccatggg tgccgcgtcc atcaccctga ccgtgcaggc ccgccagctg ctctccggca    1620
tcgtgcagca gcagtccaac ctcctgaagg ccatcggggc ccagcagcac atgctgaagc    1680
tgaccgtgtg gggcatcaag cagctgcagg ccagggtgct cgcgctcgag cgctacctga    1740
aggaccagca gctgctcggc atgtggggct gctccggcaa gctgatctgc accaccaacg    1800
tgtactggaa ctcgtcctgg tccaacaaga cctacgccga catctgggac aacatgacct    1860
ggatgcagtg ggagcgcgag atctccaact acaccgagat gatctacgag ctcctcgagg    1920
agtcccagaa ccagcaggag aagaacgagc aggatctgct cgcgctggac cgctggaact    1980
ccctgtggaa ctggttcaac atcaccaact ggctgtggta catcaagatc ttcatcatga    2040
tcgtgggcgg cctgatcggc ctgcgcatca tcttcgccgt gctgtcgctg gtgaaccgcg    2100
tgcgccaggg ctgatgagaa ttcggtgacc gggacctgga tcc                     2143
```

<210> SEQ ID NO 46
<211> LENGTH: 850
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Ala Thr Ala Ser Asn Ala Thr Ala Ser Asn Ala Thr Ala Ser Asn
    130                 135                 140

Ser Ser Ile Ile Glu Gly Met Lys Asn Cys Ser Phe Asn Ile Thr Thr
145                 150                 155                 160

Glu Leu Arg Asp Lys Arg Glu Lys Asn Ala Leu Phe Tyr Lys Leu
                165                 170                 175

```
Asp Ile Val Gln Leu Asp Gly Asn Ser Ser Gln Tyr Arg Leu Ile Asn
            180                 185                 190

Cys Asn Thr Ser Val Ile Thr Gln Ala Cys Pro Lys Val Ser Phe Asp
        195                 200                 205

Pro Ile Pro Ile His Tyr Cys Ala Pro Ala Gly Tyr Ala Ile Leu Lys
    210                 215                 220

Cys Asn Asn Lys Thr Phe Asn Gly Thr Gly Pro Cys Asn Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Gly Glu Ile Ile Ile Arg Ser Glu
            260                 265                 270

Asn Ile Thr Asp Asn Gly Lys Thr Ile Ile Val His Leu Asn Glu Ser
        275                 280                 285

Val Lys Ile Glu Cys Thr Arg Pro Ser Asn Asn Thr Arg Thr Ser Ile
    290                 295                 300

Arg Ile Gly Pro Gly Gln Ala Phe Tyr Ala Thr Gly Gln Val Ile Gly
305                 310                 315                 320

Asp Ile Arg Glu Ala His Cys Asn Ile Ser Glu Ser Lys Trp Asn Glu
                325                 330                 335

Thr Leu Gln Arg Val Ser Lys Lys Leu Lys Glu Tyr Phe Pro His Lys
            340                 345                 350

Asn Ile Thr Phe Gln Pro Ser Ser Gly Gly Asp Leu Glu Ile Thr Thr
        355                 360                 365

His Ser Phe Asn Cys Gly Gly Glu Phe Phe Tyr Cys Asn Thr Ser Ser
    370                 375                 380

Leu Phe Asn Arg Thr Tyr Met Ala Asn Ser Thr Glu Thr Asn Ser Thr
385                 390                 395                 400

Arg Ile Ile Thr Ile Arg Cys Arg Ile Lys Gln Ile Ile Asn Met Trp
                405                 410                 415

Gln Glu Val Gly Arg Ala Met Tyr Ala Pro Pro Ile Ala Gly Asn Ile
            420                 425                 430

Thr Cys Ile Ser Asn Ile Thr Gly Leu Leu Leu Thr Arg Asp Gly Gly
        435                 440                 445

Asn Asn Asn Thr Glu Thr Phe Arg Pro Gly Gly Gly Asn Met Lys Asp
450                 455                 460

Asn Trp Arg Ser Glu Leu Tyr Lys Tyr Lys Val Glu Val Lys Pro
465                 470                 475                 480

Leu Gly Val Ala Pro Thr Asn Ala Arg Arg Val Val Glu Arg Glu
                485                 490                 495

Lys Arg Ala Val Gly Met Gly Ala Val Phe Leu Gly Phe Leu Gly Ala
            500                 505                 510

Ala Gly Ser Thr Met Gly Ala Ala Ser Ile Thr Leu Thr Val Gln Ala
        515                 520                 525

Arg Gln Leu Leu Ser Gly Ile Val Gln Gln Ser Asn Leu Leu Lys
            530                 535                 540

Ala Ile Gly Ala Gln Gln His Met Leu Lys Leu Thr Val Trp Gly Ile
545                 550                 555                 560

Lys Gln Leu Gln Ala Arg Val Leu Ala Leu Glu Arg Tyr Leu Lys Asp
                565                 570                 575

Gln Gln Leu Leu Gly Met Trp Gly Cys Ser Gly Lys Leu Ile Cys Thr
            580                 585                 590

Thr Asn Val Tyr Trp Asn Ser Ser Trp Ser Asn Lys Thr Tyr Gly Asp
```

```
                595                 600                 605
Ile Trp Asp Asn Met Thr Trp Met Gln Trp Glu Arg Glu Ile Ser Asn
        610                 615                 620
Tyr Thr Glu Met Ile Tyr Glu Leu Leu Glu Glu Ser Gln Asn Gln Gln
625                 630                 635                 640
Glu Lys Asn Glu Gln Asp Leu Leu Ala Leu Asp Arg Trp Asn Ser Leu
                645                 650                 655
Trp Asn Trp Phe Asn Ile Thr Asn Trp Leu Trp Tyr Ile Lys Ile Phe
            660                 665                 670
Ile Met Ile Val Gly Gly Leu Ile Gly Leu Arg Ile Ile Phe Ala Val
            675                 680                 685
Leu Ser Leu Val Asn Arg Val Arg Gln Gly Tyr Ser Pro Leu Ser Leu
        690                 695                 700
Gln Thr Leu Ile Pro Ser Pro Arg Gly Pro Asp Arg Pro Gly Gly Ile
705                 710                 715                 720
Glu Glu Glu Gly Gly Glu Gln Asp Arg Lys Arg Ser Thr Arg Leu Val
                725                 730                 735
Ser Gly Phe Leu Ala Leu Val Trp Asp Asp Leu Arg Ser Leu Cys Leu
            740                 745                 750
Phe Ile Tyr His Arg Leu Arg Asp Phe Ile Leu Ile Ala Ala Arg Ala
            755                 760                 765
Gly Glu Leu Leu Gly Arg Ser Ser Leu Lys Gly Leu Arg Arg Gly Trp
770                 775                 780
Glu Ala Leu Lys Tyr Leu Gly Ser Leu Val Gln Tyr Trp Gly Leu Glu
785                 790                 795                 800
Leu Lys Arg Ser Ala Ile Ser Leu Leu Asp Thr Leu Ala Ile Ala Val
                805                 810                 815
Gly Glu Gly Thr Asp Arg Ile Leu Glu Phe Ala Leu Gly Ile Cys Arg
            820                 825                 830
Ala Ile Arg Asn Ile Pro Thr Arg Ile Arg Gln Gly Phe Glu Thr Ala
            835                 840                 845
Leu Leu
    850

<210> SEQ ID NO 47
<211> LENGTH: 2593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gtcgacaaga aatgcgcgtg atgggcatcc agcgcaacta cccgcagtgg tggatctggt     60
cgatgctggg cttctggatg ctcatgatct gcaacggcat gtgggtgacg gtgtactacg    120
gcgtgccggt gtggaaggag gccaagacga ccctgttctg cgcgtcggac gccaaggcct    180
acgagaagga ggtgcacaac gtgtgggcga cccacgcctg cgtgcccacg acccccaacc    240
cgcaggagat ggtgctgaag aacgtgaccg agaacttcaa catgtggaag aacgacatgg    300
tggaccagat gcacgaggac gtgatctccc tgtgggacca gtccctgaag ccctgcgtga    360
agctgacccc gctgtgcgtg accctgaact gcaccgacgc caccgcgtcc aacgcaaccg    420
cgagcaacgc cacggcgtcg aactcctcca tcatcgaggg catgaagaac tgctccttca    480
acatcacgac ggagctgcgc gacaagcgcg agaagaagaa cgccctgttc tacaagctgg    540
```

```
acatcgtgca gctggacggc aactcctcgc agtacaggct gatcaactgc aacacctccg    600
tcatcacgca ggcgtgcccc aaggtgtcct tcgaccccat ccccatccac tactgcgccc    660
ccgccggcta cgccatcctg aagtgcaaca acaagacctt caacggcacc ggcccgtgca    720
acaacgtgtc caccgtgcag tgcacgcacg ggatcaagcc cgtggtgtcc acgcagctgc    780
tcctgaacgg gtcgctggcc gagggcgaga tcatcatccg gtccgagaac atcacggaca    840
acgggaagac catcatcgtg cacctgaacg agtccgtgaa gatcgagtgc acccgcccgt    900
cgaacaacac gcgcacctcc atccggatcg gccctggcca ggccttctac gccaccggcc    960
aggtgatcgg cgacatccgc gaggcgcact gcaacatctc ggagtccaag tggaacgaga    1020
ccctgcagcg cgtgtccaag aagctgaagg agtacttccc ccacaagaac atcaccttcc    1080
agccgtcgtc cggcggcgac ctcgagatca ccacgcactc cttcaactgc ggtggcgagt    1140
tcttctactg caacacgtcg tcgctgttca accgcaccta catggccaac tccaccgaga    1200
ccaactccac gcgcatcatc acgatccgct gccgcatcaa gcagatcatc aacatgtggc    1260
aggaggtggg ccgcgccatg tacgcaccgc ccatcgccgg caacatcacc tgcatctcca    1320
acatcaccgg cctcctgctg acccgcgacg gcggcaacaa caacacggag accttcaggc    1380
caggcggagg caacatgaag gacaactggc gctccgagct gtacaagtac aaggtggtgg    1440
aggtgaagcc cctgggcgtg gcacccacca acgcccgcag gcgcgtcgtg gagcgcgaga    1500
agcgcgccgt gggcatgggc gccgtgttcc tgggcttcct gggcgctgcg ggctccacca    1560
tgggtgccgc gtccatcacc ctgaccgtgc aggcccgcca gctgctctcc ggcatcgtgc    1620
agcagcagtc caacctcctg aaggccatcg ggcccagca gcacatgctg aagctgaccg    1680
tgtggggcat caagcagctg caggccaggg tgctcgcgct cgagcgctac ctgaaggacc    1740
agcagctgct cggcatgtgg ggctgctccg gcaagctgat ctgcaccacc aacgtgtact    1800
ggaactcgtc ctggtccaac aagacctacg gcgacatctg ggacaacatg acctggatgc    1860
agtgggagcg cgagatctcc aactacaccg agatgatcta cgagctcctc gaggagtccc    1920
agaaccagca ggagaagaac gagcaggatc tgctcgcgct ggaccgctgg aactccctgt    1980
ggaactggtt caacatcacc aactggctgt ggtacatcaa gatcttcatc atgatcgtgg    2040
gcggcctgat cggcctgcgc atcatcttcg ccgtgctgtc gctggtgaac cgcgtgcgcc    2100
agggctactc cccgctgtcc ctgcaaacgc tgatcccctc cccccgggc ccggacaggc    2160 ccggtggcat cgaggaggag ggcggcgagc aggaccgcaa gcgctccacg cgcctggtgt    2220
ccggcttcct ggccctggtg tgggacgacc tgcgctccct gtgcctgttc atctaccacc    2280
gcctgcgcga cttcatcctg atcgcggccc gcgctggcga gctgctgggc cggtcctcgc    2340
tgaagggcct gcgccgcggc tgggaggccc tgaagtacct gggctcgctg gtgcagtact    2400
ggggcctgga gctgaagcgc tccgccatct ccctgctgga caccctggcc atcgccgtgg    2460
gcgagggcac cgaccgcatc ctggagttcg cgctgggcat ctgccgcgcc atccgcaaca    2520
tccccacccg catccgccag ggcttcgaga ccgccctcct gtagtaagaa ttcggtgacc    2580
gggacctgga tcc                                                      2593
```

<210> SEQ ID NO 48
<211> LENGTH: 490
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 48

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
            35                  40                  45

Tyr Glu Lys Glu Val His Asn Val Trp Ala Thr His Ala Cys Val Pro
        50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Thr Thr Asn Ala Thr Ala
            115                 120                 125

Ser Asn Ser Ser Ile Ile Glu Glu Met Lys Asn Cys Ser Phe Asn Ile
        130                 135                 140

Thr Thr Glu Leu Arg Asp Lys Arg Glu Lys Lys Asn Ala Leu Phe Tyr
145                 150                 155                 160

Lys Leu Asp Ile Val Gln Leu Asp Gly Asn Ser Ser Gln Tyr Arg Leu
                165                 170                 175

Ile Asn Cys Asn Thr Ser Val Ile Thr Gln Ala Cys Pro Lys Val Ser
            180                 185                 190

Phe Asp Pro Ile Pro Ile His Tyr Cys Ala Pro Ala Gly Tyr Ala Ile
        195                 200                 205

Leu Lys Cys Asn Asn Lys Thr Phe Thr Gly Thr Gly Pro Cys Asn Asn
210                 215                 220

Val Ser Thr Val Gln Cys Thr His Gly Ile Lys Pro Val Val Ser Thr
225                 230                 235                 240

Gln Leu Leu Leu Asn Gly Ser Leu Ala Glu Gly Glu Ile Ile Ile Arg
                245                 250                 255

Ser Glu Asn Ile Thr Asn Thr Ala Lys Thr Ile Ile Val His Leu Asn
            260                 265                 270

Glu Ser Val Lys Ile Glu Cys Thr Arg Pro Asn Asn Lys Thr Arg Thr
        275                 280                 285

Ser Ile Arg Ile Gly Pro Gly Gln Ala Phe Tyr Ala Thr Gly Gln Val
290                 295                 300

Ile Gly Asp Ile Arg Glu Ala Tyr Cys Asn Ile Ser Glu Ser Lys Trp
305                 310                 315                 320

Asn Glu Thr Leu Gln Arg Val Ser Lys Lys Leu Lys Glu Tyr Phe Pro
                325                 330                 335

His Lys Asn Ile Thr Phe Gln Pro Ser Ser Gly Gly Asp Leu Glu Ile
            340                 345                 350

Thr Thr His Ser Phe Asn Cys Gly Gly Glu Phe Phe Tyr Cys Asn Thr
        355                 360                 365

Ser Ser Leu Phe Asn Arg Thr Tyr Met Ala Asn Ser Thr Asp Met Ala
370                 375                 380

Asn Ser Thr Glu Thr Asn Ser Thr Arg Thr Ile Thr Ile Arg Cys Arg
385                 390                 395                 400

Ile Lys Gln Ile Ile Asn Met Trp Gln Glu Val Gly Arg Ala Met Tyr
                405                 410                 415
```

```
Ala Pro Pro Ile Ala Gly Asn Ile Thr Cys Ile Ser Asn Ile Thr Gly
            420                 425                 430
Leu Leu Leu Thr Arg Asp Gly Gly Glu Asn Asn Thr Glu Thr Phe Arg
        435                 440                 445
Pro Gly Gly Gly Asn Met Lys Asp Asn Trp Arg Ser Glu Leu Tyr Lys
450                 455                 460
Tyr Lys Val Val Glu Val Lys Pro Leu Gly Val Ala Pro Thr Asn Ala
465             470                 475                 480
Arg Glu Arg Val Val Glu Arg Glu Lys Glu
                485                 490
```

<210> SEQ ID NO 49
<211> LENGTH: 1519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
gtcgacaaga agccaccatg cgcgtgatgg gcatccagcg caactacccg cagtggtgga      60
tctggtcgat gctgggcttc tggatgctca tgatctgcaa cggcgtgccg gtgtggaagg     120
aggccaagac gaccctgttc tgcgcgtcgg acgccaaggc ctacgagaag gaggtgcaca     180
acgtgtgggc gacccacgcc tgcgtgccca cggaccccaa cccgcaggag atggtgctga     240
agaacgtgac cgagaacttc aacatgtgga agaacgacat ggtggaccag atgcacgagg     300
acgtgatctc cctgtgggac cagtccctga gccctgcgt gaagctgacc ccgctgtgcg     360
tgaccctgaa ctgcaccaac gcgacgacga acgccaccgc gtccaactcg tccatcatcg     420
aggagatgaa gaactgctcc ttcaacatca cgacggagct gcgcgacaag cgcgagaaga     480
agaacgccct gttctacaag ctggacatcg tgcagctgga cggcaactcc tcgcagtaca     540
ggctgatcaa ctgcaacacc tccgtcatca cgcaggcgtg cccaaggtg tccttcgacc     600
ccatccccat ccactactgc gccccgccg gctacgccat cctgaagtgc aacaacaaga     660
ccttcaccgg caccggcccg tgcaacaacg tgtccaccgt gcagtgcacg cacgggatca     720
agcccgtggt gtccacgcag ctgctcctga cgggtcgct ggccgagggc gagatcatca     780
tccggtccga gaacatcacg aacacggcga agaccatcat cgtgcacctg aacgagtccg     840
tgaagatcga gtgcacccgc ccgaacaaca gacgcgcac ctccatccgg atcggccctg     900
gccaggcctt ctacgccacc ggccaggtga tcggcgacat ccgcgaggcg tactgcaaca     960
tctcggagtc caagtggaac gagaccctgc agcgcgtgtc caagaagctg aaggagtact    1020
cccccacaa gaacatcacc ttccagccgt cgtccggcgg cgacctcgag atcaccacgc    1080
actccttcaa ctgcggtggc gagttcttct actgcaacac gtcgtcgctg ttcaaccgca    1140
cctacatggc caactccacc gacatggcca actccaccga gaccaactcc acgcgcacca    1200
tcacgatccg gtgccgcatc aagcagatca tcaacatgtg gcaggaggtg gccgcgcca    1260
tgtacgcacc gccatcgcc ggcaacatca cctgcatctc caacatcacc ggcctcctgc    1320
tgaccccgcga cggcggcgag aacaacacgg agaccttcag gccaggcgga ggcaacatga    1380
aggacaactg gcgctccgag ctgtacaagt acaaggtggt ggaggtgaag cccctgggcg    1440
tggcacccac caacgcccgc gagcgcgtcg tggagcgcga gaaggagtag taagggtccc    1500
gaattcggtt accggatcc                                                1519
```

<210> SEQ ID NO 50
<211> LENGTH: 2143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

| | | | | | |
|---|---|---|---|---|---|
| gtcgacaaga | agccaccatg | cgcgtgatgg | gcatccagcg | caactacccg | cagtggtgga | 60 |
| tctggtcgat | gctgggcttc | tggatgctca | tgatctgcaa | cggcatgtgg | gtgacggtgt | 120 |
| actacggcgt | gccggtgtgg | aaggaggcca | agacgaccct | gttctgcgcg | tcggacgcca | 180 |
| aggcctacga | gaaggaggtg | cacaacgtgt | gggcgaccca | cgcctgcgtg | cccacggacc | 240 |
| ccaacccgca | ggagatggtg | ctgaagaacg | tgaccgagaa | cttcaacatg | tggaagaacg | 300 |
| acatggtgga | ccagatgcac | gaggacgtga | tctccctgtg | gaccagtcc | ctgaagccct | 360 |
| gcgtgaagct | gaccccgctg | tgcgtgaccc | tgaactgcac | caacgcgacg | acgaacgcca | 420 |
| ccgcgtccaa | ctcgtccatc | atcgaggaga | tgaagaactg | ctccttcaac | atcacgacgg | 480 |
| agctgcgcga | caagcgcgag | aagaagaacg | ccctgttcta | caagctggac | atcgtgcagc | 540 |
| tggacggcaa | ctcctcgcag | tacaggctga | tcaactgcaa | cacctccgtc | atcacgcagg | 600 |
| cgtgccccaa | ggtgtccttc | gaccccatcc | ccatccacta | ctgcgccccc | gccggctacg | 660 |
| ccatcctgaa | gtgcaacaac | aagaccttca | ccggcaccgg | cccgtgcaac | aacgtgtcca | 720 |
| ccgtgcagtg | cacgcacggg | atcaagcccg | tggtgtccac | gcagctgctc | ctgaacgggt | 780 |
| cgctggccga | gggcgagatc | atcatccggt | ccgagaacat | cacgaacacg | gcgaagacca | 840 |
| tcatcgtgca | cctgaacgag | tccgtgaaga | tcgagtgcac | ccgcccgaac | aacaagacgc | 900 |
| gcacctccat | ccggatcggc | cctggccagg | ccttctacgc | caccggccag | gtgatcggcg | 960 |
| acatccgcga | ggcgtactgc | aacatctcgg | agtccaagtg | gaacgagacc | ctgcagcgcg | 1020 |
| tgtccaagaa | gctgaaggag | tacttccccc | acaagaacat | caccttccag | ccgtcgtccg | 1080 |
| gcggcgacct | cgagatcacc | acgcactcct | tcaactgcgg | tggcgagttc | ttctactgca | 1140 |
| acacgtcgtc | gctgttcaac | cgcacctaca | tggccaactc | caccgacatg | gccaactcca | 1200 |
| ccgagaccaa | ctccacgcgc | accatcacga | tccggtgccg | catcaagcag | atcatcaaca | 1260 |
| tgtggcagga | ggtgggccgc | gccatgtacg | caccgcccat | cgccggcaac | atcacctgca | 1320 |
| tctccaacat | caccggcctc | ctgctgaccc | gcgacggcgg | cgagaacaac | acggagacct | 1380 |
| tcaggccagg | cggaggcaac | atgaaggaca | actggcgctc | cgagctgtac | aagtacaagg | 1440 |
| tggtggaggt | gaagcccctg | ggcgtggcac | ccaccaacgc | ccgcaggcgc | gtcgtggagc | 1500 |
| gcgagaagcg | cgccgtgggc | atgggcgccg | tgttcctggg | cttcctgggc | gctgcgggct | 1560 |
| ccaccatggg | tgccgcgtcc | atcaccctga | ccgtgcaggc | ccgccagctg | ctctccggca | 1620 |
| tcgtgcagca | gcagtccaac | ctcctgaagg | ccatcgaggc | ccagcagcac | atgctgaagc | 1680 |
| tgaccgtgtg | gggcatcaag | cagctgcagg | ccagggtgct | cgcgctcgag | cgctacctga | 1740 |
| aggaccagca | gctgctcggc | atgtgggggct | gctccggcaa | gctgatctgc | accaccaacg | 1800 |
| tgtactggaa | ctcgtcctgg | tccaacaaga | cctacgcgca | catctgggac | aacatgacct | 1860 |
| ggatgcagtg | ggagcgcgag | atctccaact | acaccgagat | catctacgag | ctcctcgagg | 1920 |
| agtcccagaa | ccagcaggag | aagaacgagc | aggatctgct | cgcgctggac | cgctggaact | 1980 |
| ccctgtggaa | ctggttcaac | atcaccaact | ggctgtggta | catcaagatc | ttcatcatga | 2040 | tcgtgggcgg cctgatcggc ctgcgcatca tcttcgccgt gctgtcgctg gtgaaccgcg   2100 tgcgccaggg ctgatgaggg tcccgaattc ggttaccgga tcc                     2143

<210> SEQ ID NO 51
<211> LENGTH: 850
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Thr Asn Ala Thr Ala Ser Asn Ser Ser Ile Ile Glu Glu
    130                 135                 140

Met Lys Asn Cys Ser Phe Asn Ile Thr Thr Glu Leu Arg Asp Lys Arg
145                 150                 155                 160

Glu Lys Lys Asn Ala Leu Phe Tyr Lys Leu Asp Ile Val Gln Leu Asp
                165                 170                 175

Gly Asn Ser Ser Gln Tyr Arg Leu Ile Asn Cys Asn Thr Ser Val Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Thr Gly Thr Gly Pro Cys Asn Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Gly Glu Ile Ile Ile Arg Ser Glu Asn Ile Thr Asn Thr Ala
            260                 265                 270

Lys Thr Ile Ile Val His Leu Asn Glu Ser Val Lys Ile Glu Cys Thr
        275                 280                 285

Arg Pro Asn Asn Lys Thr Arg Thr Ser Ile Arg Ile Gly Pro Gly Gln
    290                 295                 300

Ala Phe Tyr Ala Thr Gly Gln Val Ile Gly Asp Ile Arg Glu Ala Tyr
305                 310                 315                 320

Cys Asn Ile Ser Glu Ser Lys Trp Asn Glu Thr Leu Gln Arg Val Ser
                325                 330                 335

Lys Lys Leu Lys Glu Tyr Phe Pro His Lys Asn Ile Thr Phe Gln Pro

```
                340               345               350
Ser Ser Gly Gly Asp Leu Glu Ile Thr Thr His Ser Phe Asn Cys Gly
            355               360               365

Gly Glu Phe Phe Tyr Cys Asn Thr Ser Ser Leu Phe Asn Arg Thr Tyr
    370               375               380

Met Ala Asn Ser Thr Asp Met Ala Asn Ser Thr Glu Thr Asn Ser Thr
385               390               395               400

Arg Thr Ile Thr Ile Arg Cys Arg Ile Lys Gln Ile Ile Asn Met Trp
                405               410               415

Gln Glu Val Gly Arg Ala Met Tyr Ala Pro Pro Ile Ala Gly Asn Ile
            420               425               430

Thr Cys Ile Ser Asn Ile Thr Gly Leu Leu Leu Thr Arg Asp Gly Gly
        435               440               445

Glu Asn Asn Thr Glu Thr Phe Arg Pro Gly Gly Gly Asn Met Lys Asp
    450               455               460

Asn Trp Arg Ser Glu Leu Tyr Lys Tyr Lys Val Val Glu Val Lys Pro
465               470               475               480

Leu Gly Val Ala Pro Thr Asn Ala Arg Arg Arg Val Val Glu Arg Glu
                485               490               495

Lys Arg Ala Val Gly Met Gly Ala Val Phe Leu Gly Phe Leu Gly Ala
            500               505               510

Ala Gly Ser Thr Met Gly Ala Ala Ser Ile Thr Leu Thr Val Gln Ala
        515               520               525

Arg Gln Leu Leu Ser Gly Ile Val Gln Gln Ser Asn Leu Leu Lys
    530               535               540

Ala Ile Glu Ala Gln Gln His Met Leu Lys Leu Thr Val Trp Gly Ile
545               550               555               560

Lys Gln Leu Gln Ala Arg Val Leu Ala Leu Glu Arg Tyr Leu Lys Asp
                565               570               575

Gln Gln Leu Leu Gly Met Trp Gly Cys Ser Gly Lys Leu Ile Cys Thr
            580               585               590

Thr Asn Val Tyr Trp Asn Ser Ser Trp Ser Asn Lys Thr Tyr Gly Asp
        595               600               605

Ile Trp Asp Asn Met Thr Trp Met Gln Trp Glu Arg Glu Ile Ser Asn
    610               615               620

Tyr Thr Glu Ile Ile Tyr Glu Leu Leu Glu Glu Ser Gln Asn Gln Gln
625               630               635               640

Glu Lys Asn Glu Gln Asp Leu Leu Ala Leu Asp Arg Trp Asn Ser Leu
                645               650               655

Trp Asn Trp Phe Asn Ile Thr Asn Trp Leu Trp Tyr Ile Lys Ile Phe
            660               665               670

Ile Met Ile Val Gly Gly Leu Ile Gly Leu Arg Ile Ile Phe Ala Val
        675               680               685

Leu Ser Leu Val Asn Arg Val Arg Gln Gly Tyr Ser Pro Leu Ser Leu
    690               695               700

Gln Thr Leu Ile Pro Ser Pro Arg Gly Pro Asp Arg Pro Gly Gly Ile
705               710               715               720

Glu Glu Glu Gly Gly Glu Gln Asp Arg Asn Arg Ser Thr Arg Leu Val
                725               730               735

Ser Gly Phe Leu Ala Leu Val Trp Asp Asp Leu Arg Ser Leu Cys Leu
            740               745               750

Phe Ile Tyr His Arg Leu Arg Asp Phe Ile Leu Ile Ala Ala Arg Ala
        755               760               765
```

Gly Glu Leu Leu Gly Arg Ser Ser Leu Lys Gly Leu Arg Arg Gly Trp
    770                 775                 780

Glu Ala Leu Lys Tyr Leu Gly Ser Leu Val Gln Tyr Trp Gly Leu Glu
785                 790                 795                 800

Leu Lys Arg Ser Ala Ile Ser Leu Leu Asp Thr Leu Ala Ile Ala Val
            805                 810                 815

Gly Glu Gly Thr Asp Arg Ile Leu Glu Phe Val Leu Gly Ile Cys Arg
            820                 825                 830

Ala Ile Arg Asn Ile Pro Thr Arg Ile Arg Gln Gly Phe Glu Thr Ala
            835                 840                 845

Leu Leu
    850

<210> SEQ ID NO 52
<211> LENGTH: 2593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gtcgacaaga aatgcgcgtg atgggcatcc agcgcaacta cccgcagtgg tggatctggt      60
cgatgctggg cttctggatg ctcatgatct gcaacggcat gtgggtgacg gtgtactacg     120
gcgtgccggt gtggaaggag gccaagacga ccctgttctg cgcgtcggac gccaaggcct     180
acgagaagga ggtgcacaac gtgtgggcga cccacgcctg cgtgcccacg accccaacc      240 cgcaggagat ggtgctgaag aacgtgaccg agaacttcaa catgtggaag aacgacatgg     300
tggaccagat gcacgaggac gtgatctccc tgtgggacca gtccctgaag ccctgcgtga     360
agctgacccc gctgtgcgtg accctgaact gcaccaacgc gacgacgaac gccaccgcgt     420
ccaactcgtc catcatcgag gagatgaaga actgctcctt caacatcacg acggagctgc     480
gcgacaagcg cgagaagaag aacgccctgt tctacaagct ggacatcgtg cagctggacg     540
gcaactcctc gcagtacagg ctgatcaact gcaacacctc cgtcatcacg caggcgtgcc     600
ccaaggtgtc cttcgacccc atccccatcc actactgcgc ccccgccggc tacgccatcc     660
tgaagtgcaa caacaagacc ttcaccggca ccggcccgtg caacaacgtg tccaccgtgc     720
agtgcacgca cgggatcaag cccgtggtgt ccacgcagct gctcctgaac gggtcgctgg     780
ccgagggcga gatcatcatc cggtccgaga acatcacgaa cacggcgaag accatcatcg     840
tgcacctgaa cgagtccgtg aagatcgagt gcaccccgcc gaacaacaag acgcgcacct     900
ccatccggat cggccctggc caggccttct acgccaccgg ccaggtgatc ggcgacatcc     960
gcgaggcgta ctgcaacatc tcggagtcca gtggaacga ccctgcag cgcgtgtcca       1020 agaagctgaa ggagtacttc cccacaagaa catcaccctt ccagccgtcg tccggcggcg    1080
acctcgagat caccacgcac tccttcaact gcggtggcga gttcttctac tgcaacacgt    1140
cgtcgctgtt caaccgcacc tacatggcca actccaccga catggccaac tccaccgaga    1200
ccaactccac gcgcaccatc acgatccggt gccgcatcaa gcagatcatc aacatgtggc    1260
aggaggtggg ccgcgccatg tacgcaccgc ccatcgccgg caacatcacc tgcatctcca    1320
acatcaccgg cctcctgctg acccgcgacg gcggcgagaa caacacggag accttcaggc    1380
caggcggagg caacatgaag gacaactggc gctccgagct gtacaagtac aaggtggtgg    1440
aggtgaagcc cctgggcgtg gcacccacca acgcccgcag gcgcgtcgtg agcgcgaga     1500

-continued

```
agcgcgccgt gggcatgggc gccgtgttcc tgggcttcct gggcgctgcg ggctccacca    1560
tgggtgccgc gtccatcacc ctgaccgtgc aggcccgcca gctgctctcc ggcatcgtgc    1620
agcagcagtc caacctcctg aaggccatcg aggcccagca gcacatgctg aagctgaccg    1680
tgtggggcat caagcagctg caggccaggg tgctcgcgct cgagcgctac ctgaaggacc    1740
agcagctgct cggcatgtgg ggctgctccg gcaagctgat ctgcaccacc aacgtgtact    1800
ggaactcgtc ctggtccaac aagacctacg gcgacatctg gacaacatg acctggatgc     1860 agtgggagcg cgagatctcc aactacaccg agatcatcta cgagctcctc gaggagtccc    1920
agaaccagca ggagaagaac gagcaggatc tgctcgcgct ggaccgctgg aactccctgt    1980
ggaactggtt caacatcacc aactggctgt ggtacatcaa gatcttcatc atgatcgtgg    2040
gcggcctgat cggcctgcgc atcatcttcg ccgtgctgtc gctggtgaac cgcgtgcgcc    2100
agggctactc cccgctgtcc ctgcaaacgc tgatcccctc cccccggggc ccggacaggc    2160
ccggtggcat cgaggaggag ggcggcgagc aggaccgcaa ccgctccacg cgcctggtgt    2220
ccggcttcct ggccctggtg tgggacgacc tgcgctccct gtgcctgttc atctaccacc    2280
gcctgcgcga cttcatcctg atcgcggccc gcgctggcga gctgctgggc cggtcctcgc    2340
tgaagggcct cgccgcgggc tgggaggccc tgaagtacct gggctcgctg gtgcagtact    2400
ggggcctgga gctgaagcgc tccgccatct ccctgctgga cacctggcc atcgccgtgg    2460 gcgagggcac cgaccgcatc ctggagttcg tgctgggcat ctgccgcgcc atccgcaaca    2520
tccccacccg catccgccag ggcttcgaga ccgccctcct gtagtaaggg tcccgaattc    2580
ggttaccgga tcc                                                       2593
```

<210> SEQ ID NO 53

<400> SEQUENCE: 53

000

<210> SEQ ID NO 54
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Met Arg Val Thr Gly Ile Gln Arg Asn Tyr Pro Gln Trp Trp Ile Trp
1               5                   10                  15

Ser Met Leu Gly Leu Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Ala Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Ile Asp Ala Asn Ala Thr Ala Ser Asn

```
                115                 120                 125
Ala Thr Ala Ser Asn Ser Ser Ile Ile Glu Gly Met Lys Asn Cys Ser
            130                 135                 140

Phe Asn Ile Thr Thr Glu Leu Arg Asp Lys Ile Glu Lys Lys Asn Ala
145                 150                 155                 160

Leu Phe Tyr Lys Leu Asp Ile Val Gln Leu Asp Gly Asn Ser Ser Gln
                165                 170                 175

Tyr Arg Leu Ile Asn Cys Asn Thr Ser Val Ile Thr Gln Ala Cys Pro
            180                 185                 190

Lys Val Ser Phe Asp Pro Ile Pro Ile His Tyr Cys Ala Pro Ala Gly
                195                 200                 205

Tyr Ala Ile Leu Lys Cys Asn Asn Lys Thr Phe Asn Gly Thr Gly Pro
            210                 215                 220

Cys Asn Asn Val Ser Thr Val Gln Cys Thr His Gly Ile Lys Pro Val
225                 230                 235                 240

Val Ser Thr Gln Leu Leu Leu Asn Gly Ser Leu Ala Glu Gly Glu Ile
                245                 250                 255

Ile Ile Arg Ser Glu Asn Ile Thr Asn Ser Ala Lys Thr Ile Ile Val
            260                 265                 270

His Leu Asn Glu Ser Val Lys Ile Glu Cys Thr Arg Pro Ser Asn Asn
        275                 280                 285

Thr Arg Thr Ser Ile Arg Ile Gly Pro Gly Gln Ala Phe Tyr Ala Thr
290                 295                 300

Gly Gln Val Ile Gly Asp Ile Arg Lys Ala His Cys Asn Ile Ser Glu
305                 310                 315                 320

Ser Lys Trp Asn Glu Thr Leu Gln Arg Val Ser Lys Leu Lys Glu
                325                 330                 335

Tyr Phe Pro His Lys Asn Ile Thr Phe Gln Pro Ser Ser Gly Gly Asp
            340                 345                 350

Leu Glu Ile Thr Thr His Ser Phe Asn Cys Gly Gly Glu Phe Phe Tyr
        355                 360                 365

Cys Asn Thr Ser Ser Leu Phe Asn Arg Thr Tyr Met Ala Asn Ser Thr
    370                 375                 380

Glu Thr Asn Ser Thr Arg Thr Ile Thr Leu His Cys Arg Ile Lys Gln
385                 390                 395                 400

Ile Ile Asn Met Trp Gln Glu Val Gly Arg Ala Met Tyr Ala Pro Pro
                405                 410                 415

Ile Ala Gly Asn Ile Thr Cys Ile Ser Asn Ile Thr Gly Leu Leu Leu
            420                 425                 430

Thr Arg Asp Gly Gly Asn Asn Asn Thr Thr Glu Thr Phe Arg Pro Gly
        435                 440                 445

Gly Gly Asn Met Lys Asp Asn Trp Arg Ser Glu Leu Tyr Lys Tyr Lys
    450                 455                 460

Val Val Glu Ile Lys Pro Leu Gly Val Ala Pro Thr Asn Ala Arg Glu
465                 470                 475                 480

Arg Val Val Glu Arg Glu Lys Glu
                485

<210> SEQ ID NO 55
<211> LENGTH: 1514
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 55

```
ggtcgacaag aagccaccat gcgcgtgacg ggcatccagc gcaactaccc gcagtggtgg     60
atctggtcga tgctgggcct ctggatgctc atgatctgca acggcgtgcc ggtgtggaag    120
gaggccaaga cgaccctgtt ctgcgcgtcg gacgccaagg cctacgagaa ggaggtgcac    180
aacgtgtggg cgacccacgc ctgcgtgccc acggacccca acccgcagga gatggtgctg    240
aagaacgtga ccgagaactt caacatgtgg aagaacgaca tggcggacca gatgcacgag    300
gacgtgatct ccctgtggga ccagtccctg aagccctgcg tgaagctgac cccgctgtgc    360
gtgaccctga actgcatcga cgccaacgcg accgcgtcca acgcgacggc atccaactcg    420
tccatcatcg agggatgaa gaactgctcc ttcaacatca cgacggagct gcgcgacaag    480
atcgagaaga gaacgccct gttctacaag ctggacatcg tgcagctgga cggcaactcc    540
tcgcagtaca ggctgatcaa ctgcaacacc tccgtcatca cgcaggcgtg ccccaaggtg    600
tccttcgacc ccatcccat ccactactgc gccccgccg gctacgccat cctgaagtgc    660
aacaacaaga ccttcaacgg caccggcccg tgcaacaacg tgtccaccgt gcagtgcacg    720
cacgggatca agcccgtggt gtccacgcag ctgctcctga cgggtcgct ggccgagggc    780
gagatcatca tccggtcgga gaacatcacg aacagcgcga agaccatcat cgtgcacctg    840
aacgagtccg tgaagatcga gtgcaccgc ccgagcaaca acacgcgcac ctccatccgg    900
atcggccctg gccaggcctt ctacgccacc ggccaggtga tcggcgacat ccgcaaggcg    960
cactgcaaca tctccgagtc caagtggaac gagaccctgc agcgcgtgtc caagaagctg   1020
aaggagtact cccccacaa gaacatcacc ttccagccgt cgtccggcgg cgacctcgag   1080
atcaccacgc actccttcaa ctgcggtggc gagttcttct actgcaacac gtcgtcgctg   1140
ttcaaccgca cctacatggc caactccacc gagaccaact ccacgcgcac gatcacgctc   1200
cactgccgca tcaagcagat catcaacatg tggcaggagg tgggccgcgc catgtacgca   1260
ccgcccatcg ccggcaacat cacctgcatc tccaacatca ccggcctcct gctgacccgc   1320
gacggcggca caacaacac cacgagacc ttcaggccag ggggaggcaa catgaaggac   1380
aactggcgct ccgagctgta caagtacaag gtggtggaga tcaagcccct gggcgtggca   1440
cccaccaacg cccgcgagcg cgtcgtggag cgcgagaagg agtagtaaga attcggtaac   1500
caggtcccgg atcc                                                     1514
```

<210> SEQ ID NO 56
<211> LENGTH: 2137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56

```
gtcgacaaga agccaccatg cgcgtgacgg gcatccagcg caactacccg cagtggtgga     60
tctggtcgat gctgggcctc tggatgctca tgatctgcaa cggcatgtgg gtgacggtgt    120
actacgcgt gccggtgtgg aaggaggcca agacgaccct gttctgcgcg tcggacgcca    180
aggcctacga gaaggaggtg cacaacgtgt gggcgaccca cgcctgcgtg cccacggacc    240
ccaacccgca ggagatggtg ctgaagaacg tgaccgagaa cttcaacatg tggaagaacg    300
acatggcgga ccagatgcac gaggacgtga tctccctgtg gaccagtcc ctgaagcccct    360
gcgtgaagct gaccccgctg tgcgtgaccc tgaactgcat cgacgccaac gcgaccgcgt    420
```

```
ccaacgcgac ggcatccaac tcgtccatca tcgaggggat gaagaactgc tccttcaaca      480
tcacgacgga gctgcgcgac aagatcgaga agaagaacgc cctgttctac aagctggaca      540
tcgtgcagct ggacggcaac tcctcgcagt acaggctgat caactgcaac acctccgtca      600
tcacgcaggc gtgccccaag gtgtccttcg accccatccc catccactac tgcgcccccg      660
ccggctacgc catcctgaag tgcaacaaca agaccttcaa cggcaccggc cgtgcaaca       720 acgtgtccac cgtgcagtgc acgcacggga tcaagcccgt ggtgtccacg cagctgctcc      780
tgaacgggtc gctggccgag ggcgagatca tcatccggtc ggagaacatc acgaacagcg      840
cgaagaccat catcgtgcac ctgaacgagt ccgtgaagat cgagtgcacc cgcccgagca      900
acaacacgcg cacctccatc cggatcggcc ctggccaggc cttctacgcc accggccagg      960
tgatcggcga catccgcaag gcgcactgca acatctccga gtccaagtgg aacgagaccc     1020
tgcagcgcgt gtccaagaag ctgaaggagt acttcccca  aagaacatc accttccagc     1080 cgtcgtccgg cggcgacctc gagatcacca cgcactcctt caactgcggt ggcgagttct    1140
tctactgcaa cacgtcgtcg ctgttcaacc gcacctacat ggccaactcc accgagacca    1200
actccacgcg cacgatcacg ctccactgcc gcatcaagca gatcatcaac atgtggcagg    1260
aggtgggccg cgccatgtac gcaccgccca tcgccggcaa catcacctgc atctccaaca    1320
tcaccggcct cctgctgacc cgcgacggcg caacaacaa  caccacggag ccttcaggc     1380 caggggagg  caacatgaag gacaactggc gctccgagct gtacaagtac aaggtggtgg    1440
agatcaagcc cctgggcgtg cacccacca  acgcccgcag gcgcgtcgtg gagcgcgaga    1500
agcgcgccgt gggcatgggc gccgtgttcc tgggcttcct gggcgctgcg ggctccacca    1560
tgggtgccgc gtccatcacc ctgaccgtgc aggcccgcca gctgctctcc ggcatcgtgc    1620
agcagcagtc caacctcctg aaggccatcg aggcccagca gcacatgctg aagctgaccg    1680
tgtggggcat caagcagctg caggccaggg tgctcgcgct cgagcgctac ctgaaggacc    1740
agcagctgct cggcatgtgg ggctgctccg gcaagctgat ctgcaccacc aacgtgtact    1800
ggaactcgtc ctggtccaac aagacctacg gcgacatctg gacaacatg  acctggatgc    1860 agtgggagcg cgagatctcc gactacaccg agatcatcta cgagctcctc gaggagtccc    1920
agaaccagca ggagaagaac gagcaggatc tgctcgcgct ggaccgctgg aactccctgt    1980
ggaactggtt caacatcacc aactggctgt ggtacatcaa gatcttcatc atgatcgtgg    2040
gcggcctgat cggcctgcgc atcatcttcg ccgtgctgtc gctggtgaac cgcgtgcgcc    2100
agggctgatg agaattcggt aaccaggtcc cggatcc                             2137
```

<210> SEQ ID NO 57
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Arg Val Thr Gly Ile Gln Arg Asn Tyr Pro Gln Trp Trp Ile Trp
1               5                   10                  15

Ser Met Leu Gly Leu Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

```
Phe Cys Ala Ser Asp Ala Lys Ala Tyr Glu Lys Glu Val His Asn Val
 50                  55                  60
Trp Ala Thr His Ala Cys Val Pro Thr Asp Pro Asn Pro Gln Glu Met
 65                  70                  75                  80
Val Leu Lys Asn Val Thr Glu Asn Phe Asn Met Trp Lys Asn Asp Met
                 85                  90                  95
Ala Asp Gln Met His Glu Asp Val Ile Ser Leu Trp Asp Gln Ser Leu
            100                 105                 110
Lys Pro Cys Val Lys Leu Thr Pro Leu Cys Val Thr Leu Asn Cys Ile
        115                 120                 125
Asp Ala Asn Ala Thr Ala Ser Asn Ala Thr Ala Ser Asn Ser Ser Ile
130                 135                 140
Ile Glu Gly Met Lys Asn Cys Ser Phe Asn Ile Thr Thr Glu Leu Arg
145                 150                 155                 160
Asp Lys Ile Glu Lys Lys Asn Ala Leu Phe Tyr Lys Leu Asp Ile Val
                165                 170                 175
Gln Leu Asp Gly Asn Ser Ser Gln Tyr Arg Leu Ile Asn Cys Asn Thr
            180                 185                 190
Ser Val Ile Thr Gln Ala Cys Pro Lys Val Ser Phe Asp Pro Ile Pro
        195                 200                 205
Ile His Tyr Cys Ala Pro Ala Gly Tyr Ala Ile Leu Lys Cys Asn Asn
210                 215                 220
Lys Thr Phe Asn Gly Thr Gly Pro Cys Asn Asn Val Ser Thr Val Gln
225                 230                 235                 240
Cys Thr His Gly Ile Lys Pro Val Val Ser Thr Gln Leu Leu Leu Asn
                245                 250                 255
Gly Ser Leu Ala Glu Gly Glu Ile Ile Ile Arg Ser Glu Asn Ile Thr
            260                 265                 270
Asn Ser Ala Lys Thr Ile Ile Val His Leu Asn Glu Ser Val Lys Ile
        275                 280                 285
Glu Cys Thr Arg Pro Ser Asn Asn Thr Arg Thr Ser Ile Arg Ile Gly
290                 295                 300
Pro Gly Gln Ala Phe Tyr Ala Thr Gly Gln Val Ile Gly Asp Ile Arg
305                 310                 315                 320
Lys Ala His Cys Asn Ile Ser Glu Ser Lys Trp Asn Glu Thr Leu Gln
                325                 330                 335
Arg Val Ser Lys Lys Leu Lys Glu Tyr Phe Pro His Lys Asn Ile Thr
            340                 345                 350
Phe Gln Pro Ser Ser Gly Gly Asp Leu Glu Ile Thr Thr His Ser Phe
        355                 360                 365
Asn Cys Gly Gly Glu Phe Phe Tyr Cys Asn Thr Ser Ser Leu Phe Asn
370                 375                 380
Arg Thr Tyr Met Ala Asn Ser Thr Glu Thr Asn Ser Thr Arg Thr Ile
385                 390                 395                 400
Thr Leu His Cys Arg Ile Lys Gln Ile Ile Asn Met Trp Gln Glu Val
                405                 410                 415
Gly Arg Ala Met Tyr Ala Pro Pro Ile Ala Gly Asn Ile Thr Cys Ile
            420                 425                 430
Ser Asn Ile Thr Gly Leu Leu Leu Thr Arg Asp Gly Gly Asn Asn Asn
        435                 440                 445
Thr Thr Glu Thr Phe Arg Pro Gly Gly Gly Asn Met Lys Asp Asn Trp
450                 455                 460
Arg Ser Glu Leu Tyr Lys Tyr Lys Val Val Glu Ile Lys Pro Leu Gly
```

Val Ala Pro Thr Asn Ala Arg Arg Val Glu Arg Glu Lys Arg
465                 470                 475                 480
                    485                 490                 495

Ala Val Gly Met Gly Ala Val Phe Leu Gly Phe Leu Gly Ala Ala Gly
                500                 505                 510

Ser Thr Met Gly Ala Ala Ser Ile Thr Leu Thr Val Gln Ala Arg Gln
            515                 520                 525

Leu Leu Ser Gly Ile Val Gln Gln Gln Ser Asn Leu Leu Lys Ala Ile
530                 535                 540

Glu Ala Gln Gln His Met Leu Lys Leu Thr Val Trp Gly Ile Lys Gln
545                 550                 555                 560

Leu Gln Ala Arg Val Leu Ala Leu Glu Arg Tyr Leu Lys Asp Gln Gln
                565                 570                 575

Leu Leu Gly Met Trp Gly Cys Ser Gly Lys Leu Ile Cys Thr Thr Asn
                580                 585                 590

Val Tyr Trp Asn Ser Ser Trp Ser Asn Lys Thr Tyr Gly Asp Ile Trp
            595                 600                 605

Asp Asn Met Thr Trp Met Gln Trp Glu Arg Glu Ile Ser Asp Tyr Thr
610                 615                 620

Glu Ile Ile Tyr Glu Leu Leu Glu Glu Ser Gln Asn Gln Gln Glu Lys
625                 630                 635                 640

Asn Glu Gln Asp Leu Leu Ala Leu Asp Arg Trp Asn Ser Leu Trp Asn
                645                 650                 655

Trp Phe Asn Ile Thr Asn Trp Leu Trp Tyr Ile Lys Ile Phe Ile Met
                660                 665                 670

Ile Val Gly Gly Leu Ile Gly Leu Arg Ile Ile Phe Ala Val Leu Ser
            675                 680                 685

Leu Val Asn Arg Val Arg Gln Gly Tyr Ser Pro Leu Ser Leu Gln Thr
                690                 695                 700

Leu Thr Pro Ser Pro Arg Gly Pro Asp Arg Pro Gly Gly Ile Glu Glu
705                 710                 715                 720

Glu Gly Gly Glu Gln Asp Arg Asn Arg Ser Thr Arg Leu Val Ser Gly
                725                 730                 735

Phe Leu Ala Leu Ala Trp Asp Asp Leu Arg Ser Leu Cys Leu Phe Ile
                740                 745                 750

Tyr His Arg Leu Arg Asp Phe Ile Leu Ile Ala Ala Arg Ala Gly Glu
                755                 760                 765

Leu Leu Gly Arg Ser Ser Leu Lys Gly Leu Arg Arg Gly Trp Glu Ala
770                 775                 780

Leu Lys Tyr Leu Gly Gly Leu Val Gln Tyr Trp Gly Leu Glu Leu Lys
785                 790                 795                 800

Arg Ser Ala Ile Ser Leu Leu Asp Thr Leu Ala Ile Ala Val Gly Glu
                805                 810                 815

Gly Thr Asp Arg Ile Leu Glu Phe Val Leu Gly Ile Cys Arg Ala Ile
                820                 825                 830

Arg Asn Ile Pro Thr Arg Ile Arg Gln Gly Phe Glu Thr Ala Leu Leu
                835                 840                 845

<210> SEQ ID NO 58
<211> LENGTH: 2587
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
gtcgacaaga aatgcgcgtg acgggcatcc agcgcaacta cccgcagtgg tggatctggt    60
cgatgctggg cctctggatg ctcatgatct gcaacggcat gtgggtgacg gtgtactacg   120
gcgtgccggt gtggaaggag gccaagacga ccctgttctg cgcgtcggac gccaaggcct   180
acgagaagga ggtgcacaac gtgtgggcga cccacgcctg cgtgcccacg accccaacc    240
cgcaggagat ggtgctgaag aacgtgaccg agaacttcaa catgtggaag aacgacatgg   300
cggaccagat gcacgaggac gtgatctccc tgtgggacca gtccctgaag ccctgcgtga   360
agctgacccc gctgtgcgtg accctgaact gcatcgacgc caacgcgacc gcgtccaacg   420
cgacggcatc caactcgtcc atcatcgagg ggatgaagaa ctgctccttc aacatcacga   480
cggagctgcg cgacaagatc gagaagaaga acgccctgtt ctacaagctg acatcgtgc    540
agctggacgg caactcctcg cagtacaggc tgatcaactg caacacctcc gtcatcacgc   600
aggcgtgccc caaggtgtcc ttcgacccca tccccatcca ctactgcgcc cccgccggct   660
acgccatcct gaagtgcaac aacaagacct tcaacggcac cggcccgtgc aacaacgtgt   720
ccaccgtgca gtgcacgcac gggatcaagc cgtggtgtc cacgcagctg ctcctgaacg    780
ggtcgctggc cgagggcgag atcatcatcc ggtcggagaa catcacgaac agcgcgaaga   840
ccatcatcgt gcacctgaac gagtccgtga agatcgagtg cacccgcccg agcaacaaca   900
cgcgcacctc catccggatc ggccctggcc aggccttcta cgccaccggc caggtgatcg   960
gcgacatccg caaggcgcac tgcaacatct ccgagtccaa gtggaacgag accctgcagc  1020
gcgtgtccaa gaagctgaag gagtacttcc cccacaagaa catcaccttc agccgtcgt   1080
ccggcggcga cctcgagatc accacgcact ccttcaactg cggtggcgag ttcttctact  1140
gcaacacgtc gtcgctgttc aaccgcacct acatggccaa ctccaccgag accaactcca  1200
cgcgcacgat cacgctccac tgccgcatca agcagatcat caacatgtgg caggaggtgg  1260
gccgcgccat gtacgcaccg cccatcgccg gcaacatcac ctgcatctcc aacatcaccg  1320
gcctcctgct gacccgcgac ggcggcaaca caacaccac ggagaccttc aggccagggg   1380
gaggcaacat gaaggacaac tggcgctccg agctgtacaa gtacaaggtg gtggagatca  1440
agccctggg cgtggcaccc accaacgccc gcaggcgcgt cgtggagcgc gagaagcgcg   1500
ccgtgggcat gggcgccgtg ttcctgggct tcctgggcgc tgcgggctcc accatgggtg  1560
ccgcgtccat caccctgacc gtgcaggccc gccagctgct ctccggcatc gtgcagcagc  1620
agtccaacct cctgaaggcc atcgaggccc agcagcacat gctgaagctg accgtgtggg  1680
gcatcaagca gctgcaggcc agggtgctcg cgctcgagcg ctacctgaag gaccagcagc  1740
tgctcggcat gtgggctgc tccggcaagc tgatctgcac caccaacgtg tactggaact   1800
cgtcctggtc caacaagacc tacggcgaca tctgggacaa catgacctgg atgcagtggg  1860
agcgcgagat ctccgactac accgagatca tctacgagct cctcgaggag tcccagaacc  1920
agcaggagaa gaacgagcag atctgctcg cgctggaccg ctggaactcc ctgtggaact   1980
ggttcaacat caccaactgg ctgtggtaca tcaagatctt catcatgatc gtgggcggcc  2040
tgatcggcct gcgcatcatc ttcgccgtgc tgtcgctggt gaaccgcgtg cgccaggggct 2100
actccccgct gtccctgcaa acgctgacgc cctcccccg gggccccggac aggcccggtg  2160
gcatcgagga ggagggcggc gagcaggacc gcaaccgctc cacgcgcctg gtgtccggct  2220
tcctggcccct ggcgtgggac gacctgcgct ccctgtgcct gttcatctac caccgcctgc  2280
```

-continued

```
gcgacttcat cctgatcgcg gcccgcgctg gcgagctgct gggccggtcc tcgctgaagg    2340
gcctgcgccg cggctgggag gccctgaagt acctgggcgg cctggtgcag tactggggcc    2400
tggagctgaa gcgctccgcc atctccctgc tggacaccct ggccatcgcc gtgggcgagg    2460
gcaccgaccg catcctggag ttcgtgctgg gcatctgccg cgccatccgc aacatcccca    2520
cccgcatccg ccagggcttc gagaccgccc tcctgtagta agaattcggt aaccaggtcc    2580
cggatcc                                                              2587
```

<210> SEQ ID NO 59
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Lys Asn Val Thr Glu Asn
65                  70                  75                  80

Phe Asn Met Trp Lys Asn Asp Met Val Asp Gln Met His Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Asn Ala Thr Ala Ser Asn
        115                 120                 125

Ser Ser Ile Ile Glu Gly Met Asn Ser Ser Ile Ile Glu Gly Met Lys
    130                 135                 140

Asn Cys Ser Phe Asn Ile Thr Thr Glu Leu Arg Asp Lys Arg Glu Lys
145                 150                 155                 160

Lys Asn Ala Leu Phe Tyr Lys Leu Asp Ile Val Gln Leu Asp Gly Asn
                165                 170                 175

Ser Ser Gln Tyr Arg Leu Ile Asn Cys Asn Thr Ser Val Ile Thr Gln
            180                 185                 190

Ala Cys Pro Lys Val Ser Phe Asp Pro Ile Pro Ile His Tyr Cys Ala
        195                 200                 205

Pro Ala Gly Tyr Ala Ile Leu Lys Cys Asn Asn Lys Thr Phe Asn Gly
    210                 215                 220

Thr Gly Pro Cys Asn Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Gly Glu Ile Ile Ile Arg Ser Glu Asn Ile Thr Asp Asn Gly Lys Thr
            260                 265                 270

Ile Ile Val His Leu Asn Glu Ser Val Lys Ile Glu Cys Thr Arg Pro
        275                 280                 285

Ser Asn Asn Thr Arg Thr Ser Ile Arg Ile Gly Pro Gly Gln Ala Phe
    290                 295                 300
```

```
Tyr Ala Thr Gly Gln Val Ile Gly Asp Ile Arg Glu Ala His Cys Asn
305                 310                 315                 320

Ile Ser Glu Ser Lys Trp Asn Glu Thr Leu Gln Arg Val Ser Glu Lys
            325                 330                 335

Leu Lys Glu Tyr Phe Pro His Lys Asn Ile Thr Phe Gln Pro Ser Ser
        340                 345                 350

Gly Gly Asp Leu Glu Ile Thr Thr His Ser Phe Asn Cys Gly Gly Glu
    355                 360                 365

Phe Phe Tyr Cys Asn Thr Ser Ser Leu Phe Asn Arg Thr Tyr Met Ala
370                 375                 380

Thr Ser Thr Asp Met Ala Asn Ser Thr Glu Thr Asn Ser Thr Arg Ile
385                 390                 395                 400

Ile Thr Ile Arg Cys Arg Ile Lys Gln Ile Ile Asn Met Trp Gln Glu
            405                 410                 415

Val Gly Arg Ala Met Tyr Ala Pro Pro Ile Ala Gly Asn Ile Thr Cys
        420                 425                 430

Ile Ser Asn Ile Thr Gly Leu Leu Leu Thr Arg Asp Gly Gly Lys Asn
    435                 440                 445

Asn Thr Glu Thr Phe Glu Thr Phe Arg Pro Gly Gly Gly Asn Met Lys
450                 455                 460

Asp Asn Trp Arg Ser Glu Leu Tyr Lys Tyr Lys Val Val Glu Val Lys
465                 470                 475                 480

Pro Leu Gly Val Ala Pro Thr Asn Ala Arg Glu Arg Val Val Glu Arg
        485                 490                 495

Glu Lys Glu

<210> SEQ ID NO 60
<211> LENGTH: 1547
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ggtcgacaag aagccaccat gcgcgtgatg ggcatccagc gcaactaccc gcagtggtgg     60
atctggtcga tgctgggctt ctggatgctc atgatctgca acggcgtgcc ggtgtggaag    120
gaggccaaga cgaccctgtt ctgcgcgtcg acgccaagg cctacgagaa ggaggtgcac    180
aacgtgtggg cgacccacgc ctgcgtgccc acggacccca cccgcaggag atggtgctg    240 aagaacgtga ccgagaactt caacatgtgg aagaacgaca tggtggacca gatgcacgag    300
gacgtgatct ccctgtggga ccagtccctg aagccctgcg tgaagctgac cccgctgtgc    360
gtgaccctga actgcaccaa cgcgaacgcc accgcgtcca actcctctat catcgagggg    420
atgaactcct ccatcatcga gggcatgaag aactgctcct tcaacatcac gacggagctg    480
cgcgacaagc gcgagaagaa gaacgccctg ttctacaagc tggacatcgt gcagctggac    540
ggcaactcct cgcagtacag gctgatcaac tgcaacacct ccgtcatcac gcaggcgtgc    600
cccaaggtgt ccttcgaccc catccccatc cactactgcg ccccgccgg ctacgccatc    660 ctgaagtgca caacaagac cttcaacggc accggcccgt gcaacaacgt gtccaccgtg    720
cagtgcacgc acgggatcaa gcccgtggtg tccacgcagc tgctcctgaa cgggtcgctg    780
gccgagggcg agatcatcat ccggtccgag aacatcacgg acaacgggaa gaccatcatc    840
gtgcacctga acgagtccgt gaagatcgag tgcacccgcc cgagcaacaa cacgcgcacc    900
```

| | |
|---|---|
| tccatccgga tcggccctgg ccaggccttc tacgccaccg gccaggtgat cggcgacatc | 960 |
| cgcgaggcgc actgcaacat ctcggagtcc aagtggaacg agaccctgca gcgcgtgtcc | 1020 |
| gagaagctga aggagtactt cccccacaag aacatcacct tccagccgtc gtccggcggc | 1080 |
| gacctcgaga tcaccacgca ctccttcaac tgcggtggca gttcttcta ctgcaacacg | 1140 |
| tcgtcgctgt tcaaccgcac ctacatggcc acgtccaccg acatggccaa ctccaccgag | 1200 |
| accaactcca cgcgcatcat cacgatccgg tgccgcatca agcagatcat caacatgtgg | 1260 |
| caggaggtgg gccgcgccat gtacgcaccg cccatcgccg gcaacatcac ctgcatctcc | 1320 |
| aacatcaccg gcctcctgct gacccgcgac ggcggcaaga acaacacgga gaccttcgag | 1380 |
| acgttcaggc caggcggagg caacatgaag gacaactggc gctccgagct gtacaagtac | 1440 |
| aaggtggtgg aggtgaagcc cctgggcgtg gcacccacca cgcccgcga gcgcgtcgtg | 1500 |
| gagcgcgaga aggagtagta agaattcggt gaccgggtcc cggatcc | 1547 |

<210> SEQ ID NO 61
<211> LENGTH: 2170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

| | |
|---|---|
| gtcgacaaga agccaccatg cgcgtgatgg gcatccagcg caactacccg cagtggtgga | 60 |
| tctggtcgat gctgggcttc tggatgctca tgatctgcaa cggcatgtgg gtgacggtgt | 120 |
| actacggcgt gccggtgtgg aaggaggcca agacgaccct gttctgcgcg tcggacgcca | 180 |
| aggcctacga gaaggaggtg cacaacgtgt gggcgaccca cgcctgcgtg cccacggacc | 240 |
| ccaacccgca ggagatggtg ctgaagaacg tgaccgagaa cttcaacatg tggaagaacg | 300 |
| acatggtgga ccagatgcac gaggacgtga tctccctgtg ggaccagtcc ctgaagccct | 360 |
| gcgtgaagct gaccccgctg tgcgtgaccc tgaactgcac caacgcgaac gccaccgcgt | 420 |
| ccaactcctc tatcatcgag gggatgaact cctccatcat cgagggcatg aagaactgct | 480 |
| ccttcaacat cacgacggag ctgcgcgaca gcgcgagaa gaagaacgcc ctgttctaca | 540 |
| agctggacat cgtgcagctg gacggcaact cctcgcagta caggctgatc aactgcaaca | 600 |
| cctccgtcat cacgcaggcg tgccccaagg tgtccttcga ccccatcccc atccactact | 660 |
| gcgcccccgc cggctacgcc atcctgaagt gcaacaacaa gaccttcaac ggcaccggcc | 720 |
| cgtgcaacaa cgtgtccacc gtgcagtgca cgcacgggat caagcccgtg gtgtccacgc | 780 |
| agctgctcct gaacgggtcg ctggccgagg gcgagatcat catccggtcc gagaacatca | 840 |
| cggacaacgg gaagaccatc atcgtgcacc tgaacgagtc cgtgaagatc gagtgcaccc | 900 |
| gcccgagcaa caacacgcgc acctccatcc ggatcggccc tggccaggcc ttctacgcca | 960 |
| ccggccaggt gatcggcgac atccgcgagg cgcactgcaa catctcggag tccaagtgga | 1020 |
| acgagaccct gcagcgcgtg tccgagaagc tgaaggagta cttcccccac aagaacatca | 1080 |
| ccttccagcc gtcgtccggc ggcgacctcg agatcaccac gcactccttc aactgcggtg | 1140 |
| gcgagttctt ctactgcaac acgtcgtcgc tgttcaaccg cacctacatg gccacgtcca | 1200 |
| ccgacatggc caactccacc gagaccaact ccacgcgcat catcacgatc cggtgccgca | 1260 |
| tcaagcagat catcaacatg tggcaggagg tgggccgcgc catgtacgca ccgcccatcg | 1320 |
| ccggcaacat cacctgcatc tccaacatca ccggcctcct gctgacccgc gacggcggca | 1380 |

```
agaacaacac ggagaccttc gagacgttca ggccaggcgg aggcaacatg aaggacaact    1440
ggcgctccga gctgtacaag tacaaggtgg tggaggtgaa gccccctgggc gtggcaccca   1500 ccaacgcccg caggcgcgtc gtggagcgcg agaagcgcgc cgtgggcatg ggcgccgtgt    1560
tcctgggctt cctgggcgct gcgggctcca ccatgggtgc cgcgtccatc accctgaccg    1620
tgcaggcccg ccagctgctc tccggcatcg tgcagcagca gtccaacctc ctgaaggcca    1680
tcgaggccca gcagcacatg ctgaagctga ccgtgtgggg catcaagcag ctgcaggcca    1740
gggtgctcgc gctcgagcgc tacctgaagg accagcagct gctcggcatg tggggctgct    1800
ccggcaagct gatctgcacc accaacgtgt actggaactc gtcctggtcc aacaagacct    1860
acggcgacat ctgggacaac atgacctgga tgcagtggga gcgcgagatc tccaactaca    1920
ccgagatcat ctacgagctc ctcgaggagt cccagaacca gcaggagaag aacgagcagg    1980
atctgctcgc gctggaccgc tggaactccc tgtggaactg gttcaacatc accaactggc    2040
tgtggtacat caagatcttc atcatgatcg tgggcggcct gatcggcctg cgcatcatct    2100
tcgccgtgct gtcgctggtg aaccgcgtgc gccagggctg atgagaattc ggtgaccggg    2160
tcccggatcc                                                          2170
```

<210> SEQ ID NO 62
<211> LENGTH: 859
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Asn Ala Thr Ala Ser Asn Ser Ser Ile Ile Glu Gly Met Asn
    130                 135                 140

Ser Ser Ile Ile Glu Gly Met Lys Asn Cys Ser Phe Asn Ile Thr Thr
145                 150                 155                 160

Glu Leu Arg Asp Lys Arg Glu Lys Asn Ala Leu Phe Tyr Lys Leu
                165                 170                 175

Asp Ile Val Gln Leu Asp Gly Asn Ser Ser Gln Tyr Arg Leu Ile Asn
            180                 185                 190

Cys Asn Thr Ser Val Ile Thr Gln Ala Cys Pro Lys Val Ser Phe Asp
        195                 200                 205
```

```
Pro Ile Pro Ile His Tyr Cys Ala Pro Ala Gly Tyr Ala Ile Leu Lys
210                 215                 220

Cys Asn Asn Lys Thr Phe Asn Gly Thr Gly Pro Cys Asn Asn Val Ser
225                 230                 235                 240

Thr Val Gln Cys Thr His Gly Ile Lys Pro Val Val Ser Thr Gln Leu
            245                 250                 255

Leu Leu Asn Gly Ser Leu Ala Glu Glu Ile Ile Arg Ser Glu
            260                 265                 270

Asn Ile Thr Asp Asn Gly Lys Thr Ile Val His Leu Asn Glu Ser
            275                 280                 285

Val Lys Ile Glu Cys Thr Arg Pro Ser Asn Asn Thr Arg Thr Ser Ile
290                 295                 300

Arg Ile Gly Pro Gly Gln Ala Phe Tyr Ala Thr Gly Gln Val Ile Gly
305                 310                 315                 320

Asp Ile Arg Glu Ala His Cys Asn Ile Ser Glu Ser Lys Trp Asn Glu
                325                 330                 335

Thr Leu Gln Arg Val Ser Glu Lys Leu Lys Glu Tyr Phe Pro His Lys
            340                 345                 350

Asn Ile Thr Phe Gln Pro Ser Ser Gly Gly Asp Leu Glu Ile Thr Thr
            355                 360                 365

His Ser Phe Asn Cys Gly Gly Glu Phe Phe Tyr Cys Asn Thr Ser Ser
370                 375                 380

Leu Phe Asn Arg Thr Tyr Met Ala Thr Ser Thr Asp Met Ala Asn Ser
385                 390                 395                 400

Thr Glu Thr Asn Ser Thr Arg Ile Ile Thr Ile Arg Cys Arg Ile Lys
                405                 410                 415

Gln Ile Ile Asn Met Trp Gln Glu Val Gly Arg Ala Met Tyr Ala Pro
            420                 425                 430

Pro Ile Ala Gly Asn Ile Thr Cys Ile Ser Asn Ile Thr Gly Leu Leu
            435                 440                 445

Leu Thr Arg Asp Gly Gly Lys Asn Asn Thr Glu Thr Phe Glu Thr Phe
450                 455                 460

Arg Pro Gly Gly Gly Asn Met Lys Asp Asn Trp Arg Ser Glu Leu Tyr
465                 470                 475                 480

Lys Tyr Lys Val Val Glu Val Lys Pro Leu Gly Val Ala Pro Thr Asn
                485                 490                 495

Ala Arg Arg Arg Val Val Glu Arg Glu Lys Arg Ala Val Gly Met Gly
            500                 505                 510

Ala Val Phe Leu Gly Phe Leu Gly Ala Ala Gly Ser Thr Met Gly Ala
            515                 520                 525

Ala Ser Ile Thr Leu Thr Val Gln Ala Arg Gln Leu Leu Ser Gly Ile
            530                 535                 540

Val Gln Gln Gln Ser Asn Leu Leu Lys Ala Ile Glu Ala Gln Gln His
545                 550                 555                 560

Met Leu Lys Leu Thr Val Trp Gly Ile Lys Gln Leu Gln Ala Arg Val
            565                 570                 575

Leu Ala Leu Glu Arg Tyr Leu Lys Asp Gln Gln Leu Leu Gly Met Trp
            580                 585                 590

Gly Cys Ser Gly Lys Leu Ile Cys Thr Thr Asn Val Tyr Trp Asn Ser
            595                 600                 605

Ser Trp Ser Asn Lys Thr Tyr Gly Asp Ile Trp Asp Asn Met Thr Trp
            610                 615                 620

Met Gln Trp Glu Arg Glu Ile Ser Asn Tyr Thr Glu Ile Ile Tyr Glu
```

```
                625                 630                 635                 640
Leu Leu Glu Glu Ser Gln Asn Gln Glu Lys Asn Glu Gln Asp Leu
                    645                 650                 655

Leu Ala Leu Asp Arg Trp Asn Ser Leu Trp Asn Trp Phe Asn Ile Thr
                660                 665                 670

Asn Trp Leu Trp Tyr Ile Lys Ile Phe Ile Met Ile Val Gly Gly Leu
            675                 680                 685

Ile Gly Leu Arg Ile Ile Phe Ala Val Leu Ser Leu Val Asn Arg Val
        690                 695                 700

Arg Gln Gly Tyr Ser Pro Leu Ser Leu Gln Thr Leu Ile Pro Ser Pro
705                 710                 715                 720

Arg Gly Pro Asp Arg Pro Gly Gly Ile Glu Glu Gly Gly Glu Gln
                725                 730                 735

Asp Arg Asn Arg Ser Thr Arg Leu Val Ser Gly Phe Leu Ala Leu Ala
                740                 745                 750

Trp Asp Asp Leu Arg Ser Leu Cys Leu Phe Ile Tyr His Arg Leu Arg
            755                 760                 765

Asp Phe Ile Leu Ile Ala Ala Arg Ala Gly Glu Leu Leu Gly Arg Ser
        770                 775                 780

Ser Leu Lys Gly Leu Arg Arg Gly Trp Glu Ala Leu Lys Tyr Leu Gly
785                 790                 795                 800

Ser Leu Val Gln Tyr Trp Gly Leu Glu Leu Lys Arg Ser Ala Ile Ser
                805                 810                 815

Leu Leu Asp Thr Leu Ala Ile Ala Val Gly Glu Gly Thr Asp Arg Ile
                820                 825                 830

Leu Glu Phe Val Leu Gly Ile Cys Arg Ala Ile Arg Asn Ile Pro Thr
            835                 840                 845

Arg Ile Arg Gln Gly Phe Glu Thr Ala Leu Leu
        850                 855

<210> SEQ ID NO 63
<211> LENGTH: 2620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gtcgacaaga aatgcgcgtg atgggcatcc agcgcaacta cccgcagtgg tggatctggt      60
cgatgctggg cttctggatg ctcatgatct gcaacggcat gtgggtgacg gtgtactacg     120
gcgtgccggt gtggaaggag gccaagacga ccctgttctg cgcgtcggac gccaaggcct     180
acgagaagga ggtgcacaac gtgtgggcga cccacgcctg cgtgcccacg accccaacc      240 cgcaggagat ggtgctgaag aacgtgaccg agaacttcaa catgtggaag aacgacatgg     300
tggaccagat gcacgaggac gtgatctccc tgtgggacca gtccctgaag ccctgcgtga     360
agctgacccc gctgtgcgtg accctgaact gcaccaacgc gaacgccacc gcgtccaact     420
cctctatcat cgagggggatg aactcctcca tcatcgaggg catgaagaac tgctccttca     480
acatcacgac ggagctgcgc gacaagcgcg agaagaagaa cgccctgttc tacaagctgg     540
acatcgtgca gctggacggc aactcctcgc agtacaggct gatcaactgc aacacctccg     600
tcatcacgca ggcgtgcccc aaggtgtcct tcgaccccat ccccatccac tactgcgccc     660
ccgccggcta cgccatcctg aagtgcaaca acaagacctt caacggcacc ggcccgtgca     720
```

| | |
|---|---|
| acaacgtgtc caccgtgcag tgcacgcacg ggatcaagcc cgtggtgtcc acgcagctgc | 780 |
| tcctgaacgg gtcgctggcc gagggcgaga tcatcatccg gtccgagaac atcacggaca | 840 |
| acgggaagac catcatcgtg cacctgaacg agtccgtgaa gatcgagtgc acccgcccga | 900 |
| gcaacaacac gcgcacctcc atccggatcg ccctggcca ggccttctac gccaccggcc | 960 |
| aggtgatcgg cgacatccgc gaggcgcact gcaacatctc ggagtccaag tggaacgaga | 1020 |
| ccctgcagcg cgtgtccgag aagctgaagg agtacttccc ccacaagaac atcaccttcc | 1080 |
| agccgtcgtc cggcggcgac ctcgagatca ccacgcactc cttcaactgc ggtggcgagt | 1140 |
| tcttctactg caacacgtcg tcgctgttca accgcaccta catggccacg tccaccgaca | 1200 |
| tggccaactc caccgagacc aactccacgc gcatcatcac gatccggtgc cgcatcaagc | 1260 |
| agatcatcaa catgtggcag gaggtgggcc gcgccatgta cgcaccgccc atcgccggca | 1320 |
| acatcacctg catctccaac atcaccggcc tcctgctgac ccgcgacggc ggcaagaaca | 1380 |
| acacggagac cttcgagacg ttcaggccag gcggaggcaa catgaaggac aactggcgct | 1440 |
| ccgagctgta caagtacaag gtggtggagg tgaagcccct gggcgtggca cccaccaacg | 1500 |
| cccgcaggcg cgtcgtggag cgcgagaagc gcgccgtggg catgggcgcc gtgttcctgg | 1560 |
| gcttcctggg cgctgcgggc tccaccatgg gtgccgcgtc catcaccctg accgtgcagg | 1620 |
| cccgccagct gctctccggc atcgtgcagc agcagtccaa cctcctgaag gccatcgagg | 1680 |
| cccagcagca catgctgaag ctgaccgtgt ggggcatcaa gcagctgcag gccagggtgc | 1740 |
| tcgcgctcga gcgctacctg aaggaccagc agctgctcgg catgtggggc tgctccggca | 1800 |
| agctgatctg caccaccaac gtgtactgga actcgtcctg gtccaacaag acctacggcg | 1860 |
| acatctggga caacatgacc tggatgcagt gggagcgcga gatctccaac tacaccgaga | 1920 |
| tcatctacga gctcctcgag gagtcccaga accagcagga gaagaacgag caggatctgc | 1980 |
| tcgcgctgga ccgctggaac tccctgtgga actggttcaa catcaccaac tggctgtggt | 2040 |
| acatcaagat cttcatcatg atcgtgggcg gcctgatcgg cctgcgcatc atcttcgccg | 2100 |
| tgctgtcgct ggtgaaccgc gtgcgccagg gctactcccc gctgtccctg caaacgctga | 2160 |
| tccccctcccc ccgggggcccg gacaggcccg gtggcatcga ggaggagggc ggcgagcagg | 2220 |
| accgcaaccg ctccacgcgc ctggtgtccg gcttcctggc cctggcgtgg gacgacctgc | 2280 |
| gctccctgtg cctgttcatc taccaccgcc tgcgcgactt catcctgatc gcggcccgcg | 2340 |
| ctggcgagct gctgggccgg tcctcgctga agggcctgcg ccgcggctgg gaggccctga | 2400 |
| agtacctggg ctcgctggtg cagtactggg gcctggagct gaagcgctcc gccatctccc | 2460 |
| tgctggacac cctggccatc gccgtgggcg agggcaccga ccgcatcctg gagttcgtgc | 2520 |
| tgggcatctg ccgcgccatc cgcaacatcc ccacccgcat ccgccagggc ttcgagaccg | 2580 |
| ccctcctgta gtaagaattc ggtgaccggg tcccggatcc | 2620 |

<210> SEQ ID NO 64
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Lys Val Arg Gly Ile Gln Arg Asn Tyr Pro Gln Trp Trp Ile Trp
1               5                   10                  15

Ser Met Leu Gly Leu Trp Met Leu Met Ile Cys Asn Gly Val Pro Val

-continued

```
                20                  25                  30
    Trp Lys Glu Ala Lys Thr Thr Leu Phe Cys Ala Ser Asp Ala Lys Ala
                    35                  40                  45
    Tyr Glu Lys Glu Val His Asn Val Trp Ala Thr His Ala Cys Val Pro
     50                  55                  60
    Thr Asp Pro Asn Pro Gln Met Val Leu Glu Asn Val Thr Glu Asn
     65                  70                  75                  80
    Phe Asn Met Trp Lys Asn Asp Met Ala Asp Gln Met His Glu Asp Val
                    85                  90                  95
    Ile Ser Leu Trp Asp Gln Ser Leu Lys Pro Cys Val Lys Leu Thr Pro
                    100                 105                 110
    Leu Cys Val Thr Leu Asn Cys Thr Asp Ala Asn Ala Thr Ala Ser Asn
                    115                 120                 125
    Thr Asn Ala Thr Ala Ser Asn Ile Asn Ala Thr Ala Ser Lys Ser Ser
                    130                 135                 140
    Ile Ile Glu Glu Met Lys Asn Cys Ser Phe Asn Ile Thr Thr Glu Leu
    145                 150                 155                 160
    Arg Asp Lys Arg Glu Lys Lys Tyr Ala Leu Phe Tyr Lys Leu Asp Ile
                    165                 170                 175
    Val Gln Leu Asp Gly Asn Ser Ser Gln Tyr Arg Leu Ile Asn Cys Asn
                    180                 185                 190
    Thr Ser Val Ile Thr Gln Ala Cys Pro Lys Val Ser Phe Asp Pro Ile
                    195                 200                 205
    Pro Ile His Tyr Cys Ala Pro Ala Gly Tyr Ala Ile Leu Lys Cys Asn
                    210                 215                 220
    Asn Lys Thr Phe Asn Gly Thr Gly Pro Cys Asn Asn Val Ser Thr Val
    225                 230                 235                 240
    Gln Cys Thr His Gly Ile Lys Pro Val Val Ser Thr Gln Leu Leu Leu
                    245                 250                 255
    Asn Gly Ser Leu Ala Glu Gly Glu Ile Ile Ile Arg Ser Glu Asn Ile
                    260                 265                 270
    Thr Asp Asn Ser Lys Thr Ile Ile Val His Leu Asn Glu Ser Val Lys
                    275                 280                 285
    Ile Glu Cys Thr Arg Pro Ser Asn Asn Thr Arg Thr Ser Ile Arg Ile
                    290                 295                 300
    Gly Pro Gly Gln Ala Phe Tyr Ala Thr Gly Gln Val Ile Gly Asp Ile
    305                 310                 315                 320
    Arg Glu Ala His Cys Asn Ile Ser Glu Ser Lys Trp Asn Glu Thr Leu
                    325                 330                 335
    Gln Arg Val Ser Lys Lys Leu Lys Glu Tyr Phe Pro Asp Lys Asn Ile
                    340                 345                 350
    Thr Phe Gln Pro Ser Ser Gly Gly Asp Pro Glu Ile Thr Thr His Ser
                    355                 360                 365
    Phe Asn Cys Gly Gly Glu Phe Phe Tyr Cys Asn Thr Ser Ser Leu Phe
                    370                 375                 380
    Asn Arg Thr Tyr Met Ala Asn Ser Thr Glu Thr Asn Ser Thr Arg Thr
    385                 390                 395                 400
    Ile Thr Leu His Cys Arg Ile Lys Gln Ile Ile Asn Met Trp Gln Glu
                    405                 410                 415
    Val Gly Arg Ala Met Tyr Ala Pro Pro Ile Ala Gly Asn Ile Thr Cys
                    420                 425                 430
    Ile Ser Asn Ile Thr Gly Leu Leu Leu Thr Arg Asp Gly Gly Glu Asn
                    435                 440                 445
```

```
Thr Arg Asp Gly Gly Asn Asn Thr Glu Thr Phe Arg Pro Glu Gly
    450                 455                 460

Gly Asn Met Lys Asp Asn Trp Arg Ser Glu Leu Tyr Lys Tyr Lys Val
465                 470                 475                 480

Val Glu Val Lys Pro Leu Gly Val Ala Pro Thr Lys Ala Arg Glu Arg
                485                 490                 495

Val Val Glu Arg Glu Lys Glu
            500

<210> SEQ ID NO 65
<211> LENGTH: 1559
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ggtcgacaag aagccaccat gaaggtgcgg ggcatccagc gcaactaccc gcagtggtgg      60
atctggtcga tgctgggcct ctggatgctc atgatctgca acggcgtgcc ggtgtggaag     120
gaggccaaga cgaccctgtt ctgcgcgtcg gacgccaagg cctacgagaa ggaggtgcac     180
aacgtgtggg cgacccacgc ctgcgtgccc acggacccca acccgcagga gatggtgctg     240
gagaacgtga ccgagaactt caacatgtgg aagaacgaca tggcggacca gatgcacgag     300
gacgtgatct ccctgtggga ccagtccctg aagccctgcg tgaagctgac ccgctgtgtc     360
gtgaccctga actgcacgga cgccaacgcc accgcgtcga acaccaacgc gaccgcaagc     420
aacatcaacg cggacggcgtc gaagtcctcc atcatcgagg agatgaagaa ctgctccttc     480
aacatcacga cggagctgcg cgacaagcgc gagaagaagt acgccctgtt ctacaagctg     540
gacatcgtgc agctggacgg caactcctcg cagtacaggc tgatcaactg caacacctcc     600
gtcatcacgc aggcgtgccc caaggtgtcc ttcgacccca tccccatcca ctactgcgcc     660
cccgccggct acgccatcct gaagtgcaac aacaagacct tcaacggcac cggccgtgc     720 aacaacgtgt ccaccgtgca gtgcacgcac gggatcaagc ccgtggtgtc cacgcagctg     780
ctcctgaacg ggtcgctggc cgagggcgag atcatcatcc ggtcggagaa catcacggac     840
aacagcaaga ccatcatcgt gcacctgaac gagtccgtga agatcgagtg cacccgcccg     900
agcaacaaca cgcgcacctc catccggatc ggccctggcc aggccttcta cgccaccggc     960
caagtgatcg gcgacatccg cgaggcgcac tgcaacatct ccgagtccaa gtggaacgag    1020
accctgcagc gcgtgtccaa gaagctgaag gagtacttcc ccgacaagaa catcaccttc    1080
cagccgtcgt ccggcggcga ccccgagatc accacgcact ccttcaactg cggtggcgag    1140
ttcttctact gcaacacgtc gtccctgttc aaccgcacct acatggcgaa ctccaccgag    1200
accaactcca cgcgcaccat cacgctgcac tgccgcatca agcagatcat caacatgtgg    1260
caggaggtgg gccgcgccat gtacgcaccg cccatcgccg caacatcac ctgcatctcc    1320 aacatcaccg gcctcctgct gacccgcgac ggcggcgaga cacccggga cggaggcaac    1380 aacaacacgg agaccttcag gccagaggga ggcaacatga aggacaactg cgcctccgag    1440
ctgtacaagt acaaggtggt ggaggtgaag cccctgggcg tggcacccac caaggcccgc    1500
gagcgcgtcg tggagcgcga gaaggagtag taaggtaacc gggacccgaa ttcggatcc    1559

<210> SEQ ID NO 66
<211> LENGTH: 2182
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
gtcgacaaga agccaccatg aaggtgcggg gcatccagcg caactacccg cagtggtgga      60
tctggtcgat gctgggcctc tggatgctca tgatctgcaa cggcatgtgg gtgacggtgt     120
actacggcgt gccggtgtgg aaggaggcca agacgaccct gttctgcgcg tcggacgcca     180
aggcctacga aaggaggtg cacaacgtgt gggcgaccca cgcctgcgtg cccacggacc     240
ccaacccgca ggagatggtg ctggagaacg tgaccgagaa cttcaacatg tggaagaacg     300
acatggcgga ccagatgcac gaggacgtga tctccctgtg ggaccagtcc ctgaagccct     360
gcgtgaagct gaccccgctg tgcgtgaccc tgaactgcac ggacgccaac gccaccgcgt     420
cgaacaccaa cgcgaccgca agcaacatca acgcgacggc gtcgaagtcc tccatcatcg     480
aggagatgaa gaactgctcc ttcaacatca cgacggagct gcgcgacaag cgcgagaaga     540
agtacgccct gttctacaag ctggacatcg tgcagctgga cggcaactcc tcgcagtaca     600
ggctgatcaa ctgcaacacc tccgtcatca cgcaggcgtg cccccaggtg tccttcgacc     660
ccatccccat ccactactgc gcccccgccg gctacgccat cctgaagtgc aacaacaaga     720
ccttcaacgg caccggcccg tgcaacaacg tgtccaccgt gcagtgcacg cacgggatca     780
agcccgtggt gtccacgcag ctgctcctga acgggtcgct ggccgagggc gagatcatca     840
tccggtcgga gaacatcacg gacaacgcag agaccatcat cgtgcacctg aacgagtccg     900
tgaagatcga gtgcacccgc ccgagcaaca cacgcgcac ctccatccgg atcggccctg     960
gccaggcctt ctacgccacc ggccaagtga tcggcgacat ccgcgaggcg cactgcaaca    1020
tctccgagtc caagtggaac gagaccctgc agcgcgtgtc caagaagctg aaggagtact    1080
tccccgacaa gaacatcacc ttccagccgt cgtccggcgg cgaccccgag atcaccacgc    1140
actccttcaa ctgcggtggc gagttcttct actgcaacac gtcgtccctg ttcaaccgca    1200
cctacatggc gaactccacc gagaccaact ccacgcgcac catcacgctg cactgccgca    1260
tcaagcagat catcaacatg tggcaggagg tgggccgcgc catgtacgca ccgcccatcg    1320
ccggcaacat cacctgcatc tccaacatca ccggcctcct gctgacccgc gacgcgggcg    1380
agaacacccg ggacggaggc aacaacaaca cggagacctt caggccagag ggaggcaaca    1440
tgaaggacaa ctggcgctcc gagctgtaca agtacaaggt ggtggaggtg aagcccctgg    1500
gcgtggcacc caccaaggcc cgcaggcgcg tcgtggagcg cgagaagcgc gccgtgggca    1560
tgggcgccgt gttcctgggc ttcctgggcg ctgcgggctc caccatgggt gccgcgtcca    1620
tcaccctgac cgtgcaggcc cgccagctgc tctccggcat cgtgcagcag cagtccaacc    1680
tcctgaaggc catcgaggcc cagcagcaca tgctgaagct gaccgtgtgg ggcatcaagc    1740
agctgcaggc cagggtgctc cgcgctcgag cgtacctgaa ggaccagcag ctgctcggca    1800
tgtgggctg ctccggcaag ctgatctgca ccaccaacgt gtactggaac tcgtcctggt    1860
ccaacaagac ctacgcgac atctgggaca acatgacctg gatgcagtgg gagcgcgaga    1920
tctccaacta caccgacatc atctacgacc tcctcgagga gtcccagaac cagcaggaga    1980
agaacgagca ggatctgctc gcgctggacc gctggaactc cctgtggaac tggttcaaca    2040
tcaccaagtg gctgtggtac atcaagatct tcatcatgat cgtgggcggc ctgatcggcc    2100
tgcgcatcat cttcgccgtg ctgtcgctgg tgaaccgcgt gcgccagggc tgatgaggta    2160
```

```
accgggaccc gaattcggat cc                                              2182
```

<210> SEQ ID NO 67
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Met Lys Val Arg Gly Ile Gln Arg Asn Tyr Pro Gln Trp Trp Ile Trp
1               5                   10                  15

Ser Met Leu Gly Leu Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Glu Asn Val Thr Glu Asn Phe Asn Met Trp Lys Asn Asp Met
                85                  90                  95

Ala Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Ala Asn Ala Thr Ala Ser Asn Thr Asn Ala Thr Ala Ser Asn Ile
    130                 135                 140

Asn Ala Thr Ala Ser Lys Ser Ser Ile Ile Glu Glu Met Lys Asn Cys
145                 150                 155                 160

Ser Phe Asn Ile Thr Thr Glu Leu Arg Asp Lys Arg Glu Lys Lys Tyr
                165                 170                 175

Ala Leu Phe Tyr Lys Leu Asp Ile Val Gln Leu Asp Gly Asn Ser Ser
            180                 185                 190

Gln Tyr Arg Leu Ile Asn Cys Asn Thr Ser Val Ile Thr Gln Ala Cys
        195                 200                 205

Pro Lys Val Ser Phe Asp Pro Ile Pro Ile His Tyr Cys Ala Pro Ala
    210                 215                 220

Gly Tyr Ala Ile Leu Lys Cys Asn Asn Lys Thr Phe Asn Gly Thr Gly
225                 230                 235                 240

Pro Cys Asn Asn Val Ser Thr Val Gln Cys Thr His Gly Ile Lys Pro
                245                 250                 255

Val Val Ser Thr Gln Leu Leu Leu Asn Gly Ser Leu Ala Glu Gly Glu
            260                 265                 270

Ile Ile Ile Arg Ser Glu Asn Ile Thr Asp Asn Ser Lys Thr Ile Ile
        275                 280                 285

Val His Leu Asn Glu Ser Val Lys Ile Glu Cys Thr Arg Pro Ser Asn
    290                 295                 300

Asn Thr Arg Thr Ser Ile Arg Ile Gly Pro Gly Gln Ala Phe Tyr Ala
305                 310                 315                 320

Thr Gly Gln Val Ile Gly Asp Ile Arg Glu Ala His Cys Asn Ile Ser
                325                 330                 335

Glu Ser Lys Trp Asn Glu Thr Leu Gln Arg Val Ser Lys Lys Leu Lys
            340                 345                 350
```

```
Glu Tyr Phe Pro Asp Lys Asn Ile Thr Phe Gln Pro Ser Ser Gly Gly
            355                 360                 365

Asp Pro Glu Ile Thr Thr His Ser Phe Asn Cys Gly Gly Glu Phe Phe
        370                 375                 380

Tyr Cys Asn Thr Ser Ser Leu Phe Asn Arg Thr Tyr Met Ala Asn Ser
385                 390                 395                 400

Thr Glu Thr Asn Ser Thr Arg Thr Ile Thr Leu His Cys Arg Ile Lys
                405                 410                 415

Gln Ile Ile Asn Met Trp Gln Glu Val Gly Arg Ala Met Tyr Ala Pro
            420                 425                 430

Pro Ile Ala Gly Asn Ile Thr Cys Ile Ser Asn Ile Thr Gly Leu Leu
        435                 440                 445

Leu Thr Arg Asp Gly Gly Glu Asn Thr Arg Asp Gly Gly Asn Asn Asn
    450                 455                 460

Thr Glu Thr Phe Arg Pro Glu Gly Gly Asn Met Lys Asp Asn Trp Arg
465                 470                 475                 480

Ser Glu Leu Tyr Lys Tyr Lys Val Val Glu Val Lys Pro Leu Gly Val
                485                 490                 495

Ala Pro Thr Lys Ala Arg Arg Arg Val Val Glu Arg Glu Lys Arg Ala
            500                 505                 510

Val Gly Met Gly Ala Val Phe Leu Gly Phe Leu Gly Ala Ala Gly Ser
        515                 520                 525

Thr Met Gly Ala Ala Ser Ile Thr Leu Thr Val Gln Ala Arg Gln Leu
    530                 535                 540

Leu Ser Gly Ile Val Gln Gln Gln Ser Asn Leu Leu Lys Ala Ile Glu
545                 550                 555                 560

Ala Gln Gln His Met Leu Lys Leu Thr Val Trp Gly Ile Lys Gln Leu
                565                 570                 575

Gln Ala Arg Val Leu Ala Leu Glu Arg Tyr Leu Lys Asp Gln Gln Leu
            580                 585                 590

Leu Gly Met Trp Gly Cys Ser Gly Lys Leu Ile Cys Thr Thr Asn Val
        595                 600                 605

Tyr Trp Asn Ser Ser Trp Ser Asn Lys Thr Tyr Gly Asp Ile Trp Asp
    610                 615                 620

Asn Met Thr Trp Met Gln Trp Glu Arg Glu Ile Ser Asn Tyr Thr Asp
625                 630                 635                 640

Ile Ile Tyr Asp Leu Leu Glu Glu Ser Gln Asn Gln Gln Glu Lys Asn
                645                 650                 655

Glu Gln Asp Leu Leu Ala Leu Asp Arg Trp Asn Ser Leu Trp Asn Trp
            660                 665                 670

Phe Asn Ile Thr Lys Trp Leu Trp Tyr Ile Lys Ile Phe Ile Met Ile
        675                 680                 685

Val Gly Gly Leu Ile Gly Leu Arg Ile Ile Phe Ala Val Leu Ser Leu
    690                 695                 700

Val Asn Arg Val Arg Gln Gly Tyr Ser Pro Leu Ser Leu Gln Thr Leu
705                 710                 715                 720

Ile Pro Ser Pro Arg Gly Pro Asp Arg Pro Gly Gly Ile Glu Glu Glu
                725                 730                 735

Gly Gly Glu Gln Asp Arg Asn Arg Ser Thr Arg Leu Val Ser Gly Phe
            740                 745                 750

Leu Ala Leu Ala Trp Asp Asp Leu Arg Ser Leu Cys Leu Phe Ile Tyr
        755                 760                 765
```

```
His Arg Leu Arg Asp Phe Ile Leu Ile Ala Ala Arg Ala Gly Glu Leu
        770                 775                 780

Leu Gly Arg Ser Ser Leu Lys Gly Leu Arg Arg Gly Trp Glu Ala Leu
785                 790                 795                 800

Lys Tyr Leu Gly Gly Leu Val Gln Tyr Trp Gly Leu Glu Leu Lys Arg
                805                 810                 815

Ser Ala Ile Ser Leu Leu Asp Thr Leu Ala Ile Ala Val Gly Glu Gly
            820                 825                 830

Thr Asp Arg Ile Leu Glu Phe Val Leu Gly Ile Cys Arg Ala Ile Arg
                835                 840                 845

Asn Ile Pro Thr Arg Ile Arg Gln Gly Phe Glu Thr Ala Leu Leu
        850                 855                 860

<210> SEQ ID NO 68
<211> LENGTH: 2632
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gtcgacaaga aatgaaggtg cggggcatcc agcgcaacta cccgcagtgg tggatctggt      60
cgatgctggg cctctggatg ctcatgatct gcaacggcat gtgggtgacg gtgtactacg     120
gcgtgccggt gtggaaggag gccaagacga ccctgttctg cgcgtcggac gccaaggcct     180
acgagaagga ggtgcacaac gtgtgggcga cccacgcctg cgtgcccacg accccaacc     240 cgcaggagat ggtgctggag aacgtgaccg agaacttcaa catgtggaag aacgacatgg     300
cggaccagat gcacgaggac gtgatctccc tgtgggacca gtccctgaag ccctgcgtga     360
agctgacccc gctgtgcgtg accctgaact gcacggacgc caacgccacc gcgtcgaaca     420
ccaacgcgac cgcaagcaac atcaacgcga cggcgtcgaa gtcctccatc atcgaggaga     480
tgaagaactg ctccttcaac atcacgacgg agctgcgcga caagcgcgag aagaagtacg     540
ccctgttcta caagctggac atcgtgcagc tggacggcaa ctcctcgcag tacaggctga     600
tcaactgcaa cacctccgtc atcacgcagg cgtgcccgaa ggtgtccttc gaccccatcc     660
ccatccacta ctgcgccccc gccggctacg ccatcctgaa gtgcaacaac aagaccttca     720
acggcaccgg cccgtgcaac aacgtgtcca ccgtgcagtg cacgcacggg atcaagcccg     780
tggtgtccac gcagctgctc ctgaacgggt cgctggccga gggcgagatc atcatccggt     840
cggagaacat cacggacaac agcaagacca tcatcgtgca cctgaacgag tccgtgaaga     900
tcgagtgcac ccgcccgagc aacaacacgc gcacctccat ccggatcggc cctggccagg     960
ccttctacgc caccggccaa gtgatcggcg acatccgcga ggcgcactgc aacatctccg    1020
agtccaagtg gaacgagacc ctgcagcgcg tgtccaagaa gctgaaggag tacttccccg    1080
acaagaacat caccttccag ccgtcgtccg gcggcgaccc cgagatcacc acgcactcct    1140
tcaactgcgg tggcgagttc ttctactgca acacgtcgtc cctgttcaac cgcacctaca    1200
tggcgaactc caccgagacc aactccacgc gcaccatcac gctgcactgc cgcatcaagc    1260
agatcatcaa catgtggcag gaggtgggcc gcgccatgta cgcaccgccc atcgccggca    1320
acatcacctg catctccaac atcaccggcc tcctgctgac ccgcgacggc ggcgagaaca    1380
cccgggacag aggcaacaac aacacggaga ccttcaggcc agagggaggc aacatgaagg    1440
acaactggcg ctccgagctg tacaagtaca aggtggtgga ggtgaagccc ctgggcgtgg    1500
```

```
cacccaccaa ggcccgcagg cgcgtcgtgg agcgcgagaa gcgcgccgtg ggcatgggcg    1560
ccgtgttcct gggcttcctg ggcgctgcgg gctccaccat gggtgccgcg tccatcaccc    1620
tgaccgtgca ggcccgccag ctgctctccg gcatcgtgca gcagcagtcc aacctcctga    1680
aggccatcga ggcccagcag cacatgctga agctgaccgt gtggggcatc aagcagctgc    1740
aggccagggt gctcgcgctc gagcgctacc tgaaggacca gcagctgctc ggcatgtggg    1800
gctgctccgg caagctgatc tgcaccacca cgtgtactg gaactcgtcc tggtccaaca    1860
agacctacgg cgacatctgg gacaacatga cctggatgca gtgggagcgc gagatctcca    1920
actacaccga catcatctac gacctcctcg aggagtccca gaaccagcag agaagaacg    1980 agcaggatct gctcgcgctg gaccgctgga actccctgtg gaactggttc aacatcacca    2040
agtggctgtg gtacatcaag atcttcatca tgatcgtggg cggcctgatc ggcctgcgca    2100
tcatcttcgc cgtgctgtcg ctggtgaacc gcgtgcgcca gggctactcc ccgctgtccc    2160
tgcaaacgct gatcccctcc ccccggggcc cggacaggcc cggtggcatc gaggaggagg    2220
gcggcgagca ggaccgcaac cgctccacgc gcctggtgtc cggcttcctg gcctggcgt    2280 gggacgacct cgctcccctg tgcctgttca tctaccaccg cctgcgcgac ttcatcctga    2340
tcgcggcccg cgctggcgag ctgctgggcc ggtcctcgct gaagggcctg cgccgcggct    2400
gggaggccct gaagtacctg ggcgggctgg tgcagtactg gggcctggag ctgaagcgct    2460
ccgccatctc cctgctggac accctggcca tcgccgtggg cgaggcacc gaccgcatcc    2520 tggagttcgt gctgggcatc tgccgcgcca tccgcaacat ccccacccgc atccgccagg    2580
gcttcgagac cgcccctcct gtagtaaggta accgggaccc gaattcggat cc    2632
```

<210> SEQ ID NO 69
<211> LENGTH: 846
<212> TYPE: PRT
<213> ORGANISM: Human immunodeficiency virus 1

<400> SEQUENCE: 69

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Ala Ser Asn Ser Ser Ile Ile Glu Gly Met Lys Asn Cys
    130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175
```

-continued

```
Gln Tyr Arg Leu Ile Asn Cys Asn Thr Ser Val Ile Thr Gln Ala Cys
            180                 185                 190
Pro Lys Val Ser Phe Asp Pro Ile Pro Ile His Tyr Cys Ala Pro Ala
        195                 200                 205
Gly Tyr Ala Ile Leu Lys Cys Asn Asn Lys Thr Phe Thr Gly Thr Gly
    210                 215                 220
Pro Cys Asn Asn Val Ser Thr Val Gln Cys Thr His Gly Ile Lys Pro
225                 230                 235                 240
Val Val Ser Thr Gln Leu Leu Leu Asn Gly Ser Leu Ala Glu Gly Glu
            245                 250                 255
Ile Ile Ile Arg Ser Glu Asn Ile Thr Asp Asn Gly Lys Thr Ile Ile
        260                 265                 270
Val His Leu Asn Glu Ser Val Lys Ile Glu Cys Thr Arg Pro Asn Asn
    275                 280                 285
Lys Thr Arg Thr Ser Ile Arg Ile Gly Pro Gly Gln Ala Phe Tyr Ala
290                 295                 300
Thr Gly Gln Val Ile Gly Asp Ile Arg Glu Ala Tyr Cys Asn Ile Asn
305                 310                 315                 320
Glu Ser Lys Trp Asn Glu Thr Leu Gln Arg Val Ser Lys Lys Leu Lys
            325                 330                 335
Glu Tyr Phe Pro His Lys Asn Ile Thr Phe Gln Pro Ser Ser Gly Gly
        340                 345                 350
Asp Leu Glu Ile Thr Thr His Ser Phe Asn Cys Gly Gly Glu Phe Phe
    355                 360                 365
Tyr Cys Asn Thr Ser Ser Leu Phe Asn Arg Thr Tyr Met Ala Asn Ser
370                 375                 380
Thr Asp Met Ala Asn Ser Thr Glu Thr Asn Ser Thr Arg Thr Ile Thr
385                 390                 395                 400
Ile His Cys Arg Ile Lys Gln Ile Ile Asn Met Trp Gln Glu Val Gly
            405                 410                 415
Arg Ala Met Tyr Ala Pro Pro Ile Ala Gly Asn Ile Thr Cys Ile Ser
        420                 425                 430
Asn Ile Thr Gly Leu Leu Leu Thr Arg Asp Gly Gly Lys Asn Asn Thr
    435                 440                 445
Glu Thr Phe Arg Pro Gly Gly Gly Asn Met Lys Asp Asn Trp Arg Ser
450                 455                 460
Glu Leu Tyr Lys Tyr Lys Val Val Glu Val Lys Pro Leu Gly Val Ala
465                 470                 475                 480
Pro Thr Asn Ala Arg Arg Arg Val Val Glu Arg Glu Lys Arg Ala Val
            485                 490                 495
Gly Met Gly Ala Val Phe Leu Gly Phe Leu Gly Ala Ala Gly Ser Thr
        500                 505                 510
Met Gly Ala Ala Ser Ile Thr Leu Thr Val Gln Ala Arg Gln Leu Leu
    515                 520                 525
Ser Gly Ile Val Gln Gln Ser Asn Leu Leu Lys Ala Ile Glu Ala
530                 535                 540
Gln Gln His Met Leu Lys Leu Thr Val Trp Gly Ile Lys Gln Leu Gln
545                 550                 555                 560
Ala Arg Val Leu Ala Leu Glu Arg Tyr Leu Lys Asp Gln Gln Leu Leu
            565                 570                 575
Gly Met Trp Gly Cys Ser Gly Lys Leu Ile Cys Thr Thr Asn Val Tyr
        580                 585                 590
Trp Asn Ser Ser Trp Ser Asn Lys Thr Tyr Gly Asp Ile Trp Asp Asn
```

```
                    595                 600                 605
Met Thr Trp Met Gln Trp Glu Arg Glu Ile Ser Asn Tyr Thr Glu Ile
    610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                    645                 650                 655

Asn Ile Thr Asn Trp Leu Trp Tyr Ile Lys Ile Phe Ile Met Ile Val
                660                 665                 670

Gly Gly Leu Ile Gly Leu Arg Ile Ile Phe Ala Val Leu Ser Leu Val
            675                 680                 685

Asn Arg Val Arg Gln Gly Tyr Ser Pro Leu Ser Leu Gln Thr Leu Ile
690                 695                 700

Pro Ser Pro Arg Gly Pro Asp Arg Pro Gly Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
            740                 745                 750

Arg Leu Arg Asp Phe Ile Leu Ile Ala Ala Arg Ala Gly Glu Leu Leu
        755                 760                 765

Gly Arg Ser Ser Leu Lys Gly Leu Arg Arg Gly Trp Glu Ala Leu Lys
770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
        835                 840                 845

<210> SEQ ID NO 70
<211> LENGTH: 846
<212> TYPE: PRT
<213> ORGANISM: Human immunodeficiency virus 1

<400> SEQUENCE: 70

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Val
        50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
                100                 105                 110

Lys Pro Cys Val Lys Leu Thr Pro Leu Cys Val Thr Leu Asn Cys Thr
            115                 120                 125
```

```
Asn Ala Thr Ala Ser Asn Ser Ser Ile Ile Glu Gly Met Lys Asn Cys
130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
                180                 185                 190

Pro Lys Val Ser Phe Asp Pro Ile Pro Ile His Tyr Cys Ala Pro Ala
                195                 200                 205

Gly Tyr Ala Ile Leu Lys Cys Asn Asn Lys Thr Phe Thr Gly Thr Gly
210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Val Lys Thr Ile Ile
                260                 265                 270

Val His Leu Asn Glu Ser Val Lys Ile Glu Cys Thr Arg Pro Asn Asn
275                 280                 285

Lys Thr Arg Thr Ser Ile Arg Ile Gly Pro Gly Gln Ala Phe Tyr Ala
290                 295                 300

Thr Gly Gln Val Ile Gly Asp Ile Arg Glu Ala Tyr Cys Asn Ile Asn
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
                340                 345                 350

Asp Leu Glu Ile Thr Thr His Ser Phe Asn Cys Gly Gly Glu Phe Phe
                355                 360                 365

Tyr Cys Asn Thr Ser Ser Leu Phe Asn Arg Thr Tyr Met Ala Asn Ser
370                 375                 380

Thr Asp Met Ala Asn Ser Thr Glu Thr Asn Ser Thr Arg Thr Ile Thr
385                 390                 395                 400

Ile His Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Ile Ser
                420                 425                 430

Asn Ile Thr Gly Leu Leu Leu Thr Arg Asp Gly Gly Lys Asn Asn Thr
                435                 440                 445

Glu Thr Phe Arg Pro Gly Gly Gly Asn Met Lys Asp Asn Trp Arg Ser
450                 455                 460

Glu Leu Tyr Lys Tyr Lys Val Val Glu Val Lys Pro Leu Gly Val Ala
465                 470                 475                 480

Pro Thr Asn Ala Arg Arg Arg Val Val Glu Arg Glu Lys Arg Ala Val
                485                 490                 495

Gly Met Gly Ala Val Phe Leu Gly Phe Leu Gly Ala Ala Gly Ser Thr
                500                 505                 510

Met Gly Ala Ala Ser Ile Thr Leu Thr Val Gln Ala Arg Gln Leu Leu
                515                 520                 525

Ser Gly Ile Val Gln Gln Gln Ser Asn Leu Leu Lys Ala Ile Glu Ala
                530                 535                 540

Gln Gln His Met Leu Lys Leu Thr Val Trp Gly Ile Lys Gln Leu Gln
```

```
            545                 550                 555                 560
    Ala Arg Val Leu Ala Leu Glu Arg Tyr Leu Lys Asp Gln Gln Leu Leu
                        565                 570                 575

Gly Met Trp Gly Cys Ser Gly Lys Leu Ile Cys Thr Thr Asn Val Tyr
                        580                 585                 590

Trp Asn Ser Ser Trp Ser Asn Lys Thr Tyr Gly Asp Ile Trp Asp Asn
                        595                 600                 605

Met Thr Trp Met Gln Trp Glu Arg Glu Ile Ser Asn Tyr Thr Glu Ile
                        610                 615                 620

Ile Tyr Glu Leu Leu Glu Glu Ser Gln Asn Gln Gln Glu Lys Asn Glu
    625                 630                 635                 640

Gln Asp Leu Leu Ala Leu Asp Arg Trp Asn Ser Leu Trp Asn Trp Phe
                        645                 650                 655

Asn Ile Thr Asn Trp Leu Gly Tyr Ile Lys Ile Phe Ile Met Ile Val
                        660                 665                 670

Gly Gly Leu Ile Gly Leu Arg Ile Ile Phe Ala Val Leu Ser Leu Val
                        675                 680                 685

Asn Arg Val Arg Gln Gly Tyr Ser Pro Leu Ser Leu Gln Thr Leu Ile
    690                 695                 700

Pro Ser Pro Arg Gly Pro Asp Arg Pro Gly Gly Ile Glu Glu Glu Gly
    705                 710                 715                 720

Gly Glu Gln Asp Arg Asn Arg Ser Thr Arg Leu Val Ser Gly Phe Leu
                        725                 730                 735

Ala Leu Val Trp Asp Asp Leu Arg Ser Leu Cys Leu Phe Ile Tyr His
                        740                 745                 750

Arg Leu Arg Asp Phe Ile Leu Ile Ala Ala Arg Ala Gly Glu Leu Leu
                        755                 760                 765

Gly Arg Ser Ser Leu Lys Gly Leu Arg Arg Gly Trp Glu Ala Leu Lys
                        770                 775                 780

Tyr Leu Gly Ser Leu Val Gln Tyr Trp Gly Leu Glu Leu Lys Arg Ser
    785                 790                 795                 800

Ala Ile Ser Leu Leu Asp Thr Leu Ala Ile Ala Val Gly Glu Gly Thr
                        805                 810                 815

Asp Arg Ile Leu Glu Phe Val Leu Gly Ile Cys Arg Ala Ile Arg Asn
                        820                 825                 830

Ile Pro Thr Arg Ile Arg Gln Gly Phe Glu Thr Ala Leu Leu
                        835                 840                 845

<210> SEQ ID NO 71
<211> LENGTH: 846
<212> TYPE: PRT
<213> ORGANISM: Human immunodeficiency virus 1

<400> SEQUENCE: 71

Met Arg Val Met Gly Ile Gln Arg Asn Tyr Pro Gln Trp Trp Ile Trp
    1               5                   10                  15

Ser Met Leu Gly Phe Trp Met Leu Met Ile Cys Asn Gly Met Trp Val
                        20                  25                  30

Thr Val Tyr Tyr Gly Val Pro Val Trp Lys Glu Ala Lys Thr Thr Leu
                        35                  40                  45

Phe Cys Ala Ser Asp Ala Lys Ala Tyr Glu Lys Glu Val His Asn Val
                        50                  55                  60

Trp Ala Thr His Ala Cys Val Pro Thr Asp Pro Asn Pro Gln Glu Met
    65                  70                  75                  80
```

```
Val Leu Lys Asn Val Thr Glu Asn Phe Asn Met Trp Lys Asn Asp Met
                85                  90                  95
Val Asp Gln Met His Glu Asp Val Ile Ser Leu Trp Asp Gln Ser Leu
            100                 105                 110
Lys Pro Cys Val Lys Leu Thr Pro Leu Cys Val Thr Leu Asn Cys Thr
            115                 120                 125
Asn Ala Thr Ala Ser Asn Asn Ser Ile Ile Glu Gly Met Lys Asn Cys
            130                 135                 140
Ser Phe Asn Ile Thr Thr Glu Leu Arg Asp Lys Arg Glu Lys Lys Asn
145                 150                 155                 160
Ala Leu Phe Tyr Lys Leu Asp Ile Val Gln Leu Asp Gly Asn Ser Ser
                165                 170                 175
Gln Tyr Arg Leu Ile Asn Cys Asn Thr Ser Val Ile Thr Gln Ala Cys
            180                 185                 190
Pro Lys Val Ser Phe Asp Pro Ile Pro Ile His Tyr Cys Ala Pro Ala
            195                 200                 205
Gly Tyr Ala Ile Leu Lys Cys Asn Asn Lys Thr Phe Thr Gly Thr Gly
            210                 215                 220
Pro Cys Asn Asn Val Ser Thr Val Gln Cys Thr His Gly Ile Lys Pro
225                 230                 235                 240
Val Val Ser Thr Gln Leu Leu Leu Asn Gly Ser Leu Ala Glu Gly Glu
                245                 250                 255
Ile Ile Ile Arg Ser Glu Asn Ile Thr Asn Asn Ala Lys Thr Ile Ile
            260                 265                 270
Val His Leu Asn Glu Ser Val Lys Ile Glu Cys Thr Arg Pro Asn Asn
            275                 280                 285
Lys Thr Arg Thr Ser Ile Arg Ile Gly Pro Gly Gln Ala Phe Tyr Ala
            290                 295                 300
Thr Gly Gln Val Ile Gly Asp Ile Arg Lys Ala Tyr Cys Asn Ile Ser
305                 310                 315                 320
Glu Ser Lys Trp Asn Glu Thr Leu Gln Arg Val Ser Lys Lys Leu Lys
                325                 330                 335
Glu Tyr Phe Pro His Lys Asn Ile Thr Phe Gln Pro Ser Ser Gly Gly
            340                 345                 350
Asp Leu Glu Ile Thr Thr His Ser Phe Asn Cys Gly Gly Glu Phe Phe
            355                 360                 365
Tyr Cys Asn Thr Ser Ser Leu Phe Asn Arg Thr Tyr Met Ala Asn Ser
            370                 375                 380
Thr Asp Met Ala Asn Ser Thr Glu Thr Asn Ser Thr Arg Thr Ile Thr
385                 390                 395                 400
Leu His Cys Arg Ile Lys Gln Ile Ile Asn Met Trp Gln Glu Val Gly
                405                 410                 415
Arg Ala Met Tyr Ala Pro Pro Ile Ala Gly Asn Ile Thr Cys Ile Ser
            420                 425                 430
Asn Ile Thr Gly Leu Leu Leu Thr Arg Asp Gly Gly Lys Asn Asn Thr
            435                 440                 445
Glu Thr Phe Arg Pro Gly Gly Gly Asn Met Lys Asp Asn Trp Arg Ser
            450                 455                 460
Glu Leu Tyr Lys Tyr Lys Val Val Glu Val Lys Pro Leu Gly Val Ala
465                 470                 475                 480
Pro Thr Asn Ala Arg Arg Arg Val Val Glu Arg Glu Lys Arg Ala Val
                485                 490                 495
Gly Met Gly Ala Val Phe Leu Gly Phe Leu Gly Ala Ala Gly Ser Thr
```

```
                500              505              510
Met Gly Ala Ala Ser Ile Thr Leu Thr Val Gln Ala Arg Gln Leu Leu
            515                  520                  525

Ser Gly Ile Val Gln Gln Ser Asn Leu Leu Lys Ala Ile Glu Ala
        530                  535                  540

Gln Gln His Met Leu Lys Leu Thr Val Trp Gly Ile Lys Gln Leu Gln
545                  550                  555                  560

Ala Arg Val Leu Ala Leu Glu Arg Tyr Leu Lys Asp Gln Gln Leu Leu
                565                  570                  575

Gly Met Trp Gly Cys Ser Gly Lys Leu Ile Cys Thr Thr Asn Val Tyr
            580                  585                  590

Trp Asn Ser Ser Trp Ser Asn Lys Thr Tyr Gly Asp Ile Trp Asp Asn
        595                  600                  605

Met Thr Trp Met Gln Trp Glu Arg Glu Ile Ser Asn Tyr Thr Glu Ile
    610                  615                  620

Ile Tyr Glu Leu Leu Glu Glu Ser Gln Asn Gln Gln Glu Lys Asn Glu
625                  630                  635                  640

Gln Asp Leu Leu Ala Leu Asp Arg Trp Asn Ser Leu Trp Asn Trp Phe
                645                  650                  655

Asn Ile Thr Asn Trp Leu Trp Tyr Ile Lys Ile Phe Ile Met Ile Val
            660                  665                  670

Gly Gly Leu Ile Gly Leu Arg Ile Ile Phe Ala Val Leu Ser Leu Val
        675                  680                  685

Asn Arg Val Arg Gln Gly Tyr Ser Pro Leu Ser Leu Gln Thr Leu Ile
    690                  695                  700

Pro Ser Pro Arg Gly Pro Asp Arg Pro Gly Gly Ile Glu Glu Glu Gly
705                  710                  715                  720

Gly Glu Gln Asp Arg Asn Arg Ser Thr Arg Leu Val Ser Gly Phe Leu
                725                  730                  735

Ala Leu Val Trp Asp Asp Leu Arg Ser Leu Cys Leu Phe Ile Tyr His
            740                  745                  750

Arg Leu Arg Asp Phe Ile Leu Ile Ala Ala Arg Ala Gly Glu Leu Leu
        755                  760                  765

Gly Arg Ser Ser Leu Lys Gly Leu Arg Arg Gly Trp Glu Ala Leu Lys
    770                  775                  780

Tyr Leu Gly Ser Leu Val Gln Tyr Trp Gly Leu Glu Leu Lys Arg Ser
785                  790                  795                  800

Ala Ile Ser Leu Leu Asp Thr Leu Ala Ile Ala Val Gly Glu Gly Thr
                805                  810                  815

Asp Arg Ile Leu Glu Phe Val Leu Gly Ile Cys Arg Ala Ile Arg Asn
            820                  825                  830

Ile Pro Thr Arg Ile Arg Gln Gly Phe Glu Thr Ala Leu Leu
        835                  840                  845

<210> SEQ ID NO 72
<211> LENGTH: 846
<212> TYPE: PRT
<213> ORGANISM: Human immunodeficiency virus 1

<400> SEQUENCE: 72

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30
```

```
Thr Val Tyr Tyr Gly Val Pro Val Trp Lys Glu Ala Lys Thr Thr Leu
         35                  40                  45

Phe Cys Ala Ser Asp Ala Lys Ala Tyr Glu Lys Glu Val His Asn Val
 50                  55                  60

Trp Ala Thr His Ala Cys Val Pro Thr Asp Pro Asn Pro Gln Glu Met
 65                  70                  75                  80

Val Leu Lys Asn Val Thr Glu Asn Phe Asn Met Trp Lys Asn Asp Met
                 85                  90                  95

Val Asp Gln Met His Glu Asp Val Ile Ser Leu Trp Asp Gln Ser Leu
            100                 105                 110

Lys Pro Cys Val Lys Met Thr Pro Leu Cys Val Thr Leu Asn Cys Thr
            115                 120                 125

Asn Ala Thr Ala Ile Asn Ser Ser Ile Ile Glu Gly Met Lys Asn Cys
130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
            195                 200                 205

Gly Tyr Ala Ile Leu Lys Cys Asn Asn Lys Thr Phe Thr Gly Thr Gly
            210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Asp Lys Thr Ile Ile
            260                 265                 270

Val His Leu Asn Glu Ser Val Lys Ile Glu Cys Thr Arg Pro Asn Asn
            275                 280                 285

Lys Thr Arg Thr Ser Ile Arg Ile Gly Pro Gly Gln Ala Phe Tyr Ala
            290                 295                 300

Thr Gly Gln Val Ile Gly Asp Ile Arg Glu Ala His Cys Asn Ile Ser
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
            340                 345                 350

Asp Leu Glu Ile Thr Thr His Ser Phe Asn Cys Gly Gly Glu Phe Phe
            355                 360                 365

Tyr Cys Asn Thr Ser Ser Leu Phe Asn Arg Thr Tyr Met Ala Asn Ser
370                 375                 380

Thr Asp Met Ala Asn Ser Thr Glu Thr Asn Ser Thr Arg Thr Ile Thr
385                 390                 395                 400

Ile Arg Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Ile Ser
            420                 425                 430

Asn Ile Thr Gly Leu Leu Leu Thr Arg Asp Gly Gly Lys Asn Asn Thr
            435                 440                 445

Glu Thr Phe Arg Pro Gly Gly Gly Asn Met Lys Asp Asn Trp Arg Ser
```

```
            450             455             460
Glu Leu Tyr Lys Tyr Lys Val Glu Val Lys Pro Leu Gly Val Ala
465                 470                 475                 480

Pro Thr Asn Ala Arg Arg Val Val Glu Arg Lys Arg Ala Val
                485                 490                 495

Gly Met Gly Ala Val Phe Leu Gly Phe Leu Gly Ala Ala Gly Ser Thr
                500                 505                 510

Met Gly Ala Ala Ser Ile Thr Leu Thr Val Gln Ala Arg Gln Leu Leu
                515                 520                 525

Ser Gly Ile Val Gln Gln Gln Ser Asn Leu Leu Lys Ala Ile Glu Ala
                530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
                580                 585                 590

Trp Asn Ser Ser Trp Ser Asn Lys Ser Tyr Gly Asp Ile Trp Asp Asn
                595                 600                 605

Met Thr Trp Met Gln Trp Glu Arg Glu Ile Ser Asn Tyr Thr Glu Ile
                610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                645                 650                 655

Asn Ile Thr Asn Trp Leu Trp Tyr Ile Lys Ile Phe Ile Met Ile Val
                660                 665                 670

Gly Gly Leu Ile Gly Leu Arg Ile Ile Phe Ala Val Leu Ser Leu Val
                675                 680                 685

Asn Arg Val Arg Gln Gly Tyr Ser Pro Leu Ser Leu Gln Thr Leu Ile
                690                 695                 700

Pro Ser Pro Arg Gly Pro Asp Arg Pro Gly Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
                740                 745                 750

Arg Leu Arg Asp Phe Ile Leu Ile Ala Ala Arg Ala Gly Glu Leu Leu
                755                 760                 765

Gly Arg Ser Ser Leu Lys Gly Leu Arg Arg Gly Trp Glu Ala Leu Lys
                770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
                820                 825                 830

Ile Pro Thr Arg Ile Arg Gln Gly Phe Glu Thr Ala Leu Leu
                835                 840                 845

<210> SEQ ID NO 73
<211> LENGTH: 849
<212> TYPE: PRT
<213> ORGANISM: Human immunodeficiency virus 1
```

<400> SEQUENCE: 73

| | | | | | | | | | | | | | | |
|---|---|---|---|---|---|---|---|---|---|---|---|---|---|---|
|Met|Arg|Val|Met|Gly|Ile|Gln|Arg|Asn|Tyr|Pro|Gln|Trp|Trp|Ile|Trp
1| | | |5| | | | |10| | | | |15|

Ser Met Leu Gly Phe Trp Met Leu Met Ile Cys Asn Gly Met Trp Val
               20                     25                 30

Thr Val Tyr Tyr Gly Val Pro Val Trp Lys Glu Ala Lys Thr Thr Leu
         35                 40               45

Phe Cys Ala Ser Asp Ala Lys Ala Tyr Glu Lys Glu Val His Asn Val
 50                  55                   60

Trp Ala Thr His Ala Cys Val Pro Thr Asp Pro Asn Pro Gln Glu Met
65              70                   75               80

Val Leu Lys Asn Val Thr Glu Asn Phe Asn Met Trp Lys Asn Asp Met
               85                     90               95

Val Asp Gln Met His Glu Asp Val Ile Ser Leu Trp Asp Gln Ser Leu
         100               105             110

Lys Pro Cys Val Lys Leu Thr Pro Leu Cys Val Thr Leu Asn Cys Thr
         115               120             125

Asn Ala Thr Asn Ala Thr Ala Ser Asn Ser Ile Ile Glu Gly Met
130                 135                 140

Lys Asn Cys Ser Phe Asn Ile Thr Thr Glu Leu Arg Asp Lys Arg Glu
145                 150                 155                 160

Lys Lys Asn Ala Leu Phe Tyr Lys Leu Asp Ile Val Gln Leu Asp Gly
                165                 170                 175

Asn Ser Ser Gln Tyr Arg Leu Ile Asn Cys Asn Thr Ser Val Ile Thr
                180                 185                 190

Gln Ala Cys Pro Lys Val Ser Phe Asp Pro Ile Pro Ile His Tyr Cys
                195                 200                 205

Ala Pro Ala Gly Tyr Ala Ile Leu Lys Cys Asn Asn Lys Thr Phe Thr
210                 215                 220

Gly Thr Gly Pro Cys Asn Asn Val Ser Thr Val Gln Cys Thr His Gly
225                 230                 235                 240

Ile Lys Pro Val Val Ser Thr Gln Leu Leu Leu Asn Gly Ser Leu Ala
                245                 250                 255

Glu Gly Glu Ile Ile Ile Arg Ser Glu Asn Ile Thr Asn Asn Asp Lys
                260                 265                 270

Thr Ile Ile Val His Leu Asn Glu Ser Val Lys Ile Glu Cys Thr Arg
                275                 280                 285

Pro Ser Asn Lys Thr Arg Thr Ser Ile Arg Ile Gly Pro Gly Gln Ala
                290                 295                 300

Phe Tyr Ala Thr Gly Gln Val Ile Gly Asp Ile Arg Glu Ala Tyr Cys
305                 310                 315                 320

Asn Ile Ser Glu Ser Lys Trp Asn Glu Thr Leu Gln Arg Val Ser Lys
                325                 330                 335

Lys Leu Lys Glu Tyr Phe Pro His Lys Asn Ile Thr Phe Gln Pro Ser
                340                 345                 350

Ser Gly Gly Asp Leu Glu Ile Thr Thr His Ser Phe Asn Cys Gly Gly
                355                 360                 365

Glu Phe Phe Tyr Cys Asn Thr Ser Ser Leu Phe Asn Arg Thr Tyr Met
                370                 375                 380

Ala Asn Ser Thr Asp Met Ala Asn Ser Thr Glu Thr Asn Ser Thr Arg
385                 390                 395                 400

Asn Ile Thr Ile His Cys Arg Ile Lys Gln Ile Ile Asn Met Trp Gln

-continued

```
                405                 410                 415
Glu Val Gly Arg Ala Met Tyr Ala Pro Pro Ile Ala Gly Asn Ile Thr
                420                 425                 430
Cys Ile Ser Asn Ile Thr Gly Leu Leu Leu Thr Arg Asp Gly Gly Lys
                435                 440                 445
Asn Asp Thr Glu Thr Phe Arg Pro Gly Gly Gly Asn Met Lys Asp Asn
                450                 455                 460
Trp Arg Ser Glu Leu Tyr Lys Tyr Lys Val Val Glu Val Lys Pro Leu
465                 470                 475                 480
Gly Val Ala Pro Thr Asn Ala Arg Arg Val Val Glu Arg Glu Lys
                485                 490                 495
Arg Ala Val Gly Met Gly Ala Val Phe Leu Gly Phe Leu Gly Ala Ala
                500                 505                 510
Gly Ser Thr Met Gly Ala Ala Ser Ile Thr Leu Thr Val Gln Ala Arg
                515                 520                 525
Gln Leu Leu Ser Gly Ile Val Gln Gln Gln Ser Asn Leu Leu Lys Ala
                530                 535                 540
Ile Glu Ala Gln Gln His Met Leu Lys Leu Thr Val Trp Gly Ile Lys
545                 550                 555                 560
Gln Leu Gln Ala Arg Val Leu Ala Leu Glu Arg Tyr Leu Lys Asp Gln
                565                 570                 575
Gln Leu Leu Gly Met Trp Gly Cys Ser Gly Lys Leu Ile Cys Thr Thr
                580                 585                 590
Asn Val Tyr Trp Asn Ser Ser Trp Ser Asn Lys Thr Tyr Gly Asp Ile
                595                 600                 605
Trp Asp Asn Met Thr Trp Met Gln Trp Glu Arg Glu Ile Ser Asn Tyr
                610                 615                 620
Thr Glu Ile Ile Tyr Glu Leu Leu Glu Glu Ser Gln Asn Gln Gln Glu
625                 630                 635                 640
Lys Asn Glu Gln Asp Leu Leu Ala Leu Asp Arg Trp Asn Ser Leu Trp
                645                 650                 655
Asn Trp Phe Asn Ile Thr Asn Trp Leu Trp Tyr Ile Lys Ile Phe Ile
                660                 665                 670
Met Ile Val Gly Gly Leu Ile Gly Leu Arg Ile Ile Phe Ala Val Leu
                675                 680                 685
Ser Leu Val Asn Arg Val Arg Gln Gly Tyr Ser Pro Leu Ser Leu Gln
                690                 695                 700
Thr Leu Ile Pro Ser Pro Arg Gly Pro Asp Arg Pro Gly Gly Ile Glu
705                 710                 715                 720
Glu Glu Gly Gly Glu Gln Asp Arg Asn Arg Ser Thr Arg Leu Val Ser
                725                 730                 735
Gly Phe Leu Ala Leu Val Trp Asp Asp Leu Arg Ser Leu Cys Leu Phe
                740                 745                 750
Ile Tyr His Arg Leu Arg Asp Phe Ile Leu Ile Ala Ala Arg Ala Gly
                755                 760                 765
Glu Leu Leu Gly Arg Ser Ser Leu Lys Gly Leu Arg Arg Gly Trp Glu
                770                 775                 780
Ala Leu Lys Tyr Leu Gly Ser Leu Val Gln Tyr Trp Gly Leu Glu Leu
785                 790                 795                 800
Lys Arg Ser Ala Ile Ser Leu Leu Asp Thr Leu Ala Ile Ala Val Gly
                805                 810                 815
Glu Gly Thr Asp Arg Ile Leu Glu Phe Ile Leu Gly Ile Cys Arg Ala
                820                 825                 830
```

-continued

```
Ile Arg Asn Ile Pro Thr Arg Ile Arg Gln Gly Phe Glu Thr Ala Leu
            835                 840                 845
Leu

<210> SEQ ID NO 74
<211> LENGTH: 840
<212> TYPE: PRT
<213> ORGANISM: Human immunodeficiency virus 1

<400> SEQUENCE: 74

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Ala Asn Asn Ser Asn Ile Ile Glu Glu Met Lys Asn Cys
    130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
        195                 200                 205

Gly Tyr Ala Ile Leu Lys Cys Asn Asn Lys Thr Phe Thr Gly Thr Gly
    210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Val Lys Thr Ile Ile
            260                 265                 270

Val His Leu Asn Glu Ser Val Lys Ile Glu Cys Thr Arg Pro Asn Asn
        275                 280                 285

Lys Thr Arg Thr Ser Ile Arg Ile Gly Pro Gly Gln Ala Phe Tyr Ala
    290                 295                 300

Thr Gly Gln Val Ile Gly Asp Ile Arg Glu Ala Tyr Cys Asn Ile Asn
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
            340                 345                 350
```

```
Asp Leu Glu Ile Thr Thr His Ser Phe Asn Cys Gly Gly Glu Phe Phe
            355                 360                 365

Tyr Cys Asn Thr Ser Ser Leu Phe Asn Arg Thr Asp Met Ala Asn Ser
        370                 375                 380

Thr Glu Thr Asn Asn Thr Arg Thr Ile Thr Ile His Cys Arg Ile Lys
385                 390                 395                 400

Gln Ile Ile Asn Met Trp Gln Glu Val Gly Arg Ala Met Tyr Ala Pro
                405                 410                 415

Pro Ile Ala Gly Asn Ile Thr Cys Ile Ser Asn Ile Thr Gly Leu Leu
            420                 425                 430

Leu Thr Arg Asp Gly Gly Lys Asn Asn Thr Glu Thr Phe Arg Pro Gly
        435                 440                 445

Gly Gly Asn Met Lys Asp Asn Trp Arg Ser Glu Leu Tyr Lys Tyr Lys
    450                 455                 460

Val Val Glu Val Lys Pro Leu Gly Val Ala Pro Thr Asn Ala Arg Arg
465                 470                 475                 480

Arg Val Val Glu Arg Glu Lys Arg Ala Val Gly Met Gly Ala Val Phe
                485                 490                 495

Leu Gly Phe Leu Gly Ala Ala Gly Ser Thr Met Gly Ala Ala Ser Ile
            500                 505                 510

Thr Leu Thr Val Gln Ala Arg Gln Leu Leu Ser Gly Ile Val Gln Gln
        515                 520                 525

Gln Ser Asn Leu Leu Lys Ala Ile Glu Ala Gln Gln His Met Leu Lys
    530                 535                 540

Leu Thr Val Trp Gly Ile Lys Gln Leu Gln Ala Arg Val Leu Ala Leu
545                 550                 555                 560

Glu Arg Tyr Leu Lys Asp Gln Gln Leu Leu Gly Met Trp Gly Cys Ser
                565                 570                 575

Gly Lys Leu Ile Cys Thr Thr Asn Val Tyr Trp Asn Ser Ser Trp Ser
            580                 585                 590

Asn Lys Thr Tyr Gly Asp Ile Trp Asp Asn Met Thr Trp Met Gln Trp
        595                 600                 605

Glu Arg Glu Ile Ser Asn Tyr Thr Glu Ile Ile Tyr Glu Leu Leu Glu
    610                 615                 620

Glu Ser Gln Asn Gln Gln Glu Lys Asn Glu Gln Asp Leu Leu Ala Leu
625                 630                 635                 640

Asp Arg Trp Asn Ser Leu Trp Asn Trp Phe Asn Ile Thr Asn Trp Leu
                645                 650                 655

Trp Tyr Ile Lys Ile Phe Ile Met Ile Val Gly Gly Leu Ile Gly Leu
            660                 665                 670

Arg Ile Ile Phe Ala Val Leu Ser Leu Val Asn Arg Val Arg Gln Gly
        675                 680                 685

Tyr Ser Pro Leu Ser Leu Gln Thr Leu Ile Pro Ser Pro Arg Gly Pro
    690                 695                 700

Asp Arg Pro Gly Gly Ile Glu Glu Glu Gly Gly Glu Gln Asp Arg Asn
705                 710                 715                 720

Arg Ser Thr Arg Leu Val Ser Gly Phe Leu Ala Leu Val Trp Asp Asp
                725                 730                 735

Leu Arg Ser Leu Cys Leu Phe Ile Tyr His Arg Leu Arg Asp Phe Ile
            740                 745                 750

Leu Ile Ala Ala Arg Ala Gly Glu Leu Leu Gly Arg Ser Ser Leu Lys
        755                 760                 765
```

```
Gly Leu Arg Arg Gly Trp Glu Ala Leu Lys Tyr Leu Gly Ser Leu Val
    770                 775                 780

Gln Tyr Trp Gly Leu Glu Leu Lys Arg Ser Ala Ile Ser Leu Leu Asp
785                 790                 795                 800

Thr Leu Ala Ile Ala Val Gly Glu Gly Thr Asp Arg Ile Leu Glu Phe
                805                 810                 815

Val Leu Gly Ile Cys Arg Ala Ile Arg Asn Ile Pro Thr Arg Ile Arg
            820                 825                 830

Gln Gly Phe Glu Thr Ala Leu Leu
        835                 840

<210> SEQ ID NO 75
<211> LENGTH: 846
<212> TYPE: PRT
<213> ORGANISM: Human immunodeficiency virus 1

<400> SEQUENCE: 75

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Thr Ser Asn Ser Ser Ile Ile Glu Gly Met Lys Asn Cys
130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
        195                 200                 205

Gly Tyr Ala Ile Leu Lys Cys Asn Asn Lys Thr Phe Thr Gly Thr Gly
210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Asp Lys Thr Ile Ile
            260                 265                 270

Val His Leu Asn Glu Ser Val Lys Ile Glu Cys Thr Arg Pro Asn Asn
        275                 280                 285

Asn Thr Arg Thr Ser Ile Arg Ile Gly Pro Gly Gln Ala Phe Tyr Ala
290                 295                 300
```

```
Thr Gly Gln Val Ile Gly Asp Ile Arg Glu Ala Tyr Cys Asn Ile Ser
305                 310                 315                 320

Glu Ser Lys Trp Asn Glu Thr Leu Gln Arg Val Ser Lys Lys Leu Lys
            325                 330                 335

Glu Tyr Phe Pro His Lys Asn Ile Thr Phe Gln Pro Ser Ser Gly Gly
            340                 345                 350

Asp Leu Glu Ile Thr Thr His Ser Phe Asn Cys Gly Gly Glu Phe Phe
            355                 360                 365

Tyr Cys Asn Thr Ser Ser Leu Phe Asn Arg Thr Tyr Met Ala Asn Ser
        370                 375                 380

Thr Asp Met Ala Asn Ser Thr Glu Thr Asn Ser Thr Arg Ile Ile Thr
385                 390                 395                 400

Ile His Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Ile Ser
                420                 425                 430

Asn Ile Thr Gly Leu Leu Leu Thr Arg Asp Gly Gly Lys Asn Asn Thr
            435                 440                 445

Glu Thr Phe Arg Pro Gly Gly Gly Asn Met Lys Asp Asn Trp Arg Ser
450                 455                 460

Glu Leu Tyr Lys Tyr Lys Val Val Glu Val Lys Pro Leu Gly Val Ala
465                 470                 475                 480

Pro Thr Asn Ala Arg Arg Val Val Glu Arg Glu Lys Arg Ala Val
                485                 490                 495

Gly Met Gly Ala Val Phe Leu Gly Phe Leu Gly Ala Ala Gly Ser Thr
                500                 505                 510

Met Gly Ala Ala Ser Ile Thr Leu Thr Val Gln Ala Arg Gln Leu Leu
            515                 520                 525

Ser Gly Ile Val Gln Gln Gln Ser Asn Leu Leu Lys Ala Ile Glu Ala
    530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
            580                 585                 590

Trp Asn Ser Ser Trp Ser Asn Lys Thr Tyr Gly Asp Ile Trp Asp Asn
        595                 600                 605

Met Thr Trp Met Gln Trp Glu Arg Glu Ile Ser Asn Tyr Thr Glu Ile
        610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                645                 650                 655

Asn Ile Thr Asn Trp Leu Trp Tyr Ile Lys Ile Phe Ile Met Ile Val
            660                 665                 670

Gly Gly Leu Ile Gly Leu Arg Ile Ile Phe Ala Val Leu Ser Leu Val
            675                 680                 685

Asn Arg Val Arg Gln Gly Tyr Ser Pro Leu Ser Leu Gln Thr Leu Ile
            690                 695                 700

Pro Ser Pro Arg Gly Pro Asp Arg Pro Gly Gly Ile Glu Glu Glu Gly
705                 710                 715                 720
```

```
Gly Glu Gln Asp Arg Asn Arg Ser Thr Arg Leu Val Ser Gly Phe Leu
            725                 730                 735

Ala Leu Val Trp Asp Asp Leu Arg Ser Leu Cys Leu Phe Ile Tyr His
            740                 745                 750

Arg Leu Arg Asp Phe Ile Leu Ile Ala Ala Arg Ala Gly Glu Leu Leu
            755                 760                 765

Gly Arg Ser Ser Leu Lys Gly Leu Arg Arg Gly Trp Glu Ala Leu Lys
            770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
            805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
            835                 840                 845

<210> SEQ ID NO 76
<211> LENGTH: 849
<212> TYPE: PRT
<213> ORGANISM: Human immunodeficiency virus 1

<400> SEQUENCE: 76

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Ser Cys Thr
        115                 120                 125

Asn Ala Thr Asn Ala Thr Ala Ser Asn Ser Ser Ile Leu Glu Gly Met
    130                 135                 140

Lys Asn Cys Ser Phe Asn Ile Thr Thr Glu Leu Arg Asp Lys Arg Glu
145                 150                 155                 160

Lys Lys Asn Ala Leu Phe Tyr Lys Leu Asp Ile Val Gln Leu Asp Gly
                165                 170                 175

Asn Ser Ser Gln Tyr Arg Leu Ile Asn Cys Asn Thr Ser Val Ile Thr
            180                 185                 190

Gln Ala Cys Pro Lys Val Ser Phe Asp Pro Ile Pro Ile His Tyr Cys
        195                 200                 205

Ala Pro Ala Gly Tyr Ala Ile Leu Lys Cys Asn Asn Lys Thr Phe Asn
    210                 215                 220

Gly Thr Gly Pro Cys Asn Asn Val Ser Thr Val Gln Cys Thr His Gly
225                 230                 235                 240

Ile Lys Pro Val Val Ser Thr Gln Leu Leu Leu Asn Gly Ser Leu Ala
                245                 250                 255
```

```
Glu Gly Glu Ile Ile Ile Arg Ser Lys Asn Ile Thr Asp Asn Gly Lys
            260                 265                 270

Thr Ile Ile Val His Leu Asn Glu Ser Val Lys Ile Glu Cys Thr Arg
            275                 280                 285

Pro Ser Asn Asn Thr Arg Thr Ser Ile Arg Ile Gly Pro Gly Gln Ala
            290                 295                 300

Phe Tyr Ala Thr Gly Gln Val Ile Gly Asp Ile Arg Glu Ala His Cys
305                 310                 315                 320

Asn Ile Ser Glu Ser Lys Trp Asn Glu Thr Leu Gln Arg Val Ser Glu
                325                 330                 335

Lys Leu Lys Glu Tyr Phe Pro His Lys Asn Ile Thr Phe Gln Pro Ser
            340                 345                 350

Ser Gly Gly Asp Leu Glu Ile Thr Thr His Ser Phe Asn Cys Gly Gly
            355                 360                 365

Glu Phe Phe Tyr Cys Asn Thr Ser Ser Leu Phe Asn Arg Thr Tyr Met
370                 375                 380

Ala Thr Ser Thr Asp Met Ala Asn Ser Thr Glu Thr Asn Ser Thr Arg
385                 390                 395                 400

Ile Ile Thr Ile Arg Cys Arg Ile Lys Gln Ile Ile Asn Met Trp Gln
            405                 410                 415

Glu Val Gly Arg Ala Met Tyr Ala Pro Pro Ile Ala Gly Asn Ile Thr
            420                 425                 430

Cys Ile Ser Asn Ile Thr Gly Leu Leu Leu Thr Arg Asp Gly Gly Lys
            435                 440                 445

Asn Asp Thr Asp Thr Phe Arg Pro Glu Gly Gly Asn Met Lys Asp Asn
            450                 455                 460

Trp Arg Ser Glu Leu Tyr Lys Tyr Lys Val Val Glu Val Lys Pro Leu
465                 470                 475                 480

Gly Val Ala Pro Thr Asn Ala Arg Arg Arg Val Val Glu Arg Glu Lys
            485                 490                 495

Arg Ala Val Gly Met Gly Ala Val Phe Leu Gly Phe Leu Gly Ala Ala
            500                 505                 510

Gly Ser Thr Met Gly Ala Ala Ser Ile Thr Leu Thr Val Gln Ala Arg
            515                 520                 525

Gln Leu Leu Ser Gly Ile Val Gln Gln Ser Asn Leu Leu Lys Ala
            530                 535                 540

Ile Glu Ala Gln Gln His Met Leu Lys Leu Thr Val Trp Gly Ile Lys
545                 550                 555                 560

Gln Leu Gln Ala Arg Val Leu Ala Leu Glu Arg Tyr Leu Lys Asp Gln
            565                 570                 575

Gln Leu Leu Gly Met Trp Gly Cys Ser Gly Lys Leu Ile Cys Thr Thr
            580                 585                 590

Asn Val Tyr Trp Asn Ser Ser Trp Ser Asn Lys Thr Tyr Gly Asp Ile
            595                 600                 605

Trp Asp Asn Met Thr Trp Met Gln Trp Glu Arg Glu Ile Ser Asn Tyr
            610                 615                 620

Thr Glu Leu Ile Tyr Glu Leu Leu Glu Glu Ser Gln Asn Gln Gln Glu
625                 630                 635                 640

Lys Asn Glu Gln Asp Leu Leu Ala Leu Asp Arg Trp Asn Ser Leu Trp
                645                 650                 655

Asn Trp Phe Asn Ile Thr Asn Trp Leu Trp Tyr Ile Lys Ile Phe Ile
            660                 665                 670
```

```
Met Ile Val Gly Gly Leu Ile Gly Leu Arg Ile Ile Phe Ala Val Leu
            675                 680                 685

Ser Leu Val Asn Arg Val Arg Gln Gly Tyr Ser Pro Leu Ser Leu Gln
    690                 695                 700

Thr Leu Ile Pro Ser Pro Arg Gly Pro Asp Arg Pro Gly Gly Ile Glu
705                 710                 715                 720

Glu Glu Gly Gly Glu Gln Asp Arg Asn Arg Ser Thr Arg Leu Val Ser
                725                 730                 735

Gly Phe Leu Ala Leu Ala Trp Asp Asp Leu Arg Ser Leu Cys Leu Phe
                740                 745                 750

Ile Tyr His Arg Leu Arg Asp Phe Ile Leu Ile Ala Ala Arg Ala Gly
            755                 760                 765

Glu Leu Leu Gly Arg Ser Ser Leu Lys Gly Leu Arg Arg Gly Trp Glu
    770                 775                 780

Ala Leu Lys Tyr Leu Gly Asn Leu Val Gln Tyr Trp Gly Leu Glu Leu
785                 790                 795                 800

Lys Arg Ser Ala Ile Ser Leu Leu Asp Thr Leu Ala Ile Ala Val Gly
                805                 810                 815

Glu Gly Thr Asp Arg Ile Leu Glu Phe Val Leu Gly Ile Cys Arg Ala
                820                 825                 830

Ile Arg Asn Ile Pro Thr Arg Ile Arg Gln Gly Phe Glu Thr Ala Leu
            835                 840                 845

Leu

<210> SEQ ID NO 77
<211> LENGTH: 854
<212> TYPE: PRT
<213> ORGANISM: Human immunodeficiency virus 1

<400> SEQUENCE: 77

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
    115                 120                 125

Asn Ala Thr Ala Arg Asn Cys Thr Asn Ala Thr Ala Ser Asn Ser Ser
130                 135                 140

Ile Ile Glu Gly Met Lys Asn Cys Ser Phe Asn Ile Thr Thr Glu Leu
145                 150                 155                 160

Arg Asp Lys Arg Glu Lys Lys Asn Ala Leu Phe Tyr Lys Leu Asp Ile
                165                 170                 175

Val Gln Leu Asp Gly Asn Ser Ser Gln Tyr Arg Leu Ile Asn Cys Asn
            180                 185                 190
```

```
Thr Ser Val Ile Thr Gln Ala Cys Pro Lys Val Ser Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Thr Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Arg Ser Glu Asn Ile
            260                 265                 270

Thr Asn Ser Gly Lys Thr Ile Ile Val His Leu Asn Glu Ser Val Lys
        275                 280                 285

Ile Glu Cys Thr Arg Pro Asn Asn Lys Thr Arg Thr Ser Ile Arg Ile
    290                 295                 300

Gly Pro Gly Gln Ala Phe Tyr Ala Thr Gly Gln Val Ile Gly Asp Ile
305                 310                 315                 320

Arg Glu Ala Tyr Cys Asn Ile Ser Glu Ser Lys Trp Asn Glu Thr Leu
                325                 330                 335

Gln Arg Val Ser Lys Lys Leu Lys Glu Tyr Phe Pro His Lys Asn Ile
            340                 345                 350

Thr Phe Gln Pro Ser Ser Gly Gly Asp Leu Glu Ile Thr Thr His Ser
        355                 360                 365

Phe Asn Cys Gly Gly Glu Phe Phe Tyr Cys Asn Thr Ser Ser Leu Phe
    370                 375                 380

Asn Arg Thr Tyr Met Ala Asn Ser Thr Asp Met Ala Asn Ser Thr Glu
385                 390                 395                 400

Thr Asn Ser Thr Arg Ile Ile Thr Ile His Cys Arg Ile Lys Gln Ile
                405                 410                 415

Ile Asn Met Trp Gln Glu Val Gly Arg Ala Met Tyr Ala Pro Pro Ile
            420                 425                 430

Ala Gly Asn Ile Thr Cys Ile Ser Ser Ile Thr Gly Leu Leu Leu Thr
        435                 440                 445

Arg Asp Gly Gly Glu Asn Asn Thr Glu Thr Phe Arg Pro Gly Gly Gly
    450                 455                 460

Asn Met Lys Asp Asn Trp Arg Ser Glu Leu Tyr Lys Tyr Lys Val Val
465                 470                 475                 480

Glu Val Lys Pro Leu Gly Val Ala Pro Thr Asn Ala Arg Arg Arg Val
                485                 490                 495

Val Glu Arg Glu Lys Arg Ala Val Gly Met Gly Ala Val Phe Leu Gly
            500                 505                 510

Phe Leu Gly Ala Ala Gly Ser Thr Met Gly Ala Ala Ser Ile Thr Leu
        515                 520                 525

Thr Val Gln Ala Arg Gln Leu Leu Ser Gly Ile Val Gln Gln Ser
    530                 535                 540

Asn Leu Leu Lys Ala Ile Glu Ala Gln Gln His Met Leu Lys Leu Thr
545                 550                 555                 560

Val Trp Gly Ile Lys Gln Leu Gln Ala Arg Val Leu Ala Leu Glu Arg
                565                 570                 575

Tyr Leu Lys Asp Gln Gln Leu Leu Gly Met Trp Gly Cys Ser Gly Lys
            580                 585                 590

Leu Ile Cys Thr Thr Asn Val Tyr Trp Asn Ser Ser Trp Ser Asn Lys
        595                 600                 605

Thr Tyr Gly Asp Ile Trp Asp Asn Met Thr Trp Met Gln Trp Glu Arg
```

```
                610             615             620
Glu Ile Ser Asn Tyr Thr Glu Ile Ile Tyr Glu Leu Glu Glu Ser
625                 630                 635                 640

Gln Asn Gln Gln Glu Lys Asn Glu Gln Asp Leu Leu Ala Leu Asp Arg
                    645                 650                 655

Trp Asn Ser Leu Trp Asn Trp Phe Asn Ile Thr Asn Trp Leu Trp Tyr
                660                 665                 670

Ile Lys Ile Phe Ile Met Ile Val Gly Gly Leu Ile Gly Leu Arg Ile
                675                 680                 685

Ile Phe Ala Val Phe Ser Leu Val Asn Arg Val Arg Gln Gly Tyr Ser
            690                 695                 700

Pro Leu Ser Leu Gln Thr Leu Ile Pro Ser Pro Arg Gly Pro Asp Arg
705                 710                 715                 720

Pro Gly Gly Ile Glu Glu Glu Gly Gly Glu Gln Asp Arg Asn Arg Ser
                    725                 730                 735

Thr Arg Leu Val Ser Gly Phe Leu Ala Leu Val Trp Asp Asp Leu Arg
                740                 745                 750

Ser Leu Cys Leu Phe Ile Tyr His Arg Leu Arg Asp Phe Ile Leu Ile
            755                 760                 765

Ala Ala Arg Ala Gly Glu Leu Leu Gly Arg Ser Ser Leu Lys Gly Leu
770                 775                 780

Arg Arg Gly Trp Glu Ala Leu Lys Tyr Leu Gly Ser Leu Val Gln Tyr
785                 790                 795                 800

Trp Gly Leu Glu Leu Lys Arg Ser Ala Ile Ser Leu Leu Asp Thr Leu
                    805                 810                 815

Ala Ile Ala Val Gly Glu Gly Thr Asp Arg Ile Leu Glu Phe Val Leu
                820                 825                 830

Gly Ile Cys Arg Ala Ile Arg Asn Ile Pro Thr Arg Ile Arg Gln Gly
            835                 840                 845

Phe Glu Thr Ala Leu Leu
    850

<210> SEQ ID NO 78
<211> LENGTH: 850
<212> TYPE: PRT
<213> ORGANISM: Human immunodeficiency virus 1

<400> SEQUENCE: 78

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Val
        50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125
```

-continued

```
Asn Ala Thr Thr Asn Ala Thr Ala Ser Asn Ser Ser Ile Ile Glu Glu
    130                 135                 140

Met Lys Asn Cys Ser Phe Asn Ile Thr Thr Glu Leu Arg Asp Lys Arg
145                 150                 155                 160

Glu Lys Lys Asn Ala Leu Phe Tyr Lys Leu Asp Ile Val Gln Leu Asp
                165                 170                 175

Gly Asn Ser Ser Gln Tyr Arg Leu Ile Asn Cys Asn Thr Ser Val Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
210                 215                 220

Thr Gly Thr Gly Pro Cys Asn Asn Val Ser Thr Val Gln Cys Thr His
225                 230                 235                 240

Gly Ile Lys Pro Val Val Ser Thr Gln Leu Leu Asn Gly Ser Leu
                245                 250                 255

Ala Glu Gly Glu Ile Ile Ile Arg Ser Glu Asn Ile Thr Asn Thr Ala
            260                 265                 270

Lys Thr Ile Ile Val His Leu Asn Glu Ser Val Lys Ile Glu Cys Thr
    275                 280                 285

Arg Pro Asn Asn Lys Thr Arg Thr Ser Ile Arg Ile Gly Pro Gly Gln
290                 295                 300

Ala Phe Tyr Ala Thr Gly Gln Val Ile Gly Asp Ile Arg Glu Ala Tyr
305                 310                 315                 320

Cys Asn Ile Ser Glu Ser Lys Trp Asn Glu Thr Leu Gln Arg Val Ser
                325                 330                 335

Lys Lys Leu Lys Glu Tyr Phe Pro His Lys Asn Ile Thr Phe Gln Pro
            340                 345                 350

Ser Ser Gly Gly Asp Leu Glu Ile Thr Thr His Ser Phe Asn Cys Gly
        355                 360                 365

Gly Glu Phe Phe Tyr Cys Asn Thr Ser Ser Leu Phe Asn Arg Thr Tyr
370                 375                 380

Met Ala Asn Ser Thr Asp Met Ala Asn Ser Thr Glu Thr Asn Ser Thr
385                 390                 395                 400

Arg Thr Ile Thr Ile Arg Cys Arg Ile Lys Gln Ile Ile Asn Met Trp
                405                 410                 415

Gln Glu Val Gly Arg Ala Met Tyr Ala Pro Pro Ile Ala Gly Asn Ile
            420                 425                 430

Thr Cys Ile Ser Asn Ile Thr Gly Leu Leu Leu Thr Arg Asp Gly Gly
        435                 440                 445

Glu Asn Asn Thr Glu Thr Phe Arg Pro Gly Gly Gly Asn Met Lys Asp
450                 455                 460

Asn Trp Arg Ser Glu Leu Tyr Lys Tyr Lys Val Val Glu Val Lys Pro
465                 470                 475                 480

Leu Gly Val Ala Pro Thr Asn Ala Arg Arg Val Val Glu Arg Glu
                485                 490                 495

Lys Arg Ala Val Gly Met Gly Ala Val Phe Leu Gly Phe Leu Gly Ala
            500                 505                 510

Ala Gly Ser Thr Met Gly Ala Ala Ser Ile Thr Leu Thr Val Gln Ala
        515                 520                 525

Arg Gln Leu Leu Ser Gly Ile Val Gln Gln Ser Asn Leu Leu Lys
            530                 535                 540

Ala Ile Glu Ala Gln Gln His Met Leu Lys Leu Thr Val Trp Gly Ile
```

|  |  |  |  |
|---|---|---|---|
| 545 | 550 | 555 | 560 |

Lys Gln Leu Gln Ala Arg Val Leu Ala Leu Glu Arg Tyr Leu Lys Asp
     565     570     575

Gln Gln Leu Leu Gly Met Trp Gly Cys Ser Gly Lys Leu Ile Cys Thr
    580     585     590

Thr Asn Val Tyr Trp Asn Ser Ser Trp Ser Asn Lys Thr Tyr Gly Asp
   595     600     605

Ile Trp Asp Asn Met Thr Trp Met Gln Trp Glu Arg Glu Ile Ser Asn
  610     615     620

Tyr Thr Glu Ile Ile Tyr Glu Leu Leu Glu Glu Ser Gln Asn Gln Gln
625     630     635     640

Glu Lys Asn Glu Gln Asp Leu Leu Ala Leu Asp Arg Trp Asn Ser Leu
     645     650     655

Trp Asn Trp Phe Asn Ile Thr Asn Trp Leu Trp Tyr Ile Lys Ile Phe
    660     665     670

Ile Met Ile Val Gly Gly Leu Ile Gly Leu Arg Ile Ile Phe Ala Val
   675     680     685

Leu Ser Leu Val Asn Arg Val Arg Gln Gly Tyr Ser Pro Leu Ser Leu
  690     695     700

Gln Thr Leu Ile Pro Ser Pro Arg Gly Pro Asp Arg Pro Gly Gly Ile
705     710     715     720

Glu Glu Glu Gly Gly Glu Gln Asp Arg Asn Arg Ser Thr Arg Leu Val
     725     730     735

Ser Gly Phe Leu Ala Leu Val Trp Asp Asp Leu Arg Ser Leu Cys Leu
    740     745     750

Phe Ile Tyr His Arg Leu Arg Asp Phe Ile Leu Ile Ala Ala Arg Ala
   755     760     765

Gly Glu Leu Leu Gly Arg Ser Ser Leu Lys Gly Leu Arg Arg Gly Trp
  770     775     780

Glu Ala Leu Lys Tyr Leu Gly Ser Leu Val Gln Tyr Trp Gly Leu Glu
785     790     795     800

Leu Lys Arg Ser Ala Ile Ser Leu Leu Asp Thr Leu Ala Ile Ala Val
     805     810     815

Gly Glu Gly Thr Asp Arg Ile Leu Glu Phe Val Leu Gly Ile Cys Arg
    820     825     830

Ala Ile Arg Asn Ile Pro Thr Arg Ile Arg Gln Gly Phe Glu Thr Ala
   835     840     845

Leu Leu
 850

<210> SEQ ID NO 79
<211> LENGTH: 846
<212> TYPE: PRT
<213> ORGANISM: Human immunodeficiency virus 1

<400> SEQUENCE: 79

Met Arg Val Met Gly Ile Gln Arg Asn Tyr Pro Gln Trp Trp Ile Trp
1     5     10     15

Ser Met Leu Gly Phe Trp Met Leu Met Ile Cys Asn Gly Met Trp Val
    20     25     30

Thr Val Tyr Tyr Gly Val Pro Val Trp Lys Glu Ala Lys Thr Thr Leu
   35     40     45

Phe Cys Ala Ser Asp Ala Lys Ala Tyr Glu Lys Glu Val His Asn Val
  50     55     60

-continued

```
Trp Ala Thr His Ala Cys Val Pro Thr Asp Pro Asn Pro Gln Glu Met
 65              70                  75                  80

Val Leu Lys Asn Val Thr Glu Asn Phe Asn Met Trp Lys Asn Asp Met
                 85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Ala Thr Ala Ser Asn Ser Ser Ile Ile Glu Gly Met Lys Asn Cys
    130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
        195                 200                 205

Gly Tyr Ala Ile Leu Lys Cys Asn Asn Lys Thr Phe Thr Gly Thr Gly
    210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Val Lys Thr Ile Ile
            260                 265                 270

Val His Leu Asn Glu Ser Val Lys Ile Glu Cys Thr Arg Pro Asn Asn
        275                 280                 285

Lys Thr Arg Thr Ser Ile Arg Ile Gly Pro Gly Gln Ala Phe Tyr Ala
    290                 295                 300

Thr Gly Gln Val Ile Gly Asp Ile Arg Glu Ala Tyr Cys Asn Ile Asn
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
            340                 345                 350

Asp Leu Glu Ile Thr Thr His Ser Phe Asn Cys Gly Gly Glu Phe Phe
        355                 360                 365

Tyr Cys Asn Thr Ser Ser Leu Phe Asn Arg Thr Tyr Met Ala Asn Ser
    370                 375                 380

Thr Asp Met Ala Asn Ser Thr Glu Thr Asn Ser Thr Arg Thr Ile Thr
385                 390                 395                 400

Ile His Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Ile Ser
            420                 425                 430

Asn Ile Thr Gly Leu Leu Leu Thr Arg Asp Gly Gly Lys Asn Asn Thr
        435                 440                 445

Glu Thr Phe Arg Pro Gly Gly Gly Asn Met Lys Asp Asn Trp Arg Ser
    450                 455                 460

Glu Leu Tyr Lys Tyr Lys Val Val Glu Val Lys Pro Leu Gly Val Ala
465                 470                 475                 480

Pro Thr Asn Ala Arg Arg Arg Val Val Glu Arg Glu Lys Arg Ala Val
```

```
                485                 490                 495
Gly Met Gly Ala Val Phe Leu Gly Phe Leu Gly Ala Ala Gly Ser Thr
            500                 505                 510

Met Gly Ala Ala Ser Ile Thr Leu Thr Val Gln Ala Arg Gln Leu Leu
        515                 520                 525

Ser Gly Ile Val Gln Gln Ser Asn Leu Leu Lys Ala Ile Glu Ala
    530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
            580                 585                 590

Trp Asn Ser Ser Trp Ser Asn Lys Thr Tyr Gly Asp Ile Trp Asp Asn
        595                 600                 605

Met Thr Trp Met Gln Trp Glu Arg Glu Ile Ser Asn Tyr Thr Glu Ile
    610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                645                 650                 655

Asn Ile Thr Asn Trp Leu Trp Tyr Ile Lys Ile Phe Ile Met Ile Val
            660                 665                 670

Gly Gly Leu Ile Gly Leu Arg Ile Ile Phe Ala Val Leu Ser Leu Val
        675                 680                 685

Asn Arg Val Arg Gln Gly Tyr Ser Pro Leu Ser Leu Gln Thr Leu Ile
    690                 695                 700

Pro Ser Pro Arg Gly Pro Asp Arg Pro Gly Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
            740                 745                 750

Arg Leu Arg Asp Phe Ile Leu Ile Ala Ala Arg Ala Gly Glu Leu Leu
        755                 760                 765

Gly Arg Ser Ser Leu Lys Gly Leu Arg Arg Gly Trp Glu Ala Leu Lys
    770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
        835                 840                 845

<210> SEQ ID NO 80
<211> LENGTH: 859
<212> TYPE: PRT
<213> ORGANISM: Human immunodeficiency virus 1

<400> SEQUENCE: 80

Met Arg Val Met Gly Ile Gln Arg Asn Tyr Pro Gln Trp Trp Ile Trp
1               5                   10                  15
```

-continued

```
Ser Met Leu Gly Phe Trp Met Leu Met Ile Cys Asn Gly Met Trp Val
            20                  25                  30
Thr Val Tyr Tyr Gly Val Pro Val Trp Lys Glu Ala Lys Thr Thr Leu
        35                  40                  45
Phe Cys Ala Ser Asp Ala Lys Ala Tyr Glu Lys Glu Val His Asn Val
50                  55                  60
Trp Ala Thr His Ala Cys Val Pro Thr Asp Pro Asn Pro Gln Glu Met
65                  70                  75                  80
Val Leu Lys Asn Val Thr Glu Asn Phe Asn Met Trp Lys Asn Asp Met
                85                  90                  95
Val Asp Gln Met His Glu Asp Val Ile Ser Leu Trp Asp Gln Ser Leu
            100                 105                 110
Lys Pro Cys Val Lys Leu Thr Pro Leu Cys Val Thr Leu Asn Cys Thr
        115                 120                 125
Asn Ala Asn Ala Thr Ala Ser Asn Ser Ser Ile Ile Glu Gly Met Asn
130                 135                 140
Ser Ser Ile Ile Glu Gly Met Lys Asn Cys Ser Phe Asn Ile Thr Thr
145                 150                 155                 160
Glu Leu Arg Asp Lys Arg Glu Lys Lys Asn Ala Leu Phe Tyr Lys Leu
                165                 170                 175
Asp Ile Val Gln Leu Asp Gly Asn Ser Ser Gln Tyr Arg Leu Ile Asn
            180                 185                 190
Cys Asn Thr Ser Val Ile Thr Gln Ala Cys Pro Lys Val Ser Phe Asp
        195                 200                 205
Pro Ile Pro Ile His Tyr Cys Ala Pro Ala Gly Tyr Ala Ile Leu Lys
210                 215                 220
Cys Asn Asn Lys Thr Phe Asn Gly Thr Gly Pro Cys Asn Asn Val Ser
225                 230                 235                 240
Thr Val Gln Cys Thr His Gly Ile Lys Pro Val Val Ser Thr Gln Leu
                245                 250                 255
Leu Leu Asn Gly Ser Leu Ala Glu Gly Glu Ile Ile Arg Ser Glu
            260                 265                 270
Asn Ile Thr Asp Asn Gly Lys Thr Ile Ile Val His Leu Asn Glu Ser
        275                 280                 285
Val Lys Ile Glu Cys Thr Arg Pro Ser Asn Asn Thr Arg Thr Ser Ile
290                 295                 300
Arg Ile Gly Pro Gly Gln Ala Phe Tyr Ala Thr Gly Gln Val Ile Gly
305                 310                 315                 320
Asp Ile Arg Glu Ala His Cys Asn Ile Ser Glu Ser Lys Trp Asn Glu
                325                 330                 335
Thr Leu Gln Arg Val Ser Glu Lys Leu Lys Glu Tyr Phe Pro His Lys
            340                 345                 350
Asn Ile Thr Phe Gln Pro Ser Ser Gly Gly Asp Leu Glu Ile Thr Thr
        355                 360                 365
His Ser Phe Asn Cys Gly Gly Glu Phe Phe Tyr Cys Asn Thr Ser Ser
370                 375                 380
Leu Phe Asn Arg Thr Tyr Met Ala Thr Ser Thr Asp Met Ala Asn Ser
385                 390                 395                 400
Thr Glu Thr Asn Ser Thr Arg Ile Ile Thr Ile Arg Cys Arg Ile Lys
                405                 410                 415
Gln Ile Ile Asn Met Trp Gln Glu Val Gly Arg Ala Met Tyr Ala Pro
            420                 425                 430
Pro Ile Ala Gly Asn Ile Thr Cys Ile Ser Asn Ile Thr Gly Leu Leu
```

```
                    435                 440                 445
Leu Thr Arg Asp Gly Lys Asn Asn Thr Glu Thr Phe Glu Thr Phe
450                 455                 460
Arg Pro Gly Gly Gly Asn Met Lys Asp Asn Trp Arg Ser Glu Leu Tyr
465                 470                 475                 480
Lys Tyr Lys Val Val Glu Val Lys Pro Leu Gly Val Ala Pro Thr Asn
                    485                 490                 495
Ala Arg Arg Arg Val Val Glu Arg Glu Lys Arg Ala Val Gly Met Gly
                500                 505                 510
Ala Val Phe Leu Gly Phe Leu Gly Ala Ala Gly Ser Thr Met Gly Ala
                515                 520                 525
Ala Ser Ile Thr Leu Thr Val Gln Ala Arg Gln Leu Leu Ser Gly Ile
530                 535                 540
Val Gln Gln Gln Ser Asn Leu Leu Lys Ala Ile Glu Ala Gln Gln His
545                 550                 555                 560
Met Leu Lys Leu Thr Val Trp Gly Ile Lys Gln Leu Gln Ala Arg Val
                565                 570                 575
Leu Ala Leu Glu Arg Tyr Leu Lys Asp Gln Gln Leu Leu Gly Met Trp
                580                 585                 590
Gly Cys Ser Gly Lys Leu Ile Cys Thr Thr Asn Val Tyr Trp Asn Ser
                595                 600                 605
Ser Trp Ser Asn Lys Thr Tyr Gly Asp Ile Trp Asp Asn Met Thr Trp
610                 615                 620
Met Gln Trp Glu Arg Glu Ile Ser Asn Tyr Thr Glu Ile Ile Tyr Glu
625                 630                 635                 640
Leu Leu Glu Glu Ser Gln Asn Gln Gln Glu Lys Asn Glu Gln Asp Leu
                645                 650                 655
Leu Ala Leu Asp Arg Trp Asn Ser Leu Trp Asn Trp Phe Asn Ile Thr
                660                 665                 670
Asn Trp Leu Trp Tyr Ile Lys Ile Phe Ile Met Ile Val Gly Gly Leu
                675                 680                 685
Ile Gly Leu Arg Ile Ile Phe Ala Val Leu Ser Leu Val Asn Arg Val
                690                 695                 700
Arg Gln Gly Tyr Ser Pro Leu Ser Leu Gln Thr Leu Ile Pro Ser Pro
705                 710                 715                 720
Arg Gly Pro Asp Arg Pro Gly Gly Ile Glu Glu Glu Gly Gly Glu Gln
                725                 730                 735
Asp Arg Asn Arg Ser Thr Arg Leu Val Ser Gly Phe Leu Ala Leu Ala
                740                 745                 750
Trp Asp Asp Leu Arg Ser Leu Cys Leu Phe Ile Tyr His Arg Leu Arg
                755                 760                 765
Asp Phe Ile Leu Ile Ala Ala Arg Ala Gly Glu Leu Leu Gly Arg Ser
                770                 775                 780
Ser Leu Lys Gly Leu Arg Arg Gly Trp Glu Ala Leu Lys Tyr Leu Gly
785                 790                 795                 800
Ser Leu Val Gln Tyr Trp Gly Leu Glu Leu Lys Arg Ser Ala Ile Ser
                805                 810                 815
Leu Leu Asp Thr Leu Ala Ile Ala Val Gly Glu Gly Thr Asp Arg Ile
                820                 825                 830
Leu Glu Phe Val Leu Gly Ile Cys Arg Ala Ile Arg Asn Ile Pro Thr
                835                 840                 845
Arg Ile Arg Gln Gly Phe Glu Thr Ala Leu Leu
850                 855
```

<210> SEQ ID NO 81
<211> LENGTH: 848
<212> TYPE: PRT
<213> ORGANISM: Human immunodeficiency virus 1

<400> SEQUENCE: 81

Met Arg Val Thr Gly Ile Gln Arg Asn Tyr Pro Gln Trp Trp Ile Trp
1               5                   10                  15

Ser Met Leu Gly Leu Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Ala Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Ile
        115                 120                 125

Asp Ala Asn Ala Thr Ala Ser Asn Ala Thr Ala Ser Asn Ser Ser Ile
    130                 135                 140

Ile Glu Gly Met Lys Asn Cys Ser Phe Asn Ile Thr Thr Glu Leu Arg
145                 150                 155                 160

Asp Lys Ile Glu Lys Lys Asn Ala Leu Phe Tyr Lys Leu Asp Ile Val
                165                 170                 175

Gln Leu Asp Gly Asn Ser Ser Gln Tyr Arg Leu Ile Asn Cys Asn Thr
            180                 185                 190

Ser Val Ile Thr Gln Ala Cys Pro Lys Val Ser Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Ile Thr
            260                 265                 270

Asn Ser Ala Lys Thr Ile Ile Val His Leu Asn Glu Ser Val Lys Ile
        275                 280                 285

Glu Cys Thr Arg Pro Ser Asn Asn Thr Arg Thr Ser Ile Arg Ile Gly
    290                 295                 300

Pro Gly Gln Ala Phe Tyr Ala Thr Gly Gln Val Ile Gly Asp Ile Arg
305                 310                 315                 320

Lys Ala His Cys Asn Ile Ser Glu Ser Lys Trp Asn Glu Thr Leu Gln
                325                 330                 335

Arg Val Ser Lys Lys Leu Lys Glu Tyr Phe Pro His Lys Asn Ile Thr
            340                 345                 350

Phe Gln Pro Ser Ser Gly Gly Asp Leu Glu Ile Thr Thr His Ser Phe
        355                 360                 365

Asn Cys Gly Gly Glu Phe Phe Tyr Cys Asn Thr Ser Ser Leu Phe Asn

```
                370                 375                 380
Arg Thr Tyr Met Ala Asn Ser Thr Glu Thr Asn Ser Thr Arg Thr Ile
385                 390                 395                 400

Thr Leu His Cys Arg Ile Lys Gln Ile Ile Asn Met Trp Gln Glu Val
                405                 410                 415

Gly Arg Ala Met Tyr Ala Pro Pro Ile Ala Gly Asn Ile Thr Cys Ile
                420                 425                 430

Ser Asn Ile Thr Gly Leu Leu Leu Thr Arg Asp Gly Asn Asn Asn
                435                 440                 445

Thr Thr Glu Thr Phe Arg Pro Gly Gly Asn Met Lys Asp Asn Trp
450                 455                 460

Arg Ser Glu Leu Tyr Lys Tyr Lys Val Val Glu Ile Lys Pro Leu Gly
465                 470                 475                 480

Val Ala Pro Thr Asn Ala Arg Arg Val Val Glu Arg Glu Lys Arg
                485                 490                 495

Ala Val Gly Met Gly Ala Val Phe Leu Gly Phe Leu Gly Ala Ala Gly
                500                 505                 510

Ser Thr Met Gly Ala Ala Ser Ile Thr Leu Thr Val Gln Ala Arg Gln
                515                 520                 525

Leu Leu Ser Gly Ile Val Gln Gln Ser Asn Leu Leu Lys Ala Ile
                530                 535                 540

Glu Ala Gln Gln His Met Leu Lys Leu Thr Val Trp Gly Ile Lys Gln
545                 550                 555                 560

Leu Gln Ala Arg Val Leu Ala Leu Glu Arg Tyr Leu Lys Asp Gln Gln
                565                 570                 575

Leu Leu Gly Met Trp Gly Cys Ser Gly Lys Leu Ile Cys Thr Thr Asn
                580                 585                 590

Val Tyr Trp Asn Ser Ser Trp Ser Asn Lys Thr Tyr Gly Asp Ile Trp
                595                 600                 605

Asp Asn Met Thr Trp Met Gln Trp Glu Arg Glu Ile Ser Asp Tyr Thr
                610                 615                 620

Glu Ile Ile Tyr Glu Leu Leu Glu Glu Ser Gln Asn Gln Gln Glu Lys
625                 630                 635                 640

Asn Glu Gln Asp Leu Leu Ala Leu Asp Arg Trp Asn Ser Leu Trp Asn
                645                 650                 655

Trp Phe Asn Ile Thr Asn Trp Leu Trp Tyr Ile Lys Ile Phe Ile Met
                660                 665                 670

Ile Val Gly Gly Leu Ile Gly Leu Arg Ile Ile Phe Ala Val Leu Ser
                675                 680                 685

Leu Val Asn Arg Val Arg Gln Gly Tyr Ser Pro Leu Ser Leu Gln Thr
                690                 695                 700

Leu Thr Pro Ser Pro Arg Gly Pro Asp Arg Pro Gly Gly Ile Glu Glu
705                 710                 715                 720

Glu Gly Gly Glu Gln Asp Arg Asn Arg Ser Thr Arg Leu Val Ser Gly
                725                 730                 735

Phe Leu Ala Leu Ala Trp Asp Asp Leu Arg Ser Leu Cys Leu Phe Ile
                740                 745                 750

Tyr His Arg Leu Arg Asp Phe Ile Leu Ile Ala Ala Arg Ala Gly Glu
                755                 760                 765

Leu Leu Gly Arg Ser Ser Leu Lys Gly Leu Arg Arg Gly Trp Glu Ala
                770                 775                 780

Leu Lys Tyr Leu Gly Gly Leu Val Gln Tyr Trp Gly Leu Glu Leu Lys
785                 790                 795                 800
```

Arg Ser Ala Ile Ser Leu Leu Asp Thr Leu Ala Ile Ala Val Gly Glu
            805                 810                 815

Gly Thr Asp Arg Ile Leu Glu Phe Val Leu Gly Ile Cys Arg Ala Ile
            820                 825                 830

Arg Asn Ile Pro Thr Arg Ile Arg Gln Gly Phe Glu Thr Ala Leu Leu
            835                 840                 845

<210> SEQ ID NO 82
<211> LENGTH: 863
<212> TYPE: PRT
<213> ORGANISM: Human immunodeficiency virus 1

<400> SEQUENCE: 82

Met Lys Val Arg Gly Ile Gln Arg Asn Tyr Pro Gln Trp Trp Ile Trp
1               5                   10                  15

Ser Met Leu Gly Leu Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Glu Asn Val Thr Glu Asn Phe Asn Met Trp Lys Asn Asp Met
                85                  90                  95

Ala Asp Gln Met His Glu Asp Val Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asp Ala Asn Ala Thr Ala Ser Asn Thr Asn Ala Thr Ala Ser Asn Ile
    130                 135                 140

Asn Ala Thr Ala Ser Lys Ser Ser Ile Ile Glu Glu Met Lys Asn Cys
145                 150                 155                 160

Ser Phe Asn Ile Thr Thr Glu Leu Arg Asp Lys Arg Glu Lys Lys Tyr
                165                 170                 175

Ala Leu Phe Tyr Lys Leu Asp Ile Val Gln Leu Asp Gly Asn Ser Ser
            180                 185                 190

Gln Tyr Arg Leu Ile Asn Cys Asn Thr Ser Val Ile Thr Gln Ala Cys
        195                 200                 205

Pro Lys Val Ser Phe Asp Pro Ile Pro Ile His Tyr Cys Ala Pro Ala
    210                 215                 220

Gly Tyr Ala Ile Leu Lys Cys Asn Asn Lys Thr Phe Asn Gly Thr Gly
225                 230                 235                 240

Pro Cys Asn Asn Val Ser Thr Val Gln Cys Thr His Gly Ile Lys Pro
                245                 250                 255

Val Val Ser Thr Gln Leu Leu Leu Asn Gly Ser Leu Ala Glu Gly Glu
            260                 265                 270

Ile Ile Ile Arg Ser Glu Asn Ile Thr Asp Asn Ser Lys Thr Ile Ile
        275                 280                 285

Val His Leu Asn Glu Ser Val Lys Ile Glu Cys Thr Arg Pro Ser Asn
    290                 295                 300

Asn Thr Arg Thr Ser Ile Arg Ile Gly Pro Gly Gln Ala Phe Tyr Ala
305                 310                 315                 320

Thr Gly Gln Val Ile Gly Asp Ile Arg Glu Ala His Cys Asn Ile Ser

```
                325                 330                 335
Glu Ser Lys Trp Asn Glu Thr Leu Gln Arg Val Ser Lys Lys Leu Lys
            340                 345                 350
Glu Tyr Phe Pro Asp Lys Asn Ile Thr Phe Gln Pro Ser Ser Gly Gly
            355                 360                 365
Asp Pro Glu Ile Thr Thr His Ser Phe Asn Cys Gly Gly Glu Phe Phe
            370                 375                 380
Tyr Cys Asn Thr Ser Ser Leu Phe Asn Arg Thr Tyr Met Ala Asn Ser
385                 390                 395                 400
Thr Glu Thr Asn Ser Thr Arg Thr Ile Thr Leu His Cys Arg Ile Lys
            405                 410                 415
Gln Ile Ile Asn Met Trp Gln Glu Val Gly Arg Ala Met Tyr Ala Pro
            420                 425                 430
Pro Ile Ala Gly Asn Ile Thr Cys Ile Ser Asn Ile Thr Gly Leu Leu
            435                 440                 445
Leu Thr Arg Asp Gly Gly Glu Asn Thr Arg Asp Gly Gly Asn Asn Asn
            450                 455                 460
Thr Glu Thr Phe Arg Pro Gly Gly Asn Met Lys Asp Asn Trp Arg
465                 470                 475                 480
Ser Glu Leu Tyr Lys Tyr Lys Val Val Glu Val Lys Pro Leu Gly Val
            485                 490                 495
Ala Pro Thr Lys Ala Arg Arg Arg Val Val Glu Arg Glu Lys Arg Ala
            500                 505                 510
Val Gly Met Gly Ala Val Phe Leu Gly Phe Leu Gly Ala Ala Gly Ser
            515                 520                 525
Thr Met Gly Ala Ala Ser Ile Thr Leu Thr Val Gln Ala Arg Gln Leu
            530                 535                 540
Leu Ser Gly Ile Val Gln Gln Ser Asn Leu Leu Lys Ala Ile Glu
545                 550                 555                 560
Ala Gln Gln His Met Leu Lys Leu Thr Val Trp Gly Ile Lys Gln Leu
            565                 570                 575
Gln Ala Arg Val Leu Ala Leu Glu Arg Tyr Leu Lys Asp Gln Gln Leu
            580                 585                 590
Leu Gly Met Trp Gly Cys Ser Gly Lys Leu Ile Cys Thr Thr Asn Val
            595                 600                 605
Tyr Trp Asn Ser Ser Trp Ser Asn Lys Thr Tyr Gly Asp Ile Trp Asp
            610                 615                 620
Asn Met Thr Trp Met Gln Trp Glu Arg Glu Ile Ser Asn Tyr Thr Asp
625                 630                 635                 640
Ile Ile Tyr Asp Leu Leu Glu Glu Ser Gln Asn Gln Gln Glu Lys Asn
            645                 650                 655
Glu Gln Asp Leu Leu Ala Leu Asp Arg Trp Asn Ser Leu Trp Asn Trp
            660                 665                 670
Phe Asn Ile Thr Lys Trp Leu Trp Tyr Ile Lys Ile Phe Ile Met Ile
            675                 680                 685
Val Gly Gly Leu Ile Gly Leu Arg Ile Ile Phe Ala Val Leu Ser Leu
            690                 695                 700
Val Asn Arg Val Arg Gln Gly Tyr Ser Pro Leu Ser Leu Gln Thr Leu
705                 710                 715                 720
Ile Pro Ser Pro Arg Gly Pro Asp Arg Pro Gly Ile Glu Glu Glu
            725                 730                 735
Gly Gly Glu Gln Asp Arg Asn Arg Ser Thr Arg Leu Val Ser Gly Phe
            740                 745                 750
```

```
Leu Ala Leu Ala Trp Asp Asp Leu Arg Ser Leu Cys Leu Phe Ile Tyr
            755                 760                 765

His Arg Leu Arg Asp Phe Ile Leu Ile Ala Ala Arg Ala Gly Glu Leu
        770                 775                 780

Leu Gly Arg Ser Ser Leu Lys Gly Leu Arg Arg Gly Trp Glu Ala Leu
785                 790                 795                 800

Lys Tyr Leu Gly Gly Leu Val Gln Tyr Trp Gly Leu Glu Leu Lys Arg
                805                 810                 815

Ser Ala Ile Ser Leu Leu Asp Thr Leu Ala Ile Ala Val Gly Glu Gly
            820                 825                 830

Thr Asp Arg Ile Leu Glu Phe Val Leu Gly Ile Cys Arg Ala Ile Arg
        835                 840                 845

Asn Ile Pro Thr Arg Ile Arg Gln Gly Phe Glu Thr Ala Leu Leu
    850                 855                 860

<210> SEQ ID NO 83
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65              70                  75                  80

Val Leu Lys Asn Val Thr Glu Asn Phe Asn Met Trp Lys Asn Asp Met
            85                  90                  95

Val Asp Gln Met His Glu Asp Val Ile Ser Leu Trp Asp Gln Ser Leu
        100                 105                 110

Lys Pro Cys Val Lys Leu Thr Pro Leu Cys Val Thr Leu Asn Cys Thr
    115                 120                 125

Asn Ala Thr Ala Ser Asn Ser Ser Ile Ile Glu Gly Met Lys Asn Cys
    130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
            180                 185                 190

Pro Lys Val Ser Phe Asp Pro Ile Pro Ile His Tyr Cys Ala Pro Ala
        195                 200                 205

Gly Tyr Ala Ile Leu Lys Cys Asn Asn Lys Thr Phe Thr Gly Thr Gly
    210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
```

-continued

```
                245                 250                 255
Ile Ile Ile Arg Ser Glu Asn Ile Thr Asn Asn Val Lys Thr Ile Ile
            260                 265                 270
Val His Leu Asn Glu Ser Val Lys Ile Glu Cys Thr Arg Pro Asn Asn
            275                 280                 285
Lys Thr Arg Thr Ser Ile Arg Ile Gly Pro Gly Gln Ala Phe Tyr Ala
            290                 295                 300
Thr Gly Gln Val Ile Gly Asp Ile Arg Glu Ala Tyr Cys Asn Ile Asn
305                 310                 315                 320
Glu Ser Lys Trp Asn Glu Thr Leu Gln Arg Val Ser Lys Lys Leu Lys
                325                 330                 335
Glu Tyr Phe Pro His Lys Asn Ile Thr Phe Gln Pro Ser Ser Gly Gly
            340                 345                 350
Asp Leu Glu Ile Thr Thr His Ser Phe Asn Cys Gly Gly Glu Phe Phe
            355                 360                 365
Tyr Cys Asn Thr Ser Ser Leu Phe Asn Arg Thr Tyr Met Ala Asn Ser
    370                 375                 380
Thr Asp Met Ala Asn Ser Thr Glu Thr Asn Ser Thr Arg Thr Ile Thr
385                 390                 395                 400
Ile His Cys Arg Ile Lys Gln Ile Ile Asn Met Trp Gln Glu Val Gly
                405                 410                 415
Arg Ala Met Tyr Ala Pro Pro Ile Ala Gly Asn Ile Thr Cys Ile Ser
            420                 425                 430
Asn Ile Thr Gly Leu Leu Leu Thr Arg Asp Gly Gly Lys Asn Asn Thr
            435                 440                 445
Glu Thr Phe Arg Pro Gly Gly Gly Asn Met Lys Asp Asn Trp Arg Ser
    450                 455                 460
Glu Leu Tyr Lys Tyr Lys Val Val Glu Val Lys Pro Leu Gly Val Ala
465                 470                 475                 480
Pro Thr Asn Ala Arg Arg Arg Val Val Glu Arg Glu Lys Arg Ala Val
                485                 490                 495
Gly Met Gly Ala Val Phe Leu Gly Phe Leu Gly Ala Ala Gly Ser Thr
            500                 505                 510
Met Gly Ala Ala Ser Ile Thr Leu Thr Val Gln Ala Arg Gln Leu Leu
            515                 520                 525
Ser Gly Ile Val Gln Gln Ser Asn Leu Leu Lys Ala Ile Glu Ala
            530                 535                 540
Gln Gln His Met Leu Lys Leu Thr Val Trp Gly Ile Lys Gln Leu Gln
545                 550                 555                 560
Ala Arg Val Leu Ala Leu Glu Arg Tyr Leu Lys Asp Gln Gln Leu Leu
                565                 570                 575
Gly Met Trp Gly Cys Ser Gly Lys Leu Ile Cys Thr Thr Asn Val Tyr
            580                 585                 590
Trp Asn Ser Ser Trp Ser Asn Lys Thr Tyr Gly Asp Ile Trp Asp Asn
            595                 600                 605
Met Thr Trp Met Gln Trp Glu Arg Glu Ile Ser Asn Tyr Thr Glu Ile
    610                 615                 620
Ile Tyr Glu Leu Leu Glu Glu Ser Gln Asn Gln Gln Glu Lys Asn Glu
625                 630                 635                 640
Gln Asp Leu Leu Ala Leu Asp Arg Trp Asn Ser Leu Trp Asn Trp Phe
                645                 650                 655
Asn Ile Thr Asn Trp Leu Gly Tyr Ile Lys Ile Phe Ile Met Ile Val
            660                 665                 670
```

Gly Gly Leu Ile Gly Leu Arg Ile Ile Phe Ala Val Leu Ser Leu Val
            675                 680                 685

Asn Arg Val Arg Gln Gly Tyr Ser Pro Leu Ser Leu Gln Thr Leu Ile
        690                 695                 700

Pro Ser Pro Arg Gly Pro Asp Arg Pro Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
            740                 745                 750

Arg Leu Arg Asp Phe Ile Leu Ile Ala Ala Arg Ala Gly Glu Leu Leu
        755                 760                 765

Gly Arg Ser Ser Leu Lys Gly Leu Arg Arg Gly Trp Glu Ala Leu Lys
    770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
        835                 840                 845

<210> SEQ ID NO 84
<211> LENGTH: 2562
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
gtcgacgcta gcaccatgcg cgtgatgggc atccagcgca actaccccca gtggtggatc      60
tggtccatgc tgggcttctg gatgctgatg atctgcaacg gcatgtgggt gaccgtgtac     120
tacggcgtgc ccgtgtggaa ggaggccaag accaccctgt tctgcgcctc cgacgccaag     180
gcctacgaga aggaggtgca caacgtgtgg gccacccacg cctgcgtgcc caccgacccc     240 aaccccagg agatggtgct gaagaacgtg accgagaact tcaacatgtg gaagaacgac     300
atggtggacc agatgcacga ggacgtgatc tccctgtggg accagtccct gaagccctgc     360
gtgaagctga cccccctgtg cgtgaccctg aactgcacca cgccaccgc ctccaactcc     420 tccatcatcg agggcatgaa gaactgctcc ttcaacatca ccaccgagct gcgcgacaag     480
cgcgagaaga gaacgccct gttctacaag ctggacatcg tgcagctgga cggcaactcc     540
tcccagtacc gcctgatcaa ctgcaacacc tccgtgatca cccaggcctg ccccaaggtg     600
tccttcgacc ccatccccat ccactactgc gcccccgccg gctacgccat cctgaagtgc     660
aacaacaaga ccttcaccgg caccggcccc tgcaacaacg tgtccaccgt gcagtgcacc     720
cacggcatca gcccgtggt gtccacccag ctgctgctga cggctccct ggccgagggc     780 gagatcatca tccgctccga gaacatcacc aacaacgtga gaccatcat cgtgcacctg     840 aacgagtccg tgaagatcga gtgcacccgc cccaacaaca gacccgcac ctccatccgc     900 atcggccccg gccaggcctt ctacgccacc ggccaggtga tcggcgacat ccgcgaggcc     960
tactgcaaca tcaacgagtc caagtggaac gagaccctgc agcgcgtgtc caagaagctg    1020

```
aaggagtact tcccccacaa gaacatcacc ttccagccct cctccggcgg cgacctggag    1080
atcaccaccc actccttcaa ctgcggcggc gagttcttct actgcaacac ctcctccctg    1140
ttcaaccgca cctacatggc caactccacc gacatggcca actccaccga gaccaactcc    1200
acccgcacca tcaccatcca ctgccgcatc aagcagatca tcaacatgtg caggaggtg     1260 ggccgcgcca tgtacgcccc ccccatcgcc ggcaacatca cctgcatctc caacatcacc    1320
ggcctgctgc tgacccgcga cggcggcaag aacaacaccg agaccttccg ccccggcggc    1380
ggcaacatga aggacaactg cgctccgag  ctgtacaagt acaaggtggt ggaggtgaag    1440
cccctgggcg tggcccccac caacgcccgc cgccgcgtgg tggagcgcga aagcgcgcc     1500 gtgggcatgg cgccgtgtt  cctgggcttc ctgggcgccg ccggctccac catgggcgcc    1560
gcctccatca ccctgaccgt gcaggcccgc cagctgctgt ccggcatcgt gcagcagcag    1620
tccaacctgc tgaaggccat cgaggcccag cagcacatgc tgaagctgac cgtgtgggc     1680 atcaagcagc tgcaggcccg cgtgctggcc ctggagcgct acctgaagga ccagcagctg    1740
ctgggcatgt ggggctgctc cggcaagctg atctgcacca ccaacgtgta ctggaactcc    1800
tcctggtcca acaagaccta cggcgacatc tgggacaaca tgacctggat gcagtgggag    1860
cgcgagatct ccaactacac cgagatcatc tacgagctgc tggaggagtc ccagaaccag    1920
caggagaaga cgagcagga cctgctggcc ctggaccgct ggaactccct gtggaactgg    1980
ttcaacatca ccaactggct gggctacatc aagatcttca tcatgatcgt gggcggcctg    2040
atcggcctgc gcatcatctt cgccgtgctg tccctggtga accgcgtgcg ccagggctac    2100 tccccctgt ccctgcagac cctgatcccc tcccccgcg  gccccgaccg cccggcggc     2160 atcgaggagg agggcggcga gcaggaccgc aaccgctcca cccgcctggt gtccggcttc    2220
ctggccctgg tgtgggacga cctgcgctcc ctgtgcctgt tcatctacca ccgcctgcgc    2280
gacttcatcc tgatcgccgc ccgcgccggc gagctgctgg gccgctcctc cctgaagggc    2340
ctgcgccgcg gctgggaggc cctgaagtac ctgggctccc tggtgcagta ctggggcctg    2400
gagctgaagc gctccgccat ctccctgctg gacaccctgg ccatcgccgt gggcgagggc    2460
accgaccgca tcctggagtt cgtgctgggc atctgccgcg ccatccgcaa catccccacc    2520
cgcatccgcc agggcttcga gaccgccctg ctgtagggat cc                       2562
```

<210> SEQ ID NO 85
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Met Arg Val Arg Gly Ile Pro Arg Asn Trp Pro Gln Trp Trp Ile Trp
1               5                   10                  15

Gly Ile Leu Gly Phe Trp Val Ile Ile Thr Cys Arg Val Val Gly Gln
            20                  25                  30

Leu Trp Val Thr Val Tyr Tyr Gly Val Pro Val Trp Thr Glu Ala Lys
        35                  40                  45

Thr Thr Leu Phe Cys Ala Ser Asp Ala Lys Ala Tyr Asp Lys Glu Val
    50                  55                  60

His Asn Val Trp Ala Thr His Ala Cys Val Pro Thr Asp Pro Asn Pro
65                  70                  75                  80

Gln Glu Ile Val Leu Gly Asn Ile Thr Glu Asn Phe Asn Met Trp Glu
```

-continued

```
                85                  90                  95
Asn Asp Met Val Asp Gln Met His Glu Asp Ile Ile Ser Leu Trp Asp
                100                 105                 110
Gln Ser Leu Lys Pro Cys Val Lys Leu Thr Pro Leu Cys Val Thr Leu
                115                 120                 125
Ile Cys Thr Asn Ala Asn Ile Ser Val Thr Ser Val Ser Asn Asp Ser
            130                 135                 140
Arg Ile Leu Asn Glu Glu Ile Lys Asn Cys Ser Phe Asn Thr Thr Thr
145                 150                 155                 160
Glu Ile Arg Asp Lys Lys Gln Gln Val Tyr Ala Leu Phe Tyr Arg Ser
                165                 170                 175
Asp Val Ala Pro Leu Ser Asn Ser Ser Glu Tyr Ile Leu Ile Asn Cys
                180                 185                 190
Asn Thr Ser Thr Ile Thr Gln Ala Cys Pro Lys Val Thr Phe Asp Pro
            195                 200                 205
Ile Pro Leu His Tyr Cys Ala Pro Ala Gly Tyr Ala Ile Leu Lys Cys
            210                 215                 220
Asn Asn Lys Thr Phe Asn Gly Thr Gly Pro Cys Leu Asn Val Ser Thr
225                 230                 235                 240
Val Gln Cys Thr His Gly Ile Lys Pro Val Ser Thr Gln Leu Leu
                245                 250                 255
Leu Asn Gly Ser Leu Ala Glu Glu Ile Ile Ile Lys Ser Lys Asn
            260                 265                 270
Leu Thr Asp Asp Thr Asn Thr Ile Ile Val His Leu Asn Lys Ser Ile
            275                 280                 285
Glu Ile Val Cys Thr Arg Pro Gly Asn Asn Thr Arg Lys Ser Ile Arg
            290                 295                 300
Ile Gly Pro Gly Gln Thr Phe Ala Thr Gly Asp Ile Ile Gly Asp
305                 310                 315                 320
Ile Arg Glu Ala His Cys Asn Leu Ser Lys Asp Ala Trp Asn Thr Thr
                325                 330                 335
Leu Glu Gln Ile Lys Arg Lys Leu Lys Glu His Phe Ser Ser Lys Glu
            340                 345                 350
Ile Lys Phe Ala Pro Ser Ser Gly Gly Asp Pro Glu Val Ala Thr His
            355                 360                 365
Ser Phe Asn Cys Arg Gly Glu Phe Phe Tyr Cys Asn Thr Thr Lys Leu
            370                 375                 380
Phe Asn Glu Asn Tyr Thr Leu Ser Asn Asn Ser Asn Glu Thr Ile Ile
385                 390                 395                 400
Leu Pro Cys Arg Ile Lys Gln Ile Ile Asn Met Trp Gln Gly Val Gly
                405                 410                 415
Arg Ala Met Tyr Ala Pro Pro Ile Ala Gly Asn Ile Thr Cys Asn Ser
                420                 425                 430
Ser Ile Thr Gly Leu Leu Leu Thr Arg Asp Lys Asp Ser Asn Thr Glu
            435                 440                 445
Thr Phe Arg Pro Thr Gly Gly Asn Met Lys Asp Asn Trp Arg Asn Glu
            450                 455                 460
Leu Tyr Lys Tyr Lys Val Val Glu Ile Lys Pro Leu Gly Val Ala Pro
465                 470                 475                 480
Thr Asn Ala Lys Arg Arg Val Val Glu Arg Glu Lys Arg Ala Val Gly
                485                 490                 495
Ile Gly Ala Val Leu Leu Gly Phe Leu Gly Ala Ala Gly Ser Thr Met
                500                 505                 510
```

Gly Ala Ala Ser Ile Thr Leu Thr Val Gln Ala Arg Gln Leu Leu Ser
            515                 520                 525

Gly Ile Val Gln Gln Gln Ser Asn Leu Leu Arg Ala Ile Glu Ala Gln
530                 535                 540

Gln His Met Leu Gln Leu Thr Val Trp Gly Ile Lys Gln Leu Gln Thr
545                 550                 555                 560

Arg Val Leu Ala Ile Glu Arg Tyr Leu Lys Asp Gln Gln Leu Leu Gly
            565                 570                 575

Leu Trp Gly Cys Ser Gly Arg Leu Ile Cys Thr Thr Asn Val Pro Trp
            580                 585                 590

Asn Ser Ser Trp Ser Asn Lys Ser Gln Glu Asp Ile Trp Gly Asn Met
            595                 600                 605

Thr Trp Met Gln Trp Asp Arg Glu Ile Ser Asn Tyr Thr Ser Thr Ile
            610                 615                 620

Tyr Arg Leu Leu Glu Asp Ser Gln Asn Gln Gln Glu Lys Asn Glu Lys
625                 630                 635                 640

Asp Leu Leu Ala Leu Asp Ser Trp Lys Asn Leu Trp Asn Trp Phe Asp
            645                 650                 655

Ile Thr Lys Trp Leu Trp Tyr Ile Lys Ile Phe Ile Ile Ile Val Gly
            660                 665                 670

Gly Leu Ile Gly Leu Arg Ile Val Leu Gly Val Leu Ala Ile Val Lys
            675                 680                 685

Arg Val Arg Gln Gly Tyr Ser Pro Leu Ser Phe Gln Thr Leu Ile Pro
            690                 695                 700

Ser Pro Arg Gly Leu Asp Arg Leu Gly Arg Ile Glu Glu Glu Gly Gly
705                 710                 715                 720

Glu Gln Asp Lys Asp Arg Ser Ile Arg Leu Val Asn Gly Phe Leu Ala
            725                 730                 735

Leu Ala Trp Glu Asp Leu Arg Asn Leu Cys Leu Phe Ser Tyr His Gln
            740                 745                 750

Leu Arg Asp Phe Ile Leu Ile Val Ala Arg Ala Val Glu Leu Leu Gly
            755                 760                 765

Arg Ser Ser Leu Arg Gly Leu Gln Arg Gly Trp Glu Ala Leu Lys Tyr
            770                 775                 780

Leu Gly Ala Leu Ile Gln Gln Gly Gly Leu Glu Leu Lys Lys Ser Ala
785                 790                 795                 800

Ile Ser Leu Leu Asp Thr Thr Ala Ile Ala Val Ala Glu Gly Thr Asp
            805                 810                 815

Arg Ile Leu Glu Leu Ile Gln Arg Ile Cys Arg Ala Ile Arg Asn Ile
            820                 825                 830

Pro Thr Arg Ile Arg Gln Gly Phe Glu Ala Ala Leu Leu
            835                 840                 845

<210> SEQ ID NO 86
<211> LENGTH: 2538
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atgagagtga gggggatacc gaggaattgg ccacaatggt ggatatgggg catcttaggc      60
ttttgggtga ataacttg tagggtggta gggcaattgt gggtcacagt ctattatggg      120

```
gtacctgtgt ggacagaagc aaaaactact ctattctgtg catcagatgc taaagcatat    180
gacaaagaag tgcataatgt ctgggctaca catgcctgtg tacccacaga ccccaatcca    240
caagaaatag tcttgggaaa tataacagaa aattttaaca tgtgggaaaa tgacatggtg    300
gatcagatgc atgaggatat aatcagttta tgggatcaaa gtctaaaacc atgtgtaaag    360
ttgactccac tctgtgtcac tttaatttgt acaaatgcaa atattagtgt taccagtgtg    420
agtaatgata gcaggatttt gaatgaagaa ataaaaaatt gctctttcaa tacaaccaca    480
gaaataagag ataagaaaca gcaagtgtat gcactttttt atagatctga tgtagcacca    540
cttagtaatt ctagtgagta tatattaata aattgtaata cctcaaccat aacacaagcc    600
tgtccaaagg tcacttttga cccaattcct ttgcattatt gtgctccagc tggttatgcg    660
attctaaaat gcaacaataa gacattcaat gggacaggac catgccttaa tgtcagcaca    720
gtacaatgta cacatggaat taagccagtg gtatcaactc aattactgtt aaatggtagc    780
ctagcagaag aggagataat aattaaatct aaaaatctga cagatgatac caatacaata    840
atagtacacc ttaataaatc tatagaaatt gtgtgtacaa gacctggcaa taatacaaga    900
aaaagtataa ggataggacc aggacaaaca ttctttgcaa caggtgacat aataggagac    960
ataagagaag cccattgtaa ccttagtaaa gatgcatgga cacaactctc agaacagata   1020
aaaagaaaac tcaaagaaca cttctctagt aaagaaataa aatttgctcc aagctcagga   1080
ggagatccag aagttcgcac acatagtttt aattgtagag gagaattttt ctattgcaat   1140
acaacaaaac tgtttaatga gaattataca ctgagcaata acagtaatga aacaatcata   1200
ctcccatgta gaataaaaca aattataaat atgtggcagg gggtaggacg agcaatgtat   1260
gcccctccca ttgcaggaaa cataacatgt aactcaagta tcacaggact gttattgacg   1320
cgtgacaaaa cagcaacac agagacattc agacctacag gaggaaatat gaaggacaat   1380
tggagaaatg aattatacaa atataaagtg gtagaaatta accattagg agtagcaccc   1440 actaatgcaa aaaggagagt ggtggagaga gaaaaaagag cagtaggaat aggagctgtg   1500
ctccttgggt tcttgggagc agcaggaagc actatgggcg cggcgtcaat aacgctgacg   1560
gtacaggcca gacaactgtt atctggtata gtgcaacagc aaagtaattt gctgagagct   1620
atagaggcgc aacagcacat gttgcaactc acagtctggg gcattaaaca gctccagaca   1680
agagtcttgg ctatagaaag atacctaaag gatcaacagc tcctaggact ttggggctgc   1740
tctggaagac tcatctgcac cactaatgtg ccttggaact cgagttggag taataaatct   1800
caagaagata tttgggggaa catgacctgg atgcagtggg atagagaaat tagtaattac   1860
acaagcacaa tatacaggtt acttgaagac tcgcaaaacc agcaggagaa aaatgaaaag   1920
gatttgttag cattggacag ttggaaaaat ctgtggaatt ggtttgacat aacaaaatgg   1980
ctgtggtata taaaaatatt catcataata gtaggaggtt taataggttt gagaatagtt   2040
ttgggtgtgc ttgctatagt aaaaagagtt aggcaggga actcacccttt gtcgtttcag   2100 acccttatcc caagtccgag gggactcgac aggctcggaa gaatcgaaga agaaggtgga   2160
gagcaagaca agacagatc cattcgatta gtgaacggat tcttagcact tgcttgggaa   2220
gatctgcgga atctgtgcct cttcagctac caccaattga gagactttat attgattgta   2280
gcgagagcag tggaacttct gggacgcagc agcctcaggg gactacagag ggggtgggaa   2340
gctcttaagt atctgggagc tcttatacag cagggggtc tggaactaaa gaagagtgct   2400
attagtctgc ttgataccac agcaaatgca gtagctgaag gaacagatag gattctagaa   2460
ttaatacaaa gaatttgtag agctatccgc aacataccta caagaataag acaaggcttt   2520
```
gaagcagctt tgctataa                                         2538

<210> SEQ ID NO 87
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu
65                  70                  75

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

His His His His His His His His His His
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Gly Ser Asp Thr Ile Thr Leu Pro Cys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asn Ser Thr Arg Thr Ile Thr Ile His Cys
1               5                   10

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 91
tagtaaggtc accgaattcg ggacccggat cc                                    32

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tagtaaggtg accgaattca ggtcccggat cc                                    32

<210> SEQ ID NO 93
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tagtaaggga cccgaattcg gtcaccggat cc                                    32

<210> SEQ ID NO 94
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tagtaagggt cctgaattcg gttaccggat cc                                    32

<210> SEQ ID NO 95
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tagtaagggt cccgaattcg gttaccggat cc                                    32

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tagtaagaat tcggtgaccg ggtcccggat cc                                    32

<210> SEQ ID NO 97
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 97
tagtaagaat tcggtgaccg ggacctggat cc					32

<210> SEQ ID NO 98
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tagtaagaat tcggtaacca ggtcccggat cc					32

<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tagtaagaat tcggtcaccg ggtcctggat cc					32

<210> SEQ ID NO 100
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tagtaaggta accgggaccc gaattcggat cc					32

<210> SEQ ID NO 101
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgatgaggtc accgaattcg ggacccggat cc					32

<210> SEQ ID NO 102
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tgatgaggtg accgaattca ggtcccggat cc					32

<210> SEQ ID NO 103
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tgatgaggga cccgaattcg gtcaccggat cc                                           32

<210> SEQ ID NO 104
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgatgagggt cctgaattcg gttaccggat cc                                           32

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tgatgagggt cccgaattcg gttaccggat cc                                           32

<210> SEQ ID NO 106
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgatgagaat tcggtgaccg ggtcccggat cc                                           32

<210> SEQ ID NO 107
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tgatgagaat tcggtgaccg ggacctggat cc                                           32

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tgatgagaat tcggtaacca ggtcccggat cc                                           32

<210> SEQ ID NO 109
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

```
tgatgagaat tcggtcaccg ggtcctggat cc                                    32
```

<210> SEQ ID NO 110
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
tgatgaggta accgggaccc gaattcggat cc                                    32
```